US010556062B2

(12) United States Patent
Simpson et al.

(10) Patent No.: US 10,556,062 B2
(45) Date of Patent: Feb. 11, 2020

(54) ELECTRONIC MEDICATION ORDER TRANSFER AND PROCESSING METHODS AND APPARATUS

(71) Applicant: Baxter International Inc., Deerfield, IL (US)

(72) Inventors: Thomas L. C. Simpson, Burlington, WI (US); James P. Martucci, Libertyville, IL (US); Gordon J. Wilkes, Newmarket (CA)

(73) Assignee: Baxter International Inc., Deerfield, IL (US)

( * ) Notice: Subject to any disclaimer, the term of this patent is extended or adjusted under 35 U.S.C. 154(b) by 516 days.

(21) Appl. No.: 14/830,957

(22) Filed: Aug. 20, 2015

(65) Prior Publication Data

US 2015/0356255 A1    Dec. 10, 2015

Related U.S. Application Data

(63) Continuation of application No. 14/218,542, filed on Mar. 18, 2014, now Pat. No. 10,173,008, which is a
(Continued)

(51) Int. Cl.
*A61M 5/172* (2006.01)
*G06F 19/00* (2018.01)
(Continued)

(52) U.S. Cl.
CPC ........ *A61M 5/1723* (2013.01); *A61M 1/1613* (2014.02); *A61M 5/142* (2013.01);
(Continued)

(58) Field of Classification Search
CPC .. A61M 5/1723; A61M 1/1613; A61M 5/142; A61M 5/172; A61M 2205/3334;
(Continued)

(56) References Cited

U.S. PATENT DOCUMENTS

| 3,426,150 A | 2/1969 | Tygart |
| 3,739,943 A | 6/1973 | Williamsen et al. |

(Continued)

FOREIGN PATENT DOCUMENTS

| AU | 685495 | 5/1995 |
| CA | 1293566 | 12/1991 |

(Continued)

OTHER PUBLICATIONS

Japanese Office Action—Application No. 2015-165438, dated Mar. 13, 2018—2 pages.
(Continued)

*Primary Examiner* — Christopher L Gilligan
(74) *Attorney, Agent, or Firm* — K&L Gates LLP

(57) ABSTRACT

A pharmacy system for the automated transfer and processing of electronic medication order information to and from a computerized patient care system associated with a healthcare facility includes a pharmacy engine configured to receive a first HL7 message including information relating to an electronic medication order for a medication that is to be prepared for intravenous administration to a patient, and transmit a second HL7 message including information relating to preparation of the medication corresponding to the electronic medication order, the information from the second HL7 message being used to bill for the medication corresponding to the electronic medication order. The pharmacy system also includes a pharmacy computer configured to process the electronic medication order, including identifying one or more ingredients required to prepare the medication corresponding to the electronic medication order and a pharmacy workstation configured to provide instructions for preparing the medication corresponding to the electronic medication order.

25 Claims, 59 Drawing Sheets

Related U.S. Application Data continuation of application No. 10/749,102, filed on Dec. 30, 2003, now Pat. No. 8,775,196, which is a continuation-in-part of application No. 10/659,760, filed on Sep. 10, 2003, now Pat. No. 8,489,427, which is a continuation-in-part of application No. 10/424,553, filed on Apr. 28, 2003, now Pat. No. 7,698,156, which is a continuation-in-part of application No. 10/135,180, filed on Apr. 30, 2002, now abandoned, which is a continuation-in-part of application No. 10/059,929, filed on Jan. 29, 2002, now abandoned.

(60) Provisional application No. 60/528,103, filed on Dec. 9, 2003, provisional application No. 60/528,106, filed on Dec. 8, 2003, provisional application No. 60/488,273, filed on Jul. 18, 2003, provisional application No. 60/444,350, filed on Feb. 1, 2003.

(51) Int. Cl.

| | |
|---|---|
| *G16H 10/60* | (2018.01) |
| *G16H 20/17* | (2018.01) |
| *G16H 20/40* | (2018.01) |
| *G16H 20/10* | (2018.01) |
| *G16H 40/63* | (2018.01) |
| *A61M 1/14* | (2006.01) |
| *A61M 1/16* | (2006.01) |
| *A61M 5/142* | (2006.01) |
| *A61M 1/34* | (2006.01) |

(52) U.S. Cl.
CPC ......... *A61M 5/172* (2013.01); *G06F 19/3418* (2013.01); *G06F 19/3456* (2013.01); *G06F 19/3468* (2013.01); *G06F 19/3481* (2013.01); *G16H 10/60* (2018.01); *G16H 20/10* (2018.01); *G16H 20/17* (2018.01); *G16H 20/40* (2018.01); *G16H 40/63* (2018.01); *A61M 1/14* (2013.01); *A61M 1/34* (2013.01); *A61M 2005/14208* (2013.01); *A61M 2205/18* (2013.01); *A61M 2205/33* (2013.01); *A61M 2205/3334* (2013.01); *A61M 2205/3561* (2013.01); *A61M 2205/3584* (2013.01); *A61M 2205/50* (2013.01); *A61M 2205/502* (2013.01); *A61M 2205/52* (2013.01); *A61M 2230/005* (2013.01)

(58) Field of Classification Search
CPC ................ A61M 2205/52; A61M 1/34; A61M 2005/14208; A61M 2205/18; A61M 2205/33; A61M 2205/50; A61M 2205/502; A61M 2230/005; A61M 2205/3561; A61M 2205/3584; A61M 1/14; G16H 10/60; G16H 20/17; G16H 20/40; G16H 20/10; G16H 40/63; G06F 19/3418; G06F 19/3481; G06F 19/3456; G06F 19/3468
See application file for complete search history.

(56) References Cited

U.S. PATENT DOCUMENTS

| | | |
|---|---|---|
| 3,742,938 A | 7/1973 | Stern |
| 3,756,752 A | 9/1973 | Stenner |
| 3,774,762 A | 11/1973 | Lichtenstein |
| 3,786,190 A | 1/1974 | Pori |
| 3,809,871 A | 5/1974 | Howard et al. |
| 3,810,102 A | 5/1974 | Parks, III et al. |
| 3,848,112 A | 11/1974 | Weichselbaum et al. |
| 3,858,574 A | 1/1975 | Page |
| 3,910,257 A | 10/1975 | Fletcher et al. |
| 3,910,260 A | 11/1975 | Sarnoff et al. |
| 3,921,196 A | 11/1975 | Patterson |
| 3,971,000 A | 7/1976 | Cromwell |
| 3,998,103 A | 12/1976 | Bjorklund et al. |
| 4,032,908 A | 6/1977 | Rice et al. |
| 4,078,562 A | 3/1978 | Friedman |
| 4,144,496 A | 3/1979 | Cunningham et al. |
| 4,151,407 A | 4/1979 | McBride et al. |
| 4,156,867 A | 5/1979 | Bench et al. |
| 4,164,320 A | 8/1979 | Irazoqui et al. |
| 4,173,971 A | 11/1979 | Karz |
| 4,199,307 A | 4/1980 | Jassawalla |
| 4,270,532 A | 6/1981 | Franetzki et al. |
| 4,273,121 A | 6/1981 | Jassawalla |
| 4,282,872 A | 8/1981 | Franetzki et al. |
| 4,308,866 A | 1/1982 | Jelliffe et al. |
| 4,319,338 A | 3/1982 | Grudowski et al. |
| 4,320,757 A | 3/1982 | Whitney et al. |
| 4,354,252 A | 10/1982 | Lamb et al. |
| 4,369,780 A | 1/1983 | Sakai |
| 4,370,983 A | 2/1983 | Lichtenstein |
| 4,373,527 A | 2/1983 | Fischell |
| 4,381,776 A | 5/1983 | Latham, Jr. |
| 4,385,630 A | 5/1983 | Gilcher et al. |
| 4,398,289 A | 8/1983 | Schoate |
| 4,398,908 A | 8/1983 | Siposs |
| 4,416,654 A | 11/1983 | Schoendorfer et al. |
| 4,425,114 A | 1/1984 | Schoendorfer et al. |
| 4,428,381 A | 1/1984 | Hepp |
| 4,443,216 A | 4/1984 | Chappell |
| 4,447,224 A | 5/1984 | DeCant, Jr. et al. |
| 4,449,538 A | 5/1984 | Corbitt et al. |
| 4,451,255 A | 5/1984 | Bujan et al. |
| 4,457,750 A | 7/1984 | Hill |
| 4,458,693 A | 7/1984 | Badzinski et al. |
| 4,460,358 A | 7/1984 | Somerville et al. |
| 4,464,172 A | 8/1984 | Lichtenstein |
| 4,469,481 A | 9/1984 | Kobayashi |
| 4,475,901 A | 10/1984 | Kraegen et al. |
| 4,476,381 A | 10/1984 | Rubin |
| 4,480,751 A | 11/1984 | Lueptow |
| 4,481,670 A | 11/1984 | Freeburg |
| 4,487,604 A | 12/1984 | Iwatschenko et al. |
| 4,490,798 A | 12/1984 | Franks et al. |
| 4,496,351 A | 1/1985 | Hillel et al. |
| 4,511,352 A | 4/1985 | Theeuwes et al. |
| 4,525,861 A | 6/1985 | Freeburg |
| 4,529,401 A | 7/1985 | Leslie et al. |
| 4,531,527 A | 7/1985 | Reinhold, Jr. et al. |
| 4,538,138 A | 8/1985 | Harvey et al. |
| 4,545,071 A | 10/1985 | Freeburg |
| 4,551,133 A | 11/1985 | Zegers de Beyl et al. |
| 4,559,038 A | 12/1985 | Berg et al. |
| 4,560,979 A | 12/1985 | Rosskopf |
| 4,561,443 A | 12/1985 | Hogrefe et al. |
| 4,562,751 A | 1/1986 | Nason |
| 4,590,473 A | 5/1986 | Burke et al. |
| 4,602,249 A | 7/1986 | Abbott |
| 4,619,653 A | 10/1986 | Fischell |
| 4,622,979 A | 11/1986 | Katchis et al. |
| 4,624,661 A | 11/1986 | Arimond |
| 4,636,950 A | 1/1987 | Caswell et al. |
| 4,637,817 A | 1/1987 | Archibald et al. |
| 4,650,469 A | 3/1987 | Berg et al. |
| 4,652,262 A | 3/1987 | Veracchi |
| 4,676,776 A | 6/1987 | Howson |
| 4,681,563 A | 7/1987 | Deckert et al. |
| 4,688,167 A | 8/1987 | Agarwal |
| 4,691,580 A | 9/1987 | Fosslien |
| 4,695,954 A | 9/1987 | Rose et al. |
| 4,696,671 A | 9/1987 | Epstein et al. |
| 4,697,928 A | 10/1987 | Csongor |
| 4,702,595 A | 10/1987 | Mutschler et al. |
| 4,705,506 A | 11/1987 | Archibald |
| 4,714,462 A | 12/1987 | DiComenico |
| 4,717,042 A | 1/1988 | McLaughlin |
| 4,718,576 A | 1/1988 | Tamura et al. |
| 4,722,224 A | 2/1988 | Scheller et al. |

(56) References Cited

U.S. PATENT DOCUMENTS

| | | |
|---|---|---|
| 4,722,349 A | 2/1988 | Baumberg |
| 4,722,734 A | 2/1988 | Kolln |
| 4,730,849 A | 3/1988 | Siegel |
| 4,731,058 A | 3/1988 | Doan |
| 4,732,411 A | 3/1988 | Siegel |
| 4,741,732 A | 5/1988 | Crankshaw et al. |
| 4,741,736 A | 5/1988 | Brown |
| 4,756,706 A | 7/1988 | Kerns et al. |
| 4,759,756 A | 7/1988 | Forman |
| 4,778,449 A | 10/1988 | Weber et al. |
| 4,779,626 A | 10/1988 | Peel et al. |
| 4,784,645 A | 11/1988 | Fischell |
| 4,785,799 A | 11/1988 | Schoon et al. |
| 4,785,969 A | 11/1988 | McLaughlin |
| 4,796,644 A | 1/1989 | Polaschegg |
| 4,797,840 A | 1/1989 | Fraden |
| 4,803,625 A | 2/1989 | Fu et al. |
| 4,810,090 A | 3/1989 | Boucher |
| 4,810,243 A | 3/1989 | Howson |
| 4,811,844 A | 3/1989 | Moulding, Jr. et al. |
| 4,816,208 A | 3/1989 | Woods et al. |
| 4,817,044 A | 3/1989 | Ogren |
| 4,828,545 A | 5/1989 | Epstein et al. |
| 4,830,018 A | 5/1989 | Treach |
| 4,831,562 A | 5/1989 | McIntosh et al. |
| 4,832,033 A | 5/1989 | Maher et al. |
| 4,835,372 A | 5/1989 | Gombrich et al. |
| 4,835,521 A | 5/1989 | Andrejasich et al. |
| 4,838,275 A | 6/1989 | Lee |
| 4,839,806 A | 6/1989 | Goldfischer et al. |
| 4,845,644 A | 7/1989 | Anthias et al. |
| 4,847,764 A | 7/1989 | Halvorson |
| 4,850,009 A | 7/1989 | Zook et al. |
| 4,850,972 A | 7/1989 | Schulman et al. |
| 4,853,521 A | 8/1989 | Claeys et al. |
| 4,854,324 A | 8/1989 | Hirschman et al. |
| 4,857,713 A | 8/1989 | Brown |
| 4,857,716 A | 8/1989 | Gombrich et al. |
| 4,865,584 A | 9/1989 | Epstein et al. |
| 4,871,351 A | 10/1989 | Feingold |
| 4,878,175 A | 10/1989 | Norden-Paul et al. |
| 4,889,132 A | 12/1989 | Hutcheson et al. |
| 4,889,134 A | 12/1989 | Greenwold et al. |
| 4,893,270 A | 1/1990 | Beck et al. |
| 4,897,777 A | 1/1990 | Janke et al. |
| 4,898,576 A | 2/1990 | Philip |
| 4,898,578 A | 2/1990 | Rubalcaba, Jr. |
| 4,901,728 A | 2/1990 | Hutchison |
| 4,908,017 A | 3/1990 | Howson et al. |
| 4,912,623 A | 3/1990 | Rantala et al. |
| 4,916,441 A | 4/1990 | Gombrich et al. |
| 4,922,922 A | 5/1990 | Pollock et al. |
| 4,925,444 A | 5/1990 | Orkin et al. |
| 4,933,843 A | 6/1990 | Scheller et al. |
| 4,937,777 A | 6/1990 | Flood et al. |
| 4,941,808 A | 7/1990 | Qureshi et al. |
| 4,943,279 A | 7/1990 | Samiotes et al. |
| 4,949,274 A | 8/1990 | Hollander et al. |
| 4,952,928 A | 8/1990 | Carroll et al. |
| 4,953,074 A | 8/1990 | Kametani et al. |
| 4,960,230 A | 10/1990 | Marelli |
| 4,966,579 A | 10/1990 | Polaschegg |
| 4,967,928 A | 11/1990 | Carter |
| 4,968,295 A | 11/1990 | Neumann |
| 4,977,590 A | 12/1990 | Milovancevic |
| 4,978,335 A | 12/1990 | Arthur, III |
| 4,991,091 A | 2/1991 | Allen |
| 4,992,926 A | 2/1991 | Janke et al. |
| 4,993,068 A | 2/1991 | Piosenka et al. |
| 4,998,249 A | 3/1991 | Bennett et al. |
| 5,002,055 A | 3/1991 | Merki et al. |
| 5,003,296 A | 3/1991 | Lee |
| 5,006,699 A | 4/1991 | Felkner et al. |
| 5,007,429 A | 4/1991 | Treatch et al. |
| 5,012,402 A | 4/1991 | Akiyama |
| 5,012,411 A | 4/1991 | Policastro et al. |
| 5,014,875 A | 5/1991 | McLaughlin et al. |
| 5,016,172 A | 5/1991 | Dessertine |
| 5,023,770 A | 6/1991 | Siverling |
| 5,025,374 A | 6/1991 | Roizen et al. |
| 5,036,852 A | 8/1991 | Leishman |
| 5,038,800 A | 8/1991 | Oba |
| 5,041,086 A | 8/1991 | Koenig et al. |
| 5,045,048 A | 9/1991 | Kaleskas et al. |
| 5,047,959 A | 9/1991 | Phillips et al. |
| 5,053,031 A | 10/1991 | Borsanyi |
| 5,053,990 A | 10/1991 | Kreifels et al. |
| 5,055,001 A | 10/1991 | Natwick et al. |
| 5,057,076 A | 10/1991 | Polaschegg |
| 5,061,243 A | 10/1991 | Winchell et al. |
| 5,072,356 A | 12/1991 | Watt et al. |
| 5,072,383 A | 12/1991 | Brimm et al. |
| 5,072,412 A | 12/1991 | Henderson, Jr. et al. |
| 5,078,683 A | 1/1992 | Sancoff et al. |
| 5,084,828 A | 1/1992 | Kaufman et al. |
| 5,087,245 A | 2/1992 | Doan |
| 5,088,904 A | 2/1992 | Okada |
| 5,088,981 A | 2/1992 | Howson et al. |
| 5,088,990 A | 2/1992 | Hivale et al. |
| 5,096,385 A | 3/1992 | Georgi et al. |
| 5,098,377 A | 3/1992 | Borsanyi et al. |
| 5,100,380 A | 3/1992 | Epstein et al. |
| 5,104,374 A | 4/1992 | Bishko et al. |
| 5,108,363 A | 4/1992 | Tuttle et al. |
| 5,108,367 A | 4/1992 | Epstein et al. |
| 5,108,372 A | 4/1992 | Swenson |
| 5,109,487 A | 4/1992 | Ohgomori et al. |
| 5,109,849 A | 5/1992 | Goodman et al. |
| 5,112,319 A | 5/1992 | Lai |
| 5,116,203 A | 5/1992 | Natwick et al. |
| 5,116,312 A | 5/1992 | Blankenship et al. |
| 5,131,092 A | 7/1992 | Sackmann et al. |
| 5,134,574 A | 7/1992 | Beaverstock et al. |
| 5,135,500 A | 8/1992 | Zdeb |
| 5,137,023 A | 8/1992 | Mendelson et al. |
| 5,151,978 A | 9/1992 | Bronikowski et al. |
| 5,152,296 A | 10/1992 | Simons |
| 5,153,416 A | 10/1992 | Neeley |
| 5,153,827 A | 10/1992 | Coutre et al. |
| 5,155,693 A | 10/1992 | Altmayer et al. |
| 5,157,595 A | 10/1992 | Lovrenich |
| 5,158,091 A | 10/1992 | Butterfield et al. |
| 5,159,673 A | 10/1992 | Sackmann et al. |
| 5,160,320 A | 11/1992 | Yum et al. |
| 5,161,211 A | 11/1992 | Taguchi et al. |
| 5,167,235 A | 12/1992 | Seacord et al. |
| 5,172,698 A | 12/1992 | Stanko |
| 5,176,004 A | 1/1993 | Gaudet |
| 5,179,569 A | 1/1993 | Sawyer |
| 5,179,700 A | 1/1993 | Aihara et al. |
| 5,181,910 A | 1/1993 | Scanlon |
| 5,190,185 A | 3/1993 | Blechl |
| 5,190,522 A | 3/1993 | Wojcicki et al. |
| 5,191,891 A | 3/1993 | Righter |
| 5,208,907 A | 5/1993 | Shelton et al. |
| 5,211,849 A | 5/1993 | Kitaevich et al. |
| 5,213,099 A | 5/1993 | Tripp, Jr. |
| 5,213,232 A | 5/1993 | Kraft et al. |
| 5,213,568 A | 5/1993 | Lattin et al. |
| 5,219,330 A | 6/1993 | Bollish et al. |
| 5,219,331 A | 6/1993 | Vanderveen |
| 5,225,974 A | 7/1993 | Mathews et al. |
| 5,226,425 A | 7/1993 | Righter |
| 5,228,450 A | 7/1993 | Sellers |
| 5,231,990 A | 8/1993 | Gauglitz |
| 5,234,404 A | 8/1993 | Tuttle et al. |
| 5,235,510 A | 8/1993 | Yamada et al. |
| 5,236,416 A | 8/1993 | McDaniel et al. |
| 5,238,001 A | 8/1993 | Gallant et al. |
| 5,240,007 A | 8/1993 | Pytel et al. |
| 5,244,463 A | 9/1993 | Cordner, Jr. et al. |
| 5,245,704 A | 9/1993 | Weber et al. |
| 5,254,096 A | 10/1993 | Rondelet et al. |
| 5,256,156 A | 10/1993 | Kern et al. |

(56) References Cited

U.S. PATENT DOCUMENTS

| | | |
|---|---|---|
| 5,256,157 A | 10/1993 | Samiotes et al. |
| 5,265,010 A | 11/1993 | Evans-Paganelli et al. |
| 5,265,431 A | 11/1993 | Gaudet et al. |
| 5,267,174 A | 11/1993 | Kaufman et al. |
| 5,271,405 A | 12/1993 | Boyer et al. |
| 5,272,318 A | 12/1993 | Gorman |
| 5,272,321 A | 12/1993 | Otsuka et al. |
| 5,273,517 A | 12/1993 | Barone et al. |
| 5,277,188 A | 1/1994 | Selker |
| 5,283,861 A | 2/1994 | Dangler et al. |
| 5,284,150 A | 2/1994 | Butterfield et al. |
| 5,286,252 A | 2/1994 | Tuttle et al. |
| 5,292,029 A | 3/1994 | Pearson |
| 5,297,257 A | 3/1994 | Struger et al. |
| 5,298,021 A | 3/1994 | Sherer |
| 5,304,126 A | 4/1994 | Epstein et al. |
| 5,307,263 A | 4/1994 | Brown |
| 5,307,372 A | 4/1994 | Sawyer et al. |
| 5,307,463 A | 4/1994 | Hyatt et al. |
| 5,311,908 A | 5/1994 | Barone et al. |
| 5,314,243 A | 5/1994 | McDonald et al. |
| 5,315,505 A | 5/1994 | Pratt et al. |
| 5,317,506 A | 5/1994 | Coutre et al. |
| 5,319,363 A | 6/1994 | Welch et al. |
| 5,319,543 A | 6/1994 | Wilhelm |
| 5,321,618 A | 6/1994 | Gessman |
| 5,321,829 A | 6/1994 | Zifferer |
| 5,324,422 A | 6/1994 | Colleran et al. |
| 5,325,478 A | 6/1994 | Shelton et al. |
| 5,327,341 A | 7/1994 | Whalen et al. |
| 5,331,549 A | 7/1994 | Crawford, Jr. |
| 5,336,245 A | 8/1994 | Adams et al. |
| 5,337,230 A | 8/1994 | Baumgartner et al. |
| 5,338,157 A | 8/1994 | Blomquist |
| 5,339,821 A | 8/1994 | Fujimoto |
| 5,341,291 A | 8/1994 | Roizen et al. |
| 5,341,412 A | 8/1994 | Ramot et al. |
| 5,348,008 A | 9/1994 | Bornn et al. |
| 5,348,539 A | 9/1994 | Herskowitz |
| 5,349,675 A | 9/1994 | Fitzgerald et al. |
| 5,356,378 A | 10/1994 | Doan |
| 5,361,202 A | 11/1994 | Doue |
| 5,361,758 A | 11/1994 | Hall et al. |
| 5,366,896 A | 11/1994 | Margrey et al. |
| 5,366,904 A | 11/1994 | Qureshi et al. |
| 5,367,555 A | 11/1994 | Isoyama |
| 5,368,562 A | 11/1994 | Blomquist et al. |
| 5,370,612 A | 12/1994 | Maeda et al. |
| 5,371,687 A | 12/1994 | Holmes, II et al. |
| 5,374,251 A | 12/1994 | Smith |
| 5,374,813 A | 12/1994 | Shipp |
| 5,374,965 A | 12/1994 | Kanno |
| 5,375,604 A | 12/1994 | Kelly et al. |
| 5,376,070 A | 12/1994 | Purvis et al. |
| 5,377,864 A | 1/1995 | Blechl et al. |
| 5,378,231 A | 1/1995 | Johnson et al. |
| 5,379,214 A | 1/1995 | Arbuckle et al. |
| 5,389,078 A | 2/1995 | Zalesky et al. |
| 5,390,238 A | 2/1995 | Kirk et al. |
| 5,392,951 A | 2/1995 | Gardner et al. |
| 5,395,320 A | 3/1995 | Padda et al. |
| 5,395,321 A | 3/1995 | Kawahara et al. |
| 5,398,336 A | 3/1995 | Tantry et al. |
| 5,401,059 A | 3/1995 | Ferrario |
| 5,404,292 A | 4/1995 | Hendrickson |
| 5,404,384 A | 4/1995 | Colburn et al. |
| 5,406,473 A | 4/1995 | Yoshikura et al. |
| 5,412,715 A | 5/1995 | Volpe |
| 5,415,167 A | 5/1995 | Wilk |
| 5,416,695 A | 5/1995 | Stutman et al. |
| 5,417,222 A | 5/1995 | Dempsey et al. |
| 5,420,977 A | 5/1995 | Sztipanovits et al. |
| 5,421,343 A | 6/1995 | Feng |
| 5,423,746 A | 6/1995 | Burkett et al. |
| 5,429,602 A | 7/1995 | Hauser |
| 5,431,299 A | 7/1995 | Brewer et al. |
| 5,431,627 A | 7/1995 | Pastrone et al. |
| 5,433,736 A | 7/1995 | Nilsson |
| 5,438,607 A | 8/1995 | Przygoda, Jr. et al. |
| 5,440,699 A | 8/1995 | Farrand et al. |
| 5,441,047 A | 8/1995 | David et al. |
| 5,445,294 A | 8/1995 | Gardner et al. |
| 5,445,621 A | 8/1995 | Poli et al. |
| 5,446,868 A | 8/1995 | Gardea, II et al. |
| 5,453,098 A | 9/1995 | Botts et al. |
| 5,455,851 A | 10/1995 | Chaco et al. |
| 5,458,123 A | 10/1995 | Unger |
| 5,460,294 A | 10/1995 | Williams |
| 5,460,605 A | 10/1995 | Tuttle et al. |
| 5,461,665 A | 10/1995 | Shur et al. |
| 5,462,051 A | 10/1995 | Oka et al. |
| 5,464,392 A | 11/1995 | Epstein et al. |
| 5,465,286 A | 11/1995 | Clare et al. |
| 5,467,773 A | 11/1995 | Bergelson et al. |
| 5,468,110 A | 11/1995 | McDonald et al. |
| 5,469,855 A | 11/1995 | Pompei et al. |
| 5,471,382 A | 11/1995 | Tallman et al. |
| 5,474,552 A | 12/1995 | Palti |
| 5,482,043 A | 1/1996 | Zulauf |
| 5,482,446 A | 1/1996 | Williamson et al. |
| 5,485,408 A | 1/1996 | Blomquist |
| 5,490,610 A | 2/1996 | Pearson |
| 5,494,592 A | 2/1996 | Latham, Jr. et al. |
| 5,496,265 A | 3/1996 | Langley et al. |
| 5,496,273 A | 3/1996 | Pastrone et al. |
| 5,502,944 A | 4/1996 | Kraft et al. |
| 5,507,412 A | 4/1996 | Ebert et al. |
| 5,508,912 A | 4/1996 | Schneiderman |
| 5,509,422 A | 4/1996 | Fukami |
| 5,511,594 A * | 4/1996 | Brennan .......... A61J 3/00 141/100 |
| 5,513,957 A | 5/1996 | O'Leary |
| 5,514,088 A | 5/1996 | Zakko |
| 5,514,095 A | 5/1996 | Brightbill et al. |
| 5,515,426 A | 5/1996 | Yacenda et al. |
| 5,520,450 A | 5/1996 | Colson, Jr. et al. |
| 5,520,637 A | 5/1996 | Pager et al. |
| 5,522,396 A | 6/1996 | Langer et al. |
| 5,522,798 A | 6/1996 | Johnson et al. |
| 5,526,428 A | 6/1996 | Arnold |
| 5,528,503 A | 6/1996 | Moore et al. |
| 5,529,063 A | 6/1996 | Hill |
| 5,531,680 A | 7/1996 | Dumas et al. |
| 5,531,697 A | 7/1996 | Olsen et al. |
| 5,531,698 A | 7/1996 | Olsen |
| 5,533,079 A | 7/1996 | Colburn et al. |
| 5,533,981 A | 7/1996 | Mandro et al. |
| 5,534,691 A | 7/1996 | Holdaway et al. |
| 5,536,084 A | 7/1996 | Curtis et al. |
| 5,537,313 A | 7/1996 | Pirelli |
| 5,537,853 A | 7/1996 | Finburgh et al. |
| 5,542,420 A | 8/1996 | Goldman et al. |
| 5,544,649 A | 8/1996 | David et al. |
| 5,544,651 A | 8/1996 | Wilk |
| 5,544,661 A | 8/1996 | Davis et al. |
| 5,545,140 A | 8/1996 | Conero et al. |
| 5,546,580 A | 8/1996 | Seliger et al. |
| 5,547,470 A | 8/1996 | Johnson et al. |
| 5,549,117 A | 8/1996 | Tacklind et al. |
| 5,549,460 A | 8/1996 | O'Leary |
| 5,553,609 A | 9/1996 | Chen et al. |
| 5,558,638 A | 9/1996 | Evers et al. |
| 5,558,640 A | 9/1996 | Pfeiler et al. |
| 5,560,352 A | 10/1996 | Heim et al. |
| 5,562,232 A | 10/1996 | Pearson |
| 5,562,621 A | 10/1996 | Claude et al. |
| 5,563,347 A | 10/1996 | Martin et al. |
| 5,564,803 A | 10/1996 | McDonald et al. |
| 5,568,912 A | 10/1996 | Minami et al. |
| 5,569,186 A | 10/1996 | Lord et al. |
| 5,569,187 A | 10/1996 | Kaiser |
| 5,571,258 A | 11/1996 | Pearson |
| 5,573,502 A | 11/1996 | LeCocq et al. |
| 5,573,506 A | 11/1996 | Vasko |

(56) References Cited

U.S. PATENT DOCUMENTS

| | | |
|---|---|---|
| 5,575,632 A | 11/1996 | Morris et al. |
| 5,576,952 A | 11/1996 | Stutman et al. |
| 5,579,001 A | 11/1996 | Dempsey et al. |
| 5,579,378 A | 11/1996 | Arlinghaus, Jr. |
| 5,581,369 A | 12/1996 | Righter et al. |
| 5,581,687 A | 12/1996 | Lyle et al. |
| 5,582,593 A | 12/1996 | Hultman |
| 5,583,758 A | 12/1996 | McIlroy et al. |
| 5,588,815 A | 12/1996 | Zaleski, II |
| 5,589,932 A | 12/1996 | Garcia-Rubio et al. |
| 5,590,648 A | 1/1997 | Mitchell et al. |
| 5,593,267 A | 1/1997 | McDonald et al. |
| 5,594,637 A | 1/1997 | Eisenberg et al. |
| 5,594,786 A | 1/1997 | Chaco et al. |
| 5,597,995 A | 1/1997 | Williams et al. |
| 5,598,536 A | 1/1997 | Slaughter, III et al. |
| 5,601,445 A | 2/1997 | Schipper et al. |
| 5,609,575 A | 3/1997 | Larson et al. |
| 5,609,576 A | 3/1997 | Voss et al. |
| 5,613,115 A | 3/1997 | Gihl et al. |
| 5,619,428 A | 4/1997 | Lee et al. |
| 5,619,991 A | 4/1997 | Sloane |
| 5,623,652 A | 4/1997 | Vora et al. |
| 5,623,925 A | 4/1997 | Swenson et al. |
| 5,626,144 A | 5/1997 | Tacklind et al. |
| 5,628,619 A | 5/1997 | Wilson |
| 5,630,710 A | 5/1997 | Tune et al. |
| 5,631,844 A | 5/1997 | Margrey et al. |
| 5,633,910 A | 5/1997 | Cohen |
| D380,260 S | 6/1997 | Hyman |
| 5,634,893 A | 6/1997 | Rishton |
| 5,637,082 A | 6/1997 | Pages et al. |
| 5,637,093 A | 6/1997 | Hyman et al. |
| 5,640,301 A | 6/1997 | Roecher et al. |
| 5,640,953 A | 6/1997 | Bishop et al. |
| 5,641,628 A | 6/1997 | Bianchi |
| 5,643,193 A | 7/1997 | Papillon et al. |
| 5,643,212 A | 7/1997 | Coutre et al. |
| 5,647,853 A | 7/1997 | Feldmann et al. |
| 5,647,854 A | 7/1997 | Olsen et al. |
| 5,651,775 A | 7/1997 | Walker et al. |
| 5,652,566 A | 7/1997 | Lambert |
| 5,658,240 A | 8/1997 | Urdahl et al. |
| 5,658,250 A | 8/1997 | Blomquist et al. |
| 5,661,978 A | 9/1997 | Holmes et al. |
| 5,664,270 A | 9/1997 | Bell et al. |
| 5,666,404 A | 9/1997 | Ciccotelli et al. |
| 5,678,562 A | 10/1997 | Sellers |
| 5,678,568 A | 10/1997 | Uchikubo et al. |
| 5,681,285 A | 10/1997 | Ford et al. |
| 5,682,526 A | 10/1997 | Smokoff et al. |
| 5,683,367 A | 11/1997 | Jordan et al. |
| 5,685,844 A | 11/1997 | Marttila |
| 5,687,717 A | 11/1997 | Halpern |
| 5,687,734 A | 11/1997 | Dempsey et al. |
| 5,695,473 A | 12/1997 | Olsen |
| 5,697,951 A | 12/1997 | Harpstead |
| 5,700,998 A | 12/1997 | Palti |
| 5,701,894 A | 12/1997 | Cherry et al. |
| 5,704,351 A | 1/1998 | Mortara et al. |
| 5,704,364 A | 1/1998 | Saltzstein et al. |
| 5,704,366 A | 1/1998 | Tacklind et al. |
| 5,712,798 A | 1/1998 | Langley et al. |
| 5,712,912 A | 1/1998 | Tomko et al. |
| 5,713,485 A | 2/1998 | Liff et al. |
| 5,713,856 A | 2/1998 | Eggers et al. |
| 5,715,823 A | 2/1998 | Wood et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |
| RE35,743 E | 3/1998 | Pearson |
| 5,724,025 A | 3/1998 | Tavori |
| 5,724,580 A | 3/1998 | Levin et al. |
| 5,732,709 A | 3/1998 | Tacklind et al. |
| 5,733,259 A | 3/1998 | Valcke et al. |
| 5,735,887 A | 4/1998 | Barreras, Sr. et al. |
| 5,737,539 A | 4/1998 | Edelson et al. |
| 5,740,185 A | 4/1998 | Bosse |
| 5,740,800 A | 4/1998 | Hendrickson et al. |
| 5,745,366 A | 4/1998 | Higham et al. |
| 5,745,378 A | 4/1998 | Barker et al. |
| 5,752,917 A | 5/1998 | Fuchs |
| 5,752,976 A | 5/1998 | Duffin et al. |
| 5,755,563 A | 5/1998 | Clegg et al. |
| 5,764,923 A | 6/1998 | Tallman et al. |
| 5,766,155 A | 6/1998 | Hyman et al. |
| 5,769,811 A | 6/1998 | Stacey et al. |
| 5,771,657 A | 6/1998 | Lasher et al. |
| 5,772,585 A | 6/1998 | Lavin et al. |
| 5,772,586 A | 6/1998 | Heinonen et al. |
| 5,772,635 A | 6/1998 | Dastur et al. |
| 5,772,637 A | 6/1998 | Heinzmann et al. |
| 5,776,057 A | 7/1998 | Swenson et al. |
| 5,778,345 A | 7/1998 | McCartney |
| 5,778,882 A | 7/1998 | Raymond et al. |
| 5,781,442 A | 7/1998 | Engleson et al. |
| 5,782,805 A | 7/1998 | Meinzer et al. |
| 5,782,878 A | 7/1998 | Morgan et al. |
| 5,785,650 A | 7/1998 | Akasaka et al. |
| 5,788,669 A | 8/1998 | Peterson |
| 5,790,409 A | 8/1998 | Fedor et al. |
| 5,791,342 A | 8/1998 | Woodard |
| 5,791,880 A | 8/1998 | Wilson |
| 5,793,861 A | 8/1998 | Haigh |
| 5,793,969 A | 8/1998 | Kamentsky et al. |
| 5,795,317 A | 8/1998 | Brierton et al. |
| 5,795,327 A | 8/1998 | Wilson et al. |
| 5,797,515 A | 8/1998 | Liff et al. |
| 5,800,387 A | 9/1998 | Duffy et al. |
| 5,803,906 A | 9/1998 | Pratt et al. |
| 5,805,442 A | 9/1998 | Crater et al. |
| 5,805,456 A | 9/1998 | Higham et al. |
| 5,805,505 A | 9/1998 | Zheng et al. |
| 5,807,321 A | 9/1998 | Stoker et al. |
| 5,807,322 A | 9/1998 | Lindsey et al. |
| 5,807,336 A | 9/1998 | Russo et al. |
| 5,810,747 A | 9/1998 | Brudny et al. |
| 5,814,015 A | 9/1998 | Gargano et al. |
| 5,815,566 A | 9/1998 | Ramot et al. |
| 5,822,418 A | 10/1998 | Yacenda et al. |
| 5,822,544 A | 10/1998 | Chaco et al. |
| 5,823,949 A | 10/1998 | Goltra |
| 5,826,237 A | 10/1998 | Macrae et al. |
| 5,829,438 A | 11/1998 | Gibbs et al. |
| 5,832,448 A | 11/1998 | Brown |
| 5,832,450 A | 11/1998 | Myers et al. |
| 5,833,599 A | 11/1998 | Schrier et al. |
| 5,841,975 A | 11/1998 | Layne et al. |
| 5,842,841 A | 12/1998 | Danby et al. |
| 5,842,976 A | 12/1998 | Williamson |
| 5,845,253 A | 12/1998 | Rensimer et al. |
| 5,848,593 A | 12/1998 | McGrady et al. |
| 5,851,186 A | 12/1998 | Wood et al. |
| 5,852,590 A | 12/1998 | De La Huerga |
| 5,853,387 A | 12/1998 | Clegg et al. |
| 5,855,550 A | 1/1999 | Lai et al. |
| 5,857,967 A | 1/1999 | Frid et al. |
| 5,859,972 A | 1/1999 | Subramaniam et al. |
| 5,865,745 A | 2/1999 | Schmitt et al. |
| 5,865,786 A | 2/1999 | Sibalis et al. |
| 5,867,821 A | 2/1999 | Ballantyne et al. |
| 5,871,465 A | 2/1999 | Vasko |
| 5,876,926 A | 3/1999 | Beecham |
| 5,880,443 A | 3/1999 | McDonald et al. |
| 5,882,338 A | 3/1999 | Gray |
| 5,883,370 A | 3/1999 | Walker et al. |
| 5,883,576 A | 3/1999 | De La Huerga |
| 5,885,245 A | 3/1999 | Lynch et al. |
| 5,891,035 A | 4/1999 | Wood et al. |
| 5,891,734 A | 4/1999 | Gill et al. |
| 5,893,697 A | 4/1999 | Zini et al. |
| 5,894,273 A | 4/1999 | Meador et al. |
| 5,895,371 A | 4/1999 | Levitas et al. |

(56) References Cited

U.S. PATENT DOCUMENTS

| | | |
|---|---|---|
| 5,897,493 A | 4/1999 | Brown |
| 5,897,530 A | 4/1999 | Jackson |
| 5,897,989 A | 4/1999 | Beecham |
| 5,899,665 A | 5/1999 | Makino et al. |
| 5,899,855 A | 5/1999 | Brown |
| 5,901,150 A | 5/1999 | Jhuboo et al. |
| 5,904,668 A | 5/1999 | Hyman et al. |
| 5,905,653 A | 5/1999 | Higham et al. |
| 5,907,291 A | 5/1999 | Chen et al. |
| 5,908,027 A | 6/1999 | Butterfield et al. |
| 5,910,107 A | 6/1999 | Iliff |
| 5,910,252 A | 6/1999 | Truitt et al. |
| 5,911,132 A | 6/1999 | Sloane |
| 5,911,687 A | 6/1999 | Sato et al. |
| 5,912,818 A | 6/1999 | McGrady et al. |
| 5,913,197 A | 6/1999 | Kameda |
| 5,913,310 A | 6/1999 | Brown |
| 5,915,240 A | 6/1999 | Karpf |
| 5,919,154 A | 7/1999 | Toays et al. |
| 5,921,938 A | 7/1999 | Aoyama et al. |
| 5,923,018 A | 7/1999 | Kameda et al. |
| 5,924,074 A | 7/1999 | Evans |
| 5,924,103 A | 7/1999 | Ahmed et al. |
| 5,927,540 A | 7/1999 | Godlewski |
| 5,931,791 A | 8/1999 | Saltzstein et al. |
| 5,935,060 A | 8/1999 | Iliff |
| 5,935,099 A | 8/1999 | Peterson et al. |
| 5,935,106 A | 8/1999 | Olsen |
| 5,938,413 A | 8/1999 | Makino et al. |
| 5,939,326 A | 8/1999 | Chupp et al. |
| 5,939,699 A | 8/1999 | Perttunen et al. |
| 5,940,306 A | 8/1999 | Gardner et al. |
| 5,940,802 A | 8/1999 | Hildebrand et al. |
| 5,941,829 A | 8/1999 | Saltzstein et al. |
| 5,942,986 A | 8/1999 | Shabot et al. |
| 5,943,423 A | 8/1999 | Muftic |
| 5,943,633 A | 8/1999 | Wilson et al. |
| 5,944,659 A | 8/1999 | Flach et al. |
| 5,945,651 A | 8/1999 | Chorosinski et al. |
| 5,946,083 A | 8/1999 | Melendez et al. |
| 5,946,659 A | 8/1999 | Lancelot et al. |
| 5,950,006 A | 9/1999 | Crater et al. |
| 5,951,300 A | 9/1999 | Brown |
| 5,951,510 A | 9/1999 | Barak |
| 5,954,640 A | 9/1999 | Szabo |
| 5,954,885 A | 9/1999 | Bollish et al. |
| 5,954,971 A | 9/1999 | Pages et al. |
| 5,956,023 A | 9/1999 | Lyle et al. |
| 5,957,885 A | 9/1999 | Bollish et al. |
| 5,959,529 A | 9/1999 | Kail, IV |
| 5,960,085 A | 9/1999 | de la Huerga |
| 5,960,403 A | 9/1999 | Brown |
| 5,960,991 A | 10/1999 | Ophardt |
| 5,961,446 A | 10/1999 | Beller et al. |
| 5,961,448 A | 10/1999 | Swenson et al. |
| 5,961,487 A | 10/1999 | Davis |
| 5,964,700 A | 10/1999 | Tallman et al. |
| 5,966,304 A | 10/1999 | Cook et al. |
| 5,967,975 A | 10/1999 | Ridgeway |
| 5,970,423 A | 10/1999 | Langley et al. |
| 5,971,593 A | 10/1999 | McGrady |
| 5,971,921 A | 10/1999 | Timbel |
| 5,971,948 A | 10/1999 | Pages et al. |
| 5,974,124 A | 10/1999 | Schlueter, Jr. et al. |
| 5,975,737 A | 11/1999 | Crater et al. |
| 5,980,490 A | 11/1999 | Tsoukalis |
| 5,983,193 A | 11/1999 | Heinonen et al. |
| 5,987,519 A | 11/1999 | Peifer et al. |
| 5,991,731 A | 11/1999 | Colon et al. |
| 5,993,046 A | 11/1999 | McGrady et al. |
| 5,993,420 A | 11/1999 | Hyman et al. |
| 5,995,077 A | 11/1999 | Wilcox et al. |
| 5,995,965 A | 11/1999 | Experton |
| 5,997,167 A | 12/1999 | Crater et al. |
| 5,997,476 A | 12/1999 | Brown |
| 6,003,006 A | 12/1999 | Colella et al. |
| 6,004,020 A | 12/1999 | Bartur |
| 6,004,276 A | 12/1999 | Wright et al. |
| 6,006,191 A | 12/1999 | DeRienzo |
| 6,009,333 A | 12/1999 | Chaco |
| 6,010,454 A | 1/2000 | Arieff et al. |
| 6,011,858 A | 1/2000 | Stock et al. |
| 6,011,999 A | 1/2000 | Holmes |
| 6,012,034 A | 1/2000 | Hamparian et al. |
| 6,013,057 A | 1/2000 | Danby et al. |
| 6,014,631 A | 1/2000 | Teagarden et al. |
| 6,016,444 A | 1/2000 | John |
| 6,017,318 A | 1/2000 | Gauthier et al. |
| 6,018,713 A | 1/2000 | Coli et al. |
| 6,019,745 A | 2/2000 | Gray |
| 6,021,392 A | 2/2000 | Lester et al. |
| 6,022,315 A | 2/2000 | Iliff |
| 6,023,522 A | 2/2000 | Draganoff et al. |
| 6,024,539 A | 2/2000 | Blomquist |
| 6,024,699 A | 2/2000 | Surwit et al. |
| 6,027,217 A | 2/2000 | McClure et al. |
| 6,029,138 A | 2/2000 | Khorasani et al. |
| 6,032,119 A | 2/2000 | Brown et al. |
| 6,032,155 A | 2/2000 | de la Huerga |
| 6,033,076 A | 3/2000 | Braeuning et al. |
| 6,039,251 A | 3/2000 | Holowko et al. |
| 6,039,467 A | 3/2000 | Holmes |
| 6,047,259 A | 4/2000 | Campbell et al. |
| 6,050,940 A | 4/2000 | Braun et al. |
| 6,055,487 A | 4/2000 | Margery et al. |
| 6,057,758 A | 5/2000 | Dempsey et al. |
| 6,059,736 A | 5/2000 | Tapper |
| 6,061,603 A | 5/2000 | Papadopoulos et al. |
| 6,065,819 A | 5/2000 | Holmes et al. |
| 6,068,153 A | 5/2000 | Young et al. |
| 6,073,046 A | 6/2000 | Patel et al. |
| 6,074,345 A | 6/2000 | van Oostrom et al. |
| 6,079,621 A | 6/2000 | Vardanyan et al. |
| 6,080,106 A | 6/2000 | Lloyd et al. |
| 6,081,048 A | 6/2000 | Bergmann et al. |
| 6,082,776 A | 7/2000 | Feinberg |
| 6,083,206 A | 7/2000 | Molko |
| 6,093,146 A | 7/2000 | Filangeri |
| 6,095,985 A | 8/2000 | Raymond et al. |
| 6,101,407 A | 8/2000 | Groezinger |
| 6,101,478 A | 8/2000 | Brown |
| 6,102,856 A | 8/2000 | Groff et al. |
| 6,108,399 A | 8/2000 | Hernandez-Guerra et al. |
| 6,108,588 A | 8/2000 | McGrady |
| 6,109,774 A | 8/2000 | Holmes et al. |
| 6,112,224 A | 8/2000 | Peifer et al. |
| RE36,871 E | 9/2000 | Epstein et al. |
| 6,113,554 A | 9/2000 | Gilcher et al. |
| 6,116,461 A | 9/2000 | Broadfield et al. |
| 6,117,940 A | 9/2000 | Mjalli |
| 6,123,524 A | 9/2000 | Danby et al. |
| 6,125,350 A | 9/2000 | Dirbas |
| 6,129,517 A | 10/2000 | Danby et al. |
| 6,132,371 A | 10/2000 | Dempsey et al. |
| 6,134,504 A | 10/2000 | Douglas et al. |
| 6,135,949 A | 10/2000 | Russo et al. |
| 6,139,495 A | 10/2000 | De La Huerga |
| 6,144,922 A | 11/2000 | Douglas et al. |
| 6,145,695 A | 11/2000 | Garrigues |
| 6,146,523 A | 11/2000 | Kenley et al. |
| 6,148,297 A | 11/2000 | Swor et al. |
| 6,149,063 A | 11/2000 | Reynolds et al. |
| 6,151,536 A | 11/2000 | Arnold et al. |
| 6,152,364 A | 11/2000 | Schoonen et al. |
| 6,154,668 A | 11/2000 | Pedersen et al. |
| 6,154,726 A | 11/2000 | Rensimer et al. |
| 6,157,914 A | 12/2000 | Seto et al. |
| 6,158,965 A | 12/2000 | Butterfield et al. |
| 6,160,478 A | 12/2000 | Jacobsen et al. |
| 6,161,095 A | 12/2000 | Brown |
| 6,163,737 A | 12/2000 | Fedor et al. |
| 6,165,154 A | 12/2000 | Gray et al. |
| 6,168,563 B1 | 1/2001 | Brown |
| 6,170,007 B1 | 1/2001 | Venkatraman et al. |

(56) References Cited

U.S. PATENT DOCUMENTS

| | | |
|---|---|---|
| 6,170,746 B1 | 1/2001 | Brook et al. |
| 6,171,112 B1 | 1/2001 | Clark et al. |
| 6,171,237 B1 | 1/2001 | Avitall et al. |
| 6,171,264 B1 | 1/2001 | Bader |
| 6,173,198 B1 | 1/2001 | Schulze et al. |
| 6,175,779 B1 | 1/2001 | Barrett |
| 6,175,977 B1 | 1/2001 | Schumacher et al. |
| 6,182,047 B1 | 1/2001 | Dirbas |
| 6,183,417 B1 | 2/2001 | Geheb et al. |
| 6,186,145 B1 | 2/2001 | Brown |
| 6,192,320 B1 | 2/2001 | Margrey et al. |
| 6,193,480 B1 | 2/2001 | Butterfield |
| 6,195,887 B1 | 3/2001 | Danby et al. |
| 6,198,394 B1 | 3/2001 | Jacobsen et al. |
| 6,200,264 B1 | 3/2001 | Satherley et al. |
| 6,200,289 B1 | 3/2001 | Hochman et al. |
| 6,203,495 B1 | 3/2001 | Bardy |
| 6,203,528 B1 | 3/2001 | Deckert et al. |
| 6,206,238 B1 | 3/2001 | Ophardt |
| 6,206,829 B1 | 3/2001 | Iliff |
| 6,210,361 B1 | 4/2001 | Kamen et al. |
| 6,213,391 B1 | 4/2001 | Lewis |
| 6,213,738 B1 | 4/2001 | Danby et al. |
| 6,219,439 B1 | 4/2001 | Burger |
| 6,219,587 B1 | 4/2001 | Ahlin et al. |
| 6,221,011 B1 | 4/2001 | Bardy |
| 6,221,012 B1 | 4/2001 | Maschke et al. |
| 6,222,619 B1 | 4/2001 | Herron et al. |
| 6,224,549 B1 | 5/2001 | Drongelen |
| 6,225,901 B1 | 5/2001 | Kail, IV |
| 6,226,564 B1 | 5/2001 | Stuart |
| 6,230,927 B1 | 5/2001 | Schoonen et al. |
| 6,234,997 B1 | 5/2001 | Kamen et al. |
| 6,245,013 B1 | 6/2001 | Minoz et al. |
| 6,246,473 B1 | 6/2001 | Smith, Jr. et al. |
| 6,248,063 B1 | 6/2001 | Barnhill et al. |
| 6,248,065 B1 | 6/2001 | Brown |
| 6,255,951 B1 | 7/2001 | De La Huerga |
| 6,256,643 B1 | 7/2001 | Cork et al. |
| 6,256,967 B1 | 7/2001 | Hebron et al. |
| 6,259,355 B1 | 7/2001 | Chaco et al. |
| 6,259,654 B1 | 7/2001 | De La Huerga |
| 6,266,645 B1 | 7/2001 | Simpson |
| 6,269,340 B1 | 7/2001 | Ford et al. |
| D446,854 S | 8/2001 | Cheney, II et al. |
| 6,270,455 B1 | 8/2001 | Brown |
| 6,270,457 B1 | 8/2001 | Bardy |
| 6,272,394 B1 | 8/2001 | Lipps |
| 6,272,505 B1 | 8/2001 | De La Huerga |
| 6,277,072 B1 | 8/2001 | Bardy |
| 6,283,322 B1 | 9/2001 | Liff et al. |
| 6,283,944 B1 | 9/2001 | McMullen et al. |
| 6,290,646 B1 | 9/2001 | Cosentino et al. |
| 6,290,650 B1 | 9/2001 | Butterfield et al. |
| 6,294,999 B1 | 9/2001 | Yarin et al. |
| 6,295,506 B1 | 9/2001 | Heinonen |
| 6,304,788 B1 | 10/2001 | Eady et al. |
| 6,306,088 B1 | 10/2001 | Krausman et al. |
| 6,307,956 B1 | 10/2001 | Black |
| 6,308,171 B1 | 10/2001 | De La Huerga |
| 6,311,163 B1 | 10/2001 | Sheehan et al. |
| 6,312,227 B1 | 11/2001 | Davis |
| 6,312,378 B1 | 11/2001 | Bardy |
| 6,314,384 B1 | 11/2001 | Goetz |
| 6,317,719 B1 | 11/2001 | Schrier et al. |
| 6,319,200 B1 | 11/2001 | Lai et al. |
| 6,321,203 B1 | 11/2001 | Kameda |
| 6,322,504 B1 | 11/2001 | Kirshner |
| 6,322,515 B1 | 11/2001 | Goor et al. |
| RE37,531 E | 1/2002 | Chaco et al. |
| 6,337,631 B1 | 1/2002 | Pai et al. |
| 6,338,007 B1 | 1/2002 | Broadfield et al. |
| 6,339,732 B1 | 1/2002 | Phoon et al. |
| 6,345,260 B1 | 2/2002 | Cummings, Jr. et al. |
| 6,346,886 B1 | 2/2002 | De La Huerga |
| 6,352,200 B1 | 3/2002 | Schoonen et al. |
| 6,353,817 B1 | 3/2002 | Jacobs et al. |
| 6,358,225 B1 | 3/2002 | Butterfield |
| 6,358,237 B1 | 3/2002 | Paukovits et al. |
| 6,361,263 B1 | 3/2002 | Dewey et al. |
| 6,362,591 B1 | 3/2002 | Moberg |
| 6,363,282 B1 | 3/2002 | Nichols et al. |
| 6,363,290 B1 | 3/2002 | Lyle et al. |
| 6,364,834 B1 | 4/2002 | Reuss et al. |
| 6,368,273 B1 | 4/2002 | Brown |
| 6,370,841 B1 | 4/2002 | Chudy et al. |
| 6,381,577 B1 | 4/2002 | Brown |
| 6,385,505 B1 | 5/2002 | Lipps |
| 6,393,369 B1 | 5/2002 | Carr |
| 6,397,190 B1 | 5/2002 | Goetz |
| 6,402,702 B1 | 6/2002 | Gilcher et al. |
| 6,406,426 B1 | 6/2002 | Reuss et al. |
| 6,407,335 B1 | 6/2002 | Franklin-Lees et al. |
| 6,408,330 B1 | 6/2002 | DeLaHuerga |
| 6,416,471 B1 | 7/2002 | Kumar et al. |
| 6,421,650 B1 | 7/2002 | Goetz et al. |
| 6,427,088 B1 | 7/2002 | Bowman, IV et al. |
| 6,434,531 B1 | 8/2002 | Lancelot et al. |
| 6,434,569 B1 | 8/2002 | Tomlinson et al. |
| 6,449,927 B2 | 9/2002 | Hebron et al. |
| 6,450,956 B1 | 9/2002 | Rappaport et al. |
| 6,458,102 B1 | 10/2002 | Mann et al. |
| 6,468,242 B1 | 10/2002 | Wilson et al. |
| 6,470,234 B1 | 10/2002 | McGrady |
| 6,471,089 B2 | 10/2002 | Liff et al. |
| 6,471,645 B1 | 10/2002 | Warkentin et al. |
| 6,475,146 B1 | 11/2002 | Frelburger et al. |
| 6,475,148 B1 | 11/2002 | Jackson et al. |
| 6,475,180 B2 | 11/2002 | Peterson et al. |
| 6,478,737 B2 | 11/2002 | Bardy |
| 6,485,465 B2 | 11/2002 | Moberg et al. |
| 6,511,138 B1 | 1/2003 | Gardner et al. |
| 6,519,569 B1 | 2/2003 | White et al. |
| 6,537,244 B2 | 3/2003 | Paukovits |
| 6,542,902 B2 | 4/2003 | Dulong et al. |
| 6,542,910 B2 | 4/2003 | Cork et al. |
| 6,544,174 B2 | 4/2003 | West et al. |
| 6,544,228 B1 | 4/2003 | Heitmeier |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,321 B1 | 5/2003 | Burd et al. |
| 6,561,975 B1 | 5/2003 | Pool et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,571,128 B2 | 5/2003 | Lebel et al. |
| 6,575,900 B1 | 6/2003 | Zweig et al. |
| 6,577,899 B2 | 6/2003 | Lebel et al. |
| 6,579,232 B2 | 6/2003 | Sakamaki et al. |
| 6,581,069 B1 | 6/2003 | Robinson et al. |
| 6,584,336 B1 | 6/2003 | Ali et al. |
| 6,585,157 B2 | 7/2003 | Brandt et al. |
| 6,585,644 B2 | 7/2003 | Lebel et al. |
| 6,585,675 B1 | 7/2003 | O'Mahony et al. |
| 6,592,551 B1 | 7/2003 | Cobb |
| 6,593,528 B2 | 7/2003 | Franklin-Lees et al. |
| 6,607,485 B2 | 8/2003 | Bardy |
| 6,613,009 B1 | 9/2003 | Bainbridge et al. |
| 6,635,014 B2 | 10/2003 | Starkweather et al. |
| 6,648,821 B2 | 11/2003 | Lebel et al. |
| 6,659,948 B2 | 12/2003 | Lebel et al. |
| 6,664,893 B1 | 12/2003 | Eveland et al. |
| 6,668,196 B1 | 12/2003 | Villegas et al. |
| 6,673,314 B1 | 1/2004 | Burbank et al. |
| 6,687,546 B2 | 2/2004 | Lebel et al. |
| 6,689,091 B2 | 2/2004 | Bui et al. |
| 6,694,191 B2 | 2/2004 | Starkweather et al. |
| 6,694,334 B2 | 2/2004 | DuLong et al. |
| 6,733,447 B2 | 5/2004 | Lai et al. |
| 6,740,075 B2 | 5/2004 | Lebel et al. |
| 6,746,398 B2 | 6/2004 | Hervy et al. |

(56) References Cited

U.S. PATENT DOCUMENTS

| | | |
|---|---|---|
| 6,758,810 B2 | 7/2004 | Lebel et al. |
| 6,768,425 B2 | 7/2004 | Flaherty et al. |
| 6,790,198 B1 | 9/2004 | White et al. |
| 6,804,656 B1 | 10/2004 | Rosenfeld et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,707 B2 | 11/2004 | Rovatti et al. |
| 6,813,519 B2 | 11/2004 | Lebel et al. |
| 6,820,093 B2 | 11/2004 | De La Huerga |
| 6,854,088 B2 | 2/2005 | Massengale et al. |
| 6,871,211 B2 | 3/2005 | Labounty et al. |
| 6,873,268 B2 | 3/2005 | Lebel et al. |
| 6,880,034 B2 | 4/2005 | Manke et al. |
| 6,885,288 B2 | 4/2005 | Pincus |
| 6,912,549 B2 | 6/2005 | Rotter et al. |
| 6,913,590 B2 | 7/2005 | Sorenson et al. |
| 6,928,452 B2 | 8/2005 | De La Huerga |
| 6,950,708 B2 | 9/2005 | Bowman, IV et al. |
| 6,958,705 B2 | 10/2005 | Lebel et al. |
| 6,974,437 B2 | 12/2005 | Lebel et al. |
| 6,976,628 B2 | 12/2005 | Krupa |
| 6,979,306 B2 | 12/2005 | Moll |
| 6,980,958 B1 | 12/2005 | Surwit et al. |
| 8,489,427 B2 | 7/2013 | Simpson et al. |
| 2001/0001237 A1 | 5/2001 | Stroda et al. |
| 2001/0003177 A1 | 6/2001 | Schena et al. |
| 2001/0007053 A1 | 7/2001 | Bardy |
| 2001/0007932 A1 | 7/2001 | Kamen et al. |
| 2001/0011153 A1 | 8/2001 | Bardy |
| 2001/0016699 A1 | 8/2001 | Burbank et al. |
| 2001/0017817 A1 | 8/2001 | De La Huerga |
| 2001/0021801 A1 | 9/2001 | Bardy |
| 2001/0025138 A1 | 9/2001 | Bardy |
| 2001/0025156 A1 | 9/2001 | Bui et al. |
| 2001/0027634 A1 | 10/2001 | Hebron et al. |
| 2001/0028308 A1 | 10/2001 | De La Huerga |
| 2001/0030234 A1 | 10/2001 | Wiklof |
| 2001/0031944 A1 | 10/2001 | Peterson et al. |
| 2001/0032101 A1 | 10/2001 | Statius Muller |
| 2001/0034502 A1 | 10/2001 | Moberg et al. |
| 2001/0034616 A1 | 10/2001 | Giannini |
| 2001/0037057 A1 | 11/2001 | Bardy |
| 2001/0037083 A1 | 11/2001 | Hartlaub et al. |
| 2001/0037217 A1 | 11/2001 | Abensour et al. |
| 2001/0037220 A1 | 11/2001 | Merry et al. |
| 2001/0041920 A1 | 11/2001 | Starkweather et al. |
| 2001/0044588 A1 | 11/2001 | Mault |
| 2001/0044731 A1 | 11/2001 | Coffman et al. |
| 2001/0051764 A1 | 12/2001 | Bardy |
| 2001/0053885 A1 | 12/2001 | Gielen et al. |
| 2002/0002326 A1 | 1/2002 | Causey, III et al. |
| 2002/0002473 A1 | 1/2002 | Schrier et al. |
| 2002/0004645 A1 | 1/2002 | Carlisle et al. |
| 2002/0010568 A1 | 1/2002 | Rubbert et al. |
| 2002/0013612 A1 | 1/2002 | Whitehurst |
| 2002/0016567 A1 | 2/2002 | Hochman et al. |
| 2002/0016568 A1 | 2/2002 | Lebel et al. |
| 2002/0016719 A1 | 2/2002 | Nemeth et al. |
| 2002/0016722 A1 | 2/2002 | Kameda |
| 2002/0019606 A1 | 2/2002 | Lebel et al. |
| 2002/0019748 A1 | 2/2002 | Brown |
| 2002/0022776 A1 | 2/2002 | Bardy |
| 2002/0025796 A1 | 2/2002 | Taylor et al. |
| 2002/0026104 A1 | 2/2002 | Bardy |
| 2002/0029157 A1 | 3/2002 | Marchosky |
| 2002/0029776 A1 | 3/2002 | Blomquist |
| 2002/0032602 A1 | 3/2002 | Lanzillo, Jr. et al. |
| 2002/0038392 A1 | 3/2002 | De La Huerga |
| 2002/0040208 A1 | 4/2002 | Flaherty et al. |
| 2002/0044043 A1 | 4/2002 | Chaco et al. |
| 2002/0046062 A1 | 4/2002 | Kameda |
| 2002/0046185 A1 | 4/2002 | Villart et al. |
| 2002/0046346 A1 | 4/2002 | Evans |
| 2002/0052539 A1 | 5/2002 | Haller et al. |
| 2002/0052542 A1 | 5/2002 | Bardy |
| 2002/0052574 A1 | 5/2002 | Hochman et al. |
| 2002/0065540 A1 | 5/2002 | Lebel et al. |
| 2002/0067273 A1 | 6/2002 | Jaques et al. |
| 2002/0072733 A1 | 6/2002 | Flaherty |
| 2002/0077852 A1 | 6/2002 | Ford et al. |
| 2002/0077865 A1 | 6/2002 | Sullivan |
| 2002/0082480 A1 | 6/2002 | Riff et al. |
| 2002/0082865 A1 | 6/2002 | Bianco et al. |
| 2002/0082868 A1 | 6/2002 | Pories et al. |
| 2002/0084904 A1 | 7/2002 | De La Huerga |
| 2002/0087120 A1 | 7/2002 | Rogers et al. |
| 2002/0099283 A1 | 7/2002 | Christ et al. |
| 2002/0099301 A1 | 7/2002 | Bardy |
| 2002/0100762 A1 | 8/2002 | Liff et al. |
| 2002/0107476 A1 | 8/2002 | Mann et al. |
| 2002/0107707 A1 | 8/2002 | Naparstek et al. |
| 2002/0116509 A1 | 8/2002 | De La Huerga |
| 2002/0128606 A1 | 9/2002 | Cowan et al. |
| 2002/0128871 A1 | 9/2002 | Adamson et al. |
| 2002/0128880 A1 | 9/2002 | Kunikiyo |
| 2002/0133377 A1 | 9/2002 | Brown |
| 2002/0140675 A1 | 10/2002 | Ali et al. |
| 2002/0143254 A1 | 10/2002 | Maruyama |
| 2002/0156462 A1 | 10/2002 | Stultz |
| 2002/0158128 A1 | 10/2002 | Ashiuro |
| 2002/0165491 A1 | 11/2002 | Reilly |
| 2002/0169636 A1 | 11/2002 | Eggers et al. |
| 2002/0173875 A1 | 11/2002 | Wallace et al. |
| 2002/0198513 A1 | 12/2002 | Lebel et al. |
| 2003/0023177 A1 | 1/2003 | Bardy |
| 2003/0036783 A1 | 2/2003 | Bauhahn et al. |
| 2003/0050621 A1 | 3/2003 | Lebel et al. |
| 2003/0052787 A1 | 3/2003 | Zerhusen |
| 2003/0060753 A1 | 3/2003 | Starkweather et al. |
| 2003/0060754 A1 | 3/2003 | Reilly |
| 2003/0060765 A1 | 3/2003 | Campbell et al. |
| 2003/0060768 A1 | 3/2003 | Kiyatake |
| 2003/0065287 A1 | 4/2003 | Spohn et al. |
| 2003/0078534 A1 | 4/2003 | Hochman et al. |
| 2003/0083901 A1 | 5/2003 | Bosch et al. |
| 2003/0088238 A1 | 5/2003 | Poulsen et al. |
| 2003/0097092 A1 | 5/2003 | Flaherty |
| 2003/0114836 A1 | 6/2003 | Estes et al. |
| 2003/0125611 A1 | 7/2003 | Bardy |
| 2003/0139701 A1 | 7/2003 | White et al. |
| 2003/0144878 A1 | 7/2003 | Wilkes et al. |
| 2003/0154108 A1 | 8/2003 | Fletcher-Haynes et al. |
| 2003/0160683 A1 | 8/2003 | Blomquist |
| 2003/0163088 A1 | 8/2003 | Blomquist |
| 2003/0163223 A1 | 8/2003 | Blomquist |
| 2003/0163789 A1 | 8/2003 | Blomquist |
| 2003/0167035 A1 | 9/2003 | Flaherty et al. |
| 2003/0176933 A1 | 9/2003 | Lebel et al. |
| 2003/0181851 A1 | 9/2003 | Mann et al. |
| 2003/0182164 A1 | 9/2003 | Blomquist |
| 2003/0195397 A1 | 10/2003 | Bardy |
| 2003/0201697 A1 | 10/2003 | Richardson |
| 2003/0212379 A1 | 11/2003 | Bylund et al. |
| 2003/0225596 A1 | 12/2003 | Richardson et al. |
| 2003/0225728 A1 | 12/2003 | Moura |
| 2004/0039260 A1 | 2/2004 | Bardy |
| 2004/0039264 A1 | 2/2004 | Bardy |
| 2004/0051368 A1 | 3/2004 | Caputo et al. |
| 2004/0073329 A1* | 4/2004 | Engleson ............... G06Q 50/22 700/131 |
| 2004/0088374 A1 | 5/2004 | Webb et al. |
| 2004/0111293 A1 | 6/2004 | Firanek et al. |
| 2004/0115132 A1 | 6/2004 | Young et al. |
| 2004/0116862 A1 | 6/2004 | Ray |
| 2004/0117215 A1 | 6/2004 | Marchosky |
| 2004/0172283 A1 | 9/2004 | Vanderveen et al. |
| 2004/0193328 A1 | 9/2004 | Zaitsu et al. |
| 2004/0204673 A1 | 10/2004 | Flaherty |
| 2004/0215490 A1 | 10/2004 | Duchon et al. |
| 2004/0220829 A1 | 11/2004 | Baharav et al. |
| 2004/0235446 A1 | 11/2004 | Flaherty et al. |
| 2004/0260233 A1 | 12/2004 | Garibotto et al. |

(56) References Cited

U.S. PATENT DOCUMENTS

| | | | |
|---|---|---|---|
| 2005/0038680 A1 | 2/2005 | McMahon | |
| 2005/0054923 A1 | 3/2005 | Pan | |
| 2005/0209737 A1* | 9/2005 | Kircher | B01F 13/1063 |
| | | | 700/266 |

FOREIGN PATENT DOCUMENTS

| | | |
|---|---|---|
| CA | 2133913 | 4/1995 |
| CA | 2110774 | 6/1995 |
| CA | 2145714 | 10/1995 |
| CA | 2112098 | 12/1998 |
| CA | 2309409 | 12/2000 |
| CA | 2314513 | 1/2001 |
| CA | 2314517 | 1/2001 |
| CA | 2055952 | 1/2002 |
| CN | 1516257 | 5/1999 |
| CN | 2440518 | 8/2001 |
| CN | 1131076 | 12/2003 |
| DE | 3826550 | 1/1994 |
| EP | 0237588 | 9/1987 |
| EP | 0287651 | 10/1988 |
| EP | 0302752 | 2/1989 |
| EP | 0329464 | 8/1989 |
| EP | 0366854 | 5/1990 |
| EP | 0387630 | 9/1990 |
| EP | 0429866 | 5/1991 |
| EP | 0436663 | 7/1991 |
| EP | 0462466 | 12/1991 |
| EP | 0505627 | 9/1992 |
| EP | 0522527 | 1/1993 |
| EP | 0531889 | 3/1993 |
| EP | 0544393 | 6/1993 |
| EP | 0567962 | 11/1993 |
| EP | 0580299 | 1/1994 |
| EP | 0595474 | 5/1994 |
| EP | 0439355 | 9/1994 |
| EP | 0757541 | 1/1996 |
| EP | 0784283 | 7/1997 |
| EP | 0812441 | 12/1997 |
| EP | 0833266 | 4/1998 |
| EP | 0844581 | 5/1998 |
| EP | 0847008 | 6/1998 |
| EP | 0890919 | 1/1999 |
| EP | 0365614 | 8/1999 |
| EP | 0958778 | 11/1999 |
| EP | 0960627 | 12/1999 |
| EP | 0970655 | 1/2000 |
| EP | 1048264 | 2/2000 |
| EP | 1057448 | 12/2000 |
| EP | 1072994 | 2/2001 |
| EP | 1081627 | 3/2001 |
| EP | 1107158 | 6/2001 |
| EP | 0674162 | 1/2002 |
| EP | 1593080 | 11/2005 |
| FR | 2591884 | 6/1987 |
| GB | 2210713 | 2/1987 |
| GB | 2279784 | 1/1995 |
| GB | 2285135 | 6/1995 |
| JP | 53137644 | 12/1978 |
| JP | 61066950 | 4/1986 |
| JP | 63-500546 | 2/1988 |
| JP | 63068133 | 3/1988 |
| JP | 02111375 | 4/1990 |
| JP | 06086813 | 3/1994 |
| JP | 06327636 | 11/1994 |
| JP | 10-4585 | 1/1998 |
| JP | 10014890 | 1/1998 |
| JP | 10079770 | 3/1998 |
| JP | 03055131 | 4/2000 |
| JP | 2002-011095 | 1/2002 |
| JP | 2002-092181 | 3/2002 |
| JP | 2002520718 | 7/2002 |
| JP | 2004-174235 | 6/2004 |
| JP | 2004-326436 | 11/2004 |
| WO | 8400493 | 2/1984 |
| WO | 8404685 | 12/1984 |
| WO | 8802700 | 4/1988 |
| WO | 8909017 | 9/1989 |
| WO | 9004231 | 4/1990 |
| WO | 9104704 | 4/1991 |
| WO | 9300047 | 1/1993 |
| WO | 9302720 | 2/1993 |
| WO | 9405355 | 3/1994 |
| WO | 9408647 | 4/1994 |
| WO | 9412235 | 6/1994 |
| WO | 9424929 | 11/1994 |
| WO | 9502426 | 1/1995 |
| WO | 9520804 | 8/1995 |
| WO | 9523378 | 8/1995 |
| WO | 9524010 | 9/1995 |
| WO | 9532480 | 11/1995 |
| WO | 9625214 | 8/1996 |
| WO | 9625877 | 8/1996 |
| WO | 9626670 | 9/1996 |
| WO | 9627163 | 9/1996 |
| WO | 9628209 | 9/1996 |
| WO | 9634291 | 10/1996 |
| WO | 9636923 | 11/1996 |
| WO | 9701141 | 1/1997 |
| WO | 9712680 | 4/1997 |
| WO | 9715021 | 4/1997 |
| WO | 9741525 | 11/1997 |
| WO | 9813783 | 4/1998 |
| WO | 9814275 | 4/1998 |
| WO | 9815092 | 4/1998 |
| WO | 9816893 | 4/1998 |
| WO | 9819734 | 5/1998 |
| WO | 9820793 | 5/1998 |
| WO | 9824358 | 6/1998 |
| WO | 9826365 | 6/1998 |
| WO | 9828676 | 7/1998 |
| WO | 9829790 | 7/1998 |
| WO | 9833433 | 8/1998 |
| WO | 9835747 | 8/1998 |
| WO | 9856450 | 12/1998 |
| WO | 9856451 | 12/1998 |
| WO | 9859487 | 12/1998 |
| WO | 9904043 | 1/1999 |
| WO | 9910029 | 3/1999 |
| WO | 9914882 | 3/1999 |
| WO | 9915216 | 4/1999 |
| WO | 9922330 | 5/1999 |
| WO | 9933390 | 7/1999 |
| WO | 9942933 | 8/1999 |
| WO | 9944162 | 9/1999 |
| WO | 9945490 | 9/1999 |
| WO | 9946657 | 9/1999 |
| WO | 9952025 | 10/1999 |
| WO | 9959472 | 11/1999 |
| WO | 9963886 | 12/1999 |
| WO | 9964971 | 12/1999 |
| WO | 0003344 | 1/2000 |
| WO | 0013588 | 3/2000 |
| WO | 0013726 | 3/2000 |
| WO | 0014652 | 3/2000 |
| WO | 0021590 | 4/2000 |
| WO | 0023908 | 4/2000 |
| WO | 0028460 | 5/2000 |
| WO | 0029983 | 5/2000 |
| WO | 0032098 | 6/2000 |
| WO | 0033231 | 6/2000 |
| WO | 0040145 | 7/2000 |
| WO | 0042911 | 7/2000 |
| WO | 0043941 | 7/2000 |
| WO | 0048112 | 8/2000 |
| WO | 0051519 | 9/2000 |
| WO | 0052437 | 9/2000 |
| WO | 0052438 | 9/2000 |
| WO | 0052626 | 9/2000 |
| WO | 0053082 | 9/2000 |
| WO | 0057339 | 9/2000 |
| WO | 0060522 | 10/2000 |
| WO | 0062660 | 10/2000 |

(56) References Cited

FOREIGN PATENT DOCUMENTS

| | | |
|---|---|---|
| WO | 0065522 | 11/2000 |
| WO | 0066271 | 11/2000 |
| WO | 0069331 | 11/2000 |
| WO | 0072181 | 11/2000 |
| WO | 0078374 | 12/2000 |
| WO | 0079466 | 12/2000 |
| WO | 0101305 | 1/2001 |
| WO | 0102979 | 1/2001 |
| WO | 0106468 | 1/2001 |
| WO | 0108077 | 2/2001 |
| WO | 0125972 | 4/2001 |
| WO | 0130422 | 5/2001 |
| WO | 0137786 | 5/2001 |
| WO | 0145014 | 6/2001 |
| WO | 0145774 | 6/2001 |
| WO | 0150397 | 7/2001 |
| WO | 0165232 | 9/2001 |
| WO | 0165463 | 9/2001 |
| WO | 0170301 | 9/2001 |
| WO | 0188828 | 11/2001 |
| WO | 0208941 | 1/2002 |
| WO | 0211049 | 2/2002 |
| WO | 0225566 | 3/2002 |
| WO | 0231738 | 4/2002 |
| WO | 02033961 | 4/2002 |
| WO | 0236044 | 5/2002 |
| WO | 0239250 | 5/2002 |
| WO | 0241135 | 5/2002 |
| WO | 0241232 | 5/2002 |
| WO | 0217777 | 7/2002 |
| WO | 02069099 | 9/2002 |
| WO | 02078783 | 10/2002 |
| WO | 02082984 | 10/2002 |
| WO | 02091276 | 11/2002 |
| WO | 03007816 | 1/2003 |
| WO | 03021485 | 3/2003 |
| WO | 03025826 | 3/2003 |
| WO | 03030979 | 4/2003 |
| WO | 03032827 | 4/2003 |
| WO | 03055542 | 7/2003 |
| WO | 03091836 | 11/2003 |
| WO | 03091838 | 11/2003 |
| WO | 03091840 | 11/2003 |
| WO | 2004012043 | 2/2004 |
| WO | 2004029853 | 4/2004 |
| WO | 2004030525 | 4/2004 |
| WO | 2004061745 | 7/2004 |
| WO | 2004070557 | 8/2004 |
| WO | 2004072828 | 8/2004 |
| WO | WO2004070994 | 8/2004 |
| WO | 2004088567 | 10/2004 |
| WO | 2005001739 | 1/2005 |

OTHER PUBLICATIONS

Canadian Office Action dated Jul. 10, 2015 for corresponding Canadian Application No. 2,514,571 (4 Pages).
Japanese Office Action dated Jul. 12, 2016 in corresponding Japanese application No. 2015-165438 (2 pages).
Canadian Office Action—Application No. 2,513,687, dated Mar. 13, 2018—4 pages.
Japanese Office Action—Application No. 2015-165438, dated Feb. 24, 2017—4 pages.
Canadian Office Action—Application 2,514,571 dated May 31, 2016—4 pages.
Japanese Office Action Appln. No. 2013-252772 dated Mar. 3, 2016 (4 pages)—English translation.
Canadian Office Action—Application No. 2,513,687, dated Jan. 9, 2017—7 pages.
Lefkowitz, Sheldon et al., "A Trial of the Use of Bar Code Technology to Restructure a Drug Distribution and Administration System," 1991, pp. 239-242, Hospital Pharmacy, vol. 26.
Pesce, James, "Bedside Terminals: Medtake," Clinical Computing, Jan./Feb. 1988, pp. 16-21, vol. 5, No. 1.
Hughes, Shirley, "Bedside Terminals: Clinicom," Clinical Computing, Jan./Feb. 1988, pp. 22-28, vol. 5, No. 1.
Standard Specification for Transferring Clinical Laboratory Data Messages Between Independent computer Systems, Annual Book of ASTM Standards, Mar. 25, 1988, pp. 1-16, E 1238-88, Global Engineering Documents, Philadelphia, PA.
Standard Specification for Transferring Information Between Clinical Instruments and Computer Systems, Annual Book of ASTM Standards, Jun. 1991, 15 pages, E 1394-91, Philadelphia, PA.
Standard Specification for Transferring Clinical Observations Between Independent Computer Systems, Annual Book of ASTM Standards, Jun. Mar. 1994, pp. 132.210, E 1238-94, Philadelphia, PA.
"Global Med Announces First Safetrace TX™ Sale," Apr. 1, 1999, 2 pages.
PCA II Multi-Mode Cartridge Operator's Manual, Sep. 1995, approx. 40 pages, Baxter Healthcare Corporation, Deerfield, IL.
Auto Syringe® AS40A Infusion Pump Technical Manual, 1995, 89 pages, Baxter Healthcare Corporation, Deerfield, IL.
Auto Syringe® AS40A: Model AS40A Infusion Pump Operation Manual, undated, 78 pages, Baxter Healthcare Corporation, Deerfield, IL.
Medin® Technical Overview, undated, 111 pages, Medicomp Systems.
Website information for Cartharsis Medical Technology Products, Dec. 9, 2001, 15 pages.
Website information for MedPoint™, Mar. 13, 2003, 20 pages, Bridge Medical, Solana Beach, CA.
Vincenzo Della Mae et al., "HTML generation and semantic markup for telepathology," Computer Networks and ISDN Systems, 1996, pp. 1085-1094, vol. 28, Elsevier Science B.V.
Daniel Andresen et al., "Scalability Issues for High Performance Digital Libraries on the World Wide Web," Proceedings of ADL '96, 1996, pp. 139-148, IEEE.
Michael H. Mackin, "Impact of Technology on Environmental Therapeutic Device Design," Medical Instrumentation, Feb. 1987, pp. 33-35, vol. 21, No. 1, Association for the Advancement of Medical Instrumentation.
Henry J. Lowe et al., "WebReport: A World Wide Web Based Clinical Multimedia Reporting System," 1996, pp. 314-318, AMIA, Inc.
H. Paul Hammann et al., "A World Wide Web Accessible Multi-Species ECG Database," 1997, pp. 7-12, ISA.
Valeriy Nenov et al., "Remote Analysis of Physiological Data from Neurosurgical ICU Patients," Journal of the American Medical Informatics Association, Sep./Oct. 1996, pp. 318-327, vol. 3, No. 5.
"Hospitals battle errors with bar codes," Mar. 24, 2004, 3 pages, MSNBC.
Fred Puckett, "Medication-management component of a point-of-care information system," Am. J. Health-Syst.Pharm., Jun. 15, 1995, pp. 1305-1309, vol. 52, American Society of Health-System Pharmacists, Inc.
Paul H. Perlstein et al., "Future Directions for Device Design and Infant Management," Medical Instrumentation, Feb. 1987, pp. 36-41, vol. 21, No. 1, Association for the Advancement of Medical Instrumentation.
Albert A. Cook, "An integrated nursing-pharmacy approach to a computerized medication dispensing/administration system," Hospital Pharmacy, May 1985, pp. 321-325, vol. 20, JB Lippincott Company, Philadelphia, PA.
Paul H. Perlstein et al., "Computer-Assisted Newborn Intensive Care," Pediatrics, Apr. 1976, pp. 494-501, vol. 57, No. 4, American Academy of Pediatrics, Inc., Evanston, Illinois.
Global Med Technologies, Inc. Introduces PeopleMed™.com, inc., A Chronic Disease Management Application Service Provider (ASP) Subsidiary, Jan. 11, 2000, 2 pages, Global med Technologies, Inc., Denver, CO.
Kenneth N. Barker et al., "Effect of an automated bedside dispensing machine on medication errors," American Journal of Hospital Pharmacy, Jul. 1984, pp. 1352-1358, vol. 41, No. 7, American Society of Hospital Pharmacists.

(56) References Cited

OTHER PUBLICATIONS

Darryl V. Wareham et al., "Combination Medication Cart and Computer Terminal in Decentralized Drug Distribution," American Journal of Hospital Pharmacy, Jun. 1983, pp. 976-978, vol. 40, American Society of Hospital Pharmacists.

Gretchen A. Barry et al., "Bar-code technology for documenting administration of large-volume intravenous solutions," American Journal of Hospital Pharmacy, Feb. 1989, pp. 282-287, vol. 46, American Society of Hospital Pharmacists.

Dennis D. Cote et al., "Robotic system for i.v. antineoplastic drug preparation: Description and preliminary evaluation under simulated conditions," American Journal of Hospital Pharmacy, Nov. 1989, pp. 2286-2293, vol. 46, American Society of Hospital Pharmacists.

William R. Dito et al., "Bar codes and the clinical laboratory: adaptation perspectives," Clinical Laboratory Management Review, Jan./Feb. 1992, pp. 72-85, Clinical Laboratory Management Association, Inc.

Yvonne Mari Abdoo, "Designing a Patient Care Medication and Recording System that Uses Bar Code Technology," Computers in Nursing, May/Jun. 1992, pp. 116-120, vol. 10, No. 3.

Victor J. Perini et al., Comparison of automated medication-management systems,: Am. J. Hosp. Pharm., Aug. 1, 1994, pp. 1883-1891, vol. 51, American Society of Hospital Pharmacists, Inc.

Ann Slone Endo, "Using Computers in Newborn Intensive Care Settings," American Journal of Nursing, Jul. 1981, pp. 1336-1337.

Gerald E. Meyer et al., Use of bar codes in inpatient drug distribution,: Am. J. Hosp. Pharm., May 1991, pp. 953-966, vol. 48, American Society of Hospital Pharmacists, Inc.

Standard Specification for Transferring Clinical Observations Between Independent Computer Systems, Aug. 10, 1997, 79 pages, ASTM E 1238-97, West Conshohocken, PA, United States.

Deborah J. Mayhew, "Principles and Guidelines in Software user Interface Designs," 1992, selected portions of Chapter 9, 17 pages, Prentice-Hall, Inc.

Ben Schneiderman, "Designing the User Interface: Strategies for Effective Human-Computer Interaction," 2d Ed., 1992, Chapter 5: Direct Manipulation (56 pages), Addison-Wesley Publishing Company.

Product literature, Baxter Healthcare Corporation, "MultiPlex™ Series 100 Fluid Management System," 1988, 2 pages.

Product literature, Baxter Healthcare Corporation, "MultiPlex™ Series 100 Fluid Management System," undated, 2 pages Product literature, Baxter Healthcare Corporation, "Flor-Gard® 6201 Volumetric Infusion Pump," 1992, 2 pages.

Peter Lord et al., MiniMed Technologies Programmable Implantable Infusion System, Annals New York Academy of Science, pp. 66-71, describing clinical trials from Nov. 1986.

"Block Medical: Growing with Home Infusion Therapy," taken from INVIVO, The Business and Medicine Report, Apr. 1991, pp. 7-9.

James Kazmer et al., "The Creation of Virtual Medical Record," 1996, 17pages.

Daniel J. Nigrin et al., "Glucoweb: A Case Study of Secure, Remote Biomonitoring and Communication," Proceedings of the 2000, 5 pages, American Medical Informatics Association, Bethesda, MD.

Charles Safran, M.D. et al., "Computer-Based Support for Clinical Decision Making," M.D. Computing, 1990, pp. 319-322, vol. 7, No. 5.

Gilad J. Kuperman, M.D. et al., "Innovations and research review: The impact of the HELPS computer on the LDS Hospital paper medical record," Topics in Health Record Management, 1991, pp. 76-85, vol. 12, Issue 2, Aspen Publishers, Inc.

"The Longitudinal Clinical Record: A View of the Patient," taken from Proceedings of the 1994 Annual HIMSS Conference, Feb. 14, 1994, pp. 239-250, Healthcare Information and Management Systems Society, Chicago, Illinois, USA.

Clayton M. Curtis, "A Computer-based Patient Record Emerging from the Public Sector: The Decentralized Hospital Computer Program," First Annual Nicholas E. Davies Award Proceedings of the CPR Recognition Symposium, 1995, pp. 75-132, Computer-based Patient Record Institute, Inc., Bethesda, MD.

Howard L. Bleich et al., "Clinical Computing in a Teaching Hospital," Use and Impact of Computers in Clinical Medicine, 1987, pp. 205-223 and selected pages, Springer-Verlag, New York, NY.

T.E. Bozeman et al., "The Development and Implementation of a Computer-Based Patient Record in a Rural Integrated Health System," Third Annual Nicholas E. David Award Proceedings of the CPR Recognition Symposium, 1997, pp. 101-130, Computer-based Patient Record Institute, Inc., Bethesda, MD.

Suzanne Careter, RN, Ed.D. et al., "The Computer-based Patient Record: The Jacobi Medical Center Experience," Second Annual Nicholas E. Davies Award Proceedings of the CPR Recognition Symposium, 1996, pp. 71-95, Computer-based Patient Record Institute, Inc., Bethesda, MD.

Bell Atlantic Healthcare Systems, Inc., court exhibit, StatLan Functions and Features, Specification, release 3.5, dated Nov. 12, 1992, 49 pages.

Clement J. McDonald, M.D. et al., The Regenstrief Medical Record System: 20 Years of Experience in Hospitals, Clinics, and Neighborhood Health Centers,: M.D. Computing, 1992 pp. 206-217, vol. 9, No. 4, Springer-Verlag, New York, NY.

Clement J. McDonald, M.D. et al, "The Three-Legged Stool: Regenstrief Institute for Health Care," Third Annual Nicholas E. Davies Award Proceedings of the CPR Recognition Symposium, 1997, pp. 131-158, Computer-based Patient Record Institute, Inc., Bethesda, MD.

Allan T. Pryor, "Current State of Computer-based Patient Record Systems," Aspects of the Computer-based Patient Record, 1992, pp. 67-82, Springer-Verlag, New York, NY.

Karen E. Bradshaw et al., "Physician decision-making—Evaluation of data used in a computerized ICU," International Journal of Clinical Monitoring and Computing, 1984, pp. 81-91, vol. 1, Martinus Nijhoff Publishers, Netherlands.

T. Allan Pryor et al., "help—A Total Hospital Information System," Proceedings of the Fourth Annual Symposium on Computer Applications in Medical Care, Nov. 2-5, 1980, pp. 3-7, vol. 1, Institute for Electrical and Electronics Engineers, New York, NY.

Larry B. Grandia, B.S.E. et al., "Building a computer-based Patient Record System in an Evolving Integrated Health System," First Annual Nicholas E. Davies Award Proceedings of the CPR Recognition Symposium, 1995, pp. 19-55, Computer-based Patient Record Institute, Inc., Bethesda, MD.

A.H.McMorris et al., "Are Process Control Rooms Obsolete?" taken from Control Engineering, pp. 42-47, Jul. 1971.

Specifications for Low-Level Protocol to Transfer Messages Between Clinical Laboratory Instruments and Computer Systems, Mar. 11, 1991, 7 pages, ASTM E 1381-91, Philadelphia, PA, United States.

Standard Specification for Transferring Clinical Observations Between Independent computer Systems, Nov. 14, 1991, 64 pages, ASTM E 1238-91, Philadelphia, PA, United States.

Standard Specification for Transferring Information Between Clinical Instruments and Computer Systems, Dec. 10, 1997, 15 pages, ASTM E 1394-97, West Conshohocken, PA, United States.

Web site information, Information Data Management, Inc.'s PCMS: Plasma Center Management System, Dec. 14, 2001, 11 pages.

Web site Information, Wyndgate Technologies' SafeTrace Tx™, undated, 15 pages.

Japanese Office Action dated Jul. 24, 2012, for corresponding Japanese Application No. 2009-238780.

Office Action dated Nov. 13, 2012 for corresponding Japanese Application No. 2011-154618.

Office Action dated Nov. 27, 2012 for corresponding Japanese Application No. 2006-503207.

International Search Report for International Application PCT/US2004/002821, dated May 18, 2005.

Japanese Office Action for Japanese Application No. 2011-154618, dated Aug. 8, 2013.

Canadian Office Action dated Mar. 27, 2013 for Canadian Application No. 2,556,841.

Japanese Office Action dated Apr. 23, 2012 for corresponding Japanese Patent Application No. 2006-503207.

(56) References Cited

OTHER PUBLICATIONS

Canadian Office Action for Canadian Application No. 2,513,687, dated Dec. 19, 2013.
Japanese Office Action for Japanese Application No. 2013-252772, dated Oct. 29, 2014.
Canadian Office Action dated Oct. 21, 2014 for Canadian Application No. 2,513,687.
Canadian Office Action dated Aug. 3, 2015 for corresponding Canadian Application No. 2,513,687.
Manns et al., "The acu-men™: A new device for continuous renal replacement therapy in acute renal failure," Kidney International, 1998, pp. 268-274, vol. 54.
Carson, Ewart et al., "A Systems Methodology for the Development and Evaluation of a Telematic Home Haemodialysis Service," Proceedings—19th International Conference—IEEE/EMBS Oct. 30-Nov. 2, 1997, Chicago, Illinois, pp. 907-910.
Tohme, Walid G. et al., "Design of a Multimedia PC-based Telemedicine Network for the Monitoring of Renal Dialysis Patients," SPIE vol. 3035, 1997, Downloaded from the Internet [http://proceedings.spiedigitallibrary.org] on Nov. 12, 2012, pp. 580-585.
Canadian Office Action for Canadian Application No. 2,514,571, dated Jun. 6, 2014.
Japanese Office Action—Application No. 2015-165438, dated Jul. 25, 2019—9 pages.

\* cited by examiner

Ninety-Three, James RN [Log Out]
Ninety Nine, Douglas, Mr. (MDLOC1)
MDUnit1: MDRoom1 - MDBed1
Dr.Ninety, Susan Mini-Chart: Allergies

| Allergies & Ht/Wt | Med Hx |

Lab Results

Drug Allergy
Acetaminophen

General Allergy

| Date Observed | Height | Weight |
|---|---|---|
| 8-22 14:16 | 183.00 cm | 85.00 Kg |
| | 72.05 in. | 187.39 Lbs. |

[Back]

Nurse A, RN [Log Out]
Patient, One – 101-B

Mini-Chart: Allergies(NKA)

- Administer Meds/Infusions
- STOP Infusion
- RESUME Infusion
- Titrate Infusion
- Flow Rate History
- Pump Status
- Remove Patient from Shift

Ninety-Three, James RN | Log Out

Ninety-Nine, Douglas, Mr. (MDLOC1)
MDUnit1: MDRoom1 - MDBed1
Dr.Ninety, Susan

Mini-Chart Allergies (NKA)

Allergies & Ht/Wt | Med Hx

Lab Results

All ●    Scheduled ○    PRN ○

Look Back Period: 24 ▼ hours

Order

Acetaminophen Cap 500 MG
500 MG = 1 CAP
Oral
TID
Admin Date: 6-3 12:53
Patient Refused more...

Back

Ninety-Three, James RN | Log Out

Ninety-Nine, Douglas, Mr. (MDLOC1)
MDUnit1: MDRoom1 - MDBed1
Dr.Ninety, Susan

Mini-Chart Allergies

Allergies & Ht/Wt | Med Hx

Lab Results

| Lab Test | Result | Range | H/I | Date |
|---|---|---|---|---|
| POTASSIUM | 3.1 | 3.6-5 mmol/L | Normal | 5/16/2003 9:00:00 AM |

Back

Nurse A, RN | Log Out

Patient, One – 101-B

Mini-Chart: Allergies (NKA)

MA-Continuous Infusion
Dextrose 5% W/Sodium Chloride 0.45%  ← 2629
200 ML
Route : Intravenous
Flow Rate : 50 ML/H
Estimated Admin. Period : 4 Hours ⚠ Warning : Wear Gloves  ← 2631

ⓘ Show Edubyte info here  ← 2633

RX not previously administered
Start Time : 6-2 14:54
End Time:  7-7 14:54

Nurse A, RN | Log Out

Patient, One – 101-B

Mini-Chart: Allergies (NKA)

<- 10:19 - 12:19 ->

SCHED 13

| | Time | Med | Last |
|---|---|---|---|
| ☑ | 11:30 | MORPHINE SULFATE<br>Continuous Infusion ← 2625 | 12-9<br>2:00 |
| ☐ | 13:30 NR | Continuous Infusion (De<br>⚠ | |
| ☐ | 15:30 NR | Continuous Infusion (De<br>⚠ | |
| ☐ | 17:30 NR | Continuous Infusion (De<br>⚠ | |

| Ninety-Three, James RN | Log Out |

WORKFLOW INFUSION: RESUME
Ninetyfour-Pointfive, Fred, Mr.
MDRoom1 - MDBed1
Mini-Chart: Allergies (Not Specified)

Continuous Infusion
Dextrose Inj 20%
500 ML
Route: Intravenous Flow Rate·
125 ML/H
Estimated Administration Period:
4 Hours Stopped w/o Order
Please select a reason for Resume
Infusion Site re-established ▼

Cancel

Back to Patient list

| Ninety-Three, James RN | Log Out |

WORKFLOW INFUSION: RESUME
Ninetyfour-Pointfive, Fred, Mr.
MDRoom1 - MDBed1
Mini-Chart: Allergies (Not Specified)

Scan Item

Continuous Infusion
Dextrose Inj 20%
500 ML
Route: Intravenous Flow Rate: 125
ML/H
Estimated Administration Period: 4
Hours Stopped w/o Order Back to Patient list

| ◘ | 🔍 | Nurse A, RN | Log Out |

Patient, One – 101-B

Mini-Chart : Allergies (NKA)

| 🗄 | Scan Depot: [ ] ⬆ |

Scan code is invalid

Search Items

| Item | DepotUnit | Qty |
|---|---|---|
| Morphine Sulfate Inj | | In other units |
| 2 MG/ML QA | | |
| Morphine Sulfate Inj | | In other units |
| 2 MG/ML QA | | |

Skip Scan Depot

| ◘ | 🔍 | Nurse A, RN | Log Out |

Patient, One – 101-B

Mini-Chart : Allergies (NKA)

| ℞ | Scan Item: [ ] ⬆ |

3467 — MORPHINE SULFATE
Continuous Infusion
60 MG = 30 ML
Route: Injection
Flow Rate: 30 ML/H
Estimated Admin. Period: 1 Hour Quantity: [30] ML(s)

Get: 30 ML

◆ Warning: Wear Gloves
ⓘ Show Edubyte Info here

Nurse C, RN  Log Out

Patient, Three, Mr. 100-C
Mini-Chart : Allergies

Verify Route, Line & Site

Rx Sodium Chloride 0.9%
Continuous Infusion
Rx Sodium Chloride 0.9%
1000 ML
Route. Intravenous Flow Rate: 50 ML/H
Estimated Administration Period: 20 Hours  ─ 3778

Please hang the bag
program the pump
and record the following Information
but DO NOT start the pump channel until instructed:

Route: [Intramuscular ▼] ─ 3773
Line: [Central ▼] ─ 3775
Site: [Right Forearm ▼] ─ 3777

[Compare Route] ─ 4817

Nurse A, RN  Log Out

Patient, One – 101-B
Mini-Chart . Allergies (NKA)

Scan Patient: [____]
─ 3661

If Cannot admin, select a reason: ─ 3659

Not Req Due to Monitoring Result
Patient Unavailable
Refused

[Waste/Return] ─ 3663

3657

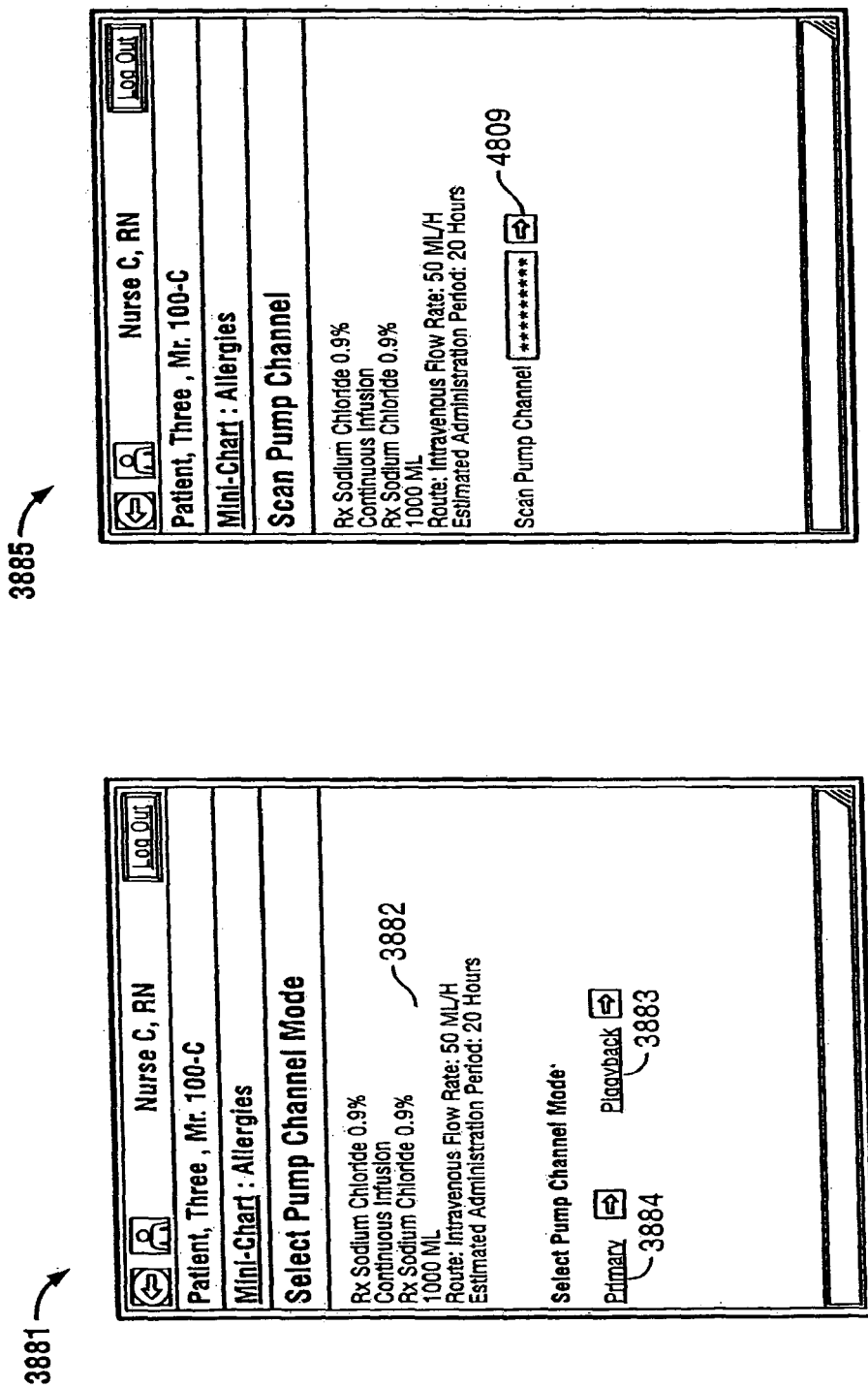

Nurse A, RN

Communication Loss Alert for the following Patients

| Rm - Bed | | Patient |
|---|---|---|
| 101 - B | ☒ | Patient, One |
| 101 - C | ☒ | Patient, Two |
| 101 - D | ☒ | Patient, Three |

Trouble Shooting Tips:
If a Yellow light is flashing on the WIRELESS MODULE and it is beeping, the system may be down. Call IT or Biomed.

- OR -

Plug in and turn on all pumps.
If that does not resolve the problem, Call IT or Biomed.

Nurse A, RN

Patient, One
Rm - Bed 101-B
Dr. One (111)111-1111 ext. 1

Flow Rate History

◊ Ancef 1 g, in Dextrose, 5% 50 mL
   run at 100 mL/hr 60 mL/h @ 10:55 AM 3/13
  70 mL/h @ 10:55 AM 3/13
  80 mL/h @ 10:54 AM 3/13

4493

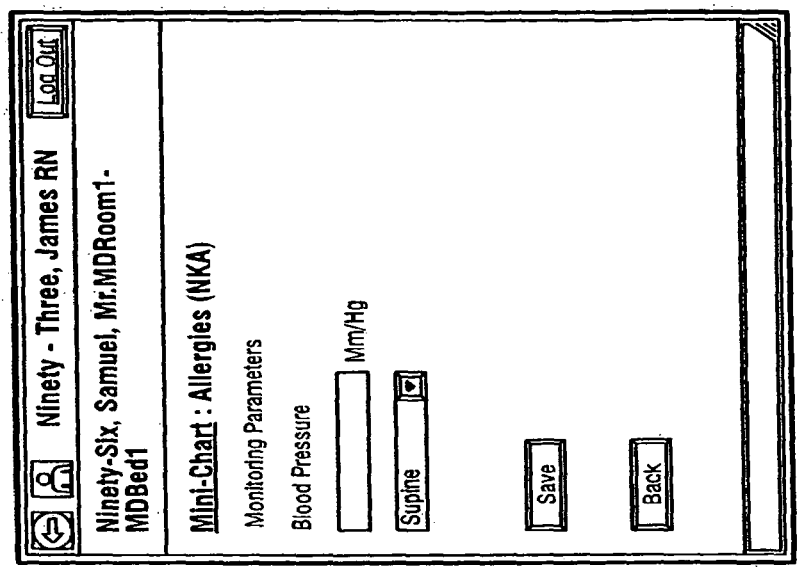
FIG. 50A
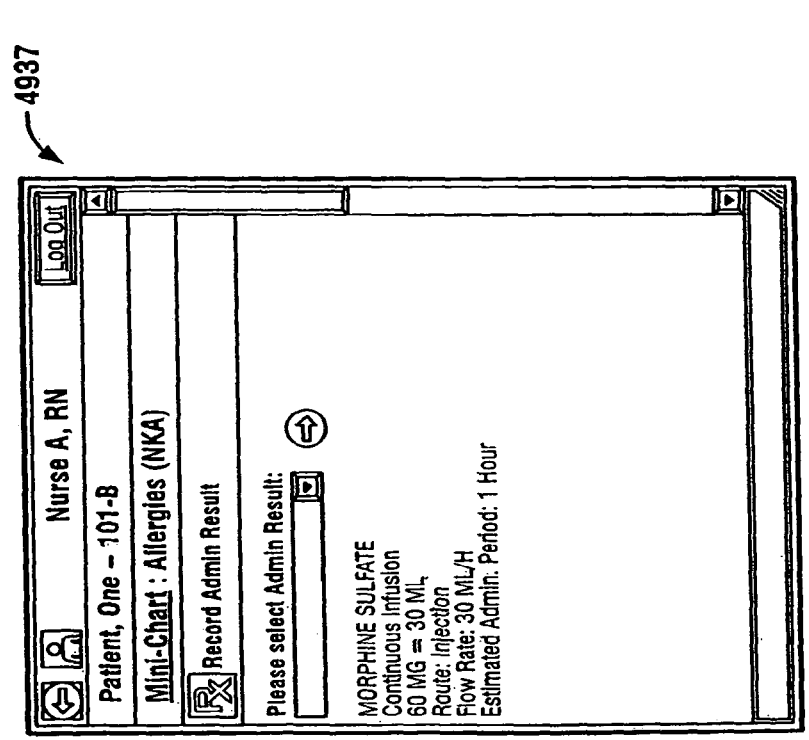
FIG. 49
FIG. 50

ELECTRONIC MEDICATION ORDER TRANSFER AND PROCESSING METHODS AND APPARATUS

PRIORITY CLAIM

This application is a continuation of U.S. patent application Ser. No. 14/218,542, filed Mar. 18, 2014, now U.S. Pat. No. 10,173,008, which is a continuation of U.S. patent application Ser. No. 10/749,102, filed Dec. 30, 2003, now U.S. Pat. No. 8,775,196, and claims the benefit of U.S. Provisional Patent Application Ser. No. 60/528,103, filed on Dec. 9, 2003. U.S. patent application Ser. No. 10/749,102, filed Dec. 30, 2003, now U.S. Pat. No. 8,775,196 claims the benefit of U.S. Provisional Patent Application Ser. No. 60/528,106, filed Dec. 8, 2003, and claims the benefit of U.S. Provisional Patent Application Ser. No. 60/488,273, filed on Jul. 18, 2003, and claims the benefit of U.S. Provisional Patent Application Ser. No. 60/444,350, filed on Feb. 1, 2003, and is a continuation-in-part of U.S. patent application Ser. No. 10/659,760, filed on Sep. 10, 2003, now U.S. Pat. No. 8,489,427 which is a continuation-in-part of U.S. patent application Ser. No. 10/424,553, filed on Apr. 28, 2003, now U.S. Pat. No. 7,698,156, which is a continuation-in-part of U.S. patent application Ser. No. 10/135,180 filed on Apr. 30, 2002, now abandoned, which is a continuation-in-part of U.S. patent application Ser. No. 10/059,929 filed on Jan. 29, 2002, now abandoned. All of which are expressly incorporated by reference and made a part hereof.

BACKGROUND

Patient care systems typically include computer networks, medical devices for treating a patient, and controls for the medical devices. Although patient care systems have improved through the use of computerized automation systems and methods, patient care systems continue to rely heavily upon manual data management processes for medical devices and controls for medical devices. For example, nursing stations are typically connected to the computer networks in modern hospitals, but it is unusual for the computer network to extend to a patient's room. Computer networks offer the opportunity for automated data management processing including the operating and monitoring of medical devices and controls for the medical devices at the point-of-care. Despite advances in the field, automated data management technology has been underutilized for point-of-care applications due to a lack of more efficient systems and methods. As dependence on automated technology grows, a need arises in providing users notifications concerning the operating status of system or subsystems, and alarm/alerts associated with the systems and subsystems.

SUMMARY

The present invention provides a system and method for reporting on notifications and alert and alarm escalations on a communication system within a healthcare environment.

According to one embodiment, a method for executing at least one of an alarm or an alert escalation process within a healthcare environment is provided. The process comprises: generating a signal that at least one of an alarm or an alert condition exists for a specific patient; transmitting the signal relating to the alarm or alert condition to a first clinician's device; indicating the alarm or alert condition on the clinician's device; operating a timer; and, escalating the signal if a response to the alarm or alert condition is not received prior to a predefined timer limit.

According to another embodiment, the alarm or alert condition signal is sent to a charge clinician.

According to another embodiment, the alarm or alert condition signal is escalated by transmitting the signal to a second clinician's device.

According to another embodiment, the system transmits the signal relating to the alarm or alert condition to a second clinician's device if the first clinician's device is not active, or if communication to the first clinician's device is lost.

According to another embodiment, the system conducts a precondition check prior to transmitting the signal to the first clinician's device. The precondition check may comprise at least one of the processes of: associating the patient with a medical device; associating the patient with a clinician and identifying the clinician as a first clinician; associating the first clinician with a clinician's device; and, establishing a relationship between the patient, the medical device, the first clinician and the first clinician's device.

According to another embodiment, the system conducts a precondition check prior to transmitting the signal to the second clinician's device.

According to another embodiment, the system provides for the charge clinician to have the authority and capability to enable or disable the escalation process.

According to another embodiment, the system terminates the signal relating to the alarm or alert condition to the clinician's devices after the alarm or alert condition is cleared.

Other embodiments, systems, methods, features, and advantages of the present invention will be, or will become, apparent to one having ordinary skill in the art upon examination of the following drawings and detailed description. It is intended that all such additional systems, methods, features, and advantages included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 25 is a view of a patient information menu interface screen;

FIG. 25A is a view of an allergies and height/weight interface screen;

FIG. 25B is a view of a medication history interface screen;

FIG. 25C is a view of a lab results interface screen;

FIG. 26 is a view of a medication delivery schedule interface screen;

FIG. 26A is another view of an interface screen of the medication delivery schedule process of FIG. 26;

FIG. 27A is a view of an interface screen of a workflow infusion stop;

FIG. 27B is another view of an interface screen of a workflow infusion stop;

FIG. 27C is a view of an interface screen of a workflow to resume an infusion;

FIG. 27D is another view of an interface screen of a workflow to resume an infusion;

FIG. 28 is another view of an interface screen of the medication delivery schedule process of FIG. 26;

FIG. 29 is a view of a missed medication interface screen;

FIG. 30 is another view of the interface screen of FIG. 29;

FIG. 31 is another view of the interface screen of FIG. 29;

FIG. 34 is a view of a scan interface screen;

FIG. 35 is a view of another scan interface screen;

FIG. 36 is a view of a medication administration interface screen;

FIG. 37 is a view of a route verification interface screen;

FIG. 38 is a view of a scan pump channel interface screen;

FIG. 38A is a view of another scan pump channel interface screen;

FIG. 39 is a view of a comparison interface screen;

FIG. 39A is another view of a comparison interface screen;

FIG. 40 is another view of a comparison interface screen;

FIG. 41 is another view of a comparison interface screen;

FIG. 44 is a view of a flow rate history interface screen;

FIG. 45A is a view of a communication loss interface screen;

FIG. 49 is a view of a record administration results interface screen;

FIG. 50 is a view of a medication order having a monitoring parameter link;

FIG. 50A is a view of a monitoring parameter entry interface screen;

DETAILED DESCRIPTION

Figure 1:
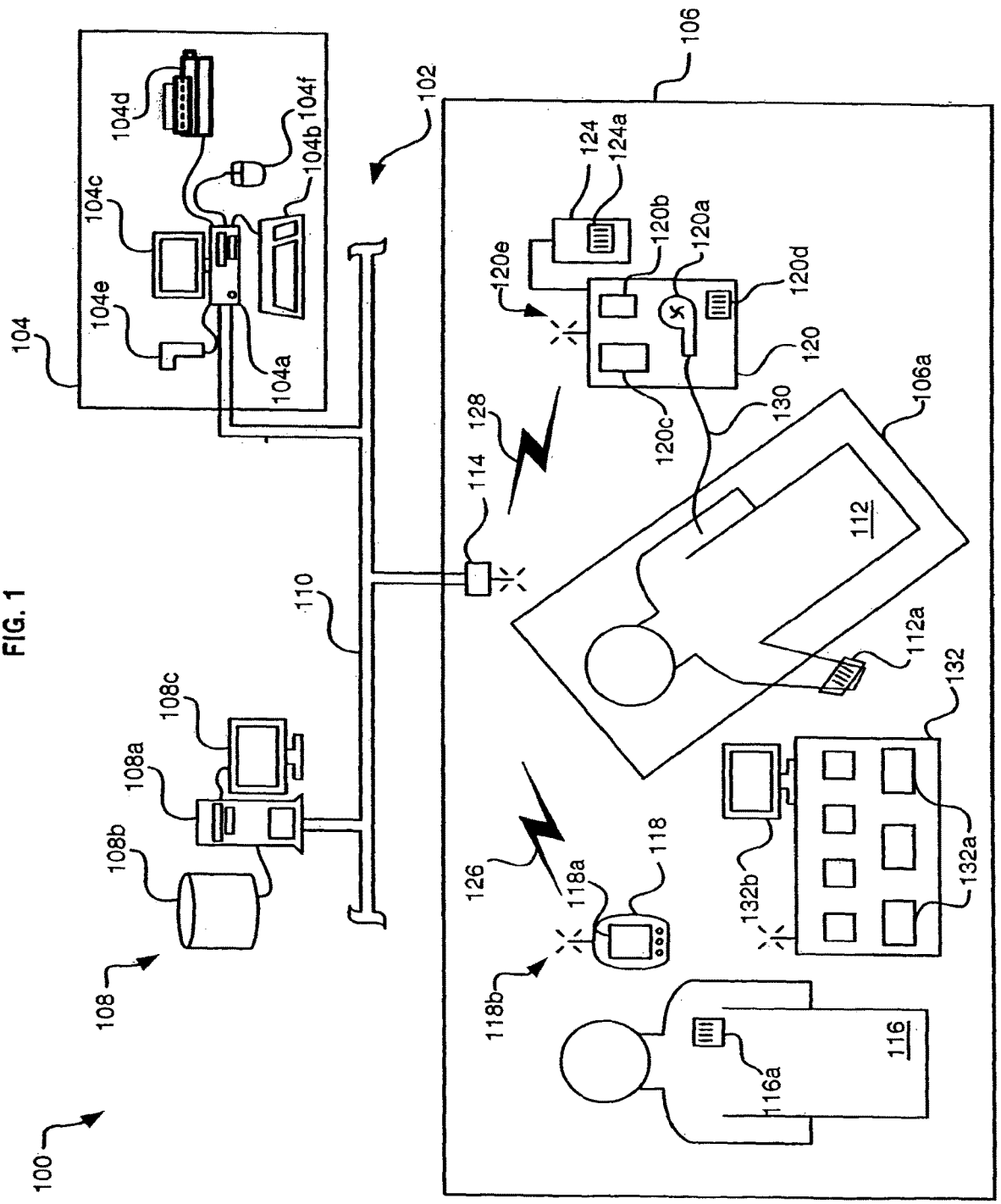
FIG. 1 is a simplified graphical representation of a patient care system. The patient care system includes a pharmacy computer, a central system, and a digital assistant at a treatment location.

While this invention is susceptible of embodiments in many different forms, there is shown in the drawings and will herein be described in detail a preferred embodiment of the invention. The present disclosure is to be considered as an exemplification of the principles of the invention and is not intended to limit the broad aspect of the invention to the embodiment illustrated.

Figure 2:
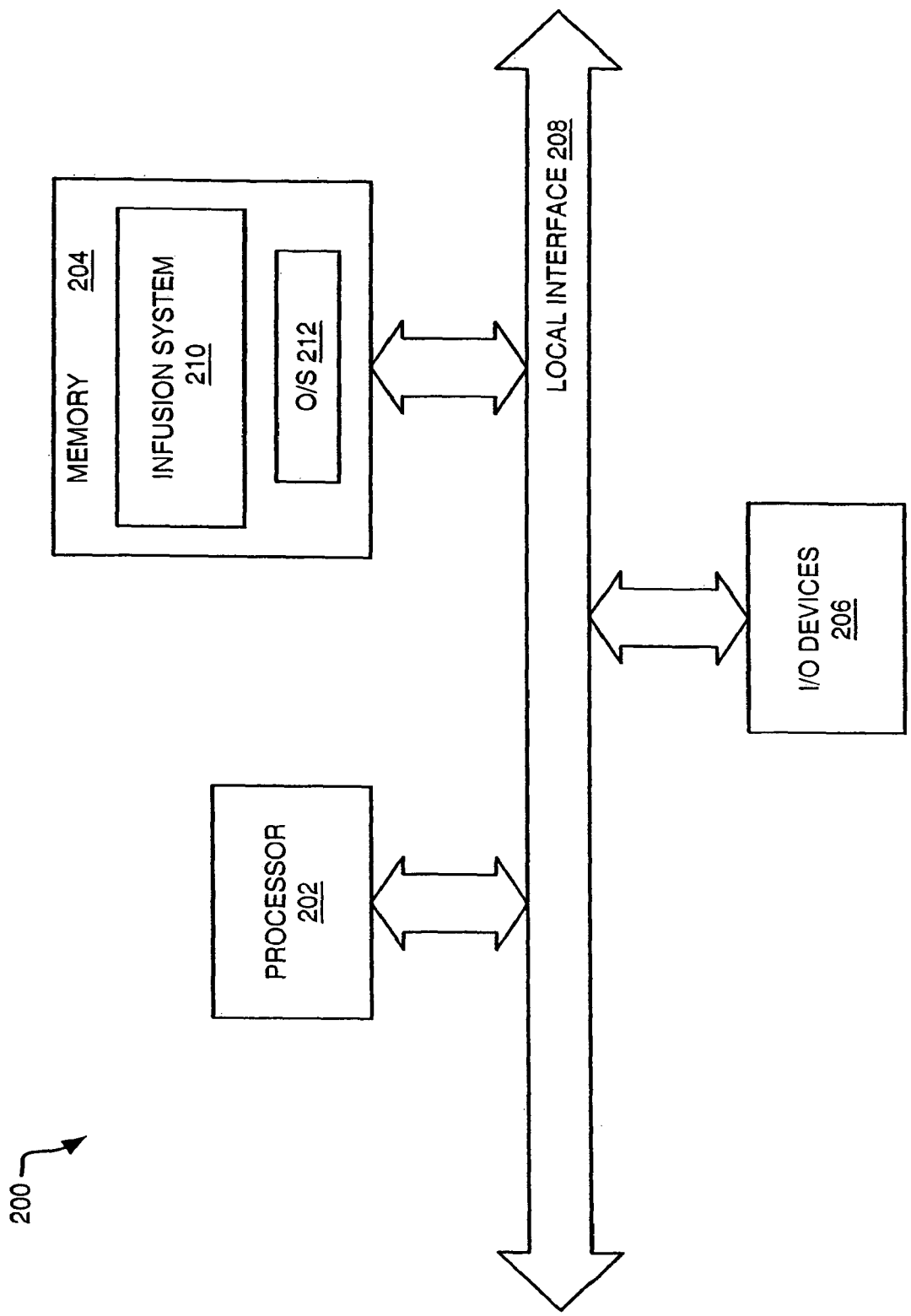
FIG. 2 is a block diagram of a computer system representative of the pharmacy computer, the central system, and/or the digital assistant of FIG. 1. The system includes an infusion system or a portion thereof.

FIG. 1 is a graphical representation of a patient care system. In one embodiment, the patient care system 100 includes a pharmacy computer 104, a central system 108, and a treatment location 106, linked by a network 102. The patient care system 100 also includes an infusion system 210, also referred to as a healthcare system, as shown in FIG. 2. Infusion system 210 is a medication system preferably implemented as a computer program, and in particular a module or application (i.e., a program or group of programs designed for end users), resident on one or more electronic computing devices within the patient care system 100. As described in detail further herein, the infusion system 210 links clinicians, such as physicians, pharmacists, and nurses, in an interdisciplinary approach to patient care.

Overall System

Figure 3:
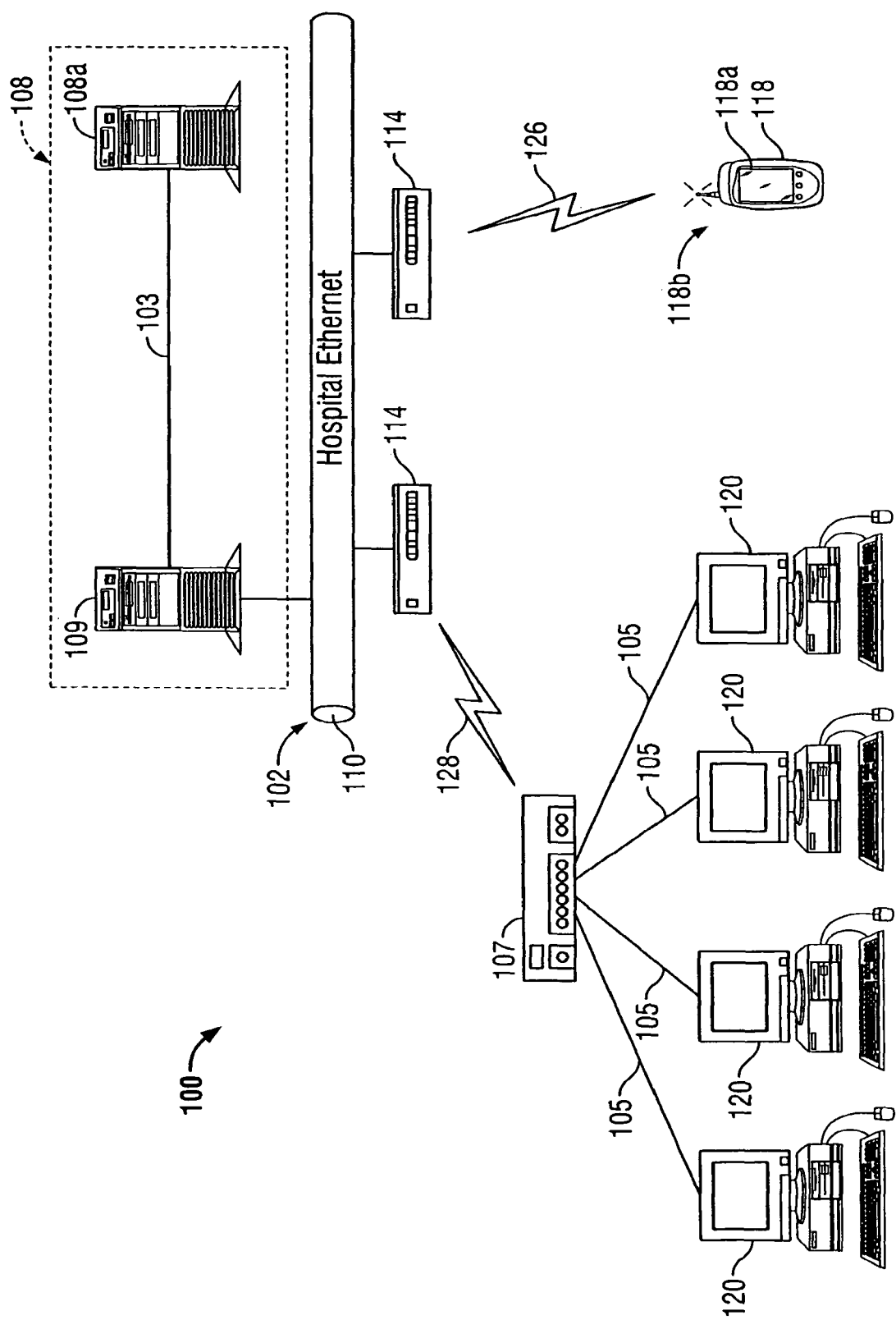
FIG. 3 is a simplified graphical representation of portions of the patient care system of FIG. 1.

Turning to FIG. 3, the patient care system 100 can include a plurality of medical 30 devices 120. In one embodiment, the medical device is an infusion pump 120. Further, in another embodiment the medical device is a controller for an infusion pump. For ease of reference, this disclosure will generally identify the medical device of the system as an infusion pump, however, it is understood that the overall system 100 may incorporate any one or more of a variety of medical devices. Accordingly, as shown in FIG. 3, a plurality of infusion pumps 120 is connected to a hub or interface 107. As explained in detail further herein, the infusion pumps 120 can be of conventional design wherein each infusion pump 120 is associated with a patient. However, as will be appreciated by those having ordinary skill in the art, the infusion pumps 120 shown in FIG. 3 do not have to be associated with the same patient or treatment location even though the infusion pumps are connected to the same hub 107. Moreover, each infusion pump 120 can be a single channel pump or a multiple channel pump, such as a triple channel pump. Typically, the pumps transmit messages containing pump status information on a periodic basis to the hub 107. A separate hub 107 can be used apart from the medical device 120 in order to centralize communications, for cost efficiencies, and/or to allow for retrofitting of existing medical devices that do not currently communicate with a central computer system 108 so that each such medical device can communicate with a central computer system 108.

Communication Hubs of the Overall System

In an embodiment, the serial port or other I/O port of the infusion pumps 120 is connected to the hub 107 using a conventional non-wireless transmission medium 105 such as twisted-pair wire, coaxial cable, fiber optic cable, or the like. Preferably, the hub 107 can connect to a plurality of infusion pumps 120 or just a single pump, through a one-way serial communications link 105. The hub 107 provides for receiving signals from the connected pumps and regenerating the received signals. In particular, the received signals from the pumps 120 are converted by the hub 107 into a format suitable for transmission onto the system network 102 via wireless communication path or link 128 and cable communication system 110. Typically, the hub 107 sends pump data to the system network 102. The hub 107 may also filter incoming information from the pumps 120 to reject duplicate messages.

Additionally, the hub 107 allows pump status information to be viewed remotely on a clinician's 116 digital assistant 118. Typically, the hub 107 sends pump data whenever the hub 107 is connected to the pump 120 and both the hub 107 and the pump 120 are turned on. As explained in detail herein, the hub 107 also provides for allowing comparisons of pharmacy-entered orders to the pump settings. In a preferred embodiment, the hub 107 is connected to the IV pole holding the pumps 120, or the hub 107 is incorporated into the infusion pump 120 to create an integrated medical/communications device as identified above.

Figure 47:
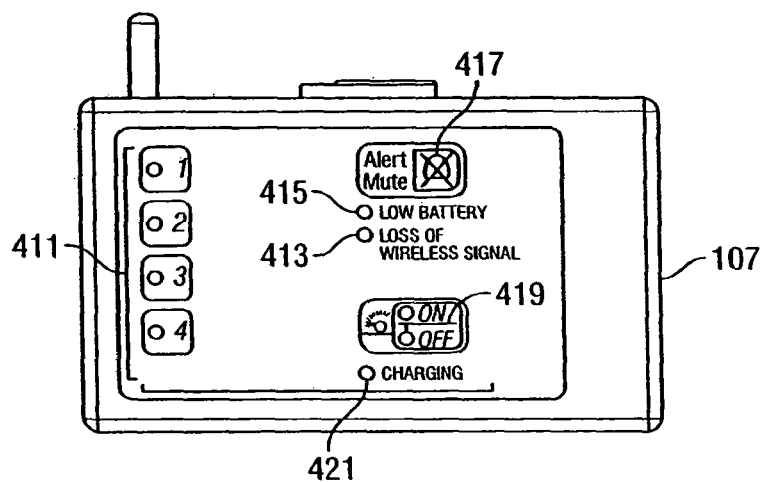
FIG. 47 is a view of a hub.

One embodiment of a hub 107 is shown in FIG. 47. In this embodiment, the hub 107 includes pump port indicators 411 for up to 4 pumps, a loss of wireless signal indicator 413, a low battery indicator 415, an alert mute key 417, an on/off key and indicator 419, and a charging indicator 421. The pump port indicators 411 provide a status indicator for each of the hub's 107 pump ports. The indicator light shows that the corresponding pump port is properly communicating with the network 102. When the indicator light is not lit, however, this indicates that the corresponding pump port is not connected to the pump 120 or the port is not communicating from the pump 120 to the network 102. The loss of wireless signal indicator 413 indicates that the hub 107 cannot communicate with the network 102 over the wireless link. If a loss of wireless signal occurs, each of the pump port indicators 411 will also turn off, indicating that the hub 107 is not communicating with the network 102. If a loss of wireless signal occurs, the hub 107 will communicate this event to the system network 102 and the central computer system 108 and server 109 for eventual transmission to the clinician 116. The alert mute key 417 allows the clinician 116 to temporarily silence all audible alerts from the hub 107. Alternate embodiments of the communications hub include a single dedicated wireless module physically within the pump, or a separate module using wireless communications to reach both the pump and server.

Additionally, in an alternate embodiment, the hub 107 may be optionally incorporated into the infusion pump 120 to create an integrated medical/communications device. The combination hub/medical device would still function identically with respect to each other.

Access Points of the Overall System

As shown in FIG. 3, a plurality of access points 114 within the healthcare facility provides an interface between the wireless communication paths and the cable communication system. Preferably, when the system network 102 is unavailable, the hub 107 stores the signals received from the pumps 120, and then transmits the converted signals to the system network 102 once the system network becomes available. In a preferred embodiment, communication between the hub 107 and the access points 114 is unidirectional from the hub 107 to the access point 114 and ultimately the network 102. As such, in the present embodiment the infusion pumps 120 can transmit data to the network 102; however, the network 102 cannot transmit data to the infusion pumps 120. It is understood, however, that in alternate embodiments also disclosed herein, communication between the hub 107 and the access points 114 is bidirectional. Accordingly, in these embodiments data and other information may be transmitted from the network 102 to the infusion pumps 120. In either case, the information transmitted between the network 102 and the hubs 107 is encoded for security purposes.

Central System Servers/Computers of the Overall System

Referring now to FIGS. 1 and 3, the central system 108 can include one or more servers or computers. While this disclosure refers generally to servers 109, 108a, it is understood that these components may be non-server computers. Preferably, but not necessarily, the central system 108 can include a first central server or computer 109 and a second central server or computer 108a. In one embodiment, a separate communication system 103 may be provided for communication between the first central server 109 and the second central server 108a. In a preferred embodiment, the separate communication system 103 is an isolated point-to-point cable communication Ethernet network. Because this communication system 103 is an isolated point-to-point system connection, the data communicated between the two servers 109, 108a is typically not encrypted. Typically, the communication system between the two servers 109 and 108a allows for bi-directional communication.

As explained in detail herein, the first central server or computer 109 has a first database 10 and a first functional feature set associated to data and functions related to the medical device and the user interface. The medical devices 120 and user interface 118 generally communicate directly with the first central computer 109. Further, as explained in detail herein, the second central server or computer 108a has a second database and a second functional feature set. The first central computer 109 is securely connected to the second computer 108a, and the medical devices 120 and user interfaces 118 do not communicate directly with the second central computer 108a. The user interface 118 can receive data from the second database relating to the second functional feature set of the second central computer 108a through the first central computer 109.

The second central server 108a, and its software subsystem, typically interface with a pharmacy system to provide information on drugs, patients and to provide the nurses and other clinicians with a typical workflow. The second central server 108a also interfaces with the first central server 109 to provide information on patients, nurses, clinicians, orders and associations between digital assistants 118 and clinicians. Some of the other functions of the second central server 108a can include patient management, item management, facility management, messaging, reporting/graphing, and various interfaces to other systems.

In particular, patient management refers to the general information about each patient that comes into a hospital or facility. This information is maintained along with information specific to each visit, and generally includes demographics, allergies, admission date, discharge date, initial diagnosis, room, bed, etc. Additionally, information about each of the medications which have been prescribed, scheduled, and administered is maintained by the second central server 108a. Functionality of the patient management function also includes prior adverse reaction checking, drug interaction checking, duplicate therapy checking, dose checking and drug-disease contraindications.

Item management refers to the information about each drug that is available in the facility. This information is managed and maintained within the second central server 108a. Such information includes drug name, strength, therapeutic classification, manufacturer, etc. Further, the second central server 108a maintains a perpetual inventory of the item contents of the medication depots and other smart storage locations on a real-time basis. The second central server 108a assists in providing for updates to be made as the depot is replenished and as doses are administered or disposed.

Facility management refers to the information that describes the overall facility. This information is managed and maintained within the second central server 108a of the system 210. This information includes: a physical breakdown of the facility into buildings, floors, units, rooms and beds; a list of programs and services that are offered and where they are offered; an identification of storage units where drug and supply items are stored and the locations they are intended to serve.

Messaging refers to the functionality of the second central server 108a, wherein the second central server 108a provides a communications link between the pharmacists and the clinicians. The second central server 108a allows for standardization of dosage and special administration instructions, and automatically sends notification of missing doses. Reporting and graphing refers to the availability of a number of operational and management reports which can be run on request or on a scheduled basis by authorized users of the system 210.

The second central server 108a also has various interfaces, such as: an ADT interface, a billing interface, a discrete results interface, a documents results interface, a formulary interface, a pharmacy orders interface, a Point of Care medication management interface and an inventory interface. These interfaces are explained in greater detail infra, however, a brief explanation is provided immediately below. The ADT interface refers to the facilities admission, transfer and discharge system (ADT). This system typically also operates the registration of pre-admittance and outpatients. The discrete results interface refers to an interface with laboratory results. Generally, after the lab results and ancillary orders are entered into an external lab information system, the discrete results interface or lab interface within the engine transfers this data to the second central server 108a. Once the lab results are saved in the second central server 108a, a user can view them from the handheld device 118, the Computerized Physician Order Entry (CPOE) system, and the second central computer 108a main application. Lab interfaces are available for at least four interfaces: radiology lab interface, microbiology lab interface, biochemistry lab interface, and pathology lab interface. These interfaces can be configured to operate either on four different ports or on the same port. The document results interface generally refers to the second central server 108a accepting radiology and pathology reports. The formulary interface generally refers to the second central server 108a being able to accept master file notifications to synchronize an external systems drug file. Changes to a formulary will trigger an outbound transaction from the server 108a to an external third-party system. The pharmacy orders interface provides for allowing medication orders to be sent to external third-party systems. The inventory interface provides for accepting pharmacy inventory changes from external third-party systems. Additionally, cart depot interfaces are available with the present system 100. The second central server 108a stores order and drug file changes in the server database, which then sends this information to any third-party cart interfaces. The third-party cart interface within the HL7 engine processes this information into HL7 MFN and RDE messages. The MFN message contains the drug file information and the RDE contains the patient orders information. The HL7 engine then transmits these messages to the third-party cart server. The HL7 engine also receives HL7 formatted DFT messages from the third-party cart server. The DFT message contains billing information for medication administration. The HL7 engine processes this information and then sends it to the second central server 108a, which can then pass this information to a billing application. The billing application may then calculate patient charges and invoice the patient. The billing interface refers to an interface with the patient charging software. The billing interface supports the optional use of billing algorithms to calculate charges. The billing interface processes internal transactions, as well as external inbound transactions from third-party systems. The billing interface provides an HL7 interface between the second central server 108a and the hospital's third-party financial system. The billed quantity may be sent directly, or patient charges may be calculated by the billing interface to send to the hospital's third-party financial system. The information is sent in real-time via HL7 messages. The Point of Care interface consists of web service communications which integrate information regarding point of care medication management for non-infusion related data. These data are communicated in real-time in order that the user interface can integrate medication management for infusion related and non-infusion related medications.

Conversely, the first central server 109 has software loaded and configured for sending and receiving data to and from multiple hubs 107, multiple digital assistants or user interfaces 118, and with the second central server 108a. As explained in detail below, the first central server 109 may perform several functions, including, but not limited to: comparing prescription parameters as received from server 108a to the applicable programmed pump settings received from the hub 107 system; relaying notifications and messages to the digital assistants 118; relaying alarm and alert information received from the hub 107 system to the appropriate digital assistant 118; relaying pharmacy and patient information as communicated from the server 108a to the appropriate digital assistant 118; and compiling pump status and alarm monitoring data and relaying this data to server 108a on a periodic basis. If required, the operations performed by the server 109 are compliant with the Health Insurance Portability Act of 1996 (August 21), Public Law 104-191. Typically, the data resident in the first central computer or server 109 is an intersection with the data resident in the second central computer or server 108a. Server 109 contains a subset of the data contained in server 108a that is required to perform its functionality. Server 109 also contains data relating to the system network 102, hubs 107 and infusion pumps 120 that are required to perform its functionality. As explained above, such data is generally that data required for the functions or performance of the digital assistants 118 and medical devices 120.

In one embodiment, a cost-effective integration of medical devices 120 or other devices and functionality with the hospital information systems in the first and second central computers 109, 108a is provided by isolating a subset of the total data mentioned above, such as patient safety-specific information, and locating such information and functionality in a validated/verified part of the system. In this context, an FDA regulatory context, verified means providing objective evidence that all requirements are tested and validated means providing objective evidence that the product meets customer needs. In the present embodiment, the validated part of the system is located within the first central computer 109. In one embodiment, the subset can include infusion pump generated alarms and/or alerts and/or medical device 120/infusion pump 120/controller 120 programming or operating parameter information. This subset is isolated and located in the validated part of the system, within the first central computer 109, and the remaining portion of the overall data is maintained in the database in the non-validated portion of the system, within the second central computer 108a. The validated database located at the first central computer 109 and non-validated database located at the second central computer 108a are kept in sync using Web services replication, as will be better understood by one of ordinary skill in the art from the details provided below. An alternate embodiment may include both the validated and unvalidated portions of the system residing on a single computer and functionally separated by means of a software firewall (e.g., operating system features or other OTS software). As will be described below, the "syncing" may be performed periodically based on time intervals, other predetermined times, and/or as needed when important data, such as patient registration status, changes occur. At intervals, a fresh new copy of the replicated data is sent to the other central computer, and validated first central computer 109 replaces its local copy with the new copy. When critical information changes, the change is propagated immediately to the validated first central computer 109 and processed as a change rather than as a replacement of the existing information. Thus, a portion or all of the subset located at the database at the first central computer 109 also exists at the second central computer 108a, as will be understood from the details provided herein. This process will be better understood with reference to the details provided below. Thus, by localizing a subset of the database, such as the patient safety-specific data at the first central computer, at least the cost of system development is further optimized, and integration with third-party non-validated systems and the respective data and information therein is made more time and cost effective.

Figure 54:
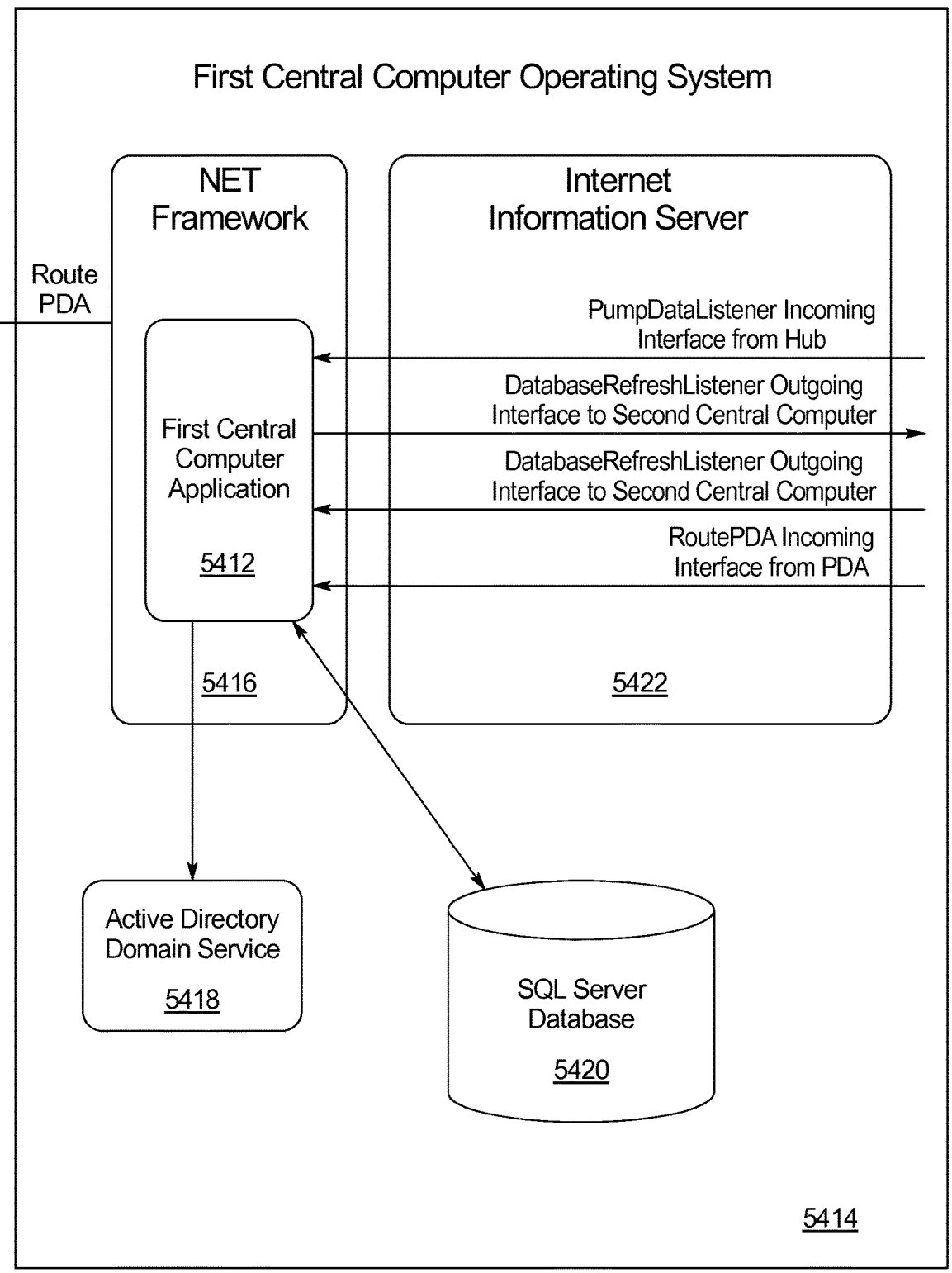
FIG. 54 is a simplified block diagram of software components loaded on the first central computer of FIG. 3.

In one embodiment, the first central computer 109 can comprise a validated server, such as a Compaq DLG-380 with Windows 2003 Server OS, running Active Directory for user and device authentication, Certificate Authority for issuance of server and client certificates, SQL Server 2000 for temporary data storage, Internet Information Server (IIS) for application hosting (Web Services and Web pages). The second central computer 108a can comprise a non-validated Server, such as an external Hospital Information System (HIS) Server connected through a dedicated Ethernet TCP/IP connection 103 accessing a data replication Web service exposed by the validated server at the other end of the dedicated connection. The second central computer 108a can alternatively comprise software for performing one or more of the various functionalities described in general herein, such as a pharmacy and other systems. Thus, the second central computer and can comprise these types of functions and have an interface with other systems, such as an external Hospital Information System (HIS) Server. The first central computer (i.e., server 109) includes a database containing a data storage package or first database. In an embodiment, the first database can be external or internal to the first central computer 109, but preferably is only accessible to users of the application 5412, as shown in FIG. 54, loaded on the first central computer. The data tables within the first database are used within the use cases described further herein. Preferably, the data tables include tables related to medical devices, digital assistants, hubs, patients, clinician, prescriptions, titration, comparison information, alarms, and escalations. Moreover, medical device tables can include tables related to pump, pump channel, pump sub-channel. Also, alarm tables can include tables related to hub alarms, pump alarms, channel alarms, an alarm history log, and the like.

In an embodiment, each table can include a key wherein data within the table is responsive to the key. For example, a key to a table regarding a pump channel information log can be a pump channel log identification wherein, in response to the key, table data is provided regarding the channel identification, pump rate, dose mode, dose, volume remaining, primary volume infused, and the like. Moreover, the tables can be linked. For instance, a patient table having patient information can be linked to a clinician table which can be linked to a digital assistant table.

The patient care system 100 of FIG. 3 can be divided into a hub subsystem, a first central computer or server subsystem, a medical device or pump subsystem, a second central computer or server subsystem, and a personal digital assistant (PDA) subsystem. The hub subsystem and the first central computer subsystem are discussed in detail further herein. Turning to the medical device subsystem, this subsystem preferably includes one or more medical devices 120 such as infusion devices for allowing delivery of medication to a patient wherein status and infusion information for each infusion device is transmitted periodically from a communication port associated with each device.

Generally, the second central computer subsystem is a server 108a having computer hardware and software for interfacing with a pharmacy system to provide information regarding drugs, patients, and typical nurse workflows. The server 108a can also have various other applications as previously discussed herein, such as an interface to a Hospital Information System (HIS). Preferably, the second central computer interfaces with the first central computer subsystem to provide the first central computer with information regarding patients, nurses, orders, and the association between a personal digital assistant and a nurse or clinician.

In one embodiment, a central computer has at least two environments: a validated environment and a non-validated environment. The validated environment may have a first operating system with a set of applications and a first database. The first database may have a first functional feature set associated with certain data therein. In one embodiment, this functional feature set has functions related to the medical device and the user interface for the medical device. The medical device and user interface communicate directly and securely with the validated environment. The non-validated environment may have a second operating system with a set of applications and a second database. The second database may have a second functional feature set associated with certain data therein. Typically, there is a logical separation between the validated environment and the non-validated environment. The user interface can receive data from the non-validation portion of the database relating to the second functional feature through validation portion of the system. In one embodiment, the validation portion is separated from the non-validation portion by a logical separation or fire wall, which may be implemented in software. Various software, such as VMware and Virtual PC, are examples of emulation software that emulates multiple environments on the same server. In another embodiment, the validation portion may be on the first central computer 109, and the non-validation portion may be on the second central computer 108a. In another embodiment, the central computer comprises a first server and a second separate server. The first and second servers are separated by a fire wall, and the central validation portion of the central computer resides in the first server, and the second non-validation portion of the central computer resides on the second server.

Preferably, as explained in detail elsewhere herein, the personal digital assistant subsystem includes one or more small portable devices 118 that provide clinicians and nurses 116 (FIG. 1) with remote information regarding: their patients—the status of infusions including the relay of alarms and alerts information; and infusion comparison results. As discussed herein, the first central computer is operably connected to one or more personal digital assistants 118 within the PDA subsystem. In an embodiment, the personal digital assistants are WINDOWS CE.NET based and used as a clinician terminal device. In particular, the personal digital assistant can be operably connected to the first central computer through a secure PKI-authenticated wireless LAN (802.1x) connection, as explained in more detail herein.

The hub subsystem preferably includes components such as one or more hubs 107 for receiving data from the medical devices 120, transmitting the pump data to the first central computer subsystem 109, and detecting conditions that can effect data communications with one or more hubs.

As indicated previously, in an embodiment, a hub 107 within the hub subsystem interfaces with up to four infusion devices 120 through a one-way serial communications link 105 wherein the infusion devices transmit messages (i.e., packets of data) containing pump status information on a periodic basis to the hub. Alternatively, the packets can be transmitted based on user defined criteria such as regular time intervals, event occurrences, a combination of time intervals and event occurrences, or the like.

Each hub 107 within the hub subsystem filters incoming information to reject duplicate messages, stores, and then forwards the pump information to the first central computer subsystem utilizing, in an embodiment, a built-in wireless network transceiver. In an embodiment, the pump information is not forwarded unless the data received from the medical device has changed.

The transceiver built into a hub 107 routes the outgoing information to a wireless access point 114 which in turn routes it to the first central computer 109 using the wired Ethernet subsystem 110. This outgoing information preferably contains XML encoded data formatted as SOAP messages specifically designed to be received by a web services type of software interface.

As will be appreciated by those having ordinary skill in the art, the term "XML" refers to a system for organizing and tagging elements of web documents wherein, with XML, customized tags can be created for enabling the definition, transmission, validation, and interpretation of data between applications and between systems or subsystems. Moreover, as used herein, the term "web services" refers to integrating web-based services using XML and SOAP wherein the term "SOAP" is a messaging protocol used to encode the information in web service request messages and response messages before sending them over the network or communication path.

The first central computer subsystem preferably consists of a server 109 with a software application loaded and configured for sending and receiving data to and from multiple hubs 107, multiple digital assistants 118, and the second central computer sub-system comprising server 108a.

Turning to FIG. 54, server 109 is preferably a COMPAQ DLG-380 with a MICROSOFT WINDOWS 2003 Server operating system 5414. In one embodiment, software components that are loaded within the memory of the first central computer 109 include a first central computer or server application 5412 within a NET framework 5416, an Active Directory Domain Service 5418 for users and device authentication, an SQL Server 5420 (show as a database) for temporary data storage, and Internet Information Server 5422 (IIS) for application hosting. The NET framework 5416 is preferably Microsoft NET framework 1.1 or greater wherein the NET framework connects the first central computer application 5412 to the operating system, Internet Information Server 5422, SQL Database 5420, and Active Directory Domain Service 5418 components. As will be appreciated by those having ordinary skill in the art, the Active Directory Domain Service 5418 provides services utilized by the Windows Server Operating System 5414 and the first central computer application 5412 to assist in ensuring that only authentic and authorized hub subsystem, second central computer subsystem and users of the personal digital assistant subsystem have access to the first central computer and thus the first central computer application 5412.

In an embodiment, the first central computer (i.e., server 109 of FIG. 3) performs several functions that include: 1) comparison of the prescription parameters as received from the second central computer subsystem to the applicable programmed pump setting received from the hub subsystem and/or program the pump; 2) relay of alarm and alert information received from the hub subsystem to the appropriate personal digital assistant 118 (FIG. 3); 3) provision of pump status and flow rate history information to the appropriate personal digital assistant 118; 4) relay of pharmacy and patient information as communicated from the second central computer 108a (FIG. 3) to the appropriate personal digital assistant 118; and, 5) compilation of pump and alarm monitoring data and relaying of this data to the second central computer 108a on a periodic basis.

The first central computer preferably includes a plurality of external software component interfaces. In an embodiment, three of these interfaces can be classified as "incoming interfaces" that receive incoming HTTP request messages and then issue outgoing HTTP response messages. The remaining two interfaces can be classified as "outgoing interfaces" that either send HTTP request messages or XML formatted response messages as explained below. As used herein, the five software interfaces are referred to as the DatabaseRefreshListener incoming and outgoing interfaces, the RoutePDA incoming and outgoing interfaces, and the PumpDataListener incoming interface.

In an embodiment, four of the external software component interfaces are paired to create two distinct bi-directional communication channels between the first central computer 109 and the second central computer 108a of FIG. 3. The first channel includes both the DatabaseRefreshListener incoming and outgoing interfaces paired together. Accordingly, the first channel is referred to herein as "DatabaseRefreshListener," and is utilized by the second central computer 108a for periodic synchronization of data in its database tables with data located in the first central computer's database tables. Using the DatabaseRefreshListener channel, the second central computer 108a updates the first central computer's database tables by sending XML encoded data formatted as SOAP messages to the first central computer's web services type of interface. Similarly, the second central computer 108a updates its own database table by sending XML encoded—requests for data to the first central computer's web services type of interface which in turn triggers the first central computer 109 to respond with XML encoded data. As indicated above, the incoming interface portion of the DatabaseRefreshListener channel is utilized by the second central computer for updating of database tables located in the first central computer with data from second central computer's database tables. Moreover, the outgoing portion of the DatabaseRefreshListener channel is utilized by the second central computer for updating its own database with data from the first central computer's database tables. Preferably, the DatabaseRefreshListener incoming interface contains several web service methods named "RefreshXXX" where "XXX" corresponds to the type of data being transferred.

In an embodiment, these methods receive incoming HTTP request messages containing XML encoded data formatted per the SOAP protocol. The XML encoded data is structure in a form that corresponds to rows in a database table. For example, the method "RefreshUsers" receives data structures consisting of pairs of user names and user passwords corresponding to rows in a database table that contains user name and user password columns.

As shown in FIG. 54, the incoming messages are routed via the Internet Information Server and the NET framework components to the application 5412 loaded on the first central computer (i.e., server 109 of FIG. 3). The first central computer application 5412 utilizes the Active Directory Domain Service 5418 to verify that the second central computer message is authentic, processes the contents, and then stores the resulting data in the SQL server database component 5420. The application 5412 loaded on the first central computer then responds to the second central computer by issuing an HTTP response method that is routed via the NET framework component 5416 and internet information server component 5422 to the second central computer. This response message indicates the success or failure of the data transfer and processing.

Preferably, the DatabaseRefreshListener incoming interface is asynchronous in nature, thus decoupling the second central computer from the first central computer to the extent practical. This decoupling allows the second central computer to be programmed for continued data processing while waiting for responses and for responding to losses in communication in a manner that is under program control. Moreover, the DatabaseRefreshListener incoming interface can also contain a web method for use by the second central computer to periodically signal the first central computer that the second central computer is functioning.

In contrast to the DatabaseRefreshListener incoming interface, the DatabaseRefreshListener outgoing interface is utilized by the second central computer for updating its own database with data from the first central computer's database tables. To ensure that the data has been captured by the second central computer before permanent removal from the first central computer, DatabaseRefreshListener outgoing interface utilizes a multi-step approach for data transfer as follows: 1) The second central computer checks for the availability of the data; 2) The second central computer requests that the first central computer send the data; 3) the second central computer confirms that the data has been received; 4) the second central computer confirms that the data has been correctly stored in its database tables.

To check for the availability of data, the second central computer first sends to the applicable web method of the DatabaseRefreshListener outgoing interface is an XML encoded request message formatted per the SOAP protocol. Preferably, the specific web method utilized is of the form "BeginGetXXXTo Archive" wherein "XXX" corresponds to the type of data being requested. For example, the method "BeginGetChannelDataToArchive" request the availability of time stamped pump channel records received by the first central computer from the pumps through the hub subsystem. The request message is passed through the Internet Information Server component 5422 and NET framework component 5416 to the application loaded within the first central computer. The application 5412 loaded within the first central computer decodes the XML contained in the request message to determine what data is being requested by the second central computer.

The application 5412 loaded within the first central computer checks for the availability of the requested data in the SQL Server Database 5420. If the data is available, the application prepares an XML encoded response message indicating that data is available. If the data cannot be obtained, the application 5412 prepares an XML encoded response message indicating that data is not available. If the data is not available, the second central computer may retry or proceed with a different transfer consistent with its processing rules. If the data is available, the second central computer initiates the data transfer by sending to the applicable web method of DatabaseRefreshListener outgoing interface a second XML encoded request message. Preferably, the specific web method utilized is of the form "EndGetXXXToAcrchive" wherein "XXX" is identical to that used above.

The application 5412 within the first central computer decodes the XML contained in the request message to determine what data to return to the second central computer and places the data in an appropriate XML encoded response message structured in a form that corresponds to rows in a database table consistent with the approach utilized by the corresponding incoming interface.

In an embodiment, the data is routed to the second central computer via the NET framework component 5416 and Internet Information Server component 5422. If the data was not correctly received, the second central computer may retry or proceed with a different transfer consistent with its processing rules. If the data was received correctly, the second central computer then sends a third request message to the applicable web method of this interface. Preferably, the specific web method utilized is of the form "BeginDeleteArchivedXXX" where "XXX" is identical to that used above.

Upon receipt of this message, the application 5412 loaded within the first central computer marks the relevant data in the SQL Server Database component as being sent to the second central computer for archiving and issues a response message acknowledging that the data has been marked. To signal the success or failure of storing the data in the second central computer database, the second central computer sends a fourth request message to the applicable web method of this interface. The specific web method utilized is of the form "EndDeleteArchivedXXX" where "XXX" is identical to that used above.

If the second central computer indicates that the transfer was unsuccessful or if sufficient time has elapsed that the first central computer determines that a loss of communication has occurred, then the relevant data is retained in the first central computer database for further transfer as requested by the second central computer.

If the second central computer indicates that the transfer was successful, then the archived data is purged from the first central computer database and the application 5412 loaded within the first central computer issues a response message confirming completion of the final step of this transfer. Preferably, the DatabaseRefreshListener outgoing interface is asynchronous in nature, thus decoupling the second central computer database from the first central computer to the extent practical.

The second bi-directional channel between the first central computer 109 and the second central computer 108*a* is referred to herein as "RoutePDA" and includes both the RoutePDA incoming and outgoing interfaces paired together. The RoutePDA channel is used by the first central computer 109 for routing of HTTP request messages originating from the PDA subsystem to the second central computer 108*a*, then receiving the corresponding HTTP response messages from the second central computer, processing if applicable, and then routing back to the originating personal digital assistant 118. In the second channel (i.e., RoutePDA), messages received from or sent to a personal digital assistant 118 are preferably transmitted to and from the first central computer 109 via the hospital or healthcare facility's wired Ethernet system 110, a wireless access point 114, an a wireless transceiver built-into each personal digital assistant 118.

Preferably, HTTP request messages are forwarded without processing through the first central computer 109 to the second central computer 108*a*. The second central computer 108*a* then issues HTTP response messages containing either XML or HTML formatted information. HTML formatted response messages are routed through the first central computer 109 to the personal digital assistant 118 without further handling. XML formatted response messages are used by the second central computer 108*a* to signal to the first central computer 109 that the user 116 (FIG. 1) has requested a web page that the first central computer 109 creates, such as a prescription comparison results page or a pump-monitoring page. The first central computer 109 examines the XML response, processes as appropriate, and issues an HTML or XML formatted response message to the sending personal digital assistant 118.

As indicated previously, the RoutePDA channel is used by the first central computer for routing of HTTP request message received from the PDA(s) 118 to the second central computer and then receiving the corresponding HTTP responses returned by the second central computer, processing if applicable, and then routing back to the sending PDA(s). Accordingly, the RoutePDA incoming interface is utilized for communication with the web browser located in the PDA(s) 118. This interface receives incoming HTTP request messages containing data encoded as name-value pairs consistent with the HTTP "GET" and "POST" protocols. The incoming messages are routed via the Internet Information Server and the NET Framework component to the application 5412 loaded within the first central computer. The application 5412 loaded on the first central computer reroutes the incoming message to the second central computer utilizing the NET framework 5416 and the RoutePDA outgoing interface as discussed below.

When an HTTP response is received at the RoutePDA outgoing interface, the application 5412 loaded on the first central computer determines whether the response utilizes HTHL or XML formatting. HTML formatted responses are rerouted by the first central computer to the PDA without further handling, via the NET framework component 5416 and Internet Information Server component 5422. XML formatted responses, however, are used by the second central computer to signal to the first central computer that the user has requested a web page that the first central computer creates, such as a prescription comparison results page or a pump-monitoring page.

The first central computer examines the XML response from the second central computer, processes as appropriate, and issues an HTML or XML formatted response to the appropriate PDA(s), via the NET framework and Internet Information Server components. Preferably, the RoutePDA interface is synchronous in nature due to the inherent synchronous behavior of the web browsers contained in the PDAs.

In contrast to the RoutePDA incoming interface, the RoutePDA outgoing interface is utilized for routing HTTP request messages received by the application 5412 loaded on the first central computer from the personal digital assistant subsystem to the second central computer for processing and then receiving the corresponding HTTP response sent by the second central computer in return. In both the DatabaseRefreshListener channel and the RoutePDA channel, the first central computer 109 sends and receives information from the second central computer 108*a* through an isolated point-to-point Ethernet sub-system 103 that is preferably dedicated to this use only.

As indicated above, in utilizing the DatabaseRefreshListener channel, the first central computer exposes a specialized Web service on the dedicated link 103 that is used by the second central computer to replicate new and updated database information (such as patient information, clinician information, pharmacy information, and the like) periodically and as needed to the first central computer. Also, data is provided from the second central computer to the first central computer. Moreover, in utilizing the RoutePDA channel at the clinician terminal device end, the first central computer 109 exposes a NET liS Server interface serving HTTP-style web pages and maintaining authenticated web session with the PDA devices 118. Stated another way, the clinician terminal device (i.e., personal digital assistant 118) receives authenticated web pages from the first central computer 109. At the first central computer end of the dedicated connection 103 to the second central computer, the first central computer establishes a virtual HTTP session for each PDA device 118 connected to the first central computer, and impersonates a Web browser to the second central computer relaying HTTP request from the PDAs as they are being received by the first central computer. Stated another way, the first central computer, through the dedicated connection 103 to the second central computer, relays requests requiring non-validation to the second central computer.

Accordingly, when the information flow between a PDA 118 and the server system requires information originating from the second central computer side or merged information be presented, the second central computer posts an XML SOAP packet to the Web service exposed by the first central computer on the dedicated link 103 and the first central computer uses the XML data to perform a merger operation with the information originating from the first central computer side of the system, converts the result to HTML, and then posts the HTML back to the clinician's PDA device 118.

The fifth external software component interface, referred to as PumpDataListener is an incoming interface for communication with the hub subsystem, as explained in more detail herein. In an embodiment, the PumpDataListener interface does not have a corresponding outgoing interface because the transfer of pump data is one-way, only, except for communication verification. However, in an alternative embodiment, an outgoing interface can be provided for transfer of pump command and control data to the medical devices 120.

The PumpDataListener incoming interface is utilized for receipt of data from the hub subsystem. Preferably, this interface contains a single web service method referred to as "SendPumpData." This method receives incoming HTTP request messages containing XML encoded data formatted per the SOAP protocol. The XML encoded data is structured in a hierarchical form such that data from several pumps and several channels per pump at several different times can be combined into a single large message structure.

The incoming messages are routed via the Internet Information Server and the Net framework components to the application 5412 loaded within the first central computer application. The first central computer application utilizes the Active Directory Domain Service component to verify that the hub subsystem message is authentic. The first central computer then processes the contents, and stores the resulting data in the SQL Server Database component. Finally, the first central computer application issues an HTTP response message to the sending hub device via the NET framework and Internet Information Server components. This response messages indicated the success or failure of data transfer and processing. Data packets received by the first central computer (i.e., server 109) from the hubs 107 are preferably stored within the first central database of the first central computer. Preferably, if an alarm or alert event is included in the packet, the first central computer can immediately dispatch the event to the appropriate clinician(s) via his or her digital assistant 118, or alternatively, the first central computer can enter the event into the first central computer database and later dispatch the information when requested by the appropriate clinician(s) via his or her digital assistant. As indicated previously, the first central computer 109 maintains a log of all clinicians that are logged onto his or her digital assistant 118 which is authenticated every time the clinician logs onto the system.

Preferably, the PumpDataListener incoming interface is asynchronous in nature, thus decoupling the hub subsystem from the first central computer subsystem to the extent practical. The decoupling allows the hubs 107 within the hub subsystem to be programmed for continued data processing while waiting for responses and for responding to losses in communication in a manner that is under program control. Nonetheless, the PumpDataListener maintains a "heartbeat" to monitor (lack of) continuity of communications between all wireless modules and/or remote pump devices and the central computer.

Communication with Clinician Handheld Devices

As described in detail further herein, pump status, alerts, alarms, patient information, chart information, comparison information, to-do lists and other data/information are provided to clinicians via a personal digital assistant or user interface 118 having a display 118a, antenna 118b, and, if desired, an audible tone or sound generator 118c. The digital assistant 118 communicates with the central system 108 via the central network 102 and, in particular, wireless communication path or link 126 and cable communication system 110. As stated previously, one or more wireless access points 114 provide an interface, in a conventional manner, between the wireless communication paths and the cable communication system. The digital assistant 118 may receive messages from both servers 109 and 108a. Preferably, communication between the central system 108 and the digital assistant 118 is bidirectional. Moreover, it is desired that the digital assistant 118 include enough memory and processing capability to store and execute a module or application (not shown) for testing the integrity of the communication link between the digital assistant and the central system 108 or the wireless access point 114.

Preferably, but not necessarily, a module or application installed on the digital assistant 118 is a script or other computer instructions (i.e., software code) written in a high-level programming language, such as JAVA, that can be executed with or without clinician intervention. The script can be automatically downloaded from the server 108a or 109 to the digital assistant 118, or to the medical device 120, as a receiver function of the system. As an example, one type of script that may be automatically downloaded from the server to the digital assistant is a script that tests the integrity of the communication link by periodically polling, or monitoring communication, including notifications and messaging, from the central system 108 or the access point 114. In a preferred embodiment, the script running on the digital assistant polls the system 108 approximately every 3 seconds. If a response is not received from the central system 108 or the access point 114, the module or application installed on the digital assistant 118 generates a time-out that results in audible tones and/or a notification on the visual display 118*a* that communication with the central system 108 has been lost. The notification on the visual display 118*a* can be, for example: the activation of an information pop-up window stating that the communication link is lost, or the changing of an active icon display on the visual display 118*a*. As used herein, and recognized by those having ordinary skill in the art, a time-out is an output generated by a module or application for indicating that the module or application has waited a certain amount of time for input, but has not received it. Another type of script may poll to determine if an alarm or alert has been triggered. Numerous other scripts may be running simultaneously. One advantage of running scripts that are downloaded from the system to the digital assistant is that there is no need to install custom code on each digital assistant 118. If any event (i.e., a message, notification, alarm, alert, etc.) is present, the digital assistant 118 automatically retrieves the event from the server and displays it on an interface screen of the digital assistant 118. Other added advantages of the script approach are 1) the script code can be easily updated at the central server instead of requiring each digital assistant to be updated, 2) the scripts can be verified/validated relatively independently of the digital assistant hardware platform because the functionality is hardware independent, thus changes or upgrades to the digital assistants have minimal effect on script operation.

As indicated previously, each clinician preferably has an associated digital assistant 118 that, in an embodiment, provides the clinician with a view of a page consisting of an HTML frame set with a dedicated frame for display of events. The dedicated frame can have a JAVA script inserted therein for display of events wherein the script interrogates the first central computer 109 for new events such as pump alarms and alerts directed to the digital assistant 118. If any new events have occurred, then the first central computer provides this information to the digital assistant 118 wherein it is displayed within the dedicated frame for display of such events.

One type of notification provided on the digital assistant 118 indicates to the clinician that data presented by the digital assistant 118 is not current, and access to alerts and alarms is not available. Conversely, the digital assistant 118 can also indicate when the digital assistant 118 is linked to the central system 108 for providing real-time access to alerts and alarms. Other notifications that are typically communicated via scripts include, but are not limited to: pump "silent shut down," overrides of pump infusion limits, end of infusion, occlusion trend information, low battery, pre-occlusion indicator, over use of bolus, keep vein open alert, stat medication notifications, change orders, lab results, radiology results, updating, change in telemetry data and/or vital signs information, doctors or pharmacy attempting to reach the nurse, patients that are requesting the nurse, loss of communication, messages from other devices, new rate for medical device based on vital information, rate following purge, etc.

As stated previously, clinicians within a healthcare facility have access to infusion alerts, alarms, and messages via the remote wireless device 118 (i.e., also referred to as a personal digital assistant (PDA) 118) or other computer devices, wireless or hardwired to the network, such as a tablet computer with a bar code reader operably attached, or a laptop computer attached to an IV pole and having a bar code reader operably attached to the computer.

Preferably, the infusion system 210 provides clinicians and other users with options for automating alert event-driven messages. Moreover, healthcare facility administrators and other users can customize the types of automated messaging to appear, via the remote wireless device, by message type or classification, severity of abnormality, and time-based reminders. Additionally, the infusion system provides clinicians and other users with the ability to configure audible messages, visual messages, or both.

The messaging provided by the infusion system 210 preferably includes a user-configurable rules engine, a scheduler, and interfaces to infusion pump systems. Moreover, it is desired that the results-driven messaging provide clinicians with real-time decision support at the point of care via a workstation, electronic tablet, wireless personal digital assistant, or the like.

Generally, the communication between the infusion pump 120 and the network 102 and, further, from the network 102 and the clinician's digital device 118 allows the clinician 116 to: view electronically-compared pharmacy-entered orders to programmed pump settings and/or program the pump, use the system as a method of remotely viewing pump alerts and alarms, view the pump status remotely, view notifications and view the history of the infusion setting changes, among other things.

Patient Care System

Turning back to FIG. 1, patient care system 100 preferably includes a computerized physician order-entry module (CPOE), an inpatient pharmacy module, a wireless nurse charting system, and an electronic patient medical record module. In one embodiment, such systems and modules are applications of the second central server or second central computer 108*a*. It is desired that patient care system 100 provide a comprehensive patient safety solution for the delivery of medication. Within patient care system 100, software modules are provided to link together existing patient care systems using interfaces such as HL7 interfaces that are known to those having ordinary skill in the art. Preferably, the patient care system 100 operates on a variety of computers and personal digital-assistant products to transmit orders, update patient medical records, and access alerts, alarms, and messages.

The computerized physician order-entry module enables physicians to enter medication orders, access alerts, alarms, messages, reminders, vital signs and results. A pharmacy module checks the prescribed drug against documented patient allergies, and for compatibility with other drugs and food. The pharmacy module also provides real-time data for inventory management. A nurse medication-charting module provides clinical information that is immediately available at the bedside, thus ensuring verification of medication and dosage at the point-of-care.

Patient care system 100 integrates drug delivery products with the information required to assist in ensuring safe and effective delivery of medication. The clinical decision support and accompanying alerts, alarms, warnings, and messaging of the patient care system 100 provide a safety net of support for clinicians as they deliver patient care under increasing time and cost pressures. This information is preferably supplied through a wireless network that supplies data in a way that improves clinician workflow, making delivery of care easier.

Overview of the Infusion System

The infusion system 210, or healthcare system 210, within the patient care system 100 provides computerized prescribing and an electronic medical administration record (eMAR), among other things. Infusion system 210 puts charting, medication history, inventory tracking, and messaging at the clinician's fingertips. Patient care system 100 combines bar-coding and real-time technology to assist in ensuring that the right patient gets the right medication and the right dosage, at the right time, via the right route. Infusion system 210 provides alerts, alarms, messages, and reminders such as, but not limited to, lab value, out of range, and missed dose.

As part of the verification of the right dosage, the system can also provide verification of the settings of an infusion pump. As explained in detail further herein, the infusion system 210 resides, at least in part, on one or more electronic computing devices such as wireless remote personal digital assistants, workstations, physician order-entry modules, electronic tablets, processor controlled infusion pumps, or the like. The infusion system 210 can be configured to display, via one or more of the electronic computing devices, numerous hospital-definable alerts and alarms in varying forms. In an embodiment, time-based alerts are provided to remind clinicians to perform a patient care function such as, but not necessarily limited to, changing an infusion rate. Further, emergency alarms are provided such as, but not necessarily limited to, an infusion being disconnected. Moreover, less urgent messages are provided such as, but not necessarily limited to, the infusion being completed or the line being occluded. In addition, the infusion status can be viewed from anywhere within the healthcare facility via one or more of wireless remote personal digital assistants or other electronic computing devices.

As disclosed in greater detail infra, the system 210 provides for the escalation of alarms or alerts that are not indicated as corrected within a predetermined period of time. Conditions that can result in the escalation of an alarm or an alert are preferably defined by the health care facility. Likewise, the time before an alarm or alert escalates can also be defined by the health care facility. Accordingly, predefined alarms or alerts that are not corrected by a clinician within a predefined period of time will result in the escalation of the associated alarms or alerts. Thus, the frequency that the clinician is notified by the system of the escalated alarms or alerts is preferably increased, as can be the volume of the audible tones associated therewith. As will be appreciated by those having skill in the art, the infusion system 210 assists in ensuring patient safety by checking the infusion being administered with the patient's order. As explained in detail further herein, a bar-coding scheme is used wherein the infusion bag and the patient ID are scanned. The infusion information is displayed on both an electronic computing device and the pump to assist in ensuring that the right infusion is being administered to the right patient at the right time, and by the right route and at the right rate. In an embodiment, an alert, audible and visual, appears on the electronic device if the above administration "rights" do not match. Moreover, through a comparison process described in greater detail infra, when the clinician sets the infusion pump rate, an audible and visual alert appears on the electronic computing device if the programmed settings do not match the patient's infusion order. In addition, at any time the clinician can, via the electronic device, check the settings of an infusion pump to confirm if the settings match the infusion order as contained within the central database 108b.

In an embodiment, the infusion system 210 provides alerts and alarms, via one or more of the electronic computing devices or the like, with differing tones or phrases for fast identification of the severity or urgency of the message. Desirably, conventional infusion pump alerts and alarms can be displayed on the electronic computing devices, such as, but not necessarily limited to, a personal digital assistant, to keep the clinicians informed of the status of the infusions for all assigned patients, thereby saving time in resolving problems and improving workflow safety.

All alarms and alerts are preferably retrievable from a central system database for, inter alia, reporting purposes. The retrievable data can assist a healthcare facility in examining and analyzing how many medication errors were avoided through alarms, alerts, and warnings. Desirably, the audible alerts and alarms are configured to sound differently according to the severity or urgency associated with the message or issue. Alarms requiring immediate attention sound different from less emergent alerts. Visual text describing the problem is preferably displayed by one or more of the electronic computing devices. In an embodiment, an alert sounds on a personal digital assistant when an infusion is nearing completion or is completed. The personal digital assistant also displays the patient, location, infusion type, and the time remaining before the infusion bag is empty. At all times the clinician can access, via the personal digital assistant, the status of infusions and thus react accordingly.

In an embodiment, before visiting a patient room, the clinician can view the status of the infusions on the personal digital assistant to determine whether another bag will be needed in the near future. If another infusion bag is needed, the clinician can save time be taking the new bag on the first visit, rather than realizing a new bag is needed after arriving in the patient room. Similarly, the pharmacy can view the status, including time remaining, in order to schedule the mixing and delivery of the next infusion bag.

If desired, and as will be appreciated by those having skill in the art, other alarms and alerts related to the infusion pump can be made available on the electronic computing devices remotely located from the infusion pump. Pertinent information can be displayed on the electronic computing devices, thus saving the nurse time and steps in resolving the problem.

As indicated above, when a pump alarms or alerts, the clinician can view patient information, drug order, and alarm or alert message on the personal digital assistant, and gather necessary items before going to the patient room to physically correct the alarm or alert condition.

In an embodiment, the infusion system 210 provides configurable time-based alerts for reminding clinicians of scheduled infusion orders. As such, a tapering order to run NS at 200 ml/hr for two hours, then reduce to 50 ml/hr, results in the infusion system 210 alerting the nurse two hours after starting the infusion to reduce the rate. Further, late alerts are provided for informing clinicians when scheduled infusions are past the time tolerance set by the facility. Moreover, time-based protocols such as alerts for conducting pain assessments, such as after starting an epidural morphine infusion, are generated.

Configurable aspects of the infusion system 210 also include the audible alerts emitted by the electronic computing devices, such as personal digital assistants. Preferably, the audible alerts can be configurable by the healthcare facility and within specific units of the healthcare facility to satisfy the unique environments within the healthcare facility.

As indicated previously, a plurality of visual alerts and messages can be displayed by the electronic computing devices, such as personal digital assistants, for indicating the importance or urgency of the message. Desirably, color, flashing, and bold text are display messaging options. Additionally, hyperlinks can be provided when messages are generated. Icons on the displays can also be utilized and emergency messages can be configured to interrupt the handheld electronic device, or the like, to immediately alert the clinician. Further, escalation of alarms/alerts is provided by the system 210. Alarms/alerts and the escalation thereof are detailed infra.

As also indicated previously, the infusion system 210 allows a clinician to view all infusions or assigned patients on the electronic computing device, such as a personal digital assistant or the like, thus reducing time spent traveling to and from patient rooms. Moreover, prescription information is displayed on the electronic computing device for verification of the drug amount, diluents, dose, and rate of the infusion. Additionally, real time status of the infusion is viewable for displaying milliliters per hour or the like, duration of the infusion, volume infused, time remaining, and volume yet to be infused. As indicated previously, the status of the infusion and flow rate history can be viewed from anywhere within the healthcare facility via the electronic computing devices.

As described in detail further herein, the infusion system 210 may calculate ordered doses based on patient weight and display the appropriate rate to run the infusion. Messages are generated if the infusion is set to run outside of the ordered dose. Moreover, pediatric dosing is available and configured for pediatric units within the healthcare facility.

In an embodiment, the status of primary infusions and secondary infusions, such as piggybacks, are displayed by the infusion system 210 on the electronic computing device, such as a personal digital assistant. The clinician can check the volume left to infuse in a piggyback at any time and a message is displayed when the piggyback is completed and the primary infusion has resumed. In addition, messages are sent to the pharmacy to replenish stocks and infusion orders.

If desired, the infusion system 210 allows for the healthcare facility to define system infusion limits for warning a clinician who programs an infusion to run outside of the set range. The warning can be configured to allow clinicians to override the warning or prohibit overrides. As will be appreciated by those having ordinary skill in the art, prohibiting overrides for certain infusions may prevent a patient from inadvertently receiving an overdose.

The infusion system 210 can also provide for displaying reference information pertinent to the needs of each specialty unit within the healthcare facility. Drug information is viewable on the electronic device, such as a personal digital assistant, in addition to specialty unit policies and procedures. Protocols and standard orders can be configured to provide messages based on patient condition. In an embodiment, for example, heparin infusion protocols are configured to alert the clinician of a new blood glucose result and to titrate the insulin infusion by a determined number of milliliters based on the sliding scale protocol.

Moreover, through configured rules, messages or notifications are sent to the nurse regarding particular infusions as they relate to the patient's condition. In an embodiment, for example, a message is generated when a patient receiving a nephrotoxic infusion has an increase in BUN and Creatinine. Additionally, protocols can be configured to generate messages when certain infusions are titrated. In an embodiment, for example, a message to document a blood pressure can be configured when a clinician titrates a dopamine infusion. Furthermore, hemodynamic monitoring parameters can be linked to infusions to generate messages.

As indicated previously, new infusion orders can be configured to provide messages alerting the clinician of a new order. Messages can be configured as audible and visual such as textual, color alerts, flashing hyperlinks, icons, and the like. Stat orders and discontinue orders can be configured as a high priority message to differentiate them from non-urgent messages. Preferably, educational messages are generated and configured by the healthcare facility.

In an embodiment, for example, an infusion requiring a specific tubing set (e.g., non-PVC) results in the display of a message informing the clinician. In a further embodiment, for example, an infusion requiring central venous access results in the display of a warning not to infuse in the peripheral vein.

In an embodiment, scheduling messages are generated and displayed on one or more electronic computing devices to remind users to complete the next task. Alerts to change infusion rates at scheduled times are sent to the electronic computing devices, such as in the case of a tapering infusion. Additionally, protocols with time-based alerts can be configured such as, for example, blood infusion protocols.

Turning again to FIG. 1, and as indicated above, patient care system 100 allows medication ordering, dispensing, and administration to take place at the patient's bedside. Physicians can order simple and complex prescriptions, intravenous therapy and total parenteral nutrition therapy (TPN) using a wireless handheld device. Infusion system 210 checks for drug interactions and other possible errors as well as correct dosage. Infusion system 210 then transmits this data in real-time to the patient care facility or local pharmacy, hospital nursing unit, home care unit, and/or clinic.

The clinician can access a medical records database using the handheld device. In an embodiment, the clinician scans the bar-coded medication and the patient's bar-coded bracelet to confirm the presence of the right medication, dosage, and time before administering any drugs. The infusion system 210 updates medical and administrative records, thereby eliminating most, if not all, time-consuming paperwork. Thus, infusion system 210 can reduce costs and improve efficiency while possibly saving lives. Patient care system 100 can include access-controlled mobile and stationary medication and supply depots, including electronic patient medical records and computerized prescribing, providing complete preparation and inventory management from the point of care to the pharmacy.

As mentioned previously. FIG. 1 is a graphical representation of patient care system 100. The patient care system 100 includes a pharmacy computer 104, a central system 108, and a treatment location 106, linked by a network 102. In an embodiment, the pharmacy computer 104 includes a processing unit 104a, a keyboard 104b, a video display 104c, a printer 104d, a bar code reader 104e, and a mouse 104f.

Although not shown in FIG. 1, the patient care system 100 can also include subsystems for hospital administration, nursing stations, a clinical information subsystem, a hospital information subsystem, an Admissions Discharge and Transfer (ADT subsystem, a billing subsystem, and/or other subsystems typically included in conventional patient care systems. Such systems are typically interfaced with the second central server 108a.

In an embodiment, the central system 108 includes a central servicing computer 108a, a database 108b, a video display 108c, input/output components, and other conventional hardware components known to those having ordinary skill in the art. The network 102 preferably includes a cable communication system 110 portion and a wireless communication system portion. The cable communication system 110 can be, but is not limited to, an Ethernet cabling system, and a thin net system.

In an embodiment, the treatment location 106 can include a treatment bed 106a, an infusion pump 120, and medical treatment cart 132. In FIG. 1, a clinician 116 and a patient 112 are shown in the treatment location 106. Medication 124 can be of a type that is administered using an infusion pump 120 or other medical device. Medication 124 can also be of a type that is administered without using a medical device. The medication can be stored in medication storage areas 132a of medical treatment cart 132. The clinician 116 uses a digital assistant 118 in the process of administering medication 124 to the patient 112.

In an embodiment, the clinician 116 uses the digital assistant 118 in the course of treating a patient 112 to communicate with the cable communication system 110 of the network 102 via a first wireless communication path 126. The infusion pump 120 has the ability to communicate with the cable communication system 110 via a second wireless communication path 128. The medication cart 132 also has the ability to communicate via a wireless communication path (not shown in FIG. 1). A wireless access point 114 interfaces with the cable communication system 110. The wireless communication system portion of the network can employ technology such as, but not limited to, known to those having ordinary skill in the art such as IEEE 802.11b "Wireless Ethernet," a local area network, wireless local area networks, a network having a tree topography, a network having a ring topography, wireless internet point of presence systems, an Ethernet, the Internet. radio communications, infrared, fiber optic, and telephone. Though shown in FIG. 1 as a wireless communication system, the communication paths can alternatively be hardwired communication paths.

In the patient care system 100, a physician can order medication 124 for patient 112. In an embodiment, the order can originate with a clinician 116 at the treatment location 106. The physician and/or clinician 116 can use a computerized physician order entry system (CPOE), the medical cart 132, or a like device, to order the medication 124 for the patient 112. Those having ordinary skill in the art are familiar with conventional computerized physician order entry systems. Despite its name, any clinician 116 can use the computerized physician order entry system. If the medication 124 is efficient to administer through infusion pump 120, the infusion order includes information for generating operating parameters for the infusion pump 120. The operating parameters are the information and/or instruction set necessary to program infusion pump 120 to operate in accordance with the infusion order.

The infusion order can be entered in a variety of locations including the pharmacy, the nursing center, the nursing floor, and treatment location 106. When the order is entered in the pharmacy, it can be entered in the pharmacy computer 104 via input/output devices such as the keyboard 104b, the mouse 104f, a touch screen display, the CPOE system and/or the medical treatment cart 132. The processing unit 104a is able to transform a manually entered order into computer-readable data. Devices such as the CPOE can transform an order into computer-readable data prior to introduction to the processing unit 104a. The operating parameters are then printed in a bar code format by the printer 104d on a medication label 124a. The medication label 124a is then affixed to a medication 124 container. Next, the medication 124 container is transported to the treatment location 106. The medication 124 can then be administered to the patient 112 in a variety of ways known in the art including orally and through an infusion pump 120. If the medication 124 is administered orally, the clinician 116 can communicate via the digital assistant 118 and/or the medical cart 132. The medical cart 132 is computerized and generally has a keyboard (not shown), a display 132b, and other input/output devices such as a bar code scanner (not shown).

As will be appreciated by those having ordinary skill in the art, the infusion bag can also be premixed, wherein a non-patient specific bar code is attached to the bag identifying the medication 124. Moreover, the infusion bag can be mixed in the pharmacy or on the floor, wherein a patient specific bar code is attached to the bag that identifies the medication 124 and, if desired, when the medication is to be administered to the patient.

At the treatment location, the medication 124 can be mounted on the infusion pump 120 with an intravenous (IV) line 130 running from the infusion pump 120 to the patient 112. The infusion pump 120 can include a pumping unit 120a, a keypad 120b, a display 120c, an infusion pump ID 120d, and an antenna 120e. Prior art infusion pumps can be provided with a wireless adaptor (not shown) in order to fully implement the system 100. The wireless adaptor can have its own battery if necessary to avoid reducing the battery life of prior art infusion pumps. The wireless adaptor can also use intelligent data management such as, but not limited to, store-and-forward data management and data compression to minimize power consumption and network traffic. The wireless adaptor can also include the ability to communicate with the digital assistant 118 even when the network 102 is not functioning.

In an embodiment, the patient care system 100 can include a variety of identifiers such 10 as, but not limited to, personnel, equipment, and medication identifiers. In FIG. 1, the clinician 116 can have a clinician badge 116a identifier, the patient 112 can have a wristband 112a identifier, the infusion pump 120 can have an infusion pump ID 120d identifier, and the medication 124 can have a medication label 124a identifier. Clinician badge 116a, wristband 112a, infusion pump ID 120d, and medication label 124a include information to identify the personnel, equipment, or medication they are associated with. The identifiers can also have additional information. For example, the medication label 124a can include information regarding the intended recipient of the medication 124, operating parameters for infusion pump 120, and information regarding the lot number and expiration of medication 124. The information included in the identifiers can be printed, but is preferably in a device readable format such as, but not limited to, an optical-readable device format such as a bar code, a radio frequency (RF) device-readable format such as an RFID, an iButton, a smart card, and a laser-readable format. The digital assistant 118 can include a display 118a and have the ability to read the identifiers, including biometric information such as a fingerprint.

The wristband 112a is typically placed on the patient 112 as the patient 112 enters a medical care facility. The wristband 112a includes a patient identifier. The patient identifier can include printed information to identify the patient and additional information such as a treating physician's name (s). The patient identifier for patient 112 can include information such as, but not limited to, the patient's name, age, social security number, the patient's blood type, address, allergies, a hospital ID number, and the name of a patient's relative.

In an embodiment, the patient identifier can contain a unique reference code or password for the patient, which is also stored in the central database for cross referencing, if needed or desired.

System Hardware/Software Architecture of the System

FIG. 2 is a block diagram of a computer 200 representative of the pharmacy computer 104, the central system 108, the CPOE, the digital assistant 118 of FIG. 1, and/or a computer included in any number of other subsystems that communicate via the network 102 such as the medication treatment cart 132. As indicated previously, the computer 200 includes an infusion system 210, or a portion of infusion system 210, for use within the patient care system 100. The infusion system as described in reference to FIG. 2 is preferably a computer program. However, the infusion system can be practiced in whole or in part as a method and system other than as a computer program.

A critical concern in the art is that the right medication is administered to the right patient. Therefore, infusion system 210 includes features to assist in assuring that the right medication is administered to the right patient in an efficient manner. Infusion system 210 can be implemented in software, firmware, hardware, or a combination thereof. In one mode, infusion system 210 is implemented in software, as an executable program, and is executed by one or more special or general purpose digital computer(s), such as a personal computer (PC; IBM-compatible, Apple-compatible, or otherwise), personal digital assistant, workstation, minicomputer, or mainframe computer. An example of a general-purpose computer that can implement the infusion system 210 is shown in FIG. 2. The infusion system 210 can reside in, or have various portions residing in, any computer such as, but not limited to, pharmacy computer 104, central system 108, medication treatment cart 132, and digital assistant 118.

Therefore, the computer 200 of FIG. 2 is representative of any computer in which the infusion system 210 resides or partially resides. Generally, in terms of hardware architecture, as shown in FIG. 2, the computer 200 includes a processor 202, memory 204, and one or more input and/or output (I/O) devices 206 (or peripherals) that are communicatively coupled via a local interface 208. The local interface 208 can be, for example, but not limited to, one or more buses or other wired or wireless connections, as is known in the art. The local interface 208 can have additional elements, which are omitted for simplicity, such as controllers, buffers (caches), drivers, repeaters, and receivers, to enable communications. Further, the local interface can include address, control, and/or data connections to enable appropriate communications among the other computer components.

Processor 202 is a hardware device for executing software, particularly software stored in memory 204. Processor 202 can be any custom made or commercially available processor, a central processing unit (CPU), an auxiliary processor among several processors associated with the computer 200, a semiconductor-based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc., or a 68xxx series microprocessor from Motorola Corporation.

Processor 202 can also represent a distributed processing architecture such as, but not limited to, SQL, Smalltalk, APL, KLisp, Snobol, Developer 200, MUMPS/Magic. Memory 204 can include any one or a combination of volatile memory elements (e.g., random access memory (RAM, such as DRAM, SRAM, SDRAM, etc.)) and non-volatile memory elements (e.g., ROM, hard drive, tape, CDROM, etc.). Moreover, memory 204 can incorporate electronic, magnetic, optical, and/or other types of storage media. Memory 204 can have a distributed architecture where various components are situated remote from one another, but are still accessed by processor 202.

The software in memory 204 can include one or more separate programs. The separate programs comprise ordered listings of executable instructions for implementing logical functions. In FIG. 2, the software in memory 204 includes the infusion system 210 in accordance with the present embodiment and a suitable operating system (O/S) 212. A non-exhaustive list of examples of suitable commercially available operating systems 212 is as follows: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run time Vxworks operating system from WindRiver Systems, Inc.; or (g) an appliance-based operating system, such as that implemented in handheld computers or personal digital assistants (PDAs) (e.g., PalmOS available from Palm Computing, Inc., and Windows CE available from Microsoft Corporation). Operating system 212 essentially controls the execution of other computer programs, such as infusion system 210, and provides scheduling, input/output control, file and data management, memory management, and communication control and related services.

Infusion system 210 can be a source program, executable program (object code), script, or any other entity comprising a set of instructions to be performed. When a source program, the program is translated via a compiler, assembler, interpreter, or the like, that may or may not be included within the memory 204, so as to operate properly in connection with the O/S 212.

Furthermore, the infusion system 210 can be written as (a) an object-oriented programming language, which has classes of data and methods, or (b) a procedural programming language, which has routines, subroutines, and/or functions, for example, but not limited to, C, C++, Pascal, Basic, Fortran, Cobol, Perl, Java, and Ada. In one embodiment, the system program 210 is written in C++.

In other embodiments, the infusion system 210 is created using Power Builder. The I/O devices 206 can include input devices, for example, but not limited to, a keyboard, mouse, scanner, microphone, touch screens, interfaces for various medical devices, bar code readers, stylus, laser readers, radio-frequency device readers, etc. Furthermore, the I/O devices 206 can also include output devices, for example, but not limited to, a printer, bar code printers, displays, etc. The I/O devices 206 can further include devices that communicate as both inputs and outputs, for instance, but not limited to, a modulator/demodulator (modem; for accessing another device, system, or network), a radio frequency (RF) or other transceiver, a telephonic interface, a bridge, a router, etc. If the computer 200 is a PC, workstation, personal digital assistant, or the like, the software in the memory 204 can further include a basic input output system (BIOS) (not shown in FIG. 2). The BIOS is a set of essential software routines that initialize and test hardware at startup, start the O/S 212, and support the transfer of data among the hardware devices. The BIOS is stored in ROM so that the BIOS can be executed when the computer 200 is activated.

When the computer 200 is in operation, processor 202 is configured to execute software stored within memory 204, to communicate data to and from memory 204, and to generally control operations of the computer 200 pursuant to the software. The infusion system 210 and the O/S 212, in whole or in part, but typically the latter, are read by processor 202, perhaps buffered within the processor 202, and then executed.

When the infusion system 210 is implemented in software, as is shown in FIG. 2, the infusion system 210 program can be stored on any computer-readable medium for use by or in connection with any computer-related system or method. As used herein, a computer-readable medium is an electronic, magnetic, optical, or other physical device or means that can contain or store a computer program for use by or in connection with a computer related system or method. The infusion system 210 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer-readable medium can be, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured via, for instance, optical scanning of the paper or other medium, then compiled, interpreted or otherwise processed in a suitable manner if necessary, and then stored in a computer memory.

In another embodiment, where the infusion system 210 is implemented in hardware, the infusion system 210 can be implemented with any, or a combination of, the following technologies, that are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Any process descriptions or blocks in figures, such as FIGS. 3-11, are to be understood as representing modules, segments, or portions of hardware, software, or the like, that can include one or more executable instructions for implementing specific logical functions or steps in the process, and alternate implementations are included within the scope of the embodiments in which functions can be executed out of order from that shown or discussed, including substantially concurrently or in reverse order, depending on the functionality involved, as would be understood by those having ordinary skill in the art.

Patient Care System Components

Figure 4:
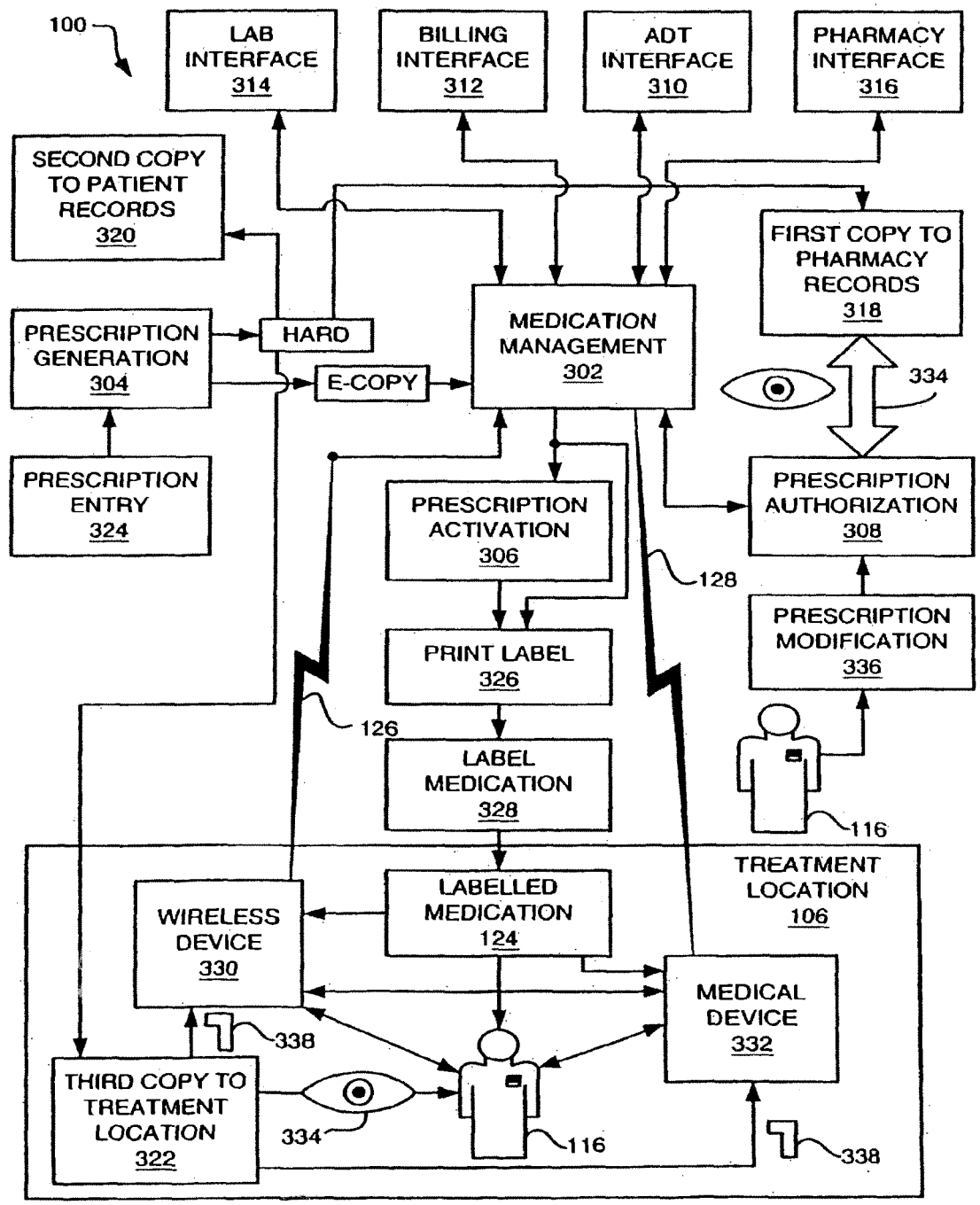
FIG. 4 is a block diagram showing functional components of the patient care system of FIG. 1.

FIG. 4 is a first block diagram showing functional components of the patient care system 100 of FIG. 1. As shown in FIG. 4, the patient care system 100 can be practiced as a modular system where the modules represent various functions of the patient care system, including the infusion system 210 (FIG. 2). The flexibility of the patient care system 100 and the infusion system can be enhanced when the systems are practiced as modular systems. The modules of the infusion system 210 (FIG. 2) can be included in various portions of the patient care system 100. In an embodiment, the patient care system functional components can include, inter alia, a medication management module 302, a prescription generation module 304, a prescription activation module 306, and a prescription authorization module 308.

The medication management module 302 can coordinate the functions of the other modules in the patient care system 100 that are involved in the administration of medical treatment. The medication management module 302 generally coordinates with other portions of the patient care system 100. The medication management module 302 can include sub-modules for operating and/or interfacing with a CPOE, for operating and/or communicating with point-of-care modules, and for operating and/or communicating with medical treatment comparison modules. In FIG. 4, an admissions, discharge, and transfer (ADT) interface 310, a billing interface 312, a lab interface 314, and a pharmacy interface 316 are shown. The ADT interface 310 is used to capture information such as the patient's demographics, size, weight, and allergies. In a preferred embodiment, the ADT system utilizes an HL7 type of interface to transfer events that are entered into the hospital's ADT system into the second central server 108a. HL7 is a protocol for formatting, transmitting and receiving data in a healthcare environment. It provides interoperability between healthcare information systems through a messaging standard that enables disparate healthcare applications, such as a variety of different third-party applications, to exchange key sets of clinical and administrative data. Typically, in the present system 100, the HL7 ADT interface consists of three applications: the HL7 ADT server, the HL7 ADT client, and the HL7 ADT viewer. The pharmacy interface 316 imports orders from the pharmacy. The pharmacy interface 316 can be an HL7-type of interface that interfaces with other systems for entering orders, such as a CPOE. This ability reduces the necessity for entering data into the patient care system 100 more than once. The pharmacy interface 316 can be configured to communicate with commercially available third-party systems such as, but not limited to Cerner, HBOC, Pyxis, Meditech, SMS, Phamous, and the like. A web services interface can provide near real-time coordination between Point of Care medication management systems supporting oral medication dosing such as McKesson AdminRx, Pyxis Verify, etc. and infusion pump related medication management. Various other interfaces are also known to those having ordinary skill in the art, but are not shown in FIG. 4.

The medication management module 302 can have additional features such as the ability to check for adverse reactions due to drug-to-drug incompatibility, duplicate drug administration, drug allergies, drug dosage limitations, drug frequency limitations, drug duration limitations, and drug disease contraindications. Food and alcohol interactions can also be noted. Drug limitations can include limitations such as, but not limited to, limitations associated with adults, children, infants, newborns, premature births, geriatric adults, age groupings, weight groupings, height groupings, and body surface area. In an embodiment, the medication management module 302 prevents the entry of the same prescription for the same patient from two different sources within the patient care system 100.

The medication management module 302 can also include the ability to generate reports. The reports include, but are not limited to, end-of-shift, titration information, patient event lists, infusion history, pump performance history, pump location history, and pump maintenance history. The end-of shift report can include the pump channel, start time, end time, primary infusion, piggyback infusion, medication, dose, rate, pump status, volume infused, volume remaining, time remaining, and the last time cleared. The infusion history report includes medications and volume infused.

The medication management module 302 can also include a medical equipment status database. The medical equipment status database includes data indicating the location of a medical device 332 within the patient care system 100. The medical equipment status database can also include data indicating the past performance of a medical device 332. The medical equipment status database can also include data indicating the maintenance schedule and/or history of a medical device 332.

Infusion prescriptions or orders are entered in prescription entry 324. Such orders can include prescriptions such as, but not limited to, single dose infusions, intermittent infusions, continuous infusions, sequencing, titrating, and alternating types. Infusion prescriptions can also include total parenteral nutritional admixtures (TPN), chemotherapy continuous infusion, piggybacks, large volume parenterals, and other infusion prescriptions. The patient care system 100 can function without end dates for orders. The patient care system 100 uses a continuous schedule generator that looks ahead a predefined time period and generates a schedule for admixture filling for the time period. The predefined time period can be defined at the patient care system 100 level or at subsystem levels such as the clinical discipline level and an organizational level. The predefined time periods can be adjustable by the clinician 116 entering the order. The schedule can be automatically extendable as long as the order is active in the patient care system 100.

The prescription generation module 304 generates hard prescriptions and electronic (E-copy) prescriptions. Hard prescriptions are generally produced in triplicate in medical facilities. A first hard copy 318 is generally sent to the pharmacy, a second hard copy 320 is generally kept for the patient's records, and a third hard copy 322 is sent to treatment location 106. An electronic prescription is sent to the medication management module 302. Prescription generation module 304 can include confirming operating parameters. The operating parameters can be based on information from prescription entry module 324.

Prescription generation 304 can occur anywhere in the patient care system 100 such as, but not limited to, the pharmacy, the treatment location 106, and a nursing center. A computerized physician order entry (CPOE) system or the like can be employed to carry out some or all of the functions of the prescription generation module 304. Clinicians 116 can enter data in a variety of manners such as, but not limited to, using a tablet wireless computer, personal digital assistant, treatment cart 132, and a workstation. The medication management module 302 can interface with more than one prescription generation module 304. The medication management module can receive orders from anywhere within the patient care system 100.

The pharmacy computer 104 is able to access the electronic copy from the medication management module 302. The prescription activation module 306 is a computer-assisted system for coordinating the filling and labeling of prescriptions. The filling of the prescription and the creation or location of medication 124 from stock is handled by the prescription activation module 306. In an embodiment, the filling process results in the creation of the medication label 124a, as opposed to the prescription activation process.

The patient care system 100 can bypass the prescription activation module 306. This can occur if the ordering clinician 116, such as the patient's physician, has the authority to immediately activate an order. If the order is immediately activated, the medication management module 302 can go directly to filling and, thus, the prescription labeling module 326.

In block 326, the patient care system 100 prints the medication label 124a. The prescription can be printed remotely and will often be printed by the pharmacy printer 104d. After block 326, the patient care system goes to block 328. In block 328, the medication label 124a is attached to the medication 124. The pharmacist generally provides a visual verification 334 that the medication label 124a matches the first hard copy 318 of the prescription. FIG. 4 shows that a visual verification 334 is also associated with prescription authorization module 308. The medication 124 can then be transported from the pharmacy to the treatment location 106. A portable medical treatment cart 132 can be used for a portion of the route from the pharmacy to the treatment location 106.

The medication label 124a can include information for preparing the infusion bag. If not generated within patient care system 100, medication label 124a can be provided by a bulk medication supplier. If provided by a bulk medication supplier, the patient care system 100 gathers the information from the medication label 124a. In addition, the patient care system 100 can add information, such as a patient identifier, to the medication label 124a.

The medication labeling module 328 places the medication label 124a on the medication 124. This can be accomplished manually. This can also be accomplished using an automatic prescription filling and packaging system (not shown). If an automatic filling and packaging system is used, medication labeling module 328 provides data for coordination of the labeling of the medication 124 to the filling and packaging system.

At the treatment location 106, the clinician 116 uses a wireless device 330, such as digital assistant 118 and/or medical treatment cart 132, to verify and administer medication 124 to the patient 112. Wireless device 330 communicates with the medication management module 302 via a communication path, such as first communication path 126.

Clinician 116 identifies him/herself by scanning badge 116a, identifies the patient 112 by scanning wristband 112a, identifies the medication 124 by scanning medication label 124a, and identifies the medical device 332, such as infusion pump 120, by scanning label 120d.

Clinician 116 can also identify him/herself by providing a fingerprint and/or password as described above and shown in the login screen 503 of FIG. 19. The medical device 332 can be a medical device capable of two-way communication with the medication management module 302. Alternatively, the medical device 332 can only be capable of providing information to the medication management module 302. The infusion system 210 assists the clinician 116 in administering and verifying the medical treatment. In an alternate embodiment, the infusion system 210 can include downloading of operating parameters to the medical device 332. Clinician 116 can provide a visual verification to confirm the third copy 322 and/or the MAR matches the labeled medication 124. Scanner 338 can be used to enter machine readable information from the third copy 322 to the wireless device 330 and the medical device 332.

The patient care system 100 can make adjustments and modifications to infusion orders. Among other modules that can include the ability to make infusion adjustments are prescription entry 324, prescription activation 306, prescription authorization 308, and prescription modification module 336. Clinician 116 accesses the prescription modification module 336 in order to make adjustments to an order. The clinician 116 can access the prescription modification module 336 throughout the patient care system 100. However, one very useful location for clinician 116 to access the prescription modification module 336 is at treatment location 106.

In prescription authorization module 308, the patient care system 100 determines whether the clinician 116 has the authority to independently modify an infusion order. The clinician 116 can be recognized by the patient care system 100 as having the authority to independently modify certain portions of the order. If the clinician 116 does not have the authority to independently modify the order, a pharmacist or physician can be requested to approve the modification entered by the clinician 116.

In one implementation of patient care system 100, an order is entered in pharmacy computer 104. The order includes a first patient identifier and an operating parameter. The pharmacy computer 104 generates a medication label 124a that is affixed to the medication bag or container. The medication 124 is sent to a treatment location 106. At treatment location 106, clinician 116 reads the clinician's badge 116a, patient's wristband 112a, and medication label 124a with a digital assistant 118. The digital assistant 118 reports, based on a determination made by the central system 108, whether medication label 124a and wristband 112a correspond to the same patient 112. The system 100 then sends the medication identifier to the pharmacy computer 104. The pharmacy computer 104 confirms the medication label 124a, identifies the same patient as the order, and sends the operating parameter to an infusion pump. The operating parameter can be sent directly to the infusion pump 120. The operating parameter is then used to program the infusion pump to administer the medication 124 to the patient 112.

Figure 5:
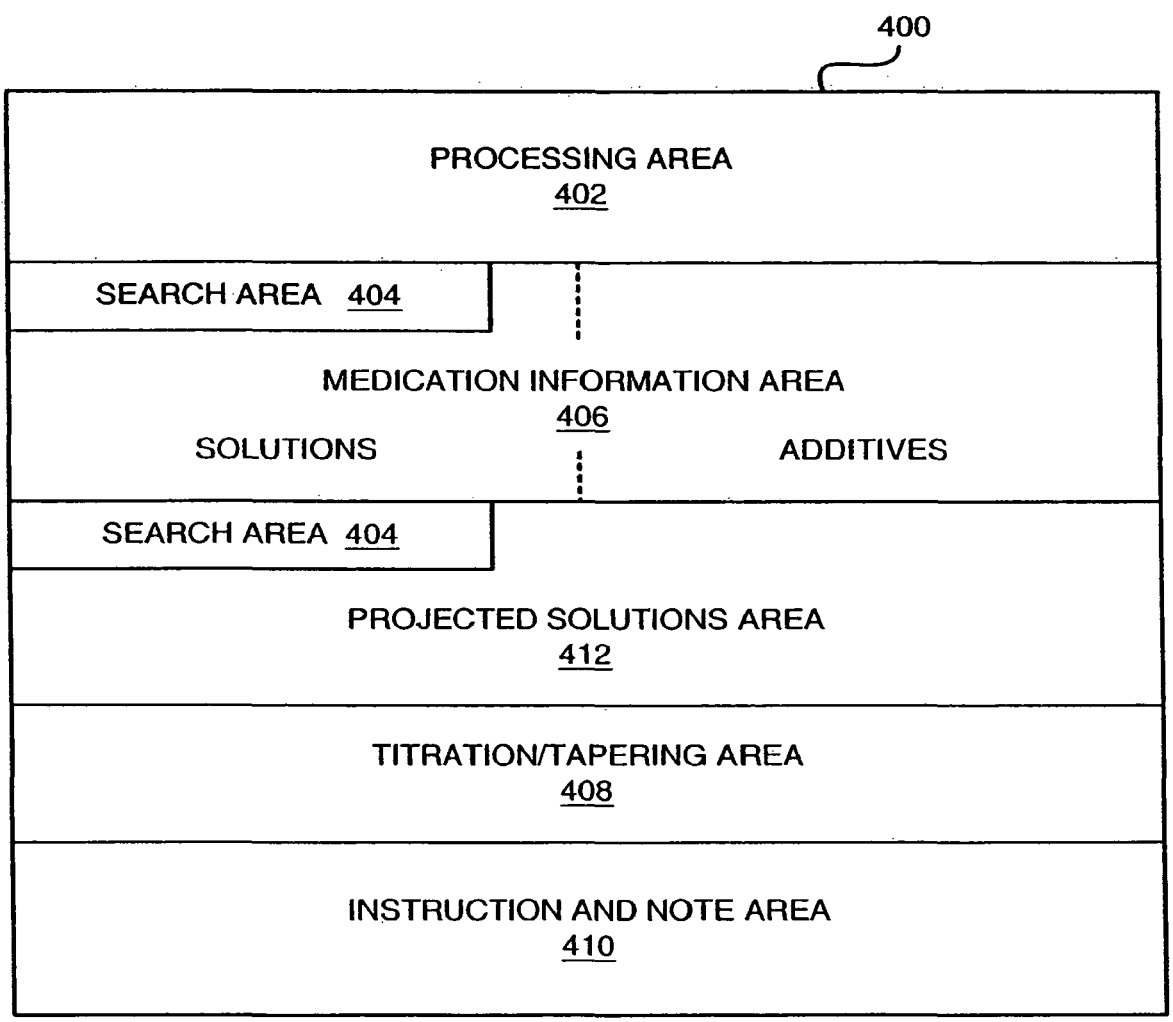
FIG. 5 is an exemplar computer screen for implementing various functions of the patient care system of FIG. 1.

FIG. 5 is an exemplar block diagram of a computer screen 400 that is useful in implementing various functions of the infusion system 210 (FIG. 2). In addition to other functions, the computer screen 400 can be used to enter new infusion orders, to modify existing infusion orders, and to stop infusion orders. Computer screen 400 preferably includes a processing area 402, search areas 404, a medication information area 406, a titration/tapering criteria area 408, an instruction and note area 410, and a projected solution ingredient area 412.

Infusion medication order types include single dose, intermittent, continuous, sequencing, and alternating. Computer screen 400 can be used with digital assistant 118, pharmacy computer 104, infusion pump 120, a CPOE system, and medical treatment cart 132. Computer screen 400 is generally designed to have the look-and-feel of clinician accessible computer screens throughout the patient care system 100 of FIG. 1. The functions of computer screen 400 are partially accomplished with database linkage techniques familiar to those having ordinary skill in the art such as, but not limited to, hyperlinks, definition boxes, and dropdown menus.

The processing area 402 includes the ability to trigger the creation of an infusion order, a save of an infusion order, the modification of an infusion order, and a cancellation of an infusion order. Clinician 116 can customize the computer screen 400 to provide the clinician's 116 preferred order entry procedures. The processing area 402 includes a status indicator for orders. The processing area 402 also includes an area for indicating whether a PRN order ("as required" or "when needed" order) can be placed by clinician 116. The processing area 402 further includes the ability to display and adjust medical device 332 operating parameters, infusion order route, infusion line, infusion administration site, infusion order start time, infusion medication order type, infusion flow rate tolerance, infusion flow rate, infusion duration and area of preparation (such as pharmacy or a remote site). The processing area 402 can also include an area for linking medical orders to other medical orders, or associated clinical monitoring, such as, linking a physician's infusion order to another medical order entered by another clinician 116. The processing area 402 can include a trigger for displaying data in other areas of the computer screen 400 such as, but not limited to, the projected solutions area 412.

Search areas 404 allow for searching for medications, solutions and/or additives for infusion orders. Default diluents can be provided for orders. If a default dosage for a medication is defined in the patient care system 100, the default dosage automatically appears with the search result that includes the medication. A search from search area 404 can result in the display of the medication name, the route of administration, the cost, the package size, the dosage form, the generic name, whether the medication is a narcotic, whether the medication is controlled, whether formulary, and whether the medication is manufactured.

Medication information area 406 can be used to define infusion order additives and solutions. Medication information area 406 can include separate additive areas and solution areas. The solution area can include a label, "Solution/Diluents." The patient care system 100 may use a medication 124 database, a solutions database, and an additive database to populate the medication information area 406 with medications 124, solutions, and additives. Substances identified in one database may also be identified in other databases. The databases may be linked to provide default values for combinations of the medications 124 and solutions.

Titration/tapering criteria area 408 generally applies to continuous infusion orders. Titration defines certain parameters of an order such as dosage and/or flow rate. Dose and flow rate can be entered as an absolute. Also, mathematical symbols such as, but not limited to, greater than ">," less than "<," and equal "=," can be used alone or in combination to enter information in titration/tapering criteria area 408. A calendar can also be used to enter data in titration/tapering criteria area 408. Dosage and flow rate can also be entered as an acceptable range. Titration/tapering criteria area 408 can be hidden when non-continuous infusion orders are entered and/or modified. The titration criteria can include values of various parameters related to patient condition such as, but not limited to, various lab results, vital signs, ability to take fluids orally, fluid input and output, and the like.

Instruction and note area 410 includes the ability to save information such as physician notes regarding a patient 112 and/or an infusion order. The instruction and note area 410 can include a display and lookup area for identifying clinicians 116 that are responsible for the patient 112, such as the patient's physician.

The projected solutions area 412 displays solution schedules and related ingredients based on the current state of the order being processed for patient 112. The time periods projected can be a patient care system 100 default. The time period can also be adjustable by the clinician 116. The projected solutions area 412 can include an adjustable display indicating the time period projected by the patient care system 100. The data displayed in the projected solutions area 412 is generally saved when an order save is triggered in the processing area 402.

The projected solutions area 412 can include the ability to look back over a period of time while modifying a previously entered order. This allows the clinician 116 to view solutions that may have already been prepared according to the unmodified infusion order.

Infusion System Components

Figure 6:
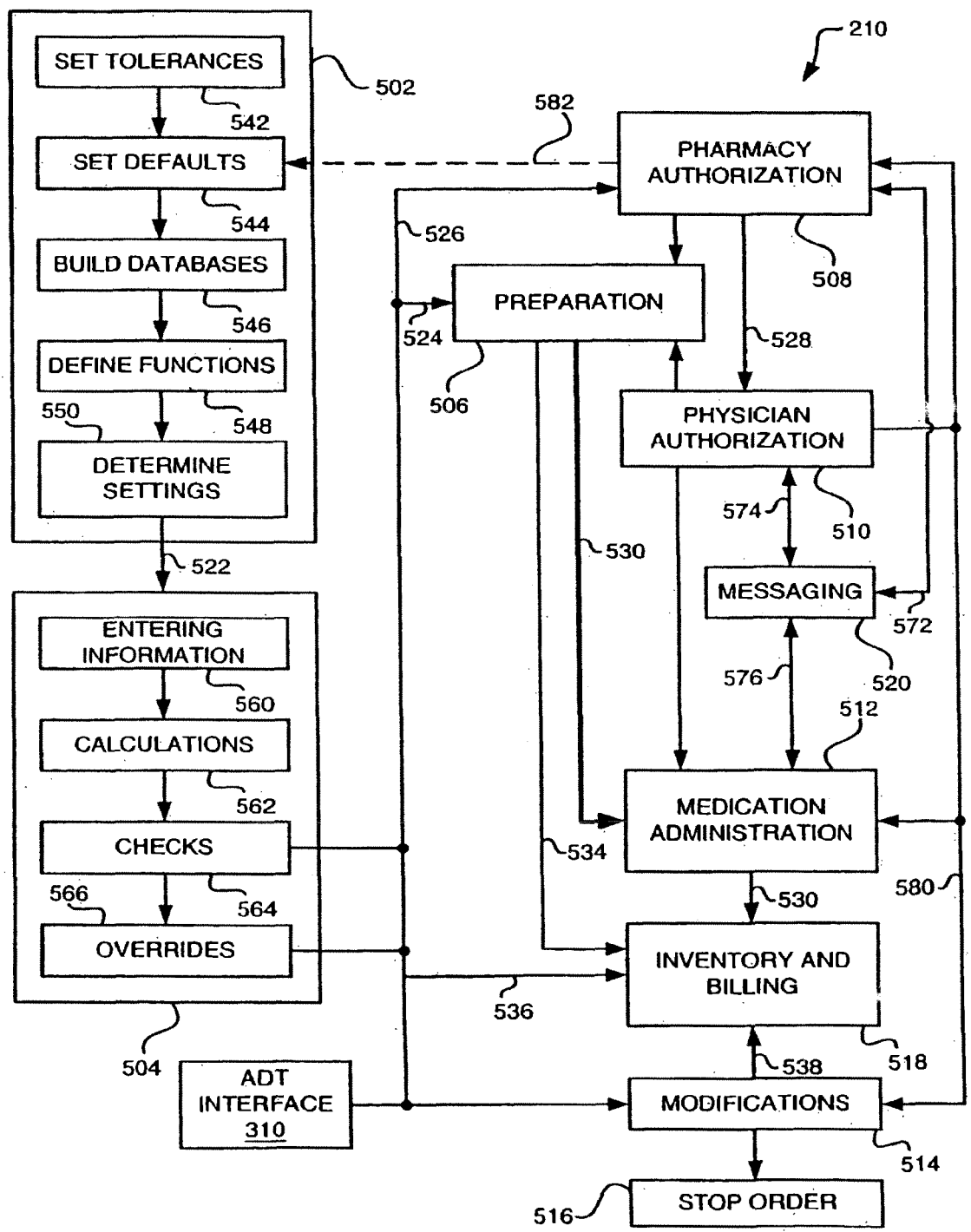
FIG. 6 is a block diagram showing functional components of the infusion system of FIG. 2. The functional components include, inter alia, blocks for setting infusion system parameters, infusion order creation, infusion order preparation, medication administration, infusion order modifications, and messaging.

FIG. 6 is a block diagram showing functional components of the infusion system 210 of FIG. 2. The functional components include blocks for setting system parameters 502, infusion order creation 504, infusion order preparation 506, medication administration 512, infusion order modifications 514, and messaging 520. FIG. 6 also includes blocks for pharmacy authorization 508, physician authorization 510, stop orders 516, and inventory and billing 518. FIG. 6 presents one description of the infusion system. However, FIG. 6 does not define a required series of processes for implementing the infusion system. One of the benefits of the infusion system is that a clinician 116 can access and enter information from a large number of locations, both physical and functional, within the patient care system 100. For example, an infusion order can be created by a physician using a CPOE, by a pharmacist using pharmacy computer 106, by a clinician 116 using digital assistant 118, and by a clinician using medication treatment cart 132. Moreover, vitals, lab results, and other records of patients can be checked from a large number of locations within the health care facility including, for instance, the inpatient pharmacy. Accordingly, a user within the inpatient pharmacy 104 (FIG. 1) can view, from a computing device 104*c*, the wards within the health care facility.

Upon selection of a ward by the user, a patient list is provided wherein the user can select a patient and associated records for display on the computing device. Alternatively, the user can enter all or part of the patient's name into the computing device, whereby the records associated with the patient are provided by the computing device for selection by the user. Upon selection, the record(s) is displayed.

In an embodiment, FIG. 6 can be viewed as first preparing the patient care system 100 for receiving infusion orders— setting system parameters 502; second, creating the infusion order—infusion order creation 504; third, preparing the infusion order—preparation 506; fourth, authorizing the infusion order—pharmacy and physician authorization 508 and 510; fifth, administering the infusion order—medication administration 512; sixth, accounting for and replenishing the inventory used to prepare the infusion order and billing the patient for the infusion order—inventory and billing 518; seventh, modifying the infusion order—modifications 514; and eighth, providing messages to various personnel and sub-systems regarding the progress of the infusion order, infusion, messages for assisting in ensuring that the right medication is efficiently prepared and provided to the right patient, in the right dose and at the right time, or the like—messages 520. Modifications 514 can include stopping the order—stop order 516—based on information provided by the transfer interface 310.

Setting system parameters 502 includes functional blocks that prepare the infusion system 210 to create and process infusion orders. Setting system parameters 502 includes, but is not limited to, setting tolerances 542, setting defaults 544, building databases 546, defining functions 548, and determining system settings 550. Setting system parameters 502 is further described below in reference to FIG. 7.

Figure 8:
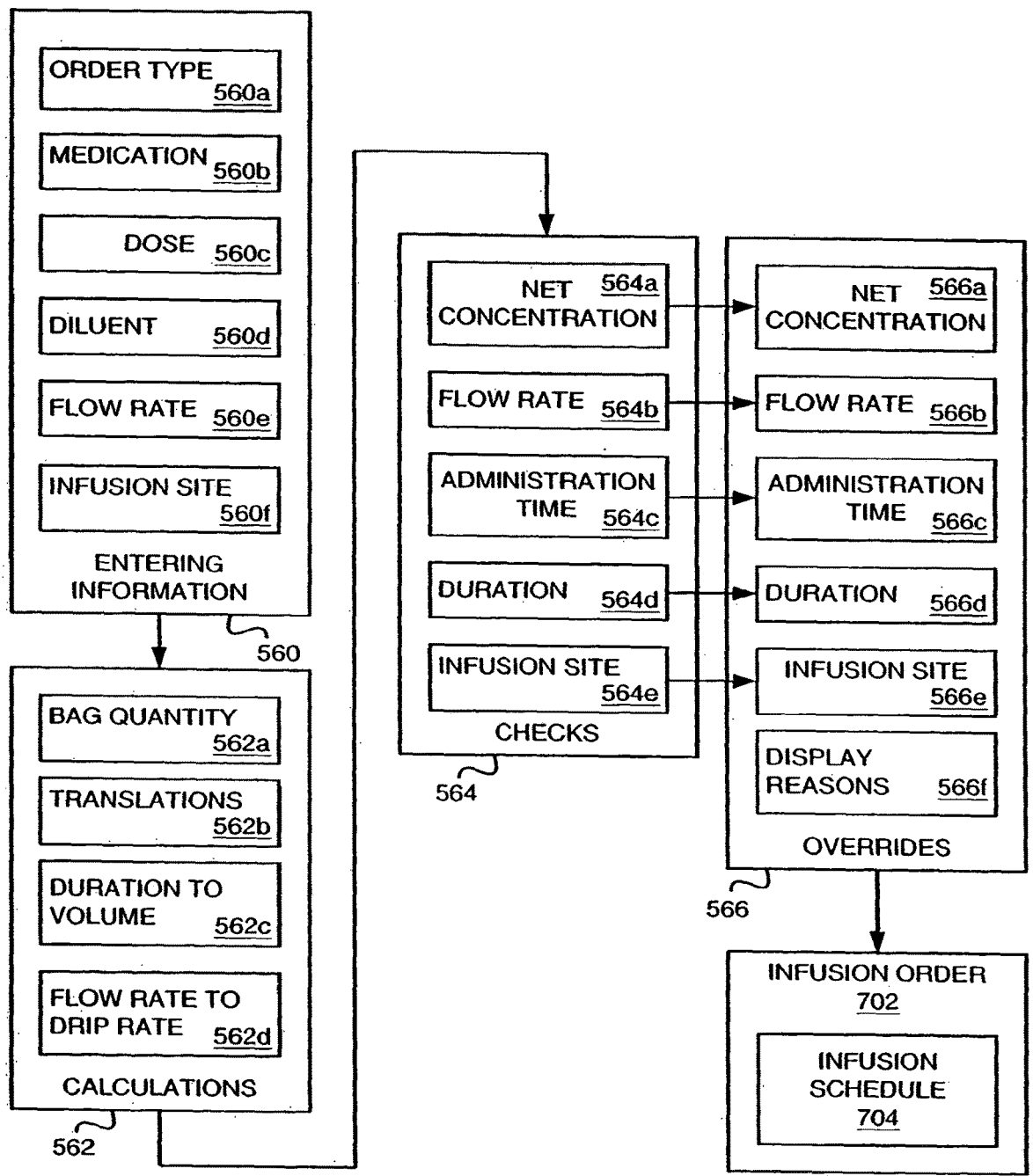
FIG. 8 is a block diagram showing functional components for the infusion order creation of FIG. 6.

Infusion order creation 504 includes functional blocks used to create infusion orders. Infusion order creation 504 includes functions similar to those described in reference to prescription generation 304 (FIG. 4). Infusion order creation 504 includes, but is not limited to, entering information 560, calculations 562, checks 564, and overrides 566. Infusion order creation is further described below in reference to FIG. 8. The result of infusion order creation is an infusion order 702 (FIG. 8). Infusion order 702 generally includes an infusion schedule 704 (FIG. 8).

Infusion orders can require authorization as described in reference to block 308 (FIG. 4). In FIG. 6, prescription authorization by the pharmacist and prescription authorization by the physician are considered separately in functional blocks for pharmacy authorization 508 and physician authorization 510. Physician authorization 510 may not be required if the infusion order is initiated by the physician. The infusion order generally requires pharmacy authorization 508 and physician authorization 510 if the order is generated by a clinician at the treatment location 106, other than the pharmacist or physician. However, if medication 124 is required immediately, the infusion system 210 allows administering clinicians to bypass prescription authorization 508 and physician authorization 510. In the case of emergency orders or non-emergency orders for routine medications, the infusion system 210 can determine there is no information stored in the patient care system 100 related to the medical treatment the clinician 116 desires to administer to the patient 112. If the infusion system 100 recognizes the clinician 116 as having the authority to initiate the desired medical treatment, the system 210 allows for the administration of the medical treatment without going to blocks 508 and 510. This authorization is then obtained following administration.

Infusion order preparation 506 can be accomplished in a number of locations throughout the medical facility such as, but not limited to, the pharmacy, the nursing center, on the floor, and the treatment location 106. Preparation 506 includes providing instructions for preparing the medication 124 and minimizing the possibility of errors in medication preparation.

Medication administration 512 takes place at the treatment location 106. The infusion system 210 is designed to make the administration of the order as efficient and accurate as possible. The infusion system 210 provides the administrating clinician with the tools to administer the right medication to the right patient in the right dose, with the right pump settings, at the right time, and via the right route. Should an alert, alarm, reminder, or other message be appropriate in assisting the clinician with the administration of the medication, the medication administration module provides a status information output to the messaging module 520. In response to the status information output, the messaging module 520 forwards a related text message, audible indicator enable, or both, to one or more electronic computing devices.

As known by those having skill in the art, infusion orders are frequently modified. Infusion system 210 provides modifications 514 to account for infusion order modifications. Modification 514 includes modifications to infusion duration, flow rate, infusion site, and stop orders 516. Modification 514 also includes the functional blocks required to implement infusion order modifications.

The infusion system 210 can include patient care system wide 100 defined stop orders 516. Changes in patient status may generate messages 520 for appropriate action. The infusion system 210 coordinates with the transfer interface 310 to automatically stop orders 516 upon discharge or death.

The system 100 includes inventory and billing module 518. Inventory and billing 518 allows the financial transactions associated with patient care to proceed with a minimum of human intervention. The completion of medication administration 512 can trigger patient billing through the billing interface 312. The billing interface can include an HL7 interface. If patients are to be charged based on completion of infusion order preparation 506, the inventory and billing system 210 includes a crediting process. The crediting process can be triggered when infusion bags are returned to the pharmacy for disposal or re-entry into the pharmacy inventory management system.

The infusion system 210 includes a messages module 520 for communicating with entities throughout the patient care system 100. In particular, the messages module 520 sends text messages, audible indication enables, or both, to one or more electronic computing devices within the patient care system 100. The messages are sent in response to a status information output provided by the medication administration module or other infusion system modules within the patient care system 100. The messages relate to the status information output and, as such, provide alerts, alarms, reminders, or other messages appropriate in assisting the clinician with medication administration.

For example, when a physician enters a new order, messaging appears in the pharmacy to alert the pharmacists that an infusion order requires authorization. Likewise, when infusion orders are appropriately authorized, the clinician 116 receives messaging on digital assistant 118 to alert the clinician 116 that the infusion order should be administered according to the infusion schedule 704. Overrides 566 may generate messages 520 for the physician and/or the pharmacy. The infusion system 100 can distinguish between system-wide and sub-system overrides in determining whether it is necessary to generate a message 520. Messaging 520 includes messages received and/or sent to the central system, the pharmacy, the physician, billing, and inventory. The system can present clinicians 116 with personal computer display views. The personal computer display provides a view summarizing outstanding clinical problems for the clinician's patients. The clinician 116 can quickly retrieve detailed information for the patients.

The system 100 can also produce an email or page to digital assistant 118, or other communication device, when certain critical patient conditions prevail.

FIG. 6 also depicts some of the communication paths that occur in patient care system 100. The highlighted communication paths are presented for ease in describing the infusion system 210. Those having ordinary skill in the art recognize that, when patient care system 100 is practiced on a network, the various functional blocks can communicate with each other via the paths highlighted in FIG. 6 and via alternate paths that are not shown in FIG. 6. Setting system parameters 502 includes communicating data related to the system parameters to infusion order creation 504, via path 522, and/or receiving data from infusion order creation 504 and providing data informing infusion order creation 504 of how the received data relates to the system parameters.

Infusion orders can be passed directly, via path 524, to infusion preparation 506. Infusion orders can also be passed to pharmacy authorization 508, via path 526 and/or to physician authorization, via path 528, before being sent to preparation 506. Path 530 highlights the delivery of the medication 124 from the preparation area to the treatment location 106.

Delivery can be accomplished using medication treatment cart 132. Paths 532, 534, 536, and 538 highlight that inventory and billing 518 transactions can be tied to a variety of other functions such as, but not limited to, infusion order creation 504, preparation 506, medication administration 512, and modifications 514. Paths 572, 574, and 576 highlight that a larger number of functions and actors involved in patient care system 100 can generate and receive information via messages 520. Path 582 highlights that system defaults 544 can be created and/or modified by the pharmacist. And, path 580 highlights that information, such as infusion orders, is available to a variety of functional units throughout the system 100.

Figure 7:
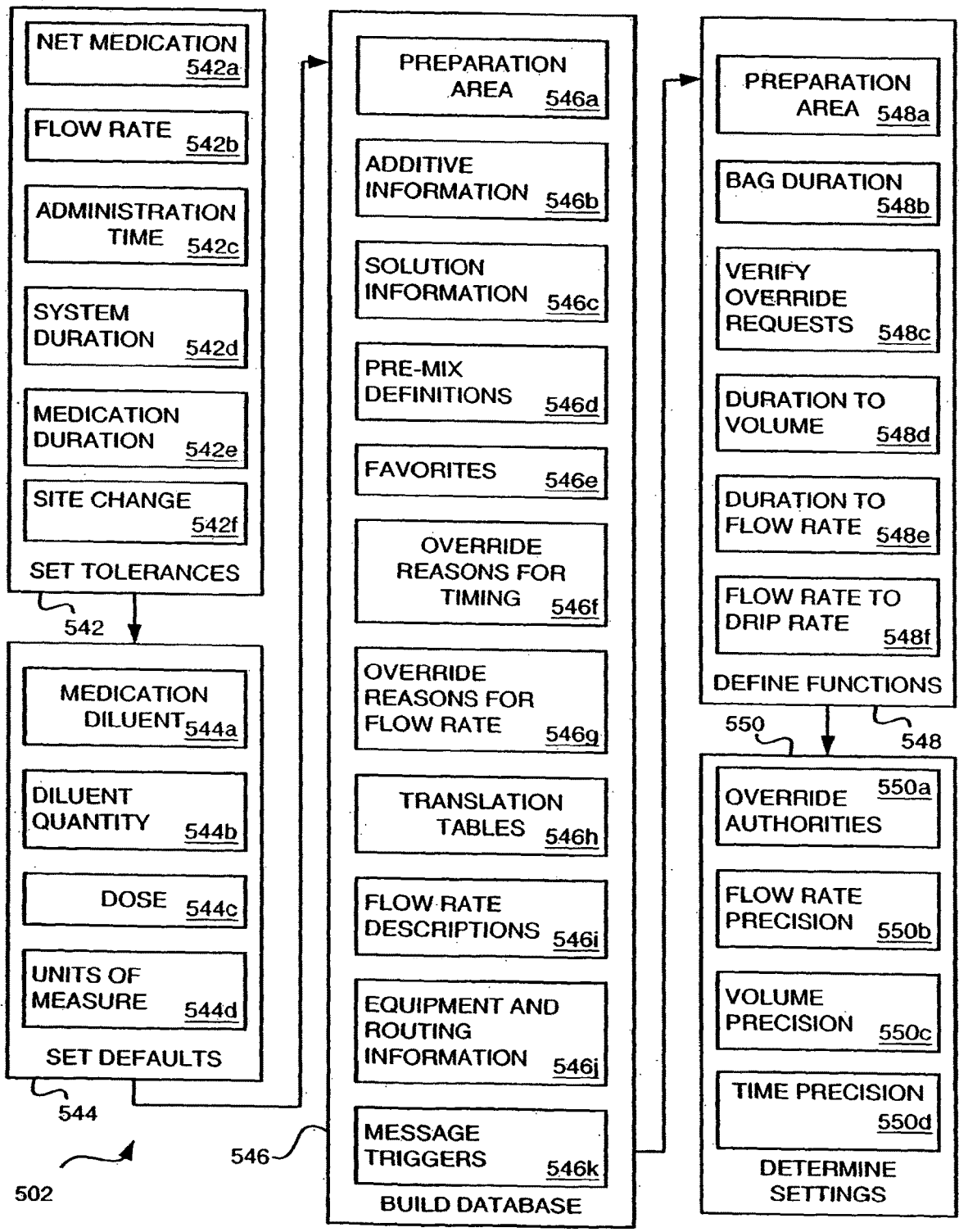
FIG. 7 is a block diagram showing functional components for the setting of infusion system parameters of FIG. 6.

FIG. 7 is a block diagram showing functional components for the setting of system parameters 502 of FIG. 6. Setting system parameters 502 includes, but is not limited to, setting tolerances 542, setting defaults 544, building databases 546, defining functions 548, and determining system settings 550. Tolerances 542 include tolerances such as, but not limited to, net medication tolerances 542a, flow rate tolerances 542b, administration time tolerances 542c, administration system duration 542d, medication duration tolerances 542e, and site change tolerances 542f. The infusion system 210 can also include separate tolerances for order entry and modifications from the ordered tolerances. For example, separate tolerances can be identified such as, but not limited to, an administration system duration 542d, an order entry maximum infusion duration override availability setting, and an administration maximum infusion duration override availability setting.

A net medication tolerance 542a is a maximum concentration of a medication that is safe to administer to a patient during a given period of time. The infusion system 210 associates the net medication tolerances with medications. Net medication tolerances 542a can be defined in medication identification files in a medication database. During infusion order creation 504, the infusion system 210 can determine the flow rate 560e, the number of infusion bags required 562a for a specified period of time, the concentration of the primary ingredient in each infusion bag, the time period over which each infusion bag is to be administered, and the total volume of each infusion bag. Flow rates can be manually entered or adjusted by altering the final concentration or the duration of each infusion bag. In an embodiment, the infusion system 210 performs a net concentration check 564a (FIG. 8) to ensure the maximum concentration of the medication is not exceeded. However, if at any time while a clinician 116 is modifying the flow rate by adjusting the final concentration resulting in the final concentration of a solution exceeding the maximum concentration of the medication, the infusion system 210 sends a message 520 to the administering clinician. The administering clinician can be authorized to override the net medication tolerance 542a. The infusion system 210 can require the clinician 116 to provide a reason for the override.

Infusion system 210 can include adjustable flow rate tolerances 542b and flow rate adjustment tolerances for administration. Flow rate tolerances 542b are optionally defined for all organizational levels of the patient care system 100. The tolerances 542b can be for the entire patient care system 100, or for sub-systems of the patient care system 100. For example, different flow rate tolerances 542b can apply to sub-systems such as, but not limited to, neonatal, pediatric, psychiatric, specific nursing units, and for specific patients. The flow rate tolerances 542b can be specified relative to the original ordered flow rate or relative to the immediately preceding flow rate. The clinician 116 can also specify a flow rate tolerance specific to a particular order.

The infusion system 210 can include a pre-defined indication of whether the administering clinician 116 is permitted to override the flow rate tolerance 542b without requiring a new order. This indication can apply to the entire patient care system 100, a sub-system, or an individual clinician 116.

The maximum infusion duration 542d can be separately definable for the various portions of the patient care system 100. The maximum infusion duration 542d can also be specific to a particular medication 124. A maximum infusion duration override 566 (FIG. 8) can be provided if it is permissible to override the maximum infusion duration 542d at the time of order entry. An administration maximum infusion duration override can be provided to set whether it is permissible to override the maximum infusion duration 542d at the time of administration and which group of users is allowed to do so. If it is permissible to override during order entry and/or administration, the infusion system 210 can define a subset of the clinicians 116 that have the authority to override the maximum infusion duration 542d.

Defaults 544 include defaults such as, but not limited to, medication diluents defaults 544a, diluents quantity defaults 544b, dose defaults 544c, and units of measure defaults 544d. Units of measurement (UOM) defaults 544d include the ability to specify the units of measurement that are most suitable for different portions of the patient care system 100. For example, medication can be measured in different units by physicians, administering clinicians, pharmacists, financial personnel, and medication screeners. The physician's UOM is generally a measurable value such as "mmol," "mEq," "ml," and/or "mg," as opposed to "vial" and/or "puff." The physician's UOM is used for tasks such as ordering and entering information 560.

The administering clinician's UOM is generally a value that reflects the UOM the medication will be administered in, such as "puff," "tbsp," and "tab." The administering clinician's UOM is used during medication administration 512. The administering clinician's UOM can also appear on documentation such as administration reports, admixture fill and manufacturing work orders.

The pharmacy UOM is generally a value that reflects the physical form the medication is dispensed in such as "tab," "vial," "inhalator," and "jar." The pharmacy UOM is used in preparation 506 and in stocking and dispensing systems. The financial UOM is generally a value used to calculate the financial figures that appear on bills and invoices. The medication screening UOM is generally used when screening the medication.

Units of measurement defaults 544d can be specified using a check-box table where checkmarks are placed in a table correlating the various UOMs with the users of the UOMs. The infusion system 210 can use the same UOM for more one function. For example, the physician's UOM can be the same as the pharmacist's UOM. Setting defaults 544 include data necessary to coordinate the various UOMs. For example, UOM defaults 544d can include the multipliers and dividers necessary to create a one-to-one correspondence between the various UOMs. The UOM defaults 544b can be changed to suit the desires of the individual clinicians. However, the one-to-one correspondence should be maintained by the patient care system 100.

The infusion system 210 can be designed to maintain a history of medication unit defaults. The infusion system 210 can also include medication measurement suffixes. The medication measurement suffixes can default during order entry. The medication measurement suffixes can be common units of measuring a medication and can include units related to patient characteristics such as body surface area and weight. Medication measurement suffixes can be designated per drug, per order type, per dose, and per UOM. Building database 546 includes building databases and/or portions of a single database such as, but not limited to, preparation area 546a, additive information 546b, solution 546c, pre-mix definitions 546d, favorites 546e, timing override reasons 546f, flow rate override reasons 546g, translation tables 546h, flow rate description 546i, equipment and routing information 546j, and message trigger 546k.

Figure 11:
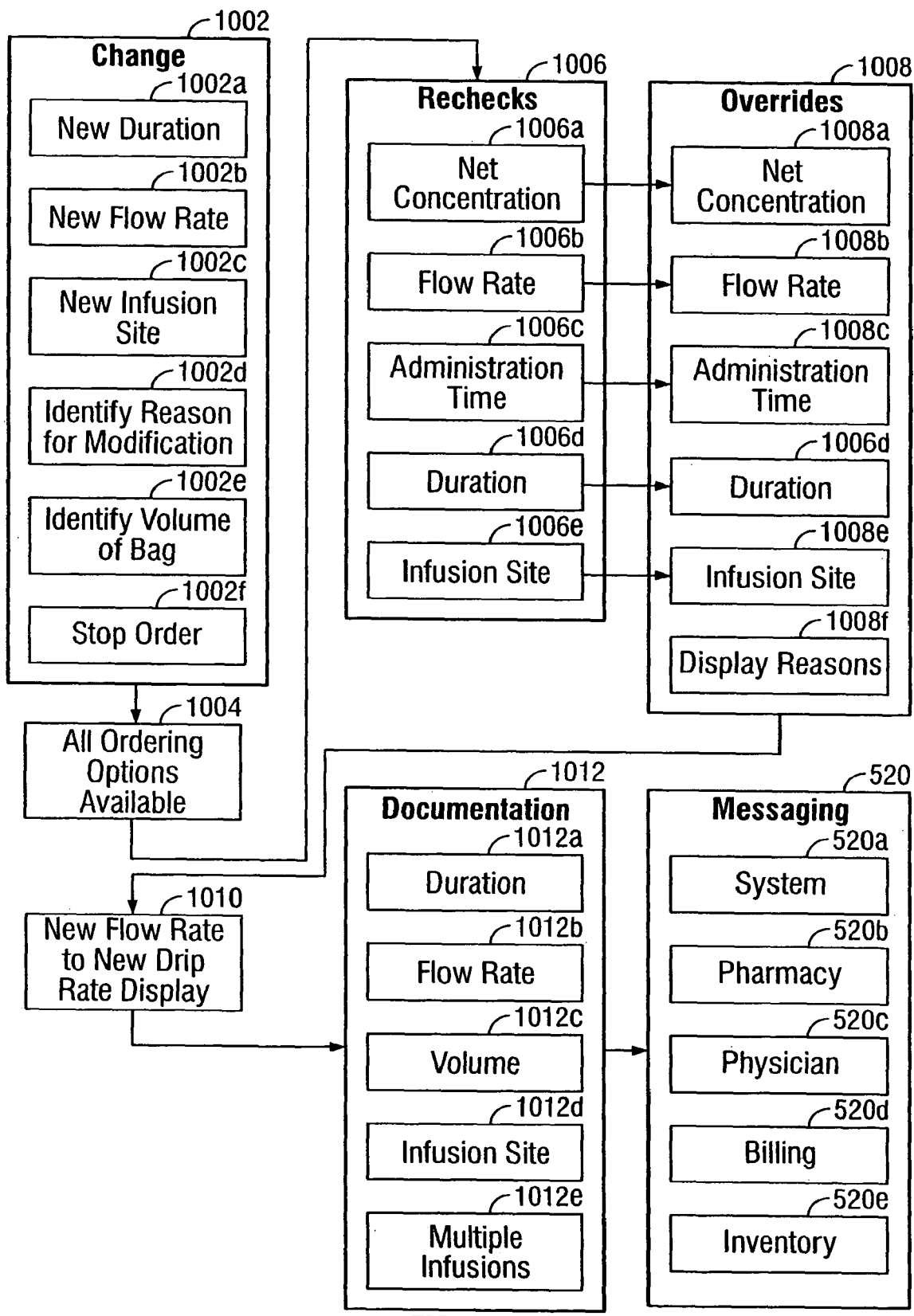
FIG. 11 is a block diagram showing functional components for infusion order documentation, infusion order modifications, and messaging of FIG. 6.

Timing override reasons 546f include displayable reasons for modifying the timing of infusion orders. For example, timing override reasons 546f can include a stylus-selectable reason for digital assistant display 118a for administering an infusion order at a time other than the time specified in the original infusion order. If the clinician 116 administers a medication outside the ordered administration time tolerance 542c, the clinician 116 can be required to choose a reason code for the modification from displayed reasons 1008f (FIG. 11).

Examples of other reason codes include, but are not limited to, PRN administration reason codes and codes for stopping an infusion.

Medications 124 and/or infusion orders can have flow rate tolerances, including system flow rate tolerances 542b. The infusion system 210 can include flow rate override reasons table 546g. Flow rate override reasons 546g are notations that the clinician 116 can choose from, and/or supply, if the clinician 116 needs to change the flow rate beyond the bounds defined by the flow rate tolerance 542b. The infusion system 210 can include a defined message trigger 546k indicating whether or not a message should be sent to the patient's physician if a clinician 116 overrides an order-defined flow rate tolerance. The infusion system 210 can also include defined message triggers 546k indicating whether or not a message should be sent, and to whom, if a clinician 116 overrides a tolerance, such as flow rate tolerances 542b, defined at a level other than the order.

The infusion system 210 can include translation tables 546h such as, but not limited to, a flow rate translation table, a varying ingredient translation table, and varying flow rate translation table. Flow rate translation includes translating an infusion order into a flow rate defined by volume/time where the order is originally specified in any way such as, but not limited to, dosage/time with a particular concentration, volume per unit of weight/time, dosage per unit of body surface area/time, and total dosage and duration.

Varying ingredient translation includes translating a plurality of flow times of infusion orders with varying ingredients in separate infusion bags into the flow rate for the infusion bag currently being administered. Orders with varying ingredients include orders such as, but not limited to, sequencing orders. In sequencing orders, different bags have different ingredients and potentially different flow rates.

Varying flow rate translation includes translation of infusion orders with varying flow rates into the flow rate for the current solution being infused. Varying flow rate orders include orders such as, but not limited to, bolus/basal, orders, tapering dose orders and alternating dose orders.

The infusion system 210 can include predefined infusion flow rates 542*b*. The predefined infusion flow rates 542*b* can be associated with flow rate descriptions 546*i* to permit selection from a drop-down list as a shortcut from keying in the flow rate. Defined functions 548 include functions such as, but not limited to, preparation area function 548*a*, bag duration function 548*b*, verify override requests function 548*c*, duration to volume function 548*d*, duration to flow rate function 548*e*, and flow rate to drip rate function 548*f*. The infusion system 210 can include a duration-to-volume function 548*d* to determine the amount to be infused per the infusion order. Flow rate to drip rate function 548*f* uses information about the medical device 330 to convert flow rates to drip rates.

Determined settings 550 include settings such as, but not limited to, override authorities 550*a*, flow rate precision 550*b*, volume precision 550*c*, and time precision 550*d*. The infusion system 210 can, if desired, determine the total volume of infusions and the flow rate(s) of the infusion order. If these numbers are determined, it is desired to round the calculated values to flow rate precisions 550*b* and volume precisions 550*c* that are comprehensible to clinicians 116 such as the physician, the pharmacist, and the nurse. Flow rate display precision 550*b* can be set to display the flow rate to a set number of decimal places. Various parts of the patient care system 100 can independently determine the precision for displayed flow rates. For example, the infusion system 210 can display to one decimal place for an adult treatment location, and to three decimal places for a neonatal treatment location. The flow rate precision 550*b* reflects the service in which the clinician's patient(s) are located. The flow rate(s) of the infusion order can be rounded to a system-defined precision. The precision can be same for all infusion orders or be dependent on the patient's service.

Volume display precision 550*c* can similarly be set to display infusion volumes to a set number of decimal places. Settable time precision 550*d* can be used to calculate the administration duration period based on flow rate if the infusion is a single dose infusion or an intermittent infusion. The total volume of each infusion bag calculated is rounded according to the volume precision 550*c*. The administration time is rounded by the infusion system 210 according to the set time precision 550*d*. The time precision 550*d* can be the same for all infusion orders regardless of the patient's service or may be service-specific.

Order Creation

FIG. 8 is a block diagram showing functional components for infusion order creation 504 of FIG. 6. Infusion order creation 504 includes functional blocks for creating infusion orders. Infusion order creation 504 includes entering information 560, calculations 562, checks 564, and overrides 566. Entering information 560 can include functions such as, but not limited to, identifying the order type 560*a*, identifying the medications 560*b*, identifying the dose 560*c*, identifying the diluent 560*d*, identifying the flow rate 560*e*, and identifying the infusion site 560*f*.

Infusion order creation 504 is linked to infusion bag preparation 506, infusion bag delivery (path 530), medication administration 512, and infusion order modifications 514. Infusion order types 560*a* include order types such as, but not limited to, single dosing, load dosing, intermittent dosing, and continuous. Continuous infusions include alternating infusions, sequencing infusions, tapering infusions, and titrating infusions. Upon selection of the first medication 560*b* in an infusion order, an infusion order type 560*a* form for the medication may default. The ordering clinician can have the option of selecting a different order type. The dose 560*c* and unit of measure 544*d* can also default. The unit of measure 544*d* can be correlated with the medication and/or the dose 544*c*. The infusion system 210 can include a default diluent, or several default diluents, for the medication. One default can be identified as a preferred diluent. A description can be associated with the diluent to assist the ordering clinician to decide which diluent to select. The diluent description can include a reference avoiding use of a particular diluent if a patient is hypertonic.

The infusion system 210 can also allow additional infusion order subtypes 560*a* based on the previously mentioned infusion order types. Additional infusion order subtypes 560*a* can include, but are not limited to, TPN infusion orders, chemotherapy continuous infusion orders, piggyback infusion orders, and large volume parenteral infusion orders. The infusion order subtypes can be accessed from different parts of the infusion system 210 allowing sorting and filtering of infusion orders according to the subtypes. A special label format for each infusion order subtype can also be defined to further customize infusion order subtype orders and associated pharmacy workflow.

When searching for a medication 124 during infusion order creation 504, the medication 124 can be flagged as additive and/or a solution to aid the clinician 116 in creating the infusion order. This designation can be made in a medication identification file. Medication dose 560*c* can be determined in a number of ways such as, but not limited to, according to body weight, body surface area, and entered according to rate. When the flow rate is not entered, the infusion system 210 calculates the flow rate according to the dose and time period specified. The ordering clinician can specify the diluent 560*d* and its quantity. The pharmacy can provide a default for such parameters—see line 582 (FIG. 6). A check 564 can be performed to ensure the net concentration 564*a* for the medication 560*b* and the flow rate 564*b* are appropriate.

The infusion system 210 can identify and/or calculate flow rates 560*e* based on the patient's weight, body surface area, and/or a specified frequency and duration of therapy. The ordered flow rate 560*e* is checked 564*b* against the flow rate tolerances, such as system flow 30 rate tolerance 542*b*. The net concentration of the medication 124 can be checked 564*a* against net concentration tolerances, such as the system net concentration tolerance 542*a*.

In an embodiment, flow rate 560*e* can also include displaying descriptions of default flow rates to facilitate the entering of orders. Flow rate 560*e* can reference flow rate descriptions database 546*i*. Calculations 562 can include calculating the dose based on patient weight and/or height (possibly provided by ADT interface 310), the drug amount, diluent volume, concentration, or rate. Calculations 562 can include, but are not limited to, calculating the flow rate, if not specified in the prescription, the bag quantity 562*a* or number of infusion bags required for a specified period of time, the time period over which each infusion bag is to be administered, and the total volume of each infusion and infusion bag based on the concentration of the ingredients in the solution. Flow rates, volume to be infused, and/or duration can be modified.

If modified, the infusion system 210 automatically calculates dependent quantities, based on calculations, if the maximum dosage for the ingredients in the concentration would be exceeded as identified in the ingredient's medication file, the patient care infusion system 210 alerts the pharmacist and/or clinician 116 and can ask for a reason code for the adjustment. Calculations 562 can include calculations such as, but not limited to, bag quantity calculations 562a, translation calculations 562b, duration to volume calculations 562c, and flow rate to drip rate calculations 562d. Checks 564 include a variety of checks that an infusion order can be subject to. The checks include checks such as, but not limited to, a net concentration check 564a, a flow rate check 564b, an administration time check 564c, a duration check 564d, and an infusion site check 564e. If an infusion order fails a check 564, the clinician 116 may be able to override the check. Overrides 566 can include overrides such as, but not limited to, a net concentration override 566a, a flow rate override 566b, an administration time override 566c, a duration override 566d, and an infusion site override 566e.

Overrides 566 can generate messages 520 for the physician and/or the pharmacy. The infusion system 210 can distinguish between system-wide and subsystem overrides in determining whether it is necessary to generate a message 520.

Overrides can include an indication of whether clinicians have the authority to override a tolerance. For example, flow rate override 566b can provide an indication of whether the clinician entering the infusion order has the authority to override the system flow rate tolerance 542b. This indication can apply to the patient care system 100 or a subsystem. Duration override 566d can provide an indication of whether the clinician 116 entering the infusion order has the authority to override the system duration 542d. This indication can apply to the patient care system 100 or a subsystem. Overrides 566 also include displaying of reasons for the override 566f. Reasons for the overrides 566f can be selected by the clinician 116 from dropdown menus.

The result of the infusion order creation 504 is an infusion order 702. Infusion order 702 can include an infusion schedule 704. The infusion system 210 can look ahead a period of time and generate the infusion schedule 704—so long as the infusion order 702 is active—for infusion bag filling for that time period, or longer if specified on demand. The ordering clinician is not required to specify an end-date for the infusion order. The infusion system 210 can include automatic scheduling of infusion bag delivery based on infusion system 210 defined tolerances 542.

Order Preparation

Figure 9:
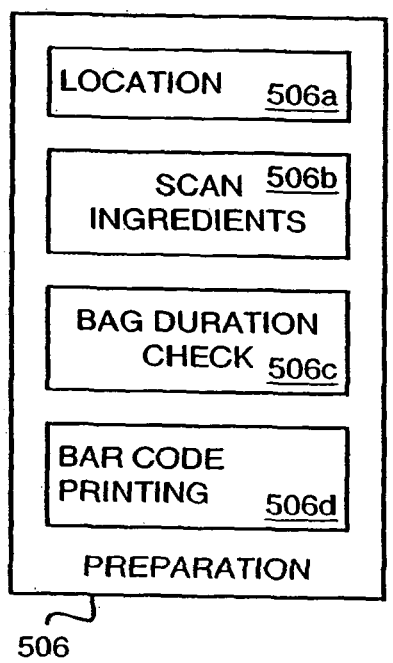
FIG. 9 is a block diagram showing functional components for the infusion order preparation of FIG. 6.

FIG. 9 is a block diagram showing functional components for infusion order preparation 506 of FIG. 6. Infusion preparation 506 includes functional blocks for preparing infusion order 702 (FIG. 8). Infusion preparation 506 can include, but is not limited to, determining preparation location 506a, scanning ingredients 506b, bag duration checking 506c, and bar code printing 506d for medication labels 124a. Bar code printing 506d can include the functions described above in reference to print label 326 (FIG. 4).

After infusion orders are entered into the infusion system 210, preparation instructions are routed to a preparation location. The preparation location depends upon the infusion system's 210 preparation program 506 and the infusion components. The infusion system 210 can include adjustable databases, such as preparation area database 546a, that specify where the infusion order is to be prepared. The infusion order can be prepared in the pharmacy or in a remote location, such as on the floor or at the treatment location 106. The clinician 116 is guided through the preparation process, including bar code verification of ingredients, using event management information that can be displayed on digital assistant 118 or another device having a display.

The medication label 124a identifies the ingredients and ingredient concentrations. The medication label 124a can be printed in any location. The medication label 124a preferably includes bar code printing 506d. Bar code printing 506d can include printing a bar code label 124a for each infusion bag. The label 124a assists in ensuring that the correct medication is administered at the correct times and/or in the correct sequence. Alternating and sequencing infusion orders are particularly vulnerable to sequencing and timing errors. Bar code printing 506d can include printing a unique bar code label for every bag in infusion order 702. Bar code printing 506d can also include printing a bar code label 124a that uniquely identifies the combination of ingredients in an infusion bag and the concentration of those ingredients. The bar code for medication 124 can include a prefix, a suffix, and the national drug code (NCD).

In an embodiment, the bar code can also include a lot and expiration date. Alternatively, a separate bar code can be provided to include the lot and expiration date. Other embodiments of the bar code, including active or passive RFID tags, magnetic strips, etc. can be used.

Medication Administration

Figure 10:
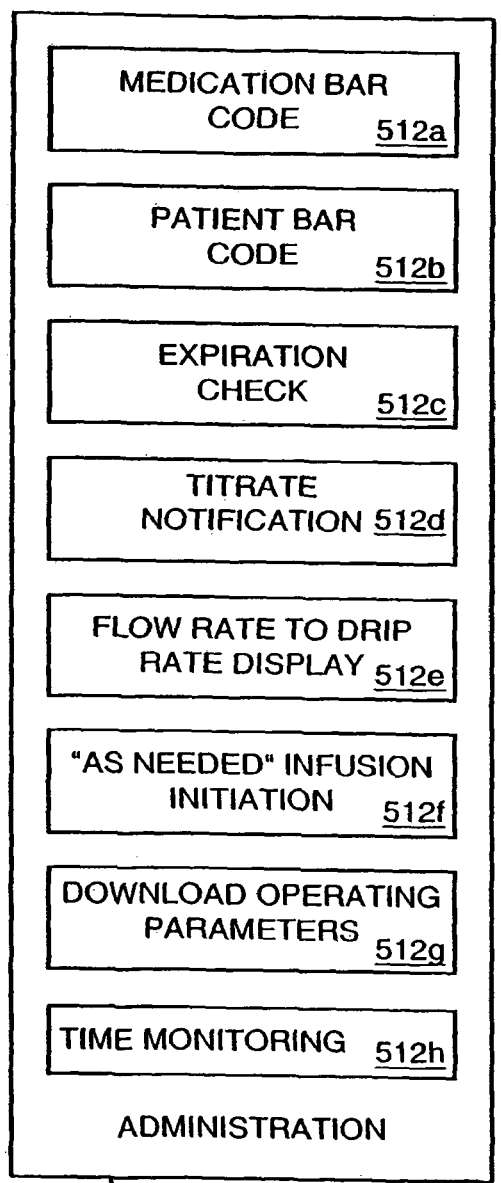
FIG. 10 is a block diagram showing functional components for the medication administration of FIG. 6.

FIG. 10 is a block diagram showing functional components for medication administration 512 of FIG. 6. Medication administration 512 includes functional blocks that are used to administer the medication to patient 112. Medication administration 512 can include reading a medication bar code 512a, reading a patient bar code 512b, running an expiration check 512c, providing titrate notification 512d, providing a flow rate to drip rate display 512e, providing "as needed" infusion initiation 512f, downloading operating parameters 512g, and time monitoring 512h. The infusion system 210 can also translate orders that may have more than one flow rate, such as tapering and alternating orders, into the flow rate for the infusion bag currently being administered. The infusion system 210 can also translate orders having infusion bags with different ingredients, such as sequencing orders, into the flow rate for the infusion bag currently being administered.

Upon administering the medication 124, the clinician 116 scans the medication label 124a. The infusion system 210 includes scanning the bar-coded label 124a when initiating the administration of the infusion order, when changing flow rates, changing bags, and/or stopping the infusion order. Infusion system 210 verifies that the infusion bag having the bar-coded label should be administered at that time and is for patient 112. The history of the medication administration, including flow rates and volumes administered, can be captured and maintained.

Some infusion orders require hanging of an infusion bag with the intent of only a partial, specific amount of the infusion bag to be administered. The infusion system 210 allows a clinician 116 to order an amount of an infusion bag to be administered. Most infusion pumps have the ability to define the volume to be administered or the flow rate and time period. Once this time has elapsed, the infusion pump will automatically prevent further administration.

Infusion system 210, as a reminder to the administering clinician, provides a message on the medication label 124a that it is to be partially administered and the appropriate volume to be administered.

Flow rate to drip rate display 512e uses data generated by flow rate to drip rate functions 548f to provide the administering clinician with drip rates for the current infusion bag.

During medication administration 512, the clinician 116 can check on the flow rate and other 30 operating parameters using the digital assistant 118. Flow rate modifications 1002b (FIG. 11) are communicated in real-time.

The infusion system 210 can include PRN or "as needed" infusion initiation 512f. "As needed" infusion initiation 512 causes the creation of a new active order and the preparation of the PRN medication. This option can include prompting the clinician 116 to select a PRN infusion from a list of anticipatory PRN orders placed for the patient and defaulting the requested infusion bags to one. The clinician 116 can have the authority to modify the requested quantity of infusion bags.

Downloading of operating parameters 512g can include determining whether the patient identifier associated with the medical treatment and/or the patient identifier retrieved from the wristband 112a, is the same as the patient identifier associated with the medical treatment at the central location. The determination often is made by the first computer, for example, the first central server 109. If the infusion system 210 determines the various patient identifiers are not the same, the system can generate an alarm message 520. If the infusion system 210 determines the various patient identifiers are the same, the infusion system 210 can download the operating parameters directly to the medical device 332. The infusion system 210 can send the operating parameters to a medical device 332, such as infusion pump 120.

One benefit of the system program 210 is that the operating parameters for the medical device 332 do not have to pass through digital assistant 118, or any other computer in the remote location, prior to the operating parameters being available to program the medical device 332. Bypassing computers at the remote location eliminates a potential source of errors in administering medication 124 to a patient 112. The operating parameters for the medical device 332 can be sent "directly" to the medical device 332 assuming the various verifications are achieved. In this context, "directly" means that the operating parameters can be sent to the medical device without passing through the digital assistant 118, or any other computer in the remote location.

In another embodiment, the infusion system 210 can include an additional block (not shown) where the central computer accepts a second medication identifier. The clinician 116 at the remote location can enter the second medication identifier. The second medication identifier can be a revised first medication identifier. For example, the second medication identifier can be part of the prescription or electronic physician order entry that is the source for the first patient ID and the operating parameters. The infusion system 210 can then confirm the first and second medication IDs are equivalent prior to sending the operating parameters to the medical device. The second medication ID can be replaced by a revised first medication ID between the time the prescription is entered and the time the medication 124 arrives at the treatment location 106. The infusion system 210 will then sound an alarm if the second medication identifier is not equivalent to the first medication identifier that was included in the medication label 124a. In a further embodiment, the infusion system 210 can include an additional block (not shown) where the operating parameter is used to program the medical device 332.

Various blocks of the infusion system 210, such as block 512, can include displaying treatment information on the digital assistant 118. This can include displaying information that mirrors the information on display 120c of infusion pump 120. The information on display 120c of infusion pump 120 can be supplemented with information about the patient 112, the patient location, and the infusion order. This information can include information regarding multiple channels of infusion pump 120. The displayed information can include information such as, but not limited to, personality, prompt line, status line, operating icons and pump head display. Operating icons include falling drop, stop sign, flow check piggyback, and delay start.

The pump head display includes information such as the drug label and the infusion rate. Those having ordinary skill in the art are familiar with the displayed information and operating icons described above.

The infusion system 210 time monitoring 512h calculates the time remaining for an order to be completed and the volume of an infusion order that remains to be administered. When the clinician 116 uses the infusion system 210 to administer the infusion order, to make flow rate changes, and to check on the status of an infusion, the infusion system 210 calculates time and volume remaining to be administered and indicates if the calculation indicates a partial bag will be used. For example, on the last bag of an order that is to be stopped before the full volume is administered, and/or on a bag within an order that must be changed before the full volume is administered, the clinician 116 is alerted on digital assistant 118 and/or cart 132. The alert can include a message such as, "Please only administer 150 mL." Time monitoring 512h includes tracking any modifications made to the flow rate using bar code scanning. The pharmacy is alerted in real time to adjust the preparation 506 of the next required infusion bag according to the modification. Monitoring of preparation 506 and medication administration 512 allows for a just-in-time delivery of medication 124. Just-in-time delivery reduces wastage attributed to discontinued or changed infusion orders.

Monitoring also ensures patient 112 safety. For titrate PRN orders, the clinician 116 is automatically notified of required flow rate changes if the titration conditions in the order indicate that the flow rate must be changed. The infusion system 210 includes defined functions for calculating a conversion of flow rates to drip rates 548f. The infusion system 210 defined values can be adjustable. The infusion system 210 can include automatic translation of flow rate to drip rate 548f to assist the clinician 116 during administration of the treatment.

Order Documentation and Modification

FIG. 11 is a block diagram showing functional components for infusion order documentation 1012, and the infusion order modifications 514 and messaging 520 of FIG. 6. Messaging 520 includes messages related to system 520a, pharmacy 520b, physician 520c, billing 520d, and inventory 520e. Modifications 514 include functional blocks used to modify existing infusion orders. Modification 514 can also be viewed as creating new orders to replace existing infusion orders.

Modification 514 can include modification changes 1002, generally all ordering options for new orders 1004 are available, rechecks 1006, recheck overrides 1008, and new flow rate to new drip rate display 1010. Infusion order modifications often lead to documentation 1012 and messaging 520. Modifications 514 include the functions described in reference to prescription modification module 336 (FIG. 4). However, modifications 514 are also accessible from other portions of the patient care system 100 such as, but not limited to, prescription entry 324, prescription activation 306, and prescription authorization 308.

Modifications 514 include modifying the duration 1002a, modifying the flow rate 1002b, using a new infusion site 1002c, identifying reasons for modifications 1002d, identifying the volume of an infusion bag 1002e, and processing stop orders 1002f. Clinicians 116 can also change an infusion rate without an order if the patient 112 is complaining of discomfort or to facilitate fluid balance, such as when the patient 112 is vomiting.

Modification changes 1002 include identifying a new duration 1002a, identifying a new flow rate 1002b, identifying a new infusion site 1002c, identifying a reason for a modification 1002d, identifying the volume remaining in the infusion bag 1002e, and stop orders 516. The ordering options available during initial infusion order creation 504 are generally available for modifying the infusion order. Ordering options available during initial infusion order creation 504 include those shown in FIG. 8. Rechecks 1006 and recheck overrides 1008 are analogous to checks 564 and overrides 566 that are described in reference to FIG. 8. New drip rate to new flow rate display 1010 assists the clinician and minimizes the possibility of errors during medication administration 512. The modified infusion order can lead to a modified infusion schedule.

Flow rates are frequently modified at the treatment location 106 for reasons such as to catch-up without changing the schedule for preparation when the infusion has been inadvertently stopped for a short time period. Such modifications may not require new infusion schedule 704 to be communicated to the pharmacy. In other cases, the new schedule 704 should be communicated to the pharmacy or other preparation staff. Flow rate modifications 1002b trigger infusion order scheduling changes and/or messages 520 for appropriate clinicians 116.

When a clinician 116 enters a flow rate modification 1002b into the infusion system 210 at treatment location 106, the clinician 116 can also elect to have the infusion schedule 704 recalculated and sent to the pharmacy. The clinician 116 has the option of requesting new medication labels 124a to be printed by bar code printing 506d module. The new medication labels 124a include data reflecting the new information for any of the previously prepared infusion bags.

The infusion system 210 and/or the clinician 116 can request a modification to the infusion site 1002c. The site can be selected from a list of anatomical representations on a computer screen. The clinician 116 can be required to identify a reason for the modification 1002d. Reasons stored in databases such as, but not limited to, override reasons for timing 546f and override reasons for flow rate 546g, can be displayed for easy identification by the clinician 116. There can be a separate hard-coded reason for physician-ordered modifications. For physician ordered modifications, the clinician 116 can be requested to identify the physician.

Prior to implementing the modification, the volume remaining in the current infusion bag is identified 1002e. The clinician 116 can be offered the option of accepting a volume calculated from a displayed value of pre-modification flow rate and/or volume. If desired, the current infusion can be stopped 1002f. If stopping the order is not required, for example the same infusion bag can be used with a new flow rate and/or a new medication added, the old flow rate can be identified and compared to the modified flow rate.

Any infusion bags that were previously prepared can be checked for expiration based on the new infusion schedule 704. When an infusion order is resumed following either a temporary stop or a hold order, the expiration check can be done regarding expiration of solutions that have already been prepared.

The new infusion schedule 704 is used to control the preparation 506 in the pharmacy or other preparation site. A system default 544 can be set for whether or not any prepared bags should be credited to the patient 112 through the billing interface 312, and whether or not they should be credited to inventory.

Infusion order changes 1002 include all ordering options available 1004 for new orders. The modified flow rate can be rechecked 1006 for rules and tolerances such as, but not limited to, net concentration 1006a, flow rate 1006b, administration time 1006c, duration 1006d, and infusion site 1006e. Overrides 1008 can be available for modifications that are outside of tolerances. Overrides 1008 include net concentration 1008a, flow rate 1008b, administration time 1008c, duration 1008d, and infusion site 1008e. The infusion system 210 can display reasons 1008f for overrides and for administering medications at times other than that specified in the original order. The clinician 116 can be required to identify a reason for the modification.

The infusion system 210 can offer the clinician 116 a display indicating the modified drip rate associated with the modified flow rate 1012. The displayed information can be calculated by the flow rate to drip rate 548f defined function. The infusion system 210 can also be provided with descriptions of typical infusion tubing used within the infusion system 210 for use in calculating drip rates.

A modification results in the infusion system 210 validating the expiration of the infusion bag and providing a message to the clinician 116 if the infusion bag expires prior to the completion of the order. The message can request that the clinician 116 contact the pharmacy. The validation of the expiration of the infusion bag for solutions such as, but not limited to, premixed solutions and solutions manufactured outside of the infusion system 210, may include parsing the scan code.

Flow rate override 1008b can provide an indication of whether the clinician 116 modifying the infusion order has the authority to override the ordered limit without requiring approval for a new infusion order. This indication can apply to the patient care system 100 or a subsystem. Documentation 1012 captures infusion order information in real-time. Documentation includes documenting multiple infusions being administered at the same time and infusion modifications such as, but not limited to, duration changes 1012a, flow rate changes 1012b, volume changes 1012c, and infusion site changes 1012d.

The infusion system 210 can assist the clinician 116 in capturing all changes in flow rate as the changes are occurring. The clinician 116 can change the flow rate as called for in the order, such as to decrease a morphine infusion flow rate from 4 ml to 2 ml. Though the infusion system 210 may recognize the change as a new order, the infusion system 210 may be configured to avoid duplication so that the modified order does not result in the generation of a new bag.

Documentation 1012 includes the ability to document changes such as, but not limited to, an infusion that is stopped temporarily, discontinued, and/or restarted. The clinician 116 may stop infusion for a variety of reasons, such as the infusion site having been compromised, the infusion has been dislodged, and/or the infusion may be heparin/saline locked to facilitate the movement of patient 112. The infusion can be resumed when a new site/infusion has been reestablished. However the length of time this may take is variable and is generally recorded by the infusion system 210.

Government regulations often require tracking of every step in the process of infusion administration. Infusion system 210 allows the administering clinician 116 to document flow rate modifications on a digital assistant 118, or other computer device, by scanning the medication label 124*a* and adjusting the flow rate 1002*a* based on a tolerance, such as a tolerance created by set tolerance 542. A flow rate modification 1002*b* corresponds in real time with the associated pharmacy's infusion schedule 704 to ensure just-in-time inventory management of infusion bags to the patient treatment area 106. Documentation 1012 may allow order backdating under some circumstances.

The infusion system 210 includes the ability to document the infusion site 1012*d* and multiple infusions 1012*e* for multiple infusion sites. In many situations, a patient 112 can have multiple medications 124 and "y-ed" infusions so that the some infusions are running into one site and other infusions are infusing into another site. For example, morphine infusion, antibiotics and normal saline infused into the right arm (site 1) and TPN and ⅔ & ⅓ running into a double lumen CVL (site 2). The infusion system 210 allows clinician 116 to document which site the various fluids are infusing through. In treatment locations 106, such as intensive care units, many more than two infusions may be running into one line or one lumen.

Clinicians 116 are able to indicate which lumen of a CVL the infusion or medication is running into. The infusion system 210 includes the ability to document the site location 1012*d* for infusions and any site location changes. Infusion sites are frequently changed due to occlusions or policy. Therefore, clinicians 116 must document a change in the site location if an infusion becomes dislodged and was subsequently restarted.

The infusion system provides for centralized device configuration. Operating parameters for medical devices, such as infusion pump 120, often include defaults and/or tolerances. The defaults and/or tolerances can reside in the infusion system 210, for example flow rate tolerance 542*b*, and/or in a memory associated with the device 332. For example, infusion pumps 120 can include a database having a table of medications having associated flow rate tolerances. If the clinician 116 enters a flow rate that is beyond the associated flow rate tolerance, the clinician 116 is warned and then can be allowed to proceed, or prohibited from proceeding. Devices 332 such as heart rate monitors can also have configurable tolerances for alerts. In addition to alerts, many other characteristics can typically be configured for devices 332 such as: network name, IP address, polling frequency, and colors. The infusion system 210 includes configuring medical devices 332 individually or in groups from one or more central computers.

System configuration parameters can be defined for a first type of medical device. The system configuration parameters are sent and accepted by the first type of device unless the particular first type of device has more specific configuration parameters that apply to that particular first type of device. For example, a first plurality of a first type medical device can be located at general care treatment locations. A second plurality of the first type of medical device can be located at an intensive care treatment location. The general care treatment location may not have specific configuration parameters while the intensive care treatment location does have specific treatment parameters. System configuration parameters will apply to all of the first type of medical devices throughout the infusion system 210, i.e. the devices in the general care treatment locations, unless specific configuration parameters apply, e.g. the intensive care treatment location.

For each type of device, specific configuration parameters that apply to all devices of that type across a particular grouping of the devices override the system configuration parameters if a particular device belongs to the group having such a definition, unless the specific configuration parameters are overridden at an even more specific level within the infusion system 210. The groups might be defined as a clinical service, a nursing unit, and/or a combination of service and nursing unit.

For each type of device, the user can define sets of configuration parameters that apply to all devices of that type being used for operations with specified ranges of attributes that override any other definition. In a hospital, the operations might consist of infusion orders and the attributes might include patient weight, drug, patient disease state, and patient acuity.

Devices can be identified as part of a general group, a specific group, and/or be associated with a particular patient by including the device address in a table in a database. General or specific configuration parameters can then be sent to the device according to the identification of the device. The specific configuration parameters can then be read back to the infusion system 210 and compared to the originally sent configuration parameters to verify the original configuration parameters were correctly received by the device 332. If the configuration parameters were not correctly received, the infusion system 210 can provide a message 520 identifying the discrepancies or the communication failure.

The infusion system 210 can detect changes to configuration parameters made at the device, rather than through a central computer, and send a message and/or alert 520. The infusion system 210 can also poll the devices to verify their configuration parameters. If system and/or specific configuration parameters change, the changes can be propagated to all devices 332 identified in the system as belonging to the group according to the groupings identified in the infusion system 210.

Throughout this document and the related claims, "central location" and "remote location" are relative terms to each other. A "remote location" is any location where a patient is receiving treatment through a controlled medical device, such as a patient treatment location 106 where patient 112 is receiving treatment through an infusion pump 120. "Central location" is any location, other than the remote location, where parameters for operating the medical device are accessible such as, but not limited to, the location of the pharmacy computer 104 and the central system 108. In a typical arrangement, several remote locations, such as treatment location 106, are in communication with a central location.

While the present disclosure has focused on the use of infusion pumps 120 within the system 210, it is understood that other medical devices may be used within the system 210 10 without departing from the scope of the present invention. For example, various types of medical devices include, but are not limited to, infusion pumps, ventilators, dialysis machines, etc. An additional type of medical device is a micro-electromechanical system (MEMS) component. MEMS is a technology used to create small or tiny devices which can be less than a millimeter in size, though they can also be larger as well. MEMS devices are typically fabricated from glass wafers or silicon, but the technology has grown far beyond its origins of the semiconductor industry. Each MEMS device is an integrated micro-system on a chip that can incorporate moving mechanical parts in addition to optical, fluidic, electrical, chemical and biomedical elements. Resulting MEMS devices or elements are responsive to many types of input, including pressure, vibration, chemical, light, and acceleration. The MEMS components can be a number of different elements including various types of pumps, a flow valve, a flow sensor, tubing, a pressure sensor or combinations of elements.

Figure 53:
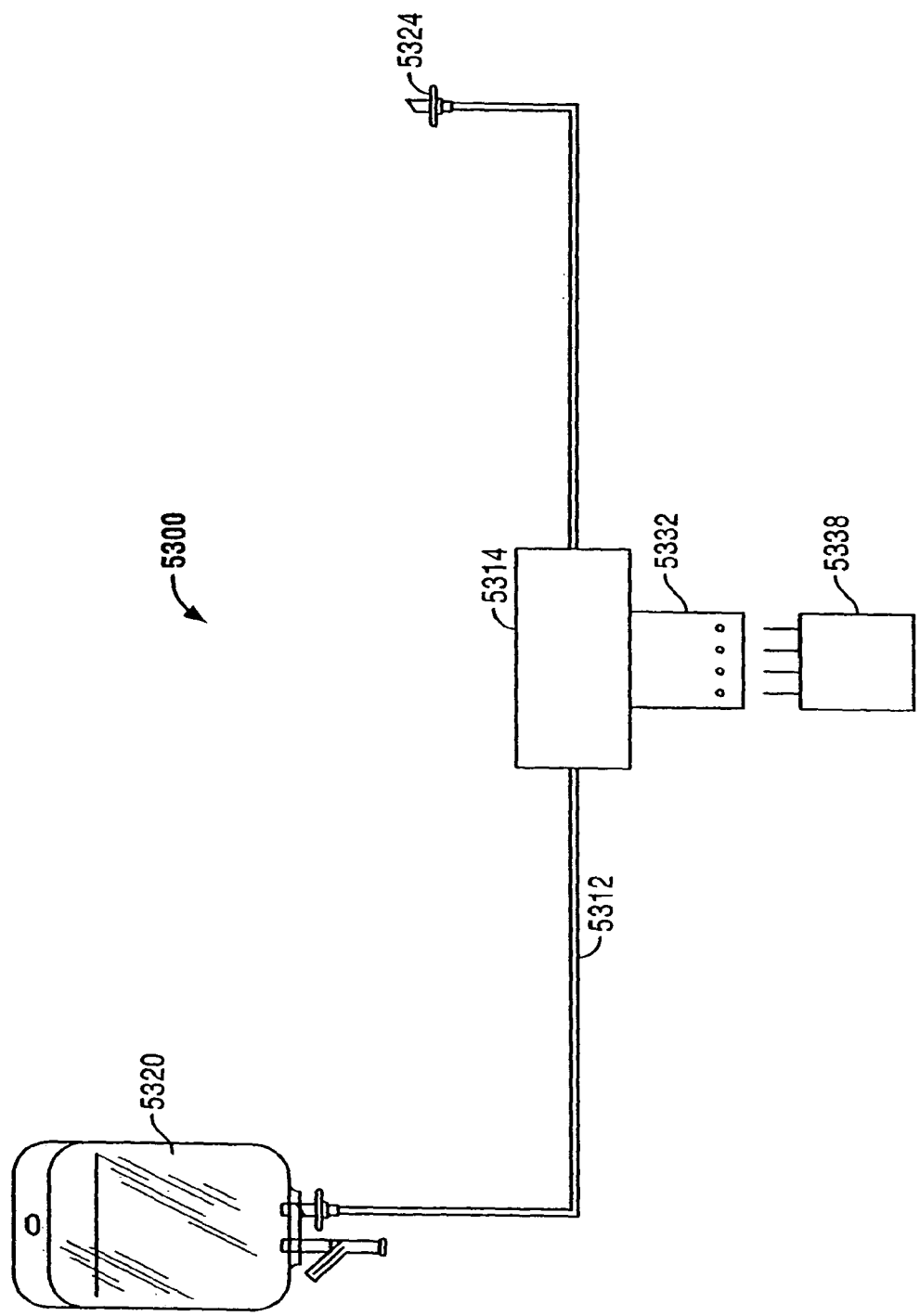
FIG. 53 is a schematic diagram of a flow control system where a micro-electromechanical system (MEMS) element is connected to a line set.

Accordingly, as explained in further detail below, one use of a MEMS component is as an in-line MEMS pump 5314, shown schematically in FIG. 53. The MEMS pump 5314 is capable of pumping fluid contained in the IV bag 5320 through the tube 5312, out through the access device 5324, and into a patient.

The MEMS component has a MEMS local electronics element attached thereto, and the MEMS electronics element connects with an external, durable MEMS controller, which can communicate with the present system 210 as does the present infusion pump 120 described herein. In one embodiment of a MEMS pump 5314, the MEMS electronics element 5332 is embedded therein and can preferably store MEMS parametric operational information. The MEMS controller, with its electronics and power source, may be physically or wirelessly connected to the MEMS electronics element. In one embodiment, the parametric operational information may be loaded from the detachable MEMS controller 5338. Preferably, the pump element 5314 generates the fluid flow through a tube 5312 based on information stored locally within the MEMS electronics 5332. This information is preferably downloaded from a wired but detachable MEMS controller 5338. Further, the MEMS components may communicate with the system 210 via wireless communication. Additionally, the MEMS controller may provide a transfer of information to and from the system 210 to fully automate the control and interrogation of the MEMS components in the present system 210 through a wireless or wired communication path.

The use of MEMS or other emerging economical fabrication techniques provides an opportunity to add a MEMS element to a disposable line-set that provides additional functionality such as pumping, valving, and sensing. Some or all of the supporting local electronics could be included in a disposable portion of a line-set as well. For example, it may be preferable to include a memory chip that contains calibration information for a pump, pressure sensor and/or flow sensor, valve, or a combination of disposable elements.

Disposability is desirable as it removes the need for costly sterilization of the components of the system between each subsequent application.

Pop-Up Windows

In an embodiment, the system can automatically provide clinicians with information associated with one or more medications via pop-up windows. Preferably, a medication table is entered into the central database 108*b*. The medication table can include the generic name of one or more medications, and any trade names associated therewith. Linked to each medication within the medication table are respective messages for display via pop-up windows. The messages can be defined by the health care facility, or predefined by the system provider.

Preferably, the messages associated with each medication pertain to: 1) hazards associated with the medication, such as in handling or exposure thereto; 2) how the medication is to be administered by a clinician; 3) physician reference information about medication; 4) the appropriate pump channel for infusing the drug; and, 5) warnings about infusion set procedures such as opening a roller clamp for a piggyback infusion.

The pop-up windows are displayed when a medication is selected or entered into a computing device such as: when the medication is being ordered by a physician via the CPOE; when the medication is being processed by the pharmacy or the like; and when the medication is being administered to a patient by a clinician. In an embodiment, when the selection or entry of a medication has been made on a computing device at a remote location, the database within the central system 108 is accessed wherein at least one of the pop-up window messages associated with the medication is provided to the remote computing device for display to the clinician.

Preferably, at least one of the pop-up window messages associated with a medication is provided for display upon the initiation of a specific step in the medication order, process, and administration procedure. For instance, upon entry of a medication order into a computing device such as the CPOE, a pop-up window is displayed with a message regarding physician reference information about the medication and, in an embodiment, another pop-up window can be displayed regarding hazards associated with the medication. Then, upon processing of the order by a pharmacy or the like, one or more pop-up windows are displayed on a computing device within the pharmacy 104 for providing general information about the medication, and possible hazards associated therewith. Next, when the order is being administered by a clinician, one or more pop-up windows are displayed on a computing device associated with the clinician (i.e., handheld 118) for providing information about administration of the medication, and, in an embodiment, possible hazards associated with the medication such as how the medication is to be handled.

Preferably, the pop-up windows displayed on a computing device are specific to the step in the medication order, process, and administration procedure that is being carried out by a clinician. For instance, the pop-up window containing physician reference information is preferably not displayed to the nurse, via handheld device 118. Nevertheless, in an embodiment, the user or hospital can define when, and if, a pop-up window should be displayed when a medication is selected or entered into a specific computing device.

It is also preferred that the pharmacy define when, and if, a pop-up window is to be displayed. For instance, pop-up windows are preferably not displayed for common medications. Instead, pop-up windows are preferably displayed for medications wherein the pharmacy or healthcare facility believes that the additional information within the pop-up window will assist in the ordering, preparing, or administration of the medication.

Administering a Medication

A method of administering a medication 124 with the infusion system 210 is described below. The method includes the ability to modify the infusion order. The modifications include modifications to the flow rate, the infusion site, temporary stops to the infusion, restarting the infusion, and hanging a new medication 124 container. The method includes: scanning a bar code associated with the patient 512*b*; scanning a bar code associated with the medication 512*a*; if the infusion is an admixture, validating the expiration 512*c*; selecting a reason for the modification 1002*d*; and recording the remaining volume of the infusion bag or accepting the value calculated from the previous volume and flow rate 1002*e*. The validation of the expiration 512*c* of the infusion bag can include the use of an admixture table and/or a bar code.

The reason for the modification may come from a defined table 546*g*. The reason for the modification may also include a hard-coded value for physician-ordered changes. When the hard-coded value is selected, the clinician 116 is prompted to select the physician from a list of physicians. The attending physician can be the default in the list of physicians. There may be a quick select feature to halt the administration of the medication 124, for example, stop order 1002*f*. If the quick select is not chosen, the following processes can be included: recording the flow rate and/or accepting the previous value for the flow rate—the previous value is displayed on the digital assistant display 118*a*, the infusion pump display 120*c*, and/or the medical cart 132 comparing the previous flow rate to the ordered flow rate—this comparison can be accomplished by using infusion system 210 or subsystem rules and tolerances; displaying appropriate messages; conversions between flow rates and drip rates can be displayed 1012—the conversions can be calculated based on infusion system 210 defined drip-rate conversion tables 548*f*. The infusion system 210 typically uses descriptions based on the tubing used to make it easy for the clinician 116 to select the correct drip rate conversion.

Changing the flow rate triggers the infusion system 210 to validate the expiration of the infusion bag(s) based on scheduled flow rate. If the solution expires before or during the administration, a message is sent to the clinician 116, such as "This solution will expire during the scheduled administration period. Please contact the pharmacy." If it is a premixed infusion bag and/or a customized infusion bag, the expiration is validated by parsing the scan code, if possible. The previous infusion site is accepted or a new infusion site location is selected from a list or a graphical anatomical representation. Then the schedule 704 is recalculated to implement pharmacy restocking. Infusion system 210 can include biometrics for identifying patients and clinicians 116.

Prior to allowing a clinician 116 to access the infusion system 210, the infusion system 210 accesses information related to the identity of the clinician 116. The infusion system 210 can identify the clinician 116 by using a device, such as a bar code reader, to read the clinicians' badge 116*a*. The system can also use biometrics to positively identify the clinician 116, to assure the clinician is an authorized user of the system, and to determine whether the clinician 116 has authority to access portions of the infusion system 210. The infusion system 210 can require a combination of the clinician badge 116*a*, or other key, and a verified biometric match in order to grant the clinician 116 access to the infusion system 210. The system can also be configured to terminate access to the infusion system 210 when the clinician badge 116*a* is removed from the vicinity of the device used to read the clinician badge 116*a*, or other key.

Biometrics is the technology and science of statistically analyzing measured biological data. One field of biometrics is that of determining unique physical characteristics, such as fingerprints. Biometrics makes it possible to identify individuals to digital systems, such as infusion system 210. A digital persona is created that makes transactions and interactions more convenient and secure. Biometric features for identification include features such as, but not limited to, fingerprint, face, iris and retina scanning, and voice identification. Biometric devices include a scanning or reading device, software to convert the scanned information into a digital format, and a memory to store the biometric information for comparison with a stored record.

Software identifies specific matched points of data that have been processed with an algorithm and compares the data. Unlike passwords, PIN codes, and smartcards, the infusion system 210 biometrics cannot be lost, forgotten, or stolen. The biometric scanner can be associated with the device for reading the clinician's badge 116*a*. For example, the biometric scanner can be a thumb print reader on the handle of a bar code reader. In other embodiments, the biometric scanner and an electronic key reader can be located on the portable medicine cart and/or the medical device. When the clinician 116 places the electronic key within a specified distance of the medical device, a processor will know the specific individual electronic biometric identification file it should expect. The infusion system 210 preferably prompts the clinician 116 to scan his biometric information.

The biometric information is entered into the infusion system 210 with some type of biometric reading or scanning device. A one-to-one comparison is made between the scanned biometric information and the previously stored specific individual electronic biometric identification file.

This one-to-one identity comparison is more efficient than comparing one-to-many identity files because it does not require searching an entire clinician database for a match. Instead, only one specific comparison is made. If there is a match, then the clinician 116 is granted access to the medical device 332. If there is no match, the clinician 116 is denied access.

Additionally, in another embodiment, the medical device does not have a controller. For example, the medical device may be a pumping unit that does not have a controller, but rather merely accepts control signals from a separate controller. In one embodiment, the controller for such a medical device can be the first central computer 109. Accordingly, the first central computer 109 may send control signals directly to the medical device for controlling the medical device.

In another embodiment, after the infusion system 210 grants access to the clinician 116, the infusion system 210 terminates that access when the electronic key is removed from the biometric scanner, or the vicinity of the biometric scanner. The vicinity within which the electronic key must be kept can be predetermined and/or may be a variable and programmable infusion system 210 parameter.

In one embodiment, the infusion system 210 includes an encrypted digital fingerprint template, a clinician's name, a login name, and a password. One technology for implementing the clinician identifier includes "IBUTTON 400" technology from Dallas Semiconductor technology. The infusion system 210 can be activated when the clinician places a finger on a fingerprint scanner. If the infusion system 210 finds a match, the infusion system 210 can request the clinician 116 login to the infusion system 210. If the infusion system 210 does not find a biometric match, the system does not allow the clinician 116 to access the infusion system 210.

In another embodiment, the database storing biometric information can be kept in the central system 108, the pharmacy computer 104, and/or the treatment location 106. At the treatment location 106, the database can be maintained in the portable cart 132, the digital assistant 118, and/or the medical device 332. Such distributed databases allow access to remote devices even if the network 102 is unable to communicate between the various locations. When network 102 communication is reestablished, the remote and central databases can be synchronized with any information modified at the other location so that both infusion system 210 databases are properly updated.

The infusion system 210 provides a closed loop infusion therapy management system. The closed loop begins with a clinician 116 order. Among other methods, the clinician 116 can enter the order through digital assistant 118 and/or medical treatment cart 132. The order is then available in real-time for pharmacy authorization 508 and physician authorization 510.

The order is available in real-time as an electronic medication administration record (eMAR). The eMAR is available to the clinician 116 for infusion administration. The infusion system 210 automatically documents medication administration 512 and modifications 514 such as flow rate changes 1002b. Through the process of medication administration 512, the infusion system 210 simultaneously adjusts infusion system 210 and/or subsystem inventory and billing 518. The infusion system 210 also provides event management and decision support data. The infusion system 210 is device independent, meaning that it can be run on workstations, wireless tablets, and handheld digital assistants 118. The infusion system 210 generally runs in real time, however, batch processing and or messaging can be used to coordinate various stages of the infusion system 210 processes.

The closed loop infusion therapy management system includes infusion order entry 560, order preparation 506, and the availability of the status of the infusion. Infusion order entry 560 can be through a number of means such as, but not limited to, the prescription entry module 324, the prescription modification module 336, and the pharmacy interface 316. Computer screen 400 can be employed in entering the infusion order. The status of the infusion provides patient 112 specific usage of infusions and alerts the pharmacy of the need for additional infusion bags.

Clinician Interaction with the Infusion System

Further, the infusion system 210 can use a login system to determine if the clinician 116 has access to the infusion system 210. One example of an interface screen of a login system for an infusion system 210 is shown in the login screen 1903 of FIG. 19. In that interface screen, the clinician 116 enters both a user name and a password, and clicks on the "Login" key.

Figure 20:
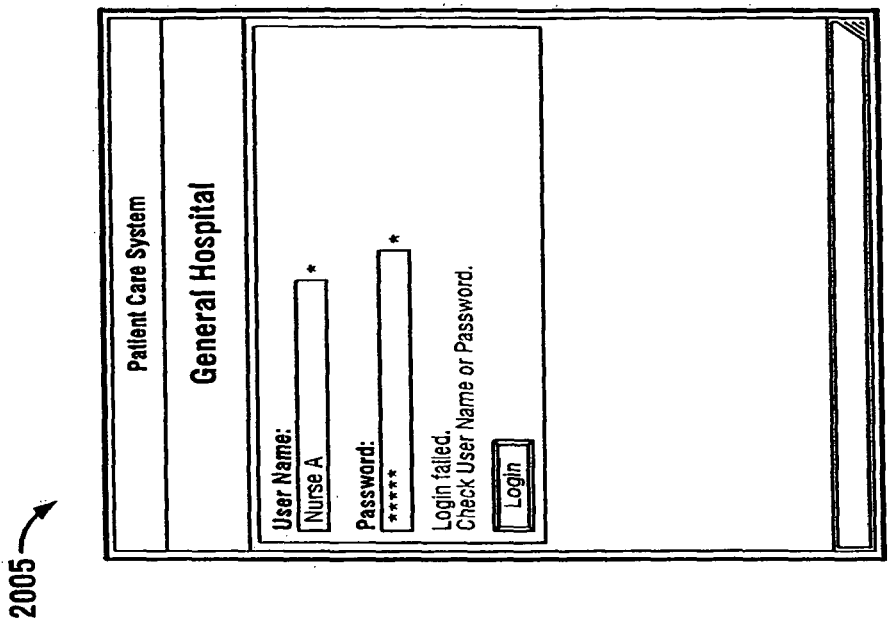
FIG. 20 is a view of another interface screen of the login process of FIG. 19.

The system 210 conducts a check to confirm that the user name and password are valid for the system 210. If either the user name or the password is not valid, the system 210 will inform the clinician 116 that the login failed in the login screen 2005 shown at FIG. 20. The clinician 116 will then have the opportunity to reenter the user name and password to correct any errors.

If the user name and password are valid, the clinician 116 will have access to the system 210. Additionally, if the clinician 116 is logged in to a digital assistant 118, but does not use it for a period of time, a security feature of the system 210 prevents the digital assistant 118 from being used further until the clinician 116 logs back in.

The charge clinician may also login to the system 210. As explained in detail herein, the charge clinician is generally a supervisor or some person whom the clinicians report to. Additionally, the charge clinician may be a person who assists in workflow for the clinicians, or who assists in monitoring alarm or alert conditions. Typically, the charge clinician maintains a supervisory or responsibility role over at least one unit. Thus, the charge clinician must login, with a login and password as explained above, and then select the units to be associated with the charge clinician.

Figure 19:
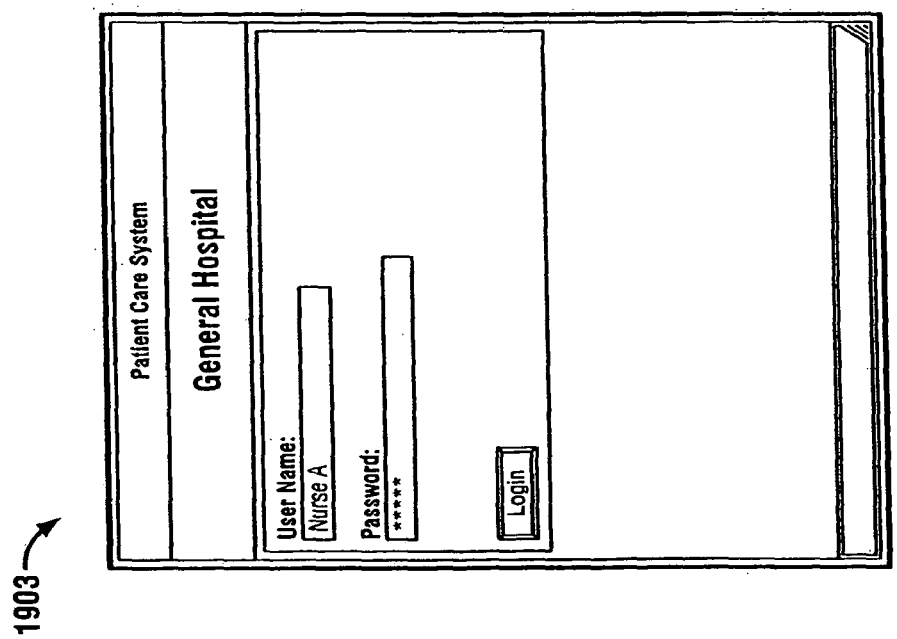
FIG. 19 is a view of an interface screen of a login process.
Figure 21:
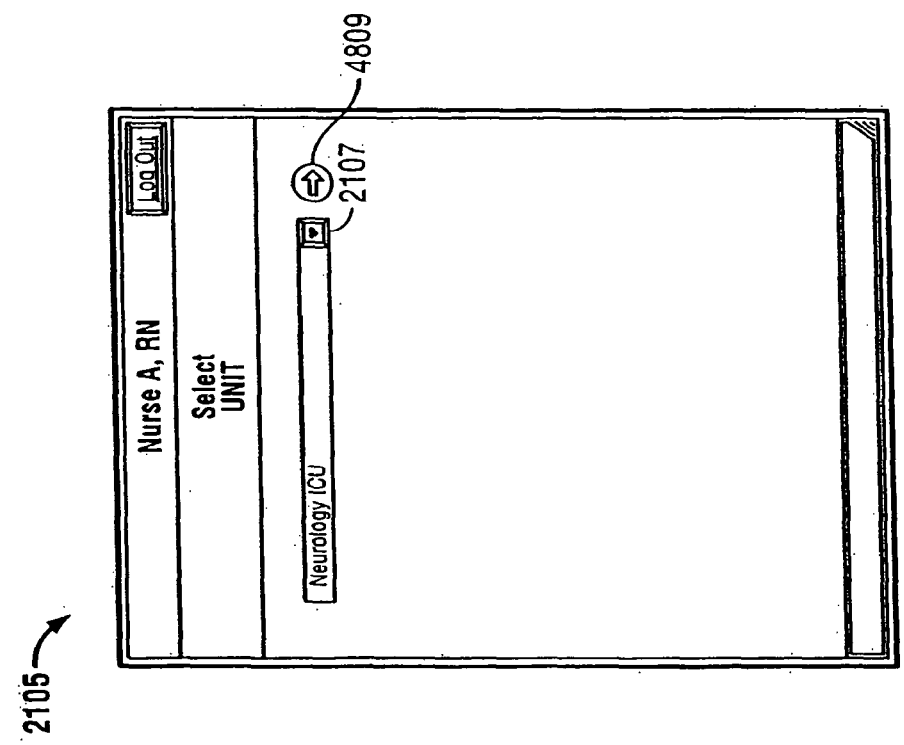
FIG. 21 is a view of a unit selection interface screen.

After the clinician 116 has completed the login process shown in FIG. 19, and has been granted access to the system 210, the clinician 116 may perform several administrative functions. One such administrative function is to select a unit. As shown in the unit selection interface screen 2105 of FIG. 21, the clinician 116 may select a unit from a drop down menu 2107. In the example illustrated in FIG. 21, the clinician has selected "Neurology ICU" as the unit. After the clinician 116 has selected the appropriate unit from the drop down menu 2107, the clinician 116 can depress the arrow key 4809 to enter the selected unit.

Figure 22:
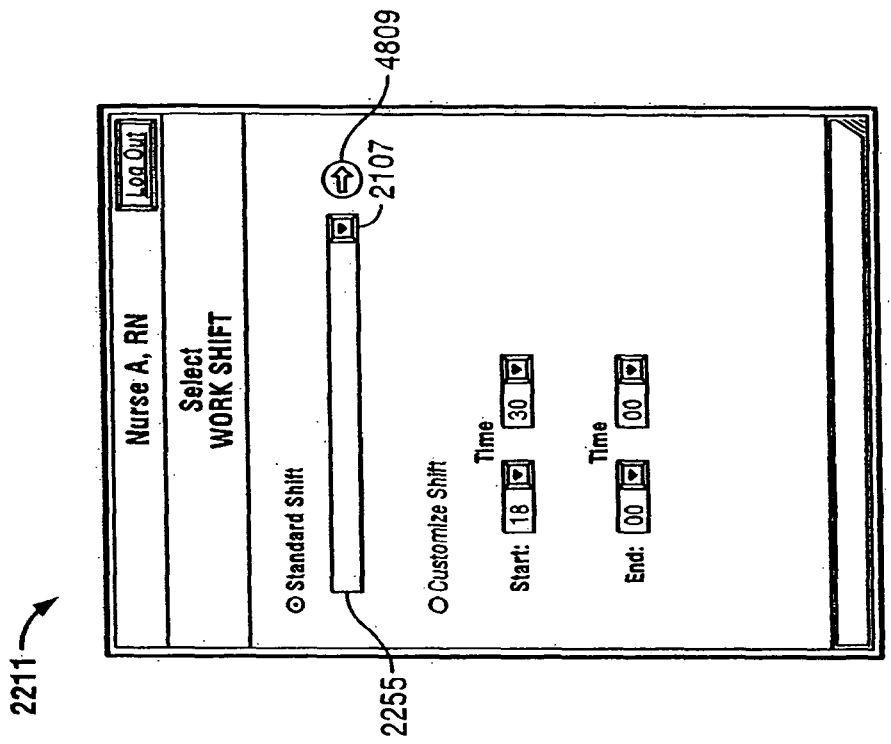
FIG. 22 is a view of a shift selection interface screen.

Another administrative function that the clinician may execute is to select the clinician's shift. As shown in select shift screen interface 2211 of FIG. 22, the clinician 116 may select either a standard shift or a customized shift. Several standard shifts which may be selected are provided in the drop down menu 2107 for that entry. If, however, the clinician 116 selects the customized shift, the clinician is requested to enter the start time and the end time for the customized shift. The clinician 116 may also enter a manual shift in the provided area 2255 and then tap the enter key 4809.

Figure 23:
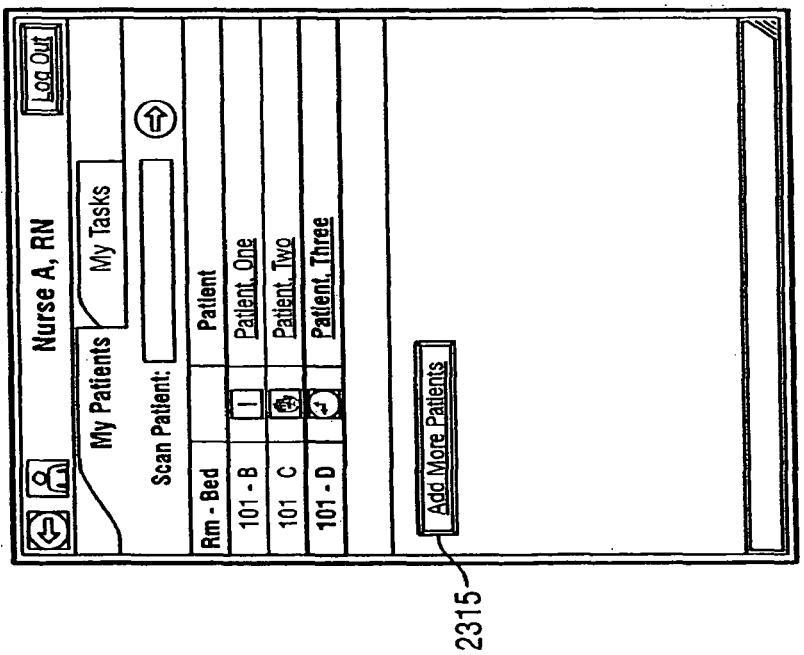
FIG. 23 is a view of a patient view interface screen.

A view patient interface screen 2313 is shown in FIG. 23. In that screen 2313, after the shift has been selected, the clinician 116 may view the patients associated with the clinician 116. The clinician 116 may also view the tasks associated with the clinician 116. Accordingly, a "to-do" list may be provided based on the patients, the clinician's tasks or both. Different levels of shading and/or coloring may be utilized to differentiate between the level of urgent care required for a specific patient. Additionally, various icons may be used in connection with the patients to provide the clinician 116 a quick understanding of the care required by a patient.

The patient view interface screen 2313 of FIG. 23 also provides the clinician 116 with the ability to add more patients at button 2315. When the clinician 116 selects the "Add More Patients" key 2315, the clinician may be provided with a list of additional patients.

Figure 24:
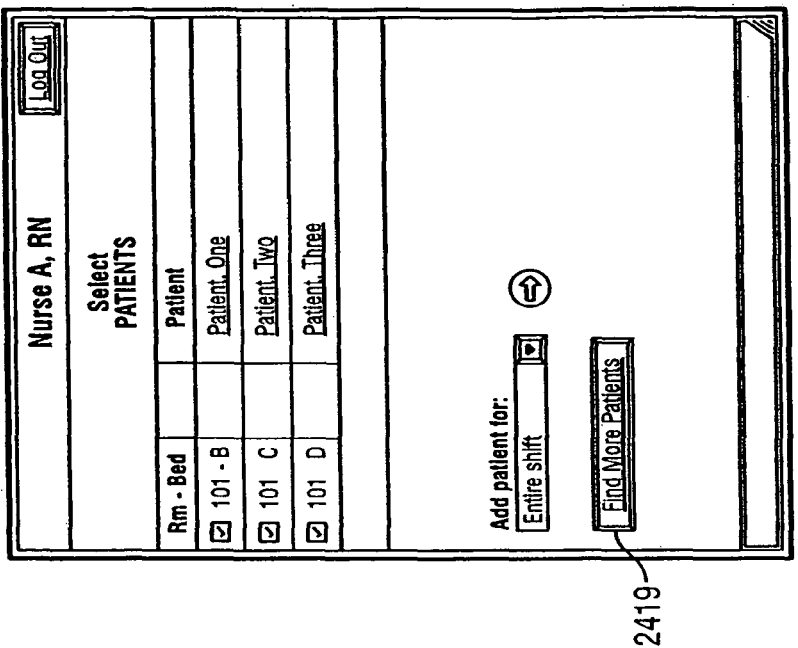
FIG. 24 is a view of a patient selection interface screen.

The clinician 116 may also be provided with a patient selection interface screen 2417 as shown in FIG. 24. At this screen 2417, the clinician 116 may select patients to be added to the clinician's shift. The patients may be from the unit associated with the clinician, or the clinician may select to add patients from different units. The clinician 116 may also select the amount of time with which they will be associated with that patient. Further, the clinician 116 may also find more patients at key 2419. It is also understood that the clinician 116 may also remove patients from a shift at any time.

The system 210 also provides messages to the clinicians 116 that are specific to the patients assigned to the clinician's shift. Typical messages may include items such as order profile changes and missed medication administrations.

A patient information menu interface screen 2521, shown in FIG. 25, is also available on the present system. The patient information menu screen 2521 provides a mini patient chart for the selected patient. The patient menu screen 2521 also provides the clinician 116 the ability to link to items relating to the patient, such as: administer medications/infusions, stop infusion, resume infusion, titrate infusion, flow rate history, pump status, and remove patient from shift. The patient menu screen 2521 also has tabs for: Allergies and Ht/Wt, Medication History, and Lab Results. An example of an Allergies & Ht/Wt interface screen 2521a is provided in FIG. 25A. Typically this screen 2521a is displayed when the mini-chart is first opened. It displays information about the patient's drug and general allergies, and the last recorded height and weight of the patient. An example of a Medication History interface screen 2521b is provided in FIG. 25B. Typically, this screen 2521b provides the clinician with a medication history of the patient within the selected look back period. The look back period may be adjusted by the clinician. Finally, an example of the lab results interface screen 2521c is provided in FIG. 25C. Lab results are made available in the system 210 through a lab interface. All available results are shown, and displayed in reverse chronological order.

An infusion schedule interface screen 2623 for a patient is shown in FIG. 26. This screen 2623 illustrates an infusion schedule for the selected patient. By clicking one of the identified orders, such as order 2625 for Morphine Sulfate on the infusion schedule screen 2623, the system 210 will link to the medication order interface screen 2627 shown in FIG. 26A. Medication order screen 2627 provides a detail of order 2625 for the specified order (i.e., Morphine Sulfate). As part of the detailed order 2625, the therapy parameters 2629 are provided, as well as any warnings 2631 and the ability to link to additional information 2633.

Figures 28, 29:
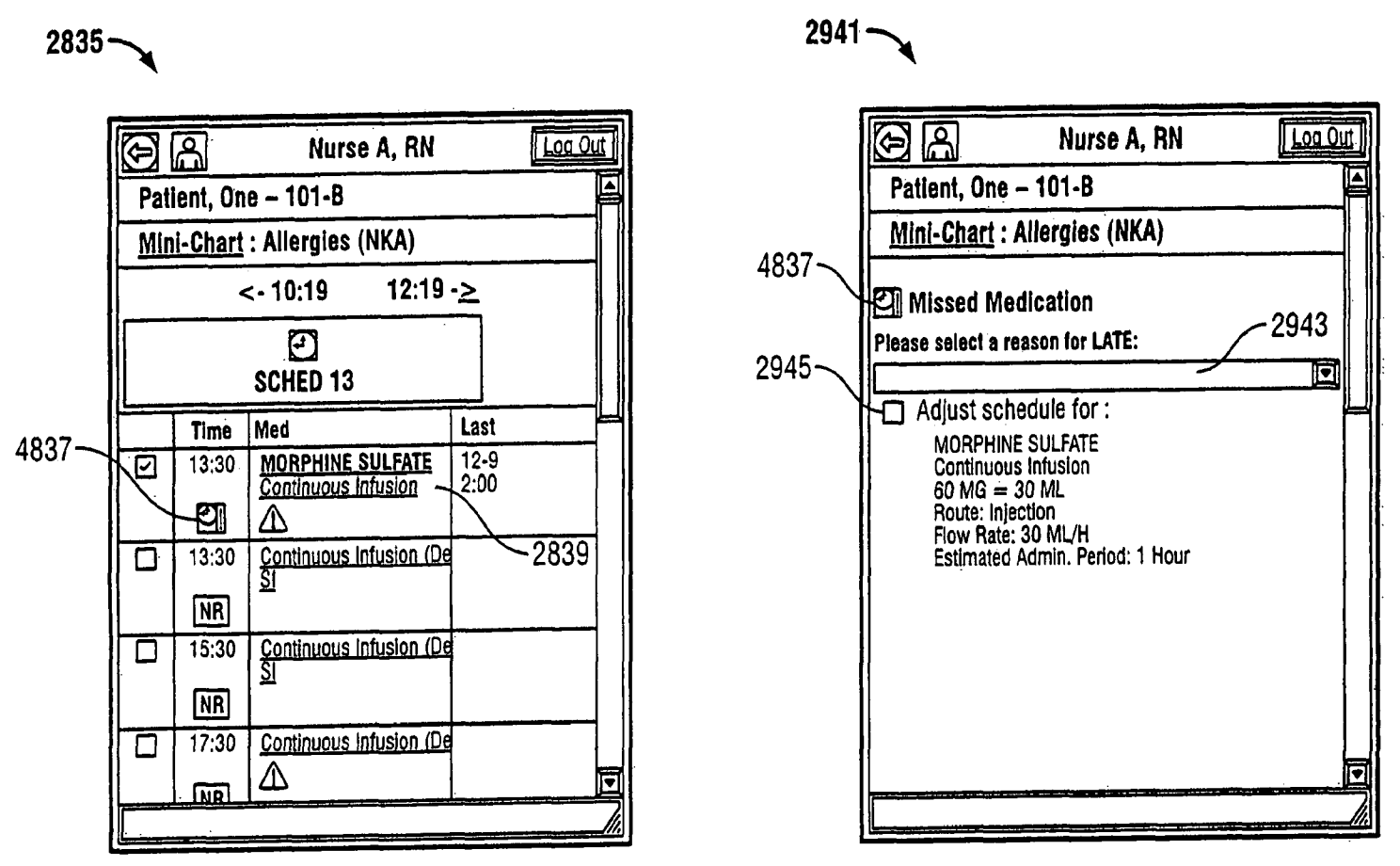
Figures 30, 31:
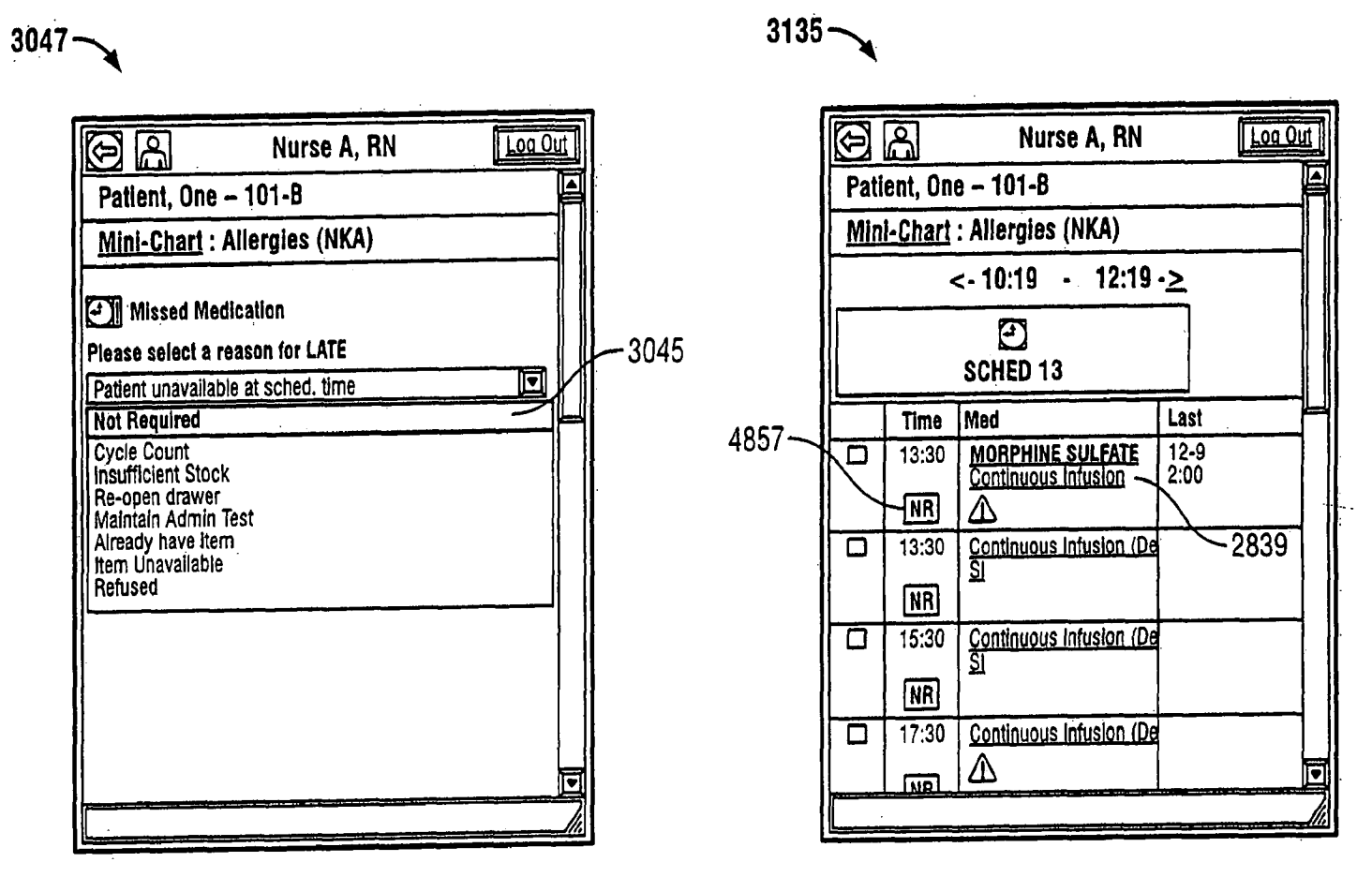

FIG. 28 illustrates a patient profile infusion schedule interface screen 2835 wherein one of the scheduled infusions was missed. As shown in screen 2835, a "missed medication" icon 4837 is shown next to the schedule Morphine Sulfate infusion order 2839. By clicking on the "missed medication" icon 4837, the system 210 links the clinician 116 to a missed medication interface screen 2941 as shown in FIG. 29. The missed medication screen 2941 requests the clinician 116 to enter, or select in the drop down menu, a reason 2943 for missing the medication. The missed medication interface screen 2941 also inquires of the clinician 116 whether the medication schedule for the order 2839 should be adjusted. To adjust the medication schedule, the clinician 116 would select box 2945 on interface screen 2941. When the clinician 116 clicks on the drop down menu to enter select a reason 2943 for missing the medication, the drop down menu will expand as shown on interface screen 3047 of FIG. 30.

Typically, if the medication is no longer needed, the clinician will select the "Not Required" reason 3045. When the clinician 116 selects the "Not Required" reason 3045 for missing the medication, the system 210 removes the missed medication icon 4837 and inserts the "Not Required" icon 4857 as shown in the infusion schedule screen 3135 of FIG. 31.

Figure 33:
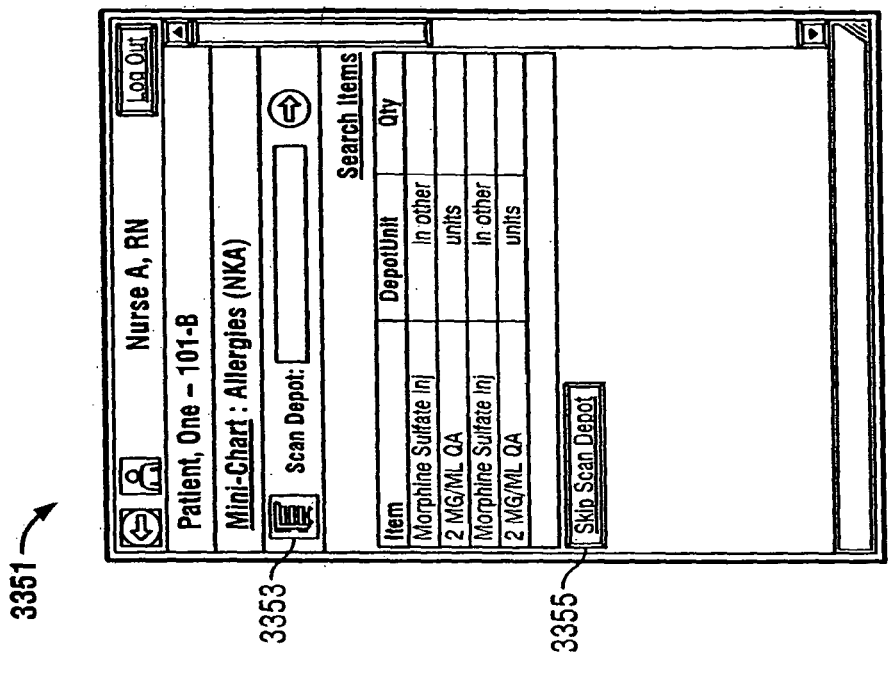
FIG. 33 is a view of a medication interface screen.
Figure 32:
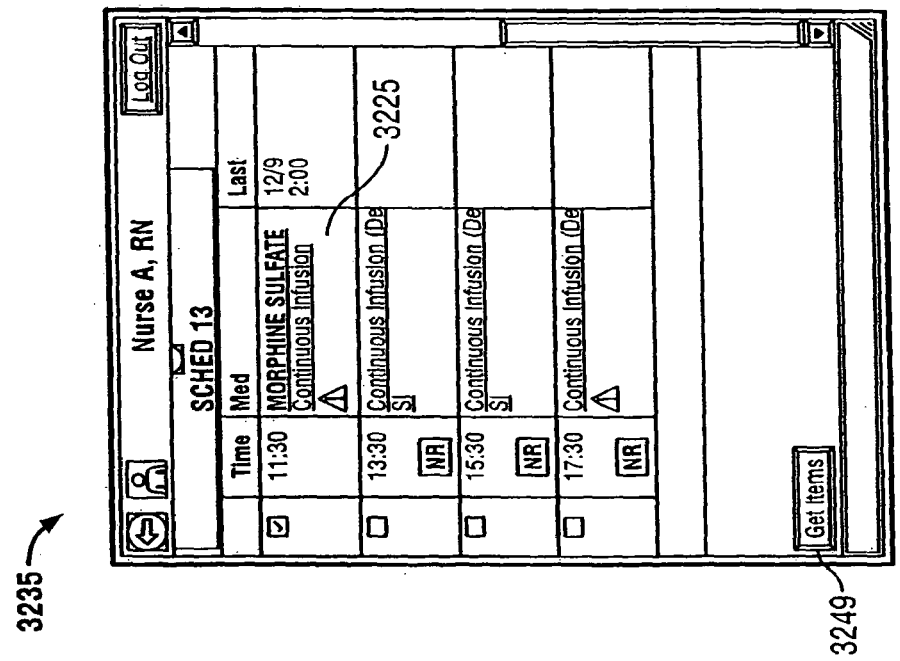
FIG. 32 is a view of a schedule interface screen.

When the clinician 116 is ready to provide a medication therapy or order for a patient, the clinician 116 will select the order 3225 in the schedule interface screen 3235, and then scroll down to the "Get Items" key 3249 as shown in FIG. 32. After the clinician 116 selects the "Get Items" key 3249, in screen 3249 of FIG. 32, the system 210 displays a medication interface screen 3351 as shown in FIG. 33. In the medication screen 3351, the clinician 116 has the ability to scan the medication selected from the medication depot as shown at the "Scan Depot" icon 3353, or to skip the scan depot block by selecting the "Skip Scan Depot" key 3355. When the clinician 116 scans an item, such as by scanning a bar code on the item, the item information is displayed on the clinician's PDA 118. An example of a scan screen 3465 is shown in FIG. 34. When, for example, the clinician 116 scans a medication, the prescription 3467 is displayed in the scan screen 3465. If, however, the scanned item does not match the order for the patient, a scan error screen 3569, such as shown in FIG. 35 will be displayed on the clinician's PDA 118. As shown on interface screen 3569, when a scanning error is detected the clinician 116 will be provided with an identification of the item to request or search for as shown on screen 3569. If a bar code cannot be scanned, for example due to a smeared or damaged bar code label, the data requested by the scan can be entered manually.

If the selected medication is in the same therapeutic class as another medication that was recently administered to the patient, the clinician's digital assistant 118 displays a warning message. Similarly, if the item has already been retrieved by another clinician, the digital assistant 118 displays a message indicating such occurrence.

If the order to be retrieved is a mix-on-floor infusion, the individual ingredients are identified on the digital assistant 118 and are to be retrieved by the clinician 116. After the items are retrieved, the system 210 generates a bag ID and prompts the clinician 116 to print a label 124a. At this point the clinician 116 also mixes the ingredients. After the clinician 116 prints out the label, the label is added to the bag and it can be scanned by the digital assistant 118.

Certain orders may be either on-call or on-hold. These orders are displayed on the patient profile screen, such as interface screen 2835 of FIG. 28. Orders that are either on-call or on-hold are available for viewing only, and not for retrieval. These orders are subsequently activated as appropriate.

The scenario may also arise where the clinician 116 has an item, including a medication item, that is not being used for a patient. Referring to interface screen 3657 in FIG. 36, the clinician 116 has the ability to identify the reason for not administering a medication, such as: not being required due to a monitoring result, the patient being unavailable, or the medication being refused. If the patient is not already identified in the screen 3657, the clinician 116 can select 3661 the patient by scanning the patient or entering the patient's name. Additionally, the clinician 116 can select to return the medical item to the medication depot by keying the "Waste/Return" selection key 3663. For certain narcotics and controlled medications, two signatures (i.e., a second authorization signature typically in the form of a login and password) may be required both to initially obtain the medication, and to return the medication to the depot.

The interface screen 3657 of FIG. 36 also provides the clinician 116 with the ability to scan the patient ID to identify the patient. If the wrong patient is scanned, or if the patient ID does not scan properly, the system 210 displays a message that the scan is invalid. Further, if the clinician 116 is unable to administer the medication, the clinician will typically have to enter a reason 3659 for not administering the medication as shown in screen 3657 of FIG. 36.

Some reasons for not administering the medication are: the medication is not required due to a monitoring result, the patient is unavailable, or the medication is refused by the patient.

After the clinician 116 has already verified the patient and the item or medication, a route verification interface screen 3771 is displayed. As shown in FIG. 37, one example of a route verification screen 3771 assists the clinician 116 in verifying the route 3773, line 3775 and site 3777. The medication therapy 3778 may also be provided in the route verification screen 3771. After the clinician enters the route 3773, line 3775 and site 3777, the clinician 116 can select the compare button 4817 and the system 210 will verify that the entered data is correct.

Next, the clinician 116 can select the pump channel mode as shown in the interface screen 3881 of FIG. 38. In the pump channel mode interface screen 3881, the therapy 3882 is shown and the clinician 116 has the option to designate the therapy 3882 as a primary therapy 3884 or a piggyback therapy 3883. Each channel of the pump has the ability to operate a primary therapy in addition to a piggyback therapy. After the pump channel mode has been selected, the clinician can conduct a pump channel scan. FIG. 38A illustrates a pump channel scan interface screen 3885. In the pump scan screen 3885, the clinician 116 scans the medical device, such as by scanning a bar code corresponding to the pump channel 121 and then clicking on the arrow key 4809.

After the clinician 116 has: (a) scanned the patient, such as on interface screen 2313 of FIG. 23, (b) scanned the medication, such as on interface screen 3465 of FIG. 34, and (c) scanned the pump channel, such as on interface screen 3885 of FIG. 38A, the clinician 116 can program the infusion pump and conduct a comparison of the programmed infusion pump parameters or settings to the parameters of the pharmacy order.

Comparison of Device Settings and Orders

Figure 52:
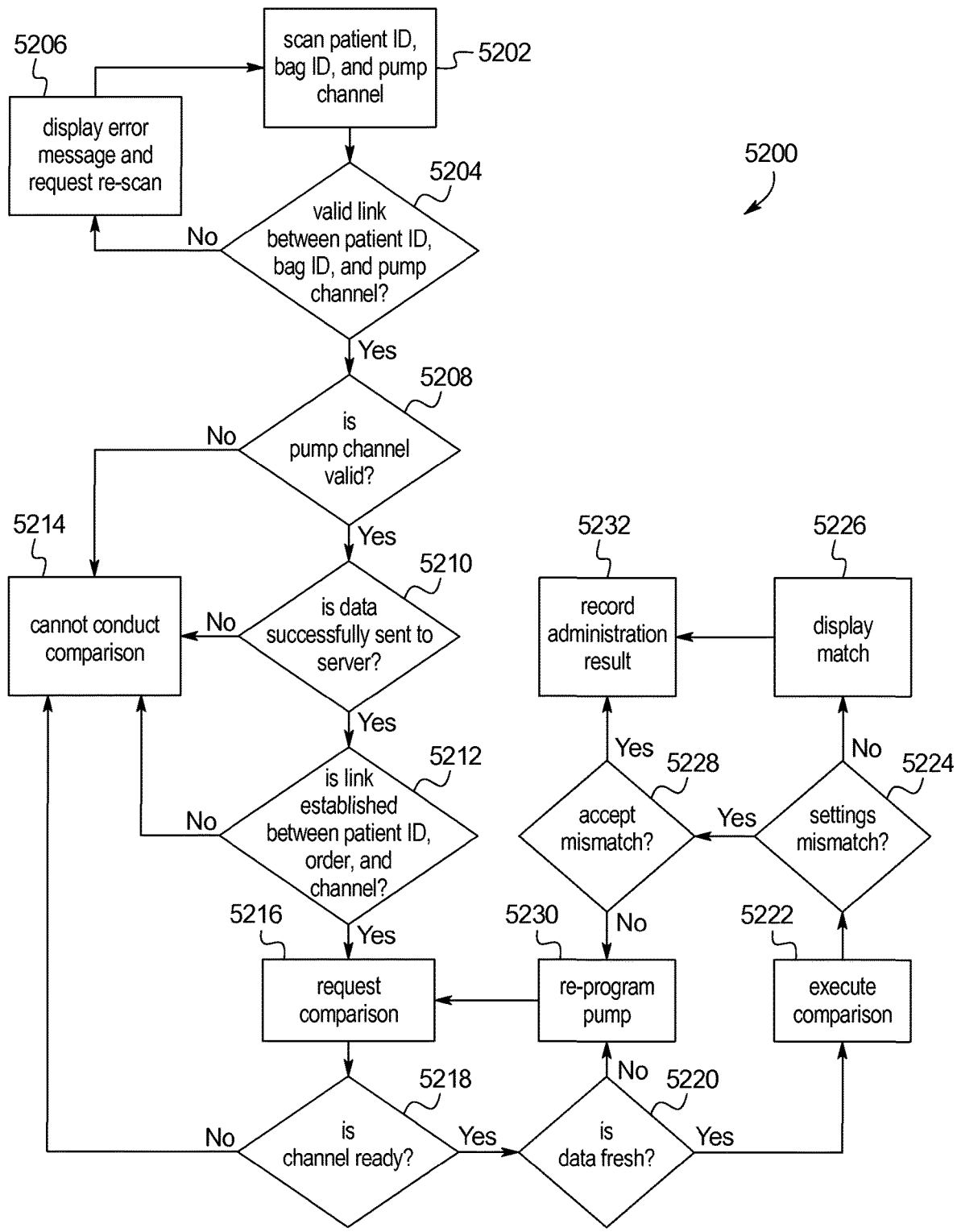
FIG. 52 is a flowchart of an order comparison process.

An exemplar flowchart of a comparison process 5200 is provided in FIG. 52. This process may also apply to programming the infusion settings remotely from the server.

Referring to FIG. 52, the comparison process 5200 is initiated at block 5202 after the clinician 116 has scanned the patient ID 112a, medication container or bag ID 124a, and the pump channel 121, as identified above. By scanning the patient, medication bag and pump channel, an association of the relevant baseline data is provided such that the system 210, and more specifically server 109, can conduct further analysis and comparison of this and additional data. First, however, the first central server 109 conducts a check at block 5204 to ensure that the scanned or entered data for the patient, medication bag and pump channel results in a valid association. If the three data items do not result in a valid association, the system 210 displays an error message at block 5206 and requests that the clinician 116 re-scan or re-enter the codes for each of the patient ID, bag ID and pump channel ID at block 5202. If the three data items result in a valid association at block 5204, the server 109 will also conduct a sequence, as explained below, to determine if the identified pump channel 121 is in the server's 109 database, and if it is available for use.

After the pump channel ID has been scanned into the system 210, the first central server 109 conducts a check at block 5208 to determine if the selected pump channel 121 is valid. Various reasons for an invalid pump channel determination is that: the pump channel does not exist in the system, the selected pump channel is already in operation, etc. If the check of the pump channel 121 results in an invalid result, an error message is displayed and the clinician is alerted that an invalid channel has been selected. Until the clinician 116 rescans the pump channel and a valid channel is recognized at block 5208, the comparison process 5200 is precluded and the system cannot conduct the comparison as identified in block 5214. If, however, the check results confirm that the selected channel 121 is a valid channel, the system progresses to block 5212 to establish the appropriate links, as explained below.

At some time during the comparison process 5200, the second central server 108a creates an XML message containing data relating to the patient ID and order ID. As shown in the flowchart for the comparison process 5200, the XML data may be created and transferred to the first central server 109, as identified at block 5210, at any point prior to block 5212. If however, the XML data received by the first central server 109 from the second central server 108a is invalid or incomplete, the comparison process is precluded and the system does not allow the comparison process to proceed as shown in block 5214. Conversely, if the XML data relating to the patient ID and order ID is complete and valid, after the first central server 109 receives the XML data from the second central server 108a, the comparison process 5200 progresses to block 5212.

At block 5212 the first central server 109 attempts to establish a link or association between the patient ID, the order ID and the pump channel 121. If the first central server 109 is not able to establish a link between the identified data at block 5212, the comparison process 5200 is precluded and the system 210 does not allow the process to proceed as shown in block 5214. Further, the system 210 displays an error message that some data is missing or inaccurate, and the system cannot conduct a comparison. If the first central server 109 properly establishes a link between the identified data at block 5212, the system 210 proceeds to block 5216 wherein the clinician 116 is requested to press the compare button 4817 on the digital assistant 118. An example of the sequence of screens occurring at block 5216 is identified below.

Figures 39, 39A:
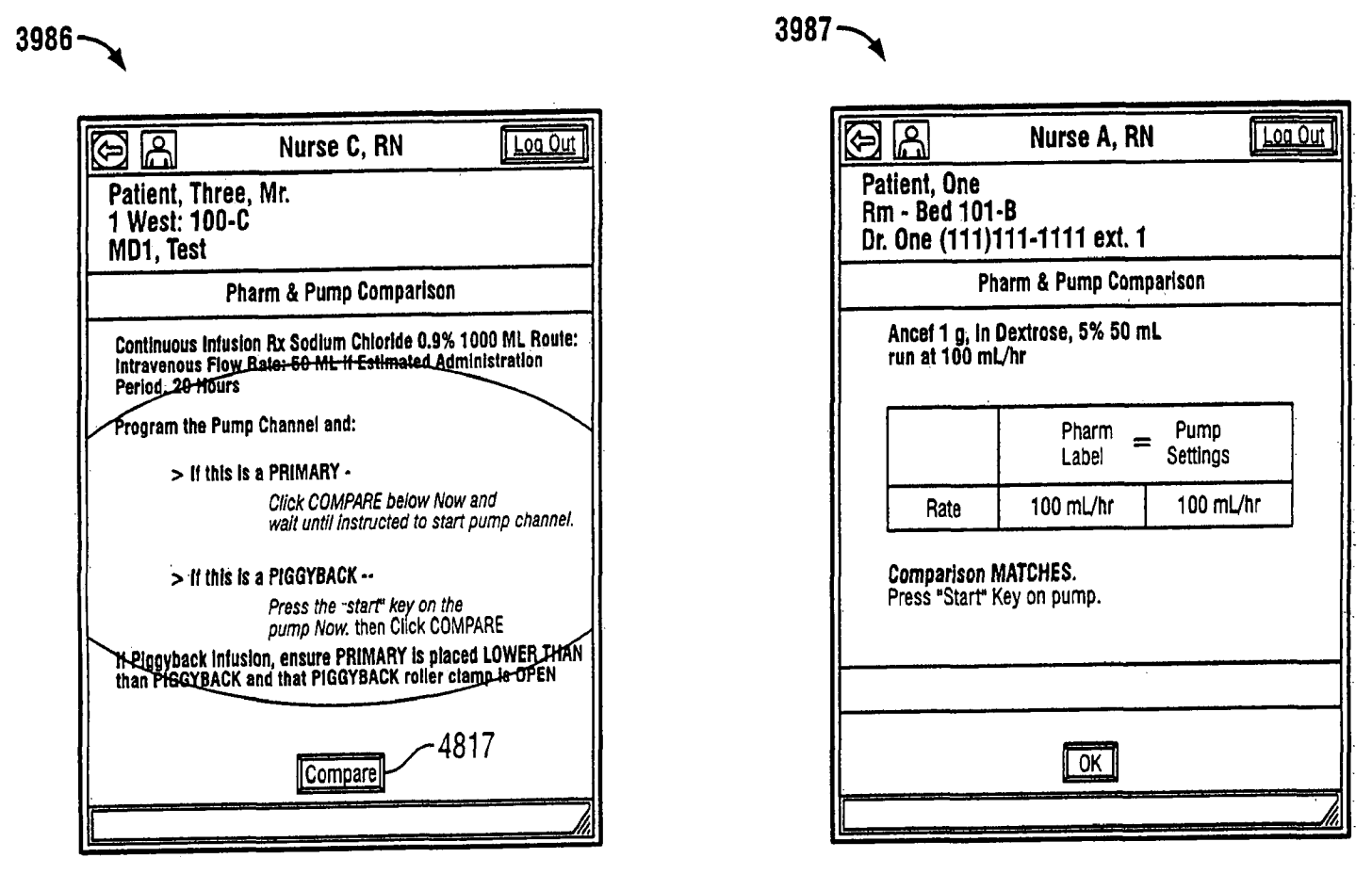

After the appropriate links have been established by the first central computer 109, the system 210 progresses to one of the comparison interface screens, such as comparison interface screen 3986 of FIG. 39. In this comparison interface screen 3986, the system 210 provides instructions to the clinician 116 to program the infusion pump prior to conducting any comparisons. Comparison may be made to ensure that the pharmacy parameters for the medication and the pump settings are in agreement. In a preferred embodiment, in the comparison process 5200 as identified herein, the system 210 conducts a rate comparison. The system may, however, conduct a single comparison or simultaneous multiple comparisons of any infusion parameter such as rate, volume, dose, etc.

Figure 42:
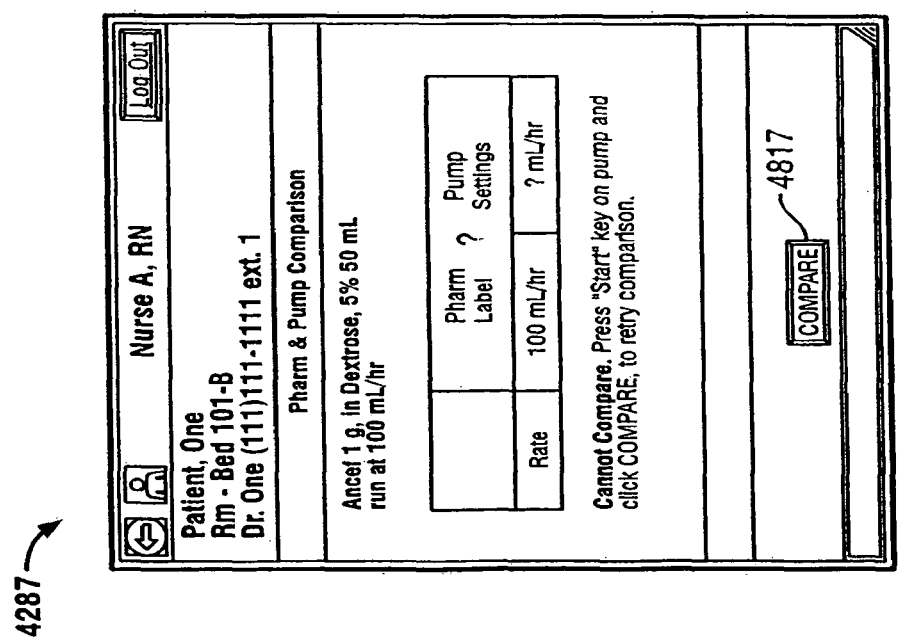
FIG. 42 is another view of a comparison interface screen.

If the infusion is a primary infusion, the instructions are provided to click the "Compare" button 4817 on the comparison interface screen 3986 and then to wait for instructions prior to starting the pump channel. If the infusion is a piggyback infusion, the instructions are provided to press the start key on the pump 120 and then to click the "Compare" button 4817. In a piggyback infusion, if the clinician 116 presses the compare button 4817 at block 5216 prior to pressing the start key on the pump, the interface screen 4287 as shown in FIG. 42 will typically be displayed providing the clinician with error instructions.

Initially, prior to conducting a comparison the system 210 polls the server 109 to ensure that the communication link between the pump 120, server 109 and digital assistant 118 is still active. If the communication link is active the comparison process 5200 proceeds. If the communication link is lost, the comparison process is not able to proceed.

Accordingly, after the clinician 116 has pressed the compare button 4817, the system 210 proceeds to block 5218 as shown in FIG. 52. At block 5218 the system 210 determines if the channel 121 is ready. For example, if the infusion has been identified as a primary infusion but the channel is already running, the system will default to block 5214 and display an error message that the system cannot conduct a comparison. Further, if the infusion has been identified as a piggyback infusion, and the start key on the pump has not been pressed, the system will default to interface screen 4287 of FIG. 42 to inform the clinician 116 to press the start key on the pump before pressing the compare button 4817.

The comparison process 5200 also checks the pump 120 to determine if the settings or operational parameters programmed into the pump 120 contains fresh data at block 5220. As an example, the system may require that the pump data have been programmed into the pump within a certain time limit (i.e., 5 minutes) prior to requesting the comparison. Such a time limit for determining if the data is fresh data can be set by the healthcare facility. If the data is not fresh data, the system will revert to block 5214 and display an error message that the data is stale. The system 210 will then request that the pump 120 be reprogrammed for the comparison process can proceed. If the data is determined to be fresh data at block 5220, the system 210 will execute the comparison at block 5222. The actual comparison of data is generally conducted at the first central server 109. As previously explained, the comparison is to determine if the parameters programmed into the pump conform with the physician's order.

Additionally, or alternatively, the pump settings can be remotely programmed by the remote controller or server. After the comparison is conducted at block 5222, the system 210 determines if there is a match or mismatch at block 5224 and returns the results to the clinician 116 via the digital assistant.

An example of a resultant comparison interface screen 3987 where the comparison results in a match is shown in FIG. 39A, and identified at block 5226 in FIG. 52. In this instance, if the pharmacy prescription parameters and the programmed pump channel settings match, the clinician 116 is instructed to start the infusion pump 120.

Figures 40, 41:
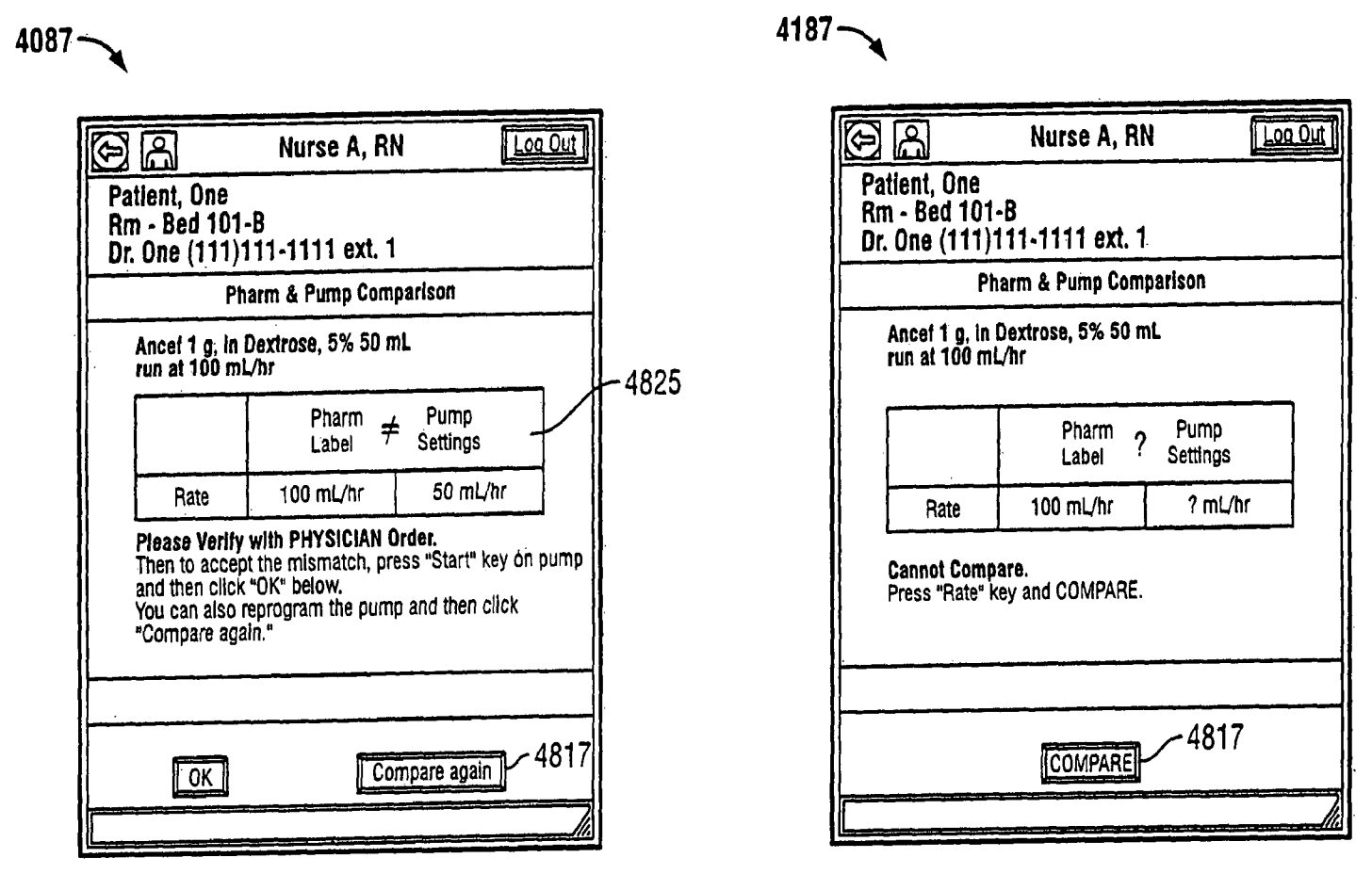

An example of a resultant comparison interface screen where the comparison of the pharmacy prescription parameters and the programmed pump settings do not match at block 5224, is depicted in the mismatch comparison interface screen 4087 of FIG. 40 with the mismatch icon 4825 shown. If this result occurs the system 210 will require the clinician 116 to either accept the mismatch, as identified at block 5228, or reprogram the infusion pump at block 5230 and conduct another comparison at block 5216. Typically, the parameters wherein the mismatch occurred will be displayed in the mismatch screen 4087. If the mismatch is accepted, it will be recorded in the system database 109 at block 5232. Further, if a mismatch is accepted at block 5228, the server 108a will navigate the clinician to the appropriate screen.

Figure 43:
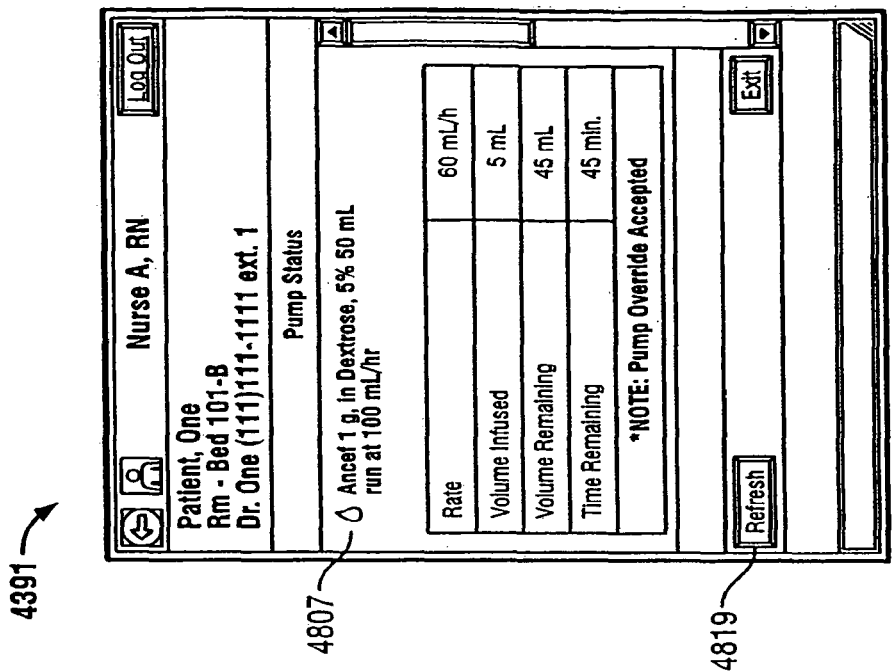
FIG. 43 is a view of a pump status interface screen.

FIG. 41 displays an example of a comparison interface screen 4187 whereby the system 210 is not able to conduct a comparison because some of the data is not available. Specifically, in the example of FIG. 41, the pump rate settings have not been entered into the system 210. Thus, the system 210 cannot conduct the comparison until additional data, such as the rate in this example, has been entered. Typically, the system 210 is not able to conduct a comparison if: an infusion is already running, the system cannot receive updated pump information, there is a system communication error, or there is missing data either from the programmed channel information or the pharmacy prescription information. Finally, the comparison screen 4287 of FIG. 42 displays another scenario whereby the system 210 cannot conduct the comparison until further steps are taken as indicated. Typically, this interface screen 4287 is provided when the infusion is a piggyback infusion, and the clinician has pressed the compare button 4817 in interface screen 3986 of FIG. 39, instead of pressing the start key on the infusion pump 120 prior to pressing the compare button 4817, as indicated in the instructions of interface screen 3986 of FIG. 39. After the infusion pump has initiated a therapy, the clinician 116 is able to view on his/her digital assistant 118 the status of the pump in a pump status interface screen 4391 as shown in FIG. 43. The pump status display 4391 displays a list of all currently active infusions for a given patient. Typically, one of five icons will be displayed in conjunction with an infusion in this screen: infusion running indicator 4807, infusion standby indicator 4810, infusion stopped indicator 4811, an unknown icon, and a delay icon. The pump status display 4391 does not update in real-time while a current screen is being displayed; however, by tapping the refresh button 4819, the most current real-time pump status screen will be displayed.

As shown in FIG. 44, the clinician 116 is also able to view a flow rate history interface screen 4493. The clinician 116 can navigate directly to the flow rate history screen 4493 by clicking on the flow rate history link on the patient menu interface screen 2521 shown in FIG. 25. The flow rate history shows the history of programmed flow rate history changes for a current infusion on a given channel. Generally, the patient information associated with the channel is displayed, as well as the current prescription information for that channel.

Further, after the clinician 116 has logged in on the digital device 118, selected the shift and selected the patients, the clinician 116 can perform a variety of tasks on the digital device 118, including but not limited to: recording an administered infusion, recording a stopped or resumed infusion, recording a discontinued infusion, viewing pump flow rate history as described above, viewing pump infusion status as described above, responding to pump alarms and alerts as described below, viewing messages/notifications and responding to messages/notifications.

Specifically, with respect to recording an administered infusion, after the clinician 116 has scanned the item bar code, the patient bar code, and the pump channel bar code, the clinician is able to compare the programmed pump settings to the pharmacy-entered order as explained in detail above. Typically, the clinician 116 will then administer the infusion using the pump 120 and record the infusion using the digital device 118.

To start an infusion, the clinician 116 typically scans the patient's wristband bar code 112a and scans the infusion bag bar code label 124a. When prompted by the digital device 118, the clinician 116 enters and compares the line, site and route for the infusion as shown in interface screen 3771 of FIG. 37. Next, in screen 3881 of FIG. 38, the clinician 116 selects a primary or piggyback infusion 3883, and scans the pump channel. The clinician 116 then programs the pumps as directed by the physician order. When the pump 120 is programmed, the clinician 116 selects to conduct a pharmacy order and pump comparison check, as shown in FIGS. 39-42. If the programmed pump settings match the pharmacy-entered order, an interface screen such as screen 4287 will indicate a match, and the clinician 116 can tap the OK button 4805 to accept the match. Finally, the clinician 116 will press the start key on the pump 120. The digital assistant 118 will then display the record administration results interface screen 4937 in FIG. 49, and the clinician 116 can enter the appropriate result from the choices in the drop-down list. These steps can be repeated for additional patients and/or additional pumps or channels.

Before administering a medication, the clinician 116 may be prompted to enter a monitoring parameter, e.g., a heart rate before administering dioxin, or a pain assessment before administering morphine. When a monitoring parameter is associated with a medication, each administration of the medication displayed on the digital assistant 118 has a link to an interface screen where the clinician 116 may enter a value. An example of such an order having a link 5001 to the entry of a monitoring parameter is shown in the order displayed in FIG. 50. After the monitoring parameter link 5001 is selected, a monitoring parameter entry interface screen 5003, as shown in FIG. 50A is displayed. There, the clinician 116 may enter into the system 210 the requested information.

Figure 51:
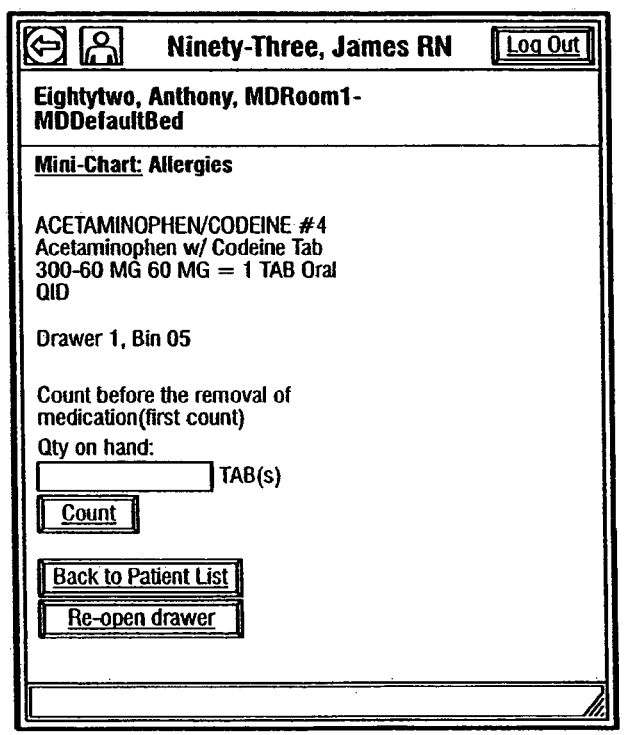
FIG. 51 is a view of a cycle count interface screen.

Additionally, the system 210 may request the clinician 116 to monitor a cycle count, typically when retrieving narcotic or controlled medications from the medication depot. As an example, when the depot drawer opens to provide the narcotic or controlled medication, the digital assistant 118 may display a cycle count interface screen 5101 as shown in FIG. 51.

This interface screen 5101 prompts the clinician to count the units of medication currently in the bin or storage area, and then to enter this data in the field provided. The system 210 then compares this quantity to the expected count. If the cycle count does not match, the digital assistant 118 displays a message indicating the mismatch, and then displays the cycle count screen 5101 again. If the cycle count does not match again, the system 210 will record the discrepancy and appropriate measures may be taken.

Figures 27A, 27B:
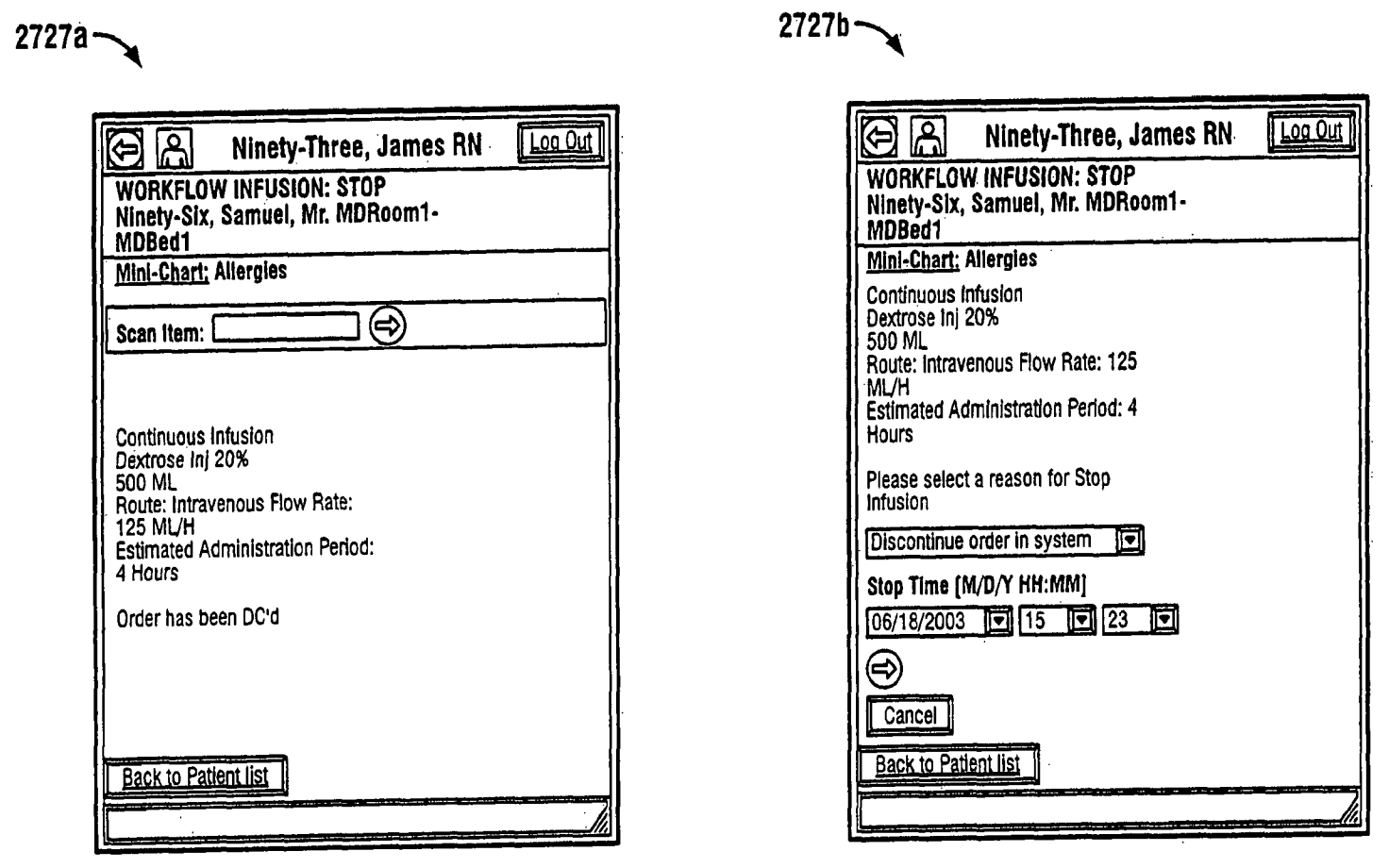

As circumstances require, a clinician may stop a running infusion before it has finished. This may be done either with or without a discontinue order in the system to stop the infusion. Infusions that have been stopped may be resumed as circumstances require, such as titrating an order. When the discontinued infusion 4813 and running infusion icons 4807 are both displayed on the digital assistant 118, the clinician 116 is instructed to navigate on the digital assistant 118 to display a list of all running infusions for the patient. An example of such a discontinue infusion interface screen 2727a is provided in FIG. 27A. In FIG. 27A the discontinued infusion order will be highlighted and indicated as being a discontinued infusion order. The clinician 116 will then scan the bar code on the solution container for the discontinued infusion, and then scan the patient's ID. Next, interface screen 2727b is provided on the clinician's digital assistant 118 as shown in FIG. 2727b. In interface screen 2727b the clinician can enter the time the infusion has been stopped, as well as the reason for stopping the infusion. The clinician 116 can then physically stop the infusion pump 120 by pressing the stop button on the infusion pump 120.

A resume infusion interface screen 2727c is provided in FIG. 27C. Infusions that are recorded as stopped, without an order to discontinue, may be resumed. To resume an infusion the clinician 116 must initially navigate to the appropriate interface screen on the digital assistant 118. By tapping on the stopped infusion icon 4811 in the patient menu, a list of all infusions currently stopped for the patient will be displayed as shown in interface screen 2727c of FIG. 27C. A prompt is provided for the clinician to select the infusion to be resumed. The clinician 116 then scans the bar code on the solution container for the infusion to be resumed. The system 210 compares the scanned ID to those for the infusions currently stopped for the patient. After the system 210 compares the ID with those that are currently stopped for the patient, the digital assistant 118 prompts the clinician 116 to scan the patient's ID. The system 210 then confirms that the scanned ID matches the patient's ID, and the system 210 will display on the digital assistant 118 the description of the scanned infusion and prompt the clinician 116 to select a facility-defined reason for resuming the infusion, as shown in interface 2727d of FIG. 27D. Once the reason is selected, the clinician 116 can restart the infusion at the pump 120 and then tap the arrow 4809 to continue. The system 210 records the infusion as having been resumed.

Figure 48:
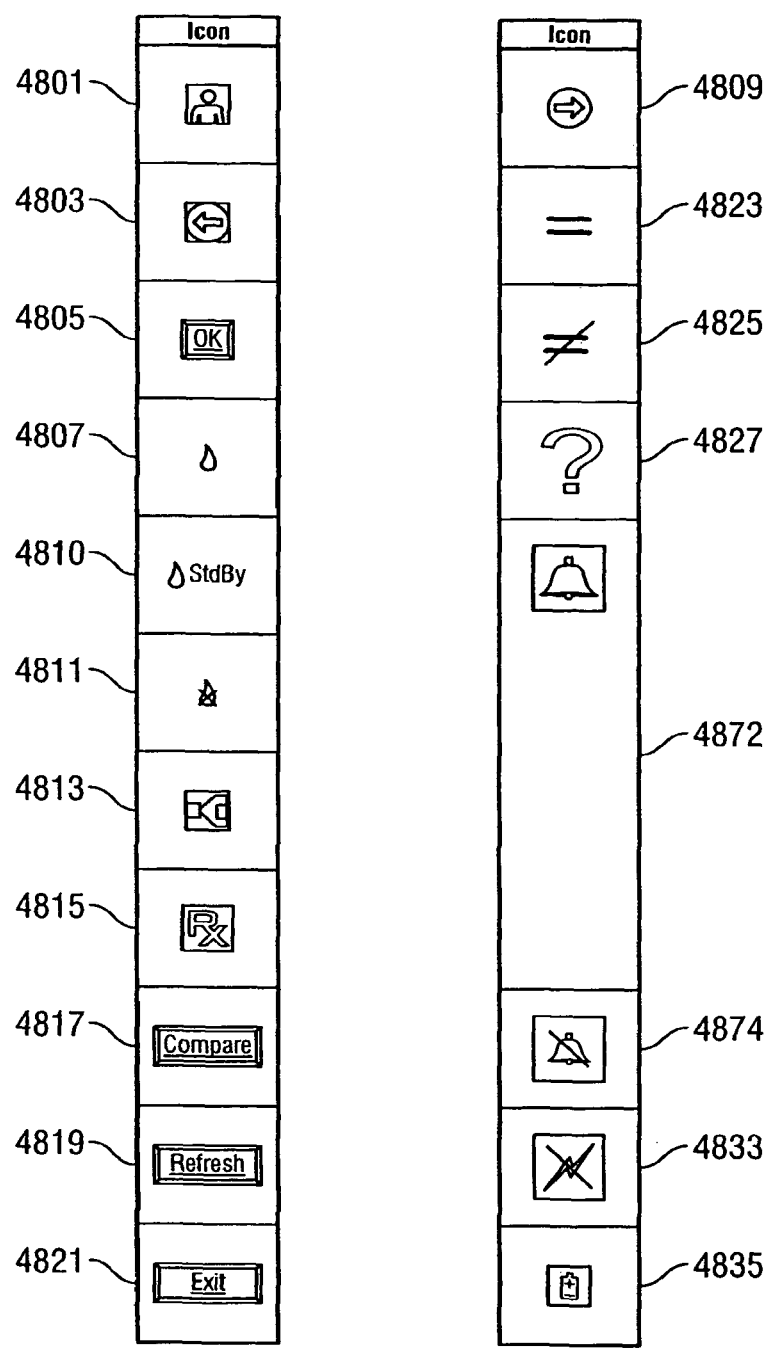
FIG. 48 is a view of a variety of icons utilized in the interface screens.

As shown in the various screen shots/interfaces for the digital assistant 118, a variety of icons are utilized to assist the clinician 116. Many of these icons are shown in FIG. 48. The patient list button 4801 is a key that, when tapped, allows the clinician 116 to navigate directly to the patient list screen, such as the patient list screen 2313 shown in FIG. 23. The back button 4803 is a key that, when tapped, returns the screen on the digital assistant 118 to the previous screen. The OK button 4805 is tapped to acknowledge data shown on the digital device 118. When the OK button 4805 is tapped the next screen is usually displayed. The infusion running indicator button 4807 indicates that a programmed infusion is now running for the selected pump 120 and channel. The infusion standby indicator 4810 indicates that a programmed infusion has been put on standby for the selected patient, pump 120 and channel.

The infusion stopped indicator 4811 indicates that the programmed infusion has been stopped for the selected patient, pump 120 and channel. The infusion discontinue order indicator 4813 indicates that a pharmacy-entered order will discontinue an infusion for the selected patient, pump 120 and channel. The physician's notes indicator 4815 indicates the presence of physician's notes for the selected patient, pump 120 and channel. The clinician 116 can tap the notes indicator 4815 to view the notes. The compare button 4817 is provided in various screens, and when tapped has the system 210 perform a comparison of the scanned item with the pharmacy-entered order, as well as additional comparisons. The refresh button 4819 is tapped to update and show the latest data on the screen. The exit button 4821 allows the clinician to exit the current screen, and return to the previously displayed screen. The enter button 4809 is also the OK button and is tapped to acknowledge and enter either data selected from choices within a drop-down list, or data manually entered in a field. The comparison match indicator 4823 indicates that programmed pump settings match pharmacy-entered order information. The comparison mismatch indicator 4825 indicates that programmed pump settings do not match pharmacy-entered order information. The cannot compare indicator 4827 indicates that the system cannot compare the programmed pump settings to the pharmacy-entered order information. The pump alarm/alert indicator 4872 indicates that an alarm or alert condition is occurring. When the alarm/alert indicator 4872 is tapped, an expanded pump alarm and alert screen is displayed. On the alarm and alert screen, a red alarm/alert icon 4872 indicates an alarm condition, and a yellow alarm/alert icon 4872 indicates an alert condition.

The alarm/alert silence button 4874 is tapped to temporarily silence the audible alert on the digital device 118. The loss of communication indicator 4833 indicates that the pump 120 and/or the hub 107 is not properly communicating with the system 210. A message accompanying this indication describes the steps to take to resolve the problem. The wireless module low battery alert indicator 4835 indicates that the hub 107 is presently running on a backup battery that has less than 30 minutes of battery power remaining.

The above disclosure relating to the setup and use of the digital assistant 118 has been discussed with respect to a clinician 116 performing these functions. It is understood, however, that these tasks may be performed by any hospital administrative or staff individual, whether or not that individual is a clinician 116.

Emergency Notification Process

Figure 12:
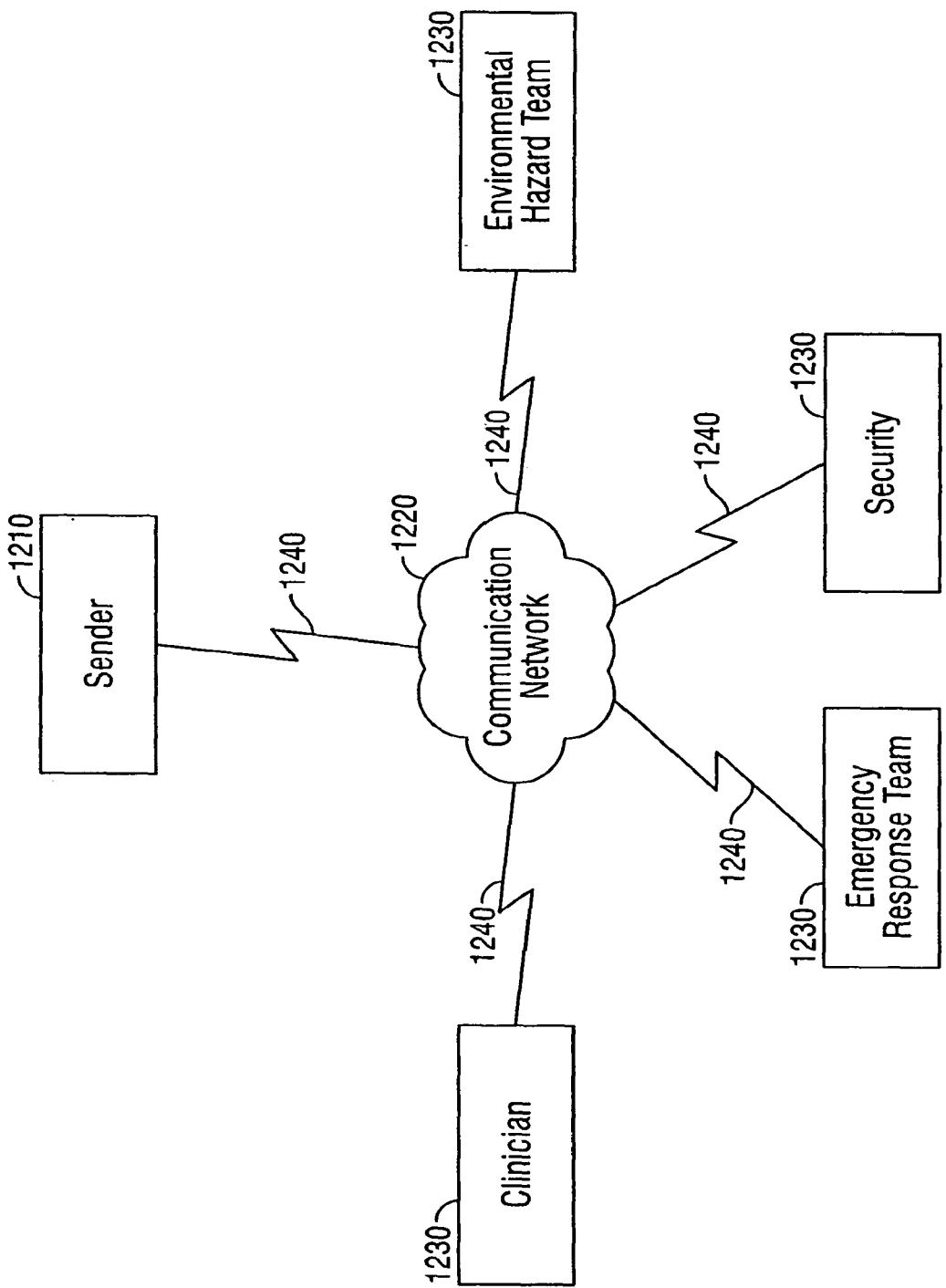
FIG. 12 is a view of an emergency notification system, illustrating communication.

Referring to FIG. 12, there is shown a preferred embodiment of an emergency notification system 1200. A notifying party 1210 is in communication with a communication network 1220. One of skill in the art will appreciate the variety of communication networks are operable including, but not limited to, an Ethernet network, a coaxial cable network, a wireless local area network, and a wireless wide area network. Additionally, a variety of communication network protocols are operable, but not limited to, Transfer Control Protocol I Internet Protocol ("TCP/IP"), Wireless Area Protocol ("WAP"), and Uniform Data Protocol ("UDP").

Additionally, the communication network 1220 is operable as a part of a larger communication network; for example, the communication network 1220 may be a wireless communication network in communication with a wired communication network existing in, for example, a hospital.

In communication with the communication network 1220 is a notifying party 1210. The notifying party 1210 may be a hospital clinician, for example, a nurse, doctor, hospital administrator, or security officer. The notifying party 1210 may also be a patient. Additionally, the notifying party 1210 may be an automated process, for example, a computer program or a medical device. The automated process acting as a notifying party 1210 may be programmed to broadcast an emergency notification across the communication network 1220 upon the fulfillment of a certain condition or an event. For example, the automated process may be programmed to broadcast an emergency notification upon the sensing of a patient condition.

The emergency notification is received by one or more target parties 1230. Target parties 1230 may be clinicians, for example, doctors and nurses. The target parties 1230 may also be an emergency response officer or security officer, or an environmental hazard team. The target party 1230 may be any individual in communication with the communication network 1220. The present embodiment provides the notifying party 1210 with the option of sending the emergency notification only to a certain target party 1230 or target parties 1230, or to all target parties 1230; the embodiment allows for the notifying party 1210 to choose which target parties 1230 receive the emergency notification.

The target parties 1230 and notifying party 1210 are in communication with the communication network 1220. One skilled in the art will appreciate the variety of modes of communication 1240 which may provide for the notifying party 1210 and target parties 1230 to be in communication with the communication network 1220. For example, the mode of communication 1240 may be a wired connection, for example, a personal computer or programmable controller. The mode of communication 1240 may also be a wireless network connection enabled through a handheld computer or a cellular phone.

Figure 13:
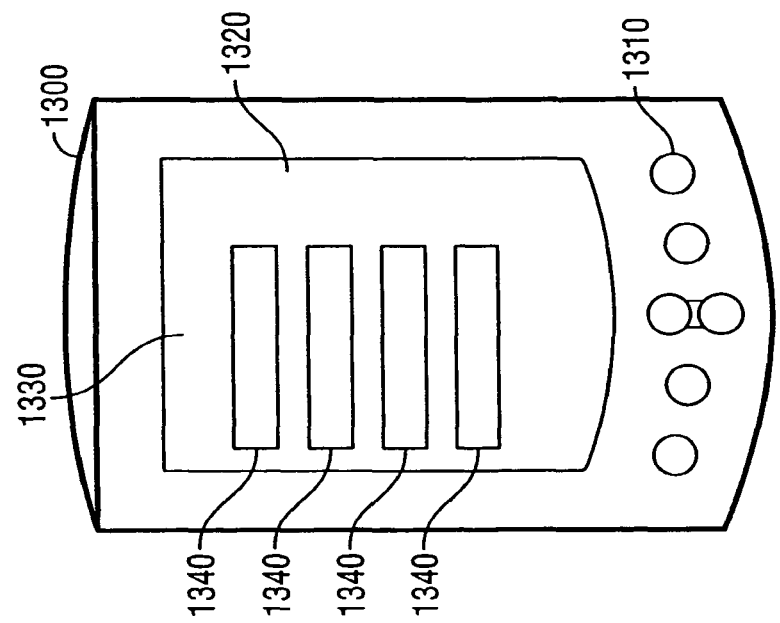
FIG. 13 is a view of an emergency notification interface from the perspective of a notifying party, illustrating the preferred notification options made available to the notifying party by the emergency notification system.

Referring now to FIG. 13, there is shown a notification interface 1300 from the perspective of the notifying party 1210. One skilled in the art will appreciate the variety of interfaces which will enable the notifying party 1210 to broadcast an emergency notification via the communication network 1220. The notification interface may be a website connected to an intranet or the Internet. The notification interface may also be activated by a cellular phone or other telephone, or by an electronic email. In one embodiment, the notification interface 1300 is a handheld computer of the type found widely commercially available and includes screen 1320. Examples include the Palm devices manufactured by Palm, Inc., the Visor devices manufactured by Handspring, Inc., the Jornada devices manufactured by Hewlett Packard, Inc., the Axim devices manufactured by Dell, Inc., the Clie devices manufactured by Sony, Inc., and the PocketPC devices manufactured by Toshiba, Inc., Compaq and Symbol.

In one embodiment, the notification interface 1300 comprises a menu 1330 listing one or more options 1340. For example, one notification option 1340 may allow the notifying party 1210 to select a specific clinician or type of clinician to be the target party 1230 of the emergency notification. Another notification option 1340 may allow the notifying party 1210 to choose to cancel the emergency notification, in the event that the emergency notification was sent erroneously. Additional notification options 1340 may include entries for patient identification information, patient location, the type of the emergency, and the expected time for response.

Figure 14:
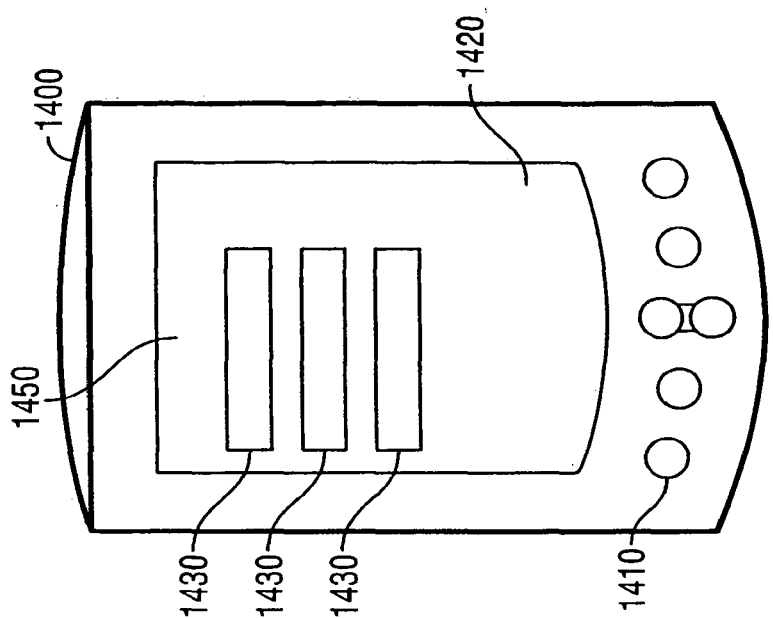
FIG. 14 is a view of an emergency notification interface from the perspective of a target party, illustrating the preferred emergency information received by the target party.

Referring now to FIG. 14, there is shown one embodiment of a receiving interface 1400 from the perspective of the target party 1230. Similar to the notification interface 1300, the receiving interface 1400 may be operable on a variety of different platforms and remain practicable under the principles of the present invention. In one embodiment illustrated in FIG. 13, the receiving interface 1400 is a handheld computer. The interface 1400 includes a screen 1420 for displaying configurable information 2350. The information 2350 may include emergency notification information such as patient identification, location of the emergency, the type of the emergency, and the expected time for a response. In one embodiment, the receiving interface includes one or more options 1430.

Both the notification interface 1300 and the receiving interface 1400 are optionally configured with a hotkey 1310, 1410. With respect to the notification interface 1300, the hotkey 1310 may be configured to send an emergency notification containing information obtained automatically from the notification interface 1300 itself. For example, pressing the hotkey 1310 on the notification interface 1300 may be configured to automatically send an emergency notification containing the information.

Messaging & Notifications, Including Alarm/Alert Notifications

The system provides for transmitting notifications and messages. Notifications may include, but are not limited to: patient status lists, alarms, alerts, infusion schedules, orders, overrides, warnings, therapy parameters, links to additional information, missed medications, route verifications, comparisons, flow rate information, physician notes, loss of communication, low battery, administration results, etc. The system also provides for displaying these and additional notifications. One way in which a notification is displayed is on the digital assistants 118. Notifications may be provided to any one of numerous clinicians and/or charge clinicians.

Figure 15:
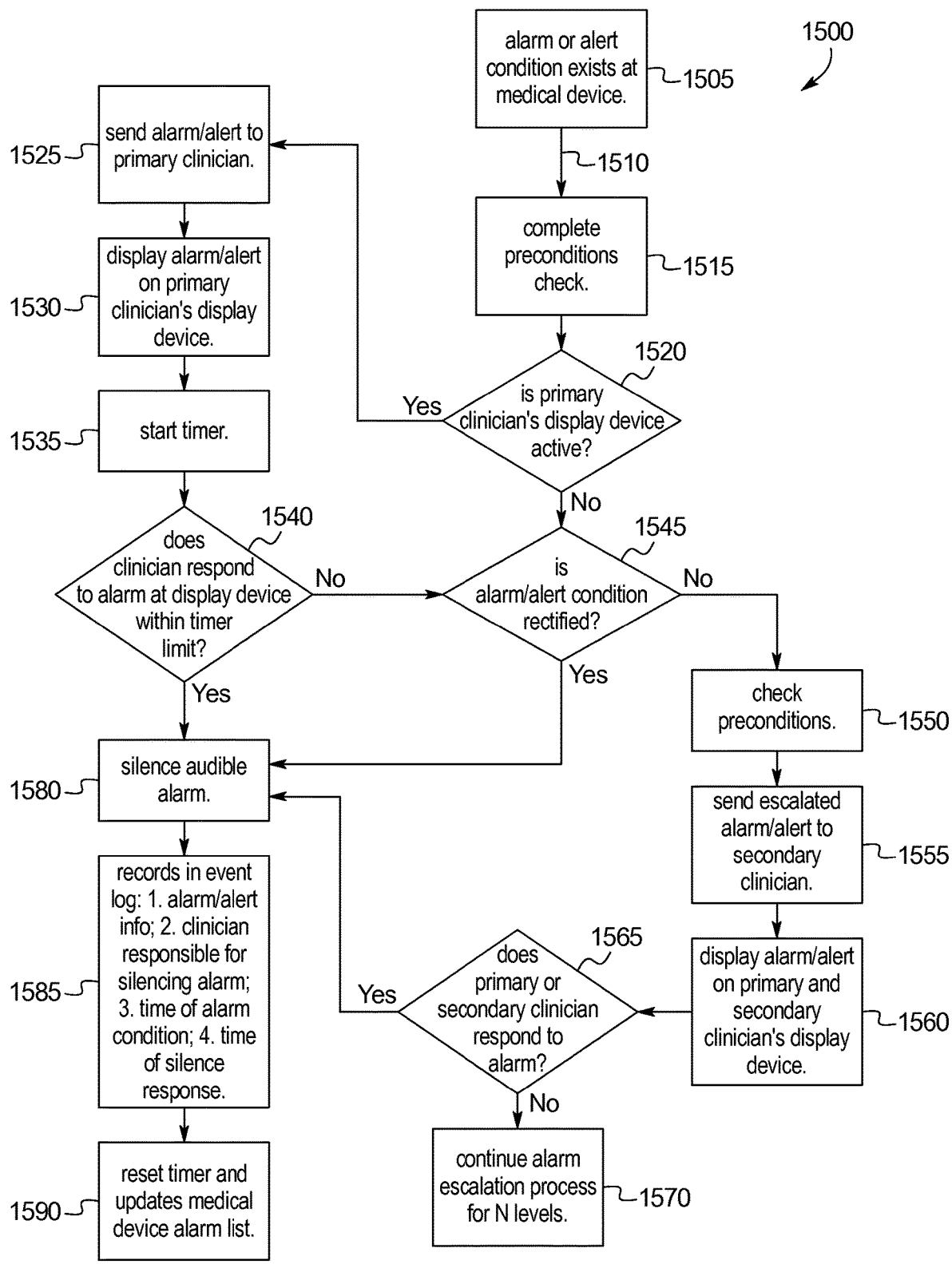
FIG. 15 is one embodiment of a flowchart of an alarm/alert escalation process.

As explained above, one type of notification is an alarm/alert notification. In the present system, notifications may be escalated. A specific alarm/alert escalation process is shown in FIG. 15. Typically, a notification process is provided to transmit notifications to any number of clinicians 116. The identified alarm/alert escalation process 1500 of FIG. 15 provides for notifying a series of clinicians via a clinician device 118 when an alarm or alert is active on a medical device such as an infusion pump 120. In a preferred embodiment, the clinician's device is a personal digital assistant ("PDA") 118, such as shown in FIGS. 1 and 3, typically having a display 118*a* and an audible tone or sound generator 118*c*. For illustrative purposes only, the clinician's device will hereinafter be identified in this detailed description as a digital assistant 118. Further, the alarm/alert escalation process 1500 provides an escalation process when the clinician fails to respond to the alarm/alert notification on the digital assistant 118. When an escalation process is started, a notification is provided to another or second clinician's digital assistant 118 as specified in the escalation procedure. While the alarm/alert notification is sent to the digital assistants 118, it is understood that typically the pump alarms and alerts can only be resolved at the pump. As explained herein, silencing of the alarm or alert at the digital assistant 118, such as in block 1580 of FIG. 15, may or may not affect the pump.

The alarm/alert escalation process 1500 commences at block 1505 when at least one or both of an alarm or an alert condition is triggered at the medical device 120. In a preferred embodiment, shown in FIG. 3, following the triggering of an alarm or an alert at the medical device 120, a signal containing data relating to the alarm or alert condition is generated and sent at block 1510 from the medical device 120, to the server 109. In a wireless environment, either a medical device 120 having a wireless transmitter is provided or a medical device 120 connected to a wireless hub 107 is provided. In the latter example, shown in FIG. 3, the hub 107 receives signals from the medical devices 120 and converts the signals into a format suitable for transmission onto the system network 102 via wireless communication path or link 128. Further, if the hub 107 recognizes that the alarm, alert or other notification is a duplicate, it may discard the duplicate notification. The transmitted signal is received by a wireless access point 114 within the healthcare environment. The wireless access points 114 provide an interface between the wireless communication paths (i.e., wireless path 128) and cable communication paths such as cable communication path 110 shown in FIG. 3.

After the server 109 receives the data relating to the alarm or alert condition, sent at block 1510, the server 109 conducts a precondition check at block 1515. The precondition check may include: associating the alarm or alert condition at the medical device 120 with a specific patient; associating the patient with a primary clinician, also referred to as a first clinician (this association may be conducted at the central system servicing unit 108a); and, associating the first clinician with that clinician's digital assistant 118. The server 109 uses the information gained in its precondition check at block 1515 to establish a relationship between the medical device 120 (and in one embodiment the specific channel 121 of the infusion pump 120) the patient, the primary or first clinician and the first clinician's digital assistant 118. It is understood that there is a many to many relationship between patients 112 and clinicians 116.

Accordingly, numerous first clinicians, numerous second clinicians, and numerous n-level clinicians may be associated with a specific patient. Further, n-level escalations are also possible within this system.

Typically, the server 108a has stored therein the patient to clinician many-to-many associations, and the patient to unit associations. The server 108a transmits these associations to server 109, and the server 109 stores these associations. Similarly, the server 108a sends the charge clinician to unit associations to the server 109 for storage.

Following the precondition check at block 1515, the server 109 determines the appropriate channel 121 to patient 112 to clinician 116 mapping. Once the mapping is complete, the server 109 determines if the first clinician's digital assistant 118 is active at block 1520. If the first clinician's digital assistant 118 is active, then the server 109 generates a signal representative of the alarm or alert condition that exist. The signal includes data such as the patient's name, patient's location, room identification, bed identification, alarm or alert type, condition description, time, date, clinician identification and/or prescription. In the preferred embodiment, the signal is transmitted from the server 109 to the wireless access point 114. The wireless access point 114 then transmits the signal relating to the alarm or alert condition via a wireless communication transmission to the clinician's digital assistant 118 at block 1525.

The signal relating to the alarm or alert condition may also be transmitted at block 1525 to a charge clinician, a secondary first clinician, or a secondary clinician. Such a signal may be transmitted via a wireless or wired communication. Further, the charge clinician may be utilizing a digital assistant 118, a desktop computer, or some other electronic device. The charge clinician is generally a supervisor or some person to whom the clinicians report.

Figures 16A, 16B:
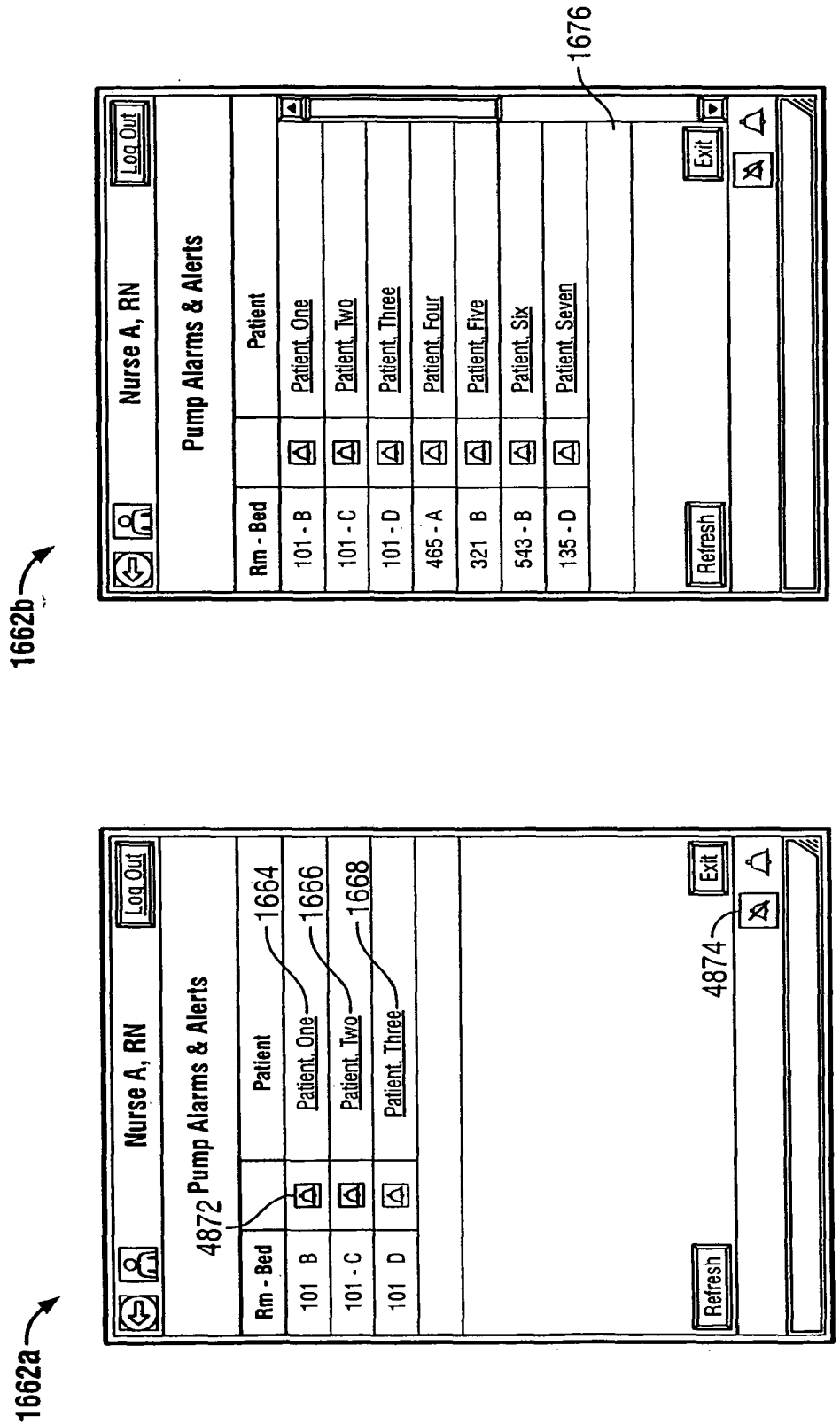
FIG. 16A is a view of an alarm/alert interface screen.
FIG. 16B is another view of an alarm/alert interface screen.
Figure 17:
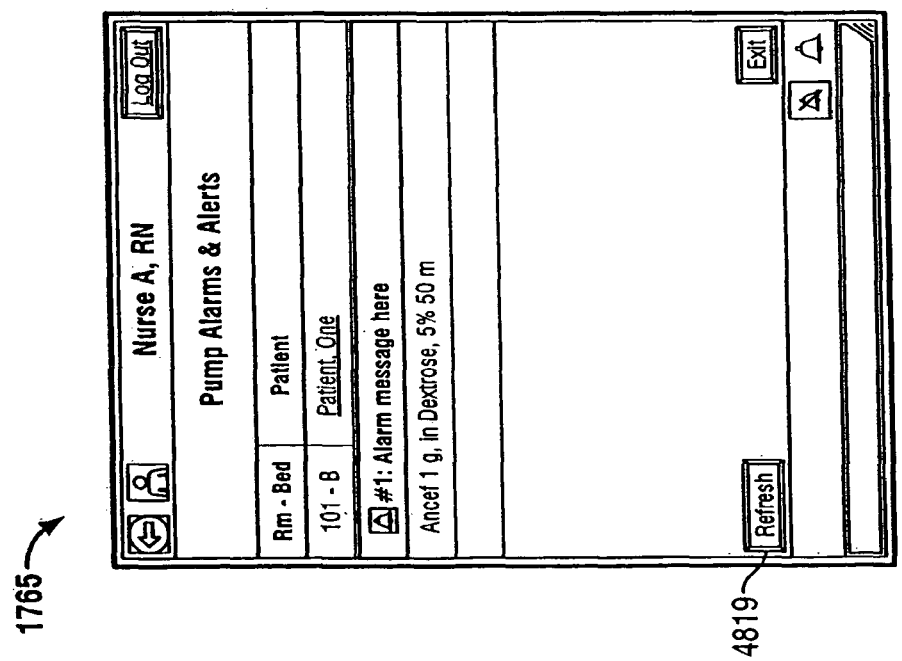
FIG. 17 is another view of an alarm/alert interface screen.

Additionally, the charge clinician may be a person who assists in workflow for the clinicians, or who assists in monitoring alarm or alert conditions. The signal is received by the clinician's digital assistant 118, and subsequently displayed at block 1530 in FIG. 15. This block provides for indicating the alarm or alert condition on the clinician's digital assistant 118. The indication on the clinician's digital assistant may be visual, audible, or both visual and audible. Further, the visual indication may include one or more of text, icons, symbols, etc. Similarly, as explained above, the audible indication may include a variety of audible tones at a variety of decibel levels. The visual and audible indicators are configurable by the hospital. FIG. 16A discloses an exemplar screen shot of an alarm/alert interface list screen 1662a on the clinician's digital assistant 118. The alarm/alert list interface 1662a contains a list of patients that are currently associated to active channel alarm/alerts. As shown in FIG. 16A, this clinician's digital assistant 118 currently has three active alarm/alert indications. There is an alarm condition for patient one 1664, an alarm condition for patient two 1666, and an alert condition for patient three 1668. Each patient name and corresponding alarm/alert icon is a hyperlink to the appropriate pump alarm details interface screen, as shown in FIG. 17. In one embodiment, the list of patients is filtered to only include the patients that are currently associated to the clinician 116 logged into the digital assistant 118 displaying this interface screen. This clinician-to-patient association can be as a primary clinician or as a temporary coverage clinician. A secondary clinician can also be accessed through the escalation process. The alarm/alert list interface 1662 is typically accessed by clicking on an alarm/alert icon 4872 displayed on the clinician's 116 digital assistant 118 during normal clinician workflow.

As explained above, when the alarm or alert condition is indicated on the clinician's digital assistant at block 1530, this indication may be provided visually, audibly or both. When an audible indication is provided at the clinician's digital assistant 118, the alarm icon 4872 appears on the display 118a of the clinician's digital assistant 118. If an audible indication is provided, the clinician may have the ability to mute the audible indication even though the clinician has not responded to the alarm or alert condition. If the clinician does silence the alarm, the server 109 will initiate a silence timer. The visual indication will remain even though the audible indication has been muted. As shown in FIG. 16A, if an alarm/alert would be providing an audible indication at the clinician's digital assistant 118 but for the muting by the clinician, a muted alarm/alert icon 4874 is provided. Further, upon escalation of the alarm/alert condition, if the clinician does not respond to the alarm within the timer limit, the muting of the audible indication may be disengaged. An alternate embodiment of the audible indication may be a vibration alert.

Further, it is understood that multiple alarm/alert conditions may occur simultaneously or in overlapping periods. Accordingly, simultaneous or overlapping signals containing data relating to the specific alarm or alert condition are generated and sent at block 1510 from the medical device 120, to the server 109. The alarm/alert signals may originate from the same or different medical devices 120. Further, the alarm/alert signals may relate to the same or different patients. Each of the alarm/alert signals, however, is individually routed in the alarm/alert escalation process 1500 as herein described for an individual alarm/alert condition.

As shown in FIG. 16A, a specific clinician may have numerous alarm/alert indications on his/her digital assistant 118. Another example of an alarm/alert screen is shown on interface screen 1662b of FIG. 16B. As is typical in the present system, the line referenced as 1676 in interface screen 1662b of FIG. 16B indicates the end of a list, and specifically the alarm/alert indication list for a specific clinician in this interface.

Figure 18:
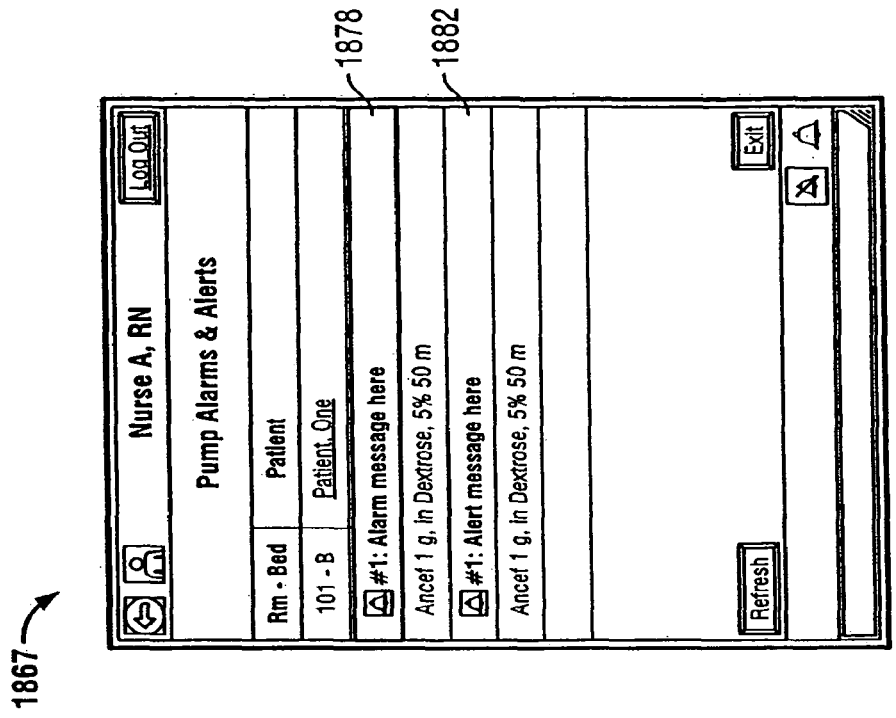
FIG. 18 is a view of an interface screen from the clinician's handheld device.

FIG. 17 illustrates a detailed patient alarm/alert interface 1765 after the clinician has selected to view one of the alarm/alert indications for the patient hyperlink on the clinician's digital assistant 118 from the interface list 1662a of FIG. 16A. Here, the clinician has selected the alarm indication for patient one 1664. The alarm/alert detail screen 1765 provides the clinician with a message detailing the reason for the alarm/alert. The clinician can click on the refresh button 4819 to update the current information displayed on the screen 1765. As shown on interface 1867 of FIG. 18, multiple alarms or alerts 1878, 1882 may exist for the same patient. This alarm/alert interface 1867 provides a list of all active pump alarm/alerts that are currently associated to a given patient. These active pump alarm/alerts can be from multiple channels 121 and/or pumps 120, and even spread across multiple hubs 107. This interface screen 1867 is accessed by specifying a given patient on the pump alarm list screen 1662.

After the signal is sent to the clinician's digital assistant at block 1525, and received by the primary clinician's digital assistant 118 at block 1530, a timer is initiated at block 1535 at the server 109. The timer has a timer limit. A typical escalation timer limit is approximately 2 minutes; however, this limit is configurable by the hospital. At block 1540, the system determines if a response is provided to the alert or alarm within the timer limit. If the timer limit is reached without acknowledgment from the primary clinician's digital assistant 118, the process proceeds to block 1545. At block 1545, the system makes the further inquiry as to whether an acknowledgment or response to the alarm/alert condition has been made at the medical device 120. If no response has been made at either the primary clinician's digital assistant 118, the medical device 120, or by the charge clinician, then at block 1545 the alarm/alert process is escalated.

If at any time a loss of communication occurs after an alarm/alert condition is triggered, but prior to the acknowledgment of the alarm/alert condition, the alarm/alert condition will reassert once the loss of communication has been fixed. Similarly, if an alarm/alert condition is triggered after a loss of communication, the alarm/alert condition will reassert once the communication has been re-established.

When an alarm is escalated, the server 109 conducts another precondition check at block 1550. This precondition check 1550 may include: associating the patient with a secondary clinician (this association may be conducted at the central system servicing unit 108a); and, associating the second clinician with that clinician's digital assistant 118, also referred to as the second clinician's device or second clinician's digital assistant 118. The server 109 uses the information gained in its precondition check at block 1550 to establish a relationship between the medical device 120, the patient, the secondary clinician and the second clinician's digital assistant 118.

Following the second precondition check at block 1550, the server 109 may also determine if the second clinician's digital assistant 118 is active. If the second clinician's digital assistant 118 is active, then the server 109 generates an escalated signal representative of the alarm or alert condition that exists. The escalated signal similarly includes data such as the patient's name, patient's location, room identification, bed identification, alarm or alert type, condition description, time, date, clinician identification and/or prescription. In the preferred embodiment, the escalated signal is transmitted from the server 109 to the wireless access point 114. The wireless access point 114 then transmits the escalated signal relating to the alarm or alert condition via a wireless communication transmission to the second clinician's digital assistant 118 at block 1555.

The escalated signal relating to the alarm or alert condition may also be transmitted at block 1555 to a charge clinician. Such an escalated signal may be via a wireless or wired communication. Further, the charge clinician may be utilizing a digital assistant, a desktop computer, or some other electronic device. As explained above, the charge clinician is generally a supervisor or some person to whom the clinicians report, or a person who assists in workflow for the clinicians, or who assists in monitoring alarm or alert conditions.

The escalated signal is received by the second clinician's digital assistant 118, and subsequently displayed at block 1560 in FIG. 15. This block provides for indicating the alarm or alert condition on the second clinician's digital assistant 118. The indication on the second clinician's device may be visual, audible, or both visual and audible. Further, the visual indication may include one or more of text, icons, symbols, etc. Similarly, as explained above, the audible indication may include a variety of audible tones. It is understood, however, that the original signal, see block 1525, sent to the first clinician is still maintained at the first clinician's digital assistant, as shown in block 1530 of FIG. 15. The signal at the first clinician's digital assistant 118 may be elevated (i.e., it may be shown in a larger size or font, it may be flashing, the volume of the audible alert may be louder, etc.).

After the secondary signal is sent to the clinician's digital assistant at block 1555 and received by the secondary clinician's digital assistant 118 at block 1560, there are at least two individuals (the first clinician and/or the charge clinician) and at least two devices that have the alarm/alert conditions active. Accordingly, any of these clinicians may respond to the alarm/alert condition as shown in blocks 1540 and 1565 The escalated alarm process will continue, at block 1570, until the alarm/alert condition is cleared either at one of the clinician's digital assistant 118, the charge clinician's computer or device, or at the medical device 120.

Referring back to block 1520, if the server 109 determines that the primary clinician's digital assistant 118 is not active, and if at block 1545 the server 109 determines that the alarm/alert condition still exists, the server 109 will proceed to block 1550 as discussed above to determine the appropriate secondary or charge clinician to send the alarm/alert signal.

Additionally, it is understood that block 1520 may occur at any time during the alarm/alert escalation process 1500. One reason for a clinician's digital assistant 118 being inactive could be a loss of a signal from the server 109. As shown in the communication loss interface screen 4501 of FIGS. 45A and 45B, when the signal is lost the digital assistant 118 will provide the clinician 116 with a screen 4501, and/or an audible/vibratory indication, indicating a lost signal. The communication loss screen 4501 also informs the clinician 116 as to which patients the signal has been lost. At screen 4501 the system 210 also provides the clinician 116 with trouble shooting tips to regain a signal. When a hub 107 or digital assistant 118 is outside of the wireless range, pump alarms and alerts cannot be received at the digital assistant 118.

Figure 46:
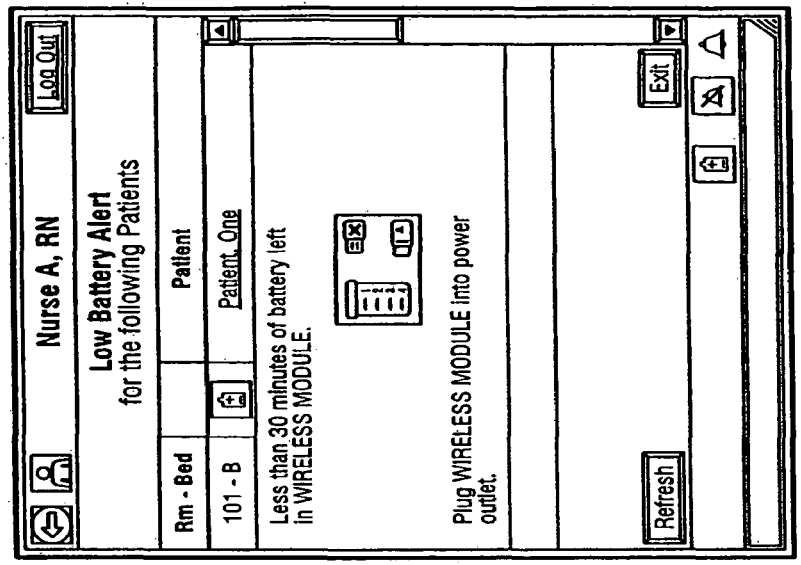
FIG. 46 is a view of a low battery interface screen.
Figure 45B:
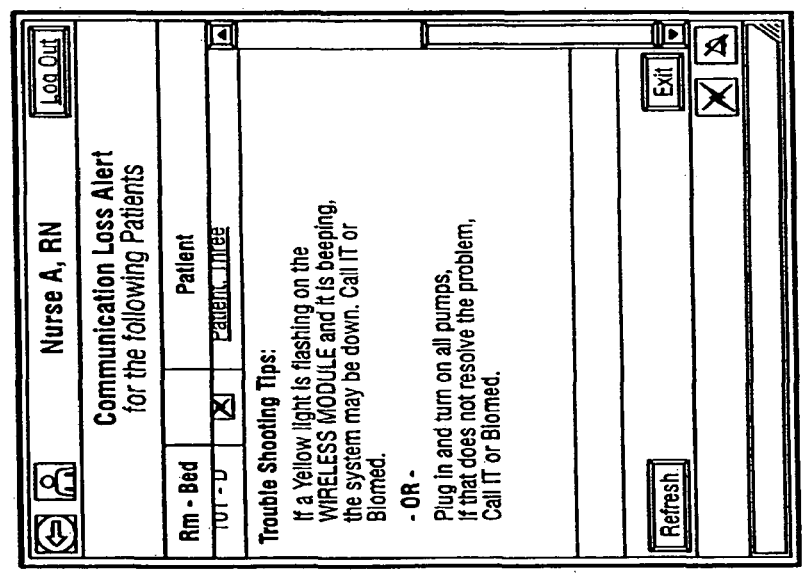
FIG. 45B is a view of a communication loss interface screen.

Other reasons for the digital assistant 118 being inactive could be the loss of battery power at the digital assistant 118, a loss of battery power at the wireless hub 107, or the digital assistant losing a signal with the access point 114. The system 210 does provide the clinician 116 with a low battery screen. As shown in interface screen 4603 of FIG. 46, one type of low battery screen is a screen to alert the clinician that a low battery situation exists on a wireless hub 107 connected to a patient's infusion pump. When a low battery screen is provided, the screen contains a list of patients for which infusions are associated with that specific hub 107. The list of patients is generally filtered to include only the patients that are currently associated to the clinician logged into the digital assistant 118 displaying the screen 4603, and also all patients that share the same infusion pump 120/hub 107 with the logged-in clinician. This clinician-to-patient association can be as a first clinician or as a secondary clinician through the escalation process. It is understood that other reasons for the clinician's digital assistant 118 being inactive are possible. Nevertheless, if at any time the clinician's digital assistant 118 becomes inactive, the process 1500 may proceed to block 3100 such that the signal may be sent to a secondary clinician and/or to the charge clinician. Further, as explained above with respect to a time-out feature and other features of this disclosure, if a communication signal is lost from either the server 109 or the medical device 120, a signal lost message may be provided on the digital assistant 118 as shown in FIGS. 45A and 45B.

At any time during the alarm/alert process, the primary clinician may respond to the alarm/alert signal. If the primary clinician responded to the alarm/alert signal at block 1540, the escalated process will be avoided. If, however, an escalated process has been initiated at block 1550, either the primary physician or the secondary clinician may respond to the alarm/alert signal at block 1565. Similarly, the alarm/alert condition may be resolved at the medical device 120, or by the charge clinician at any time, either before or during an alarm/alert escalation process. After the alarm/alert condition has been resolved, either at block 1540, block 1565, at the medical device 120 or by the charge clinician, the audible alarm at the medical device 120 and at the clinician's digital assistant 118 will be terminated at block 1540.

The server 109 records all alarm/alert conditions as an event at block 1585. Recording the event may include: recording information on the alarm/alert condition; recording the clinician who responded to the alarm/alert condition; recording the initial time of the alarm/alert condition (see block 1505); and, recording the time when the alarm/alert condition was rectified. Additionally, at block 1590, the server 109 will reset the timer and update a medical device alarm list. The alarm/alert condition may also be recorded in the pump's event history.

Example Use Cases

FIG. 55A-FIG. 62 are flowcharts of example operations that may be performed using the system described herein. Example operations include administering a new infusion, scanning a pump channel, changing the channel a pump is assigned to, stopping/discontinuing an infusion, resuming an infusion, and removing a pump. In general, each of these operations receives inputs from an electronic device, such as a digital assistant 118, which includes information indicating the operation to be performed, information identifying which patient 112 is to be affected (e.g., patient ID), and information identifying which medication 124 for that patient 112 is to be affected (e.g., Rx ID). This information is then sent to the first central server 109, which confirms that channel identification information matches the infusion order information and confirms that the correct infusion operation occurred.

Administer Infusion Process

Figure 55A:
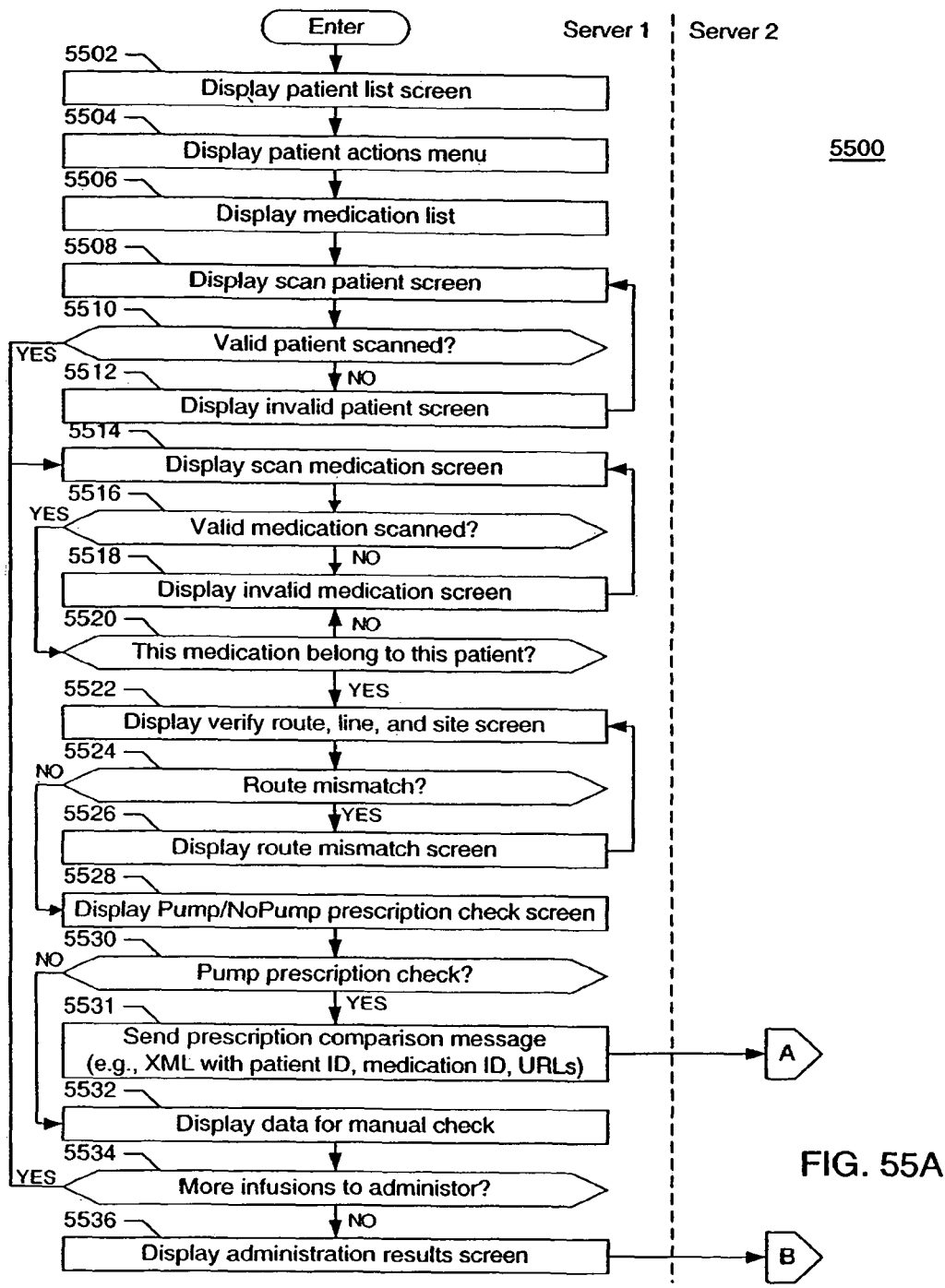
FIG. 55A-FIG. 55C is a flowchart of an example administer infusion process.

FIG. 55A illustrates an example of an administer infusion process 5500. Portions of the administer infusion process 5500 are an alternate embodiment of the comparison procedure 5200 outlined above. The administer infusion process 5500 may be used to start a new infusion. In general, the administer infusion process 5500 receives inputs from an electronic device, such as a digital assistant 118, which includes information indicating an administer infusion process is to be performed, information identifying which patient 112 is to be affected (e.g., patient ID), and information identifying which medication 124 for that patient 112 is to be started (e.g., Rx ID). The process 5500 then sends this information to the first central server 109, which confirms that channel identification information matches the infusion order information and confirms that the correct infusion is started.

More specifically, the example administer infusion process 5500 begins when the second central server 108a causes the digital assistant 118 to display a list of patients at block 5502. An example of a digital assistant display 118a showing a list of patients is illustrated in FIG. 24. The list of patients is preferably limited to patients associated with the user (e.g., a clinician 116) who is logged into that digital assistant 118 at the time. Once the user selects a patient 112, information identifying the selection and/or the patient 112 is transmitted from the digital assistant 118 back to the second central server 108a. Communication between the digital assistant 118 and the second central server 108a may be via any suitable communication channel such as the wireless/wired network 102 described above. The second central server 108a then causes the digital assistant 118 to display a list of actions at block 5504. An example of a digital assistant display 118a showing a list of actions is illustrated in FIG. 25. The list of actions is preferably limited to actions associated with the selected patient 112. For example, an "administer infusion" action would only be available if at least one infusion was currently associated with the selected patient 112.

When the user selects the "administer infusion" action from the list of actions, information identifying the action selected is sent to the second central server 108a. In response, the second central server 108a causes the digital assistant 118 to display a screen prompting the user to select a medication 124 to be infused from a list of medications displayed on the digital assistant 118 at block 5506. An example of a digital assistant display 118a showing a list of medications is illustrated in FIG. 26. The list of medications is preferably retrieved from the second central server 108a database based on actual orders for this patient 112. Of course, the list may have any number of items including no infusions to administer or one infusion to administer. Data indicative of the selected medication 124 is then sent to the second central server 108a.

Next, the second central server 108a causes the digital assistant 118 to display a screen prompting the user to scan a machine-readable identifier associated with the patient 112 at block 5508. An example of a digital assistant display 118a prompting the user to scan a machine-readable identifier associated with the patient 112 is illustrated in FIG. 36. The user may use the scanner of the digital assistant 118 to scan a barcode label on the patient's wristband 112a. Alternatively, the user may manually enter the patient identifier into the digital assistant 118. The patient identifier is then sent to the second central server 108a for verification at block 5510. The second central server 108a then attempts to lookup the patient identifier in a database. If the patient identifier (e.g., wristband ID) does not exist as a valid patient identifier in the database, the second central server 108a causes the digital assistant 118 to display an invalid patient notification at block 5512. Once the user acknowledges the invalid patient notification (or the notification times out), the digital assistant 118 re-displays the screen prompting the user to scan a machine-readable identifier associated with the patient 112 at block 5508.

If the patient identifier (e.g., wristband ID) does exist as a valid patient identifier in the database at block 5510, the second central server 108a causes the digital assistant 118 to display a screen prompting the user to scan a machine-readable identifier associated with the medication 124 to be administered at block 5514. An example of a digital assistant display 118a prompting the user to scan a machine-readable identifier associated with the medication 124 is illustrated in FIG. 34. The user may use the scanner of the digital assistant 118 to scan the medication label 124a on a bag of medication 124 (e.g., a barcode on an infusion bag).

Alternatively, the user may manually enter the medication identifier into the digital assistant 118. The medication identifier is then sent to the second central server 108a for verification at block 5516. The second central server 108a attempts to lookup the medication identifier in the database. If the medication identifier (e.g., bag ID) does not exist as a valid medication identifier in the database, the second central server 108a causes the digital assistant 118 to display an invalid item notification at block 5518. Once the user acknowledges the invalid item notification (or the notification times out), the digital assistant 118 re-displays the screen prompting the user to scan a machine-readable identifier associated with the medication 124 to be resumed at block 5514.

Once a valid medication identifier is obtained, the second central server 108a uses the medication identifier to look up a patient identifier in the database. The patient identifier from the database is then compared to the scanned (or manually entered) patient identifier to determine if the scanned (or manually entered) medication 124 belongs to the scanned (or manually entered) patient 112 at block 5520. If the two patient identifiers do not match, the second central server 108a causes the digital assistant 118 to display the invalid item notification at block 5518.

If the two patient identifiers do match (i.e., this patient 112 goes with this medication 124), the second central server 108a causes the digital assistant 118 to display a screen prompting the user to enter a route, a line, and a site at block 5522. An example of a digital assistant display 118a prompting the user to enter a route, a line, and a site is illustrated in FIG. 37. Data indicative of the route, line, and site is then sent to the second central server 108a for verification at block 5524. If a route mismatch occurs, the second central server 108a causes the digital assistant 118 to display a route mismatch notification at block 5526. An example of a digital assistant display 118a with a mismatch notification is illustrated in FIG. 40. Once the user acknowledges the route mismatch notification (or the notification times out), the digital assistant 118 re-displays the screen prompting the user to enter a route, a line, and a site at block 5522. If a route mismatch does not occur, the second central server 108a causes the digital assistant 118 to display a screen asking the user to select between a manual prescription comparison and an automatic prescription comparison at block 5528. If a manual prescription comparison is selected at block 5530, the second central server 108a causes the digital assistant 118 to display an indication of the parameters to be manually verified by the user at block 5532.

Figure 57A:
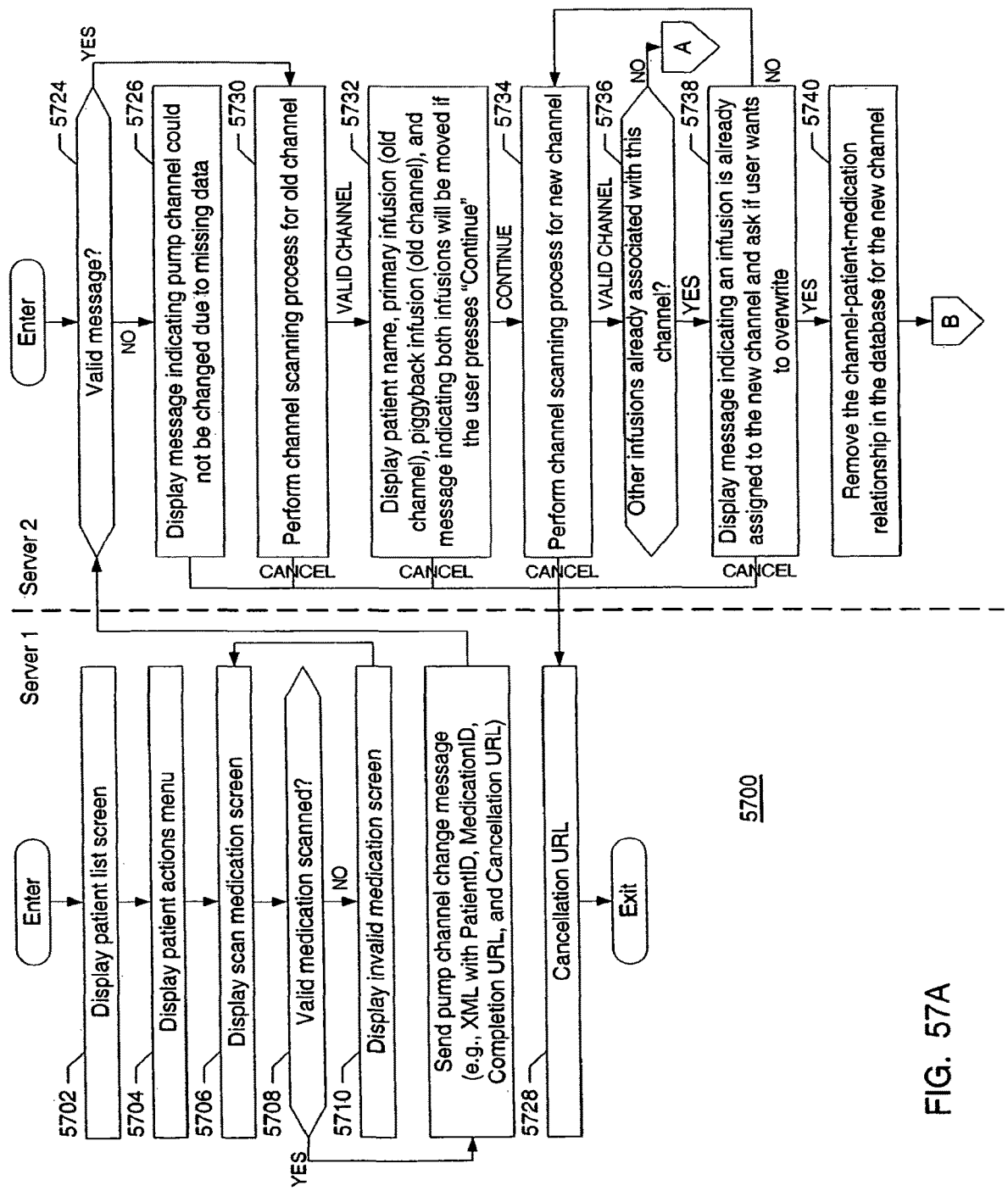
FIG. 57A-FIG. 57B is a flowchart of an example change pump channel process.
Figure 57B:
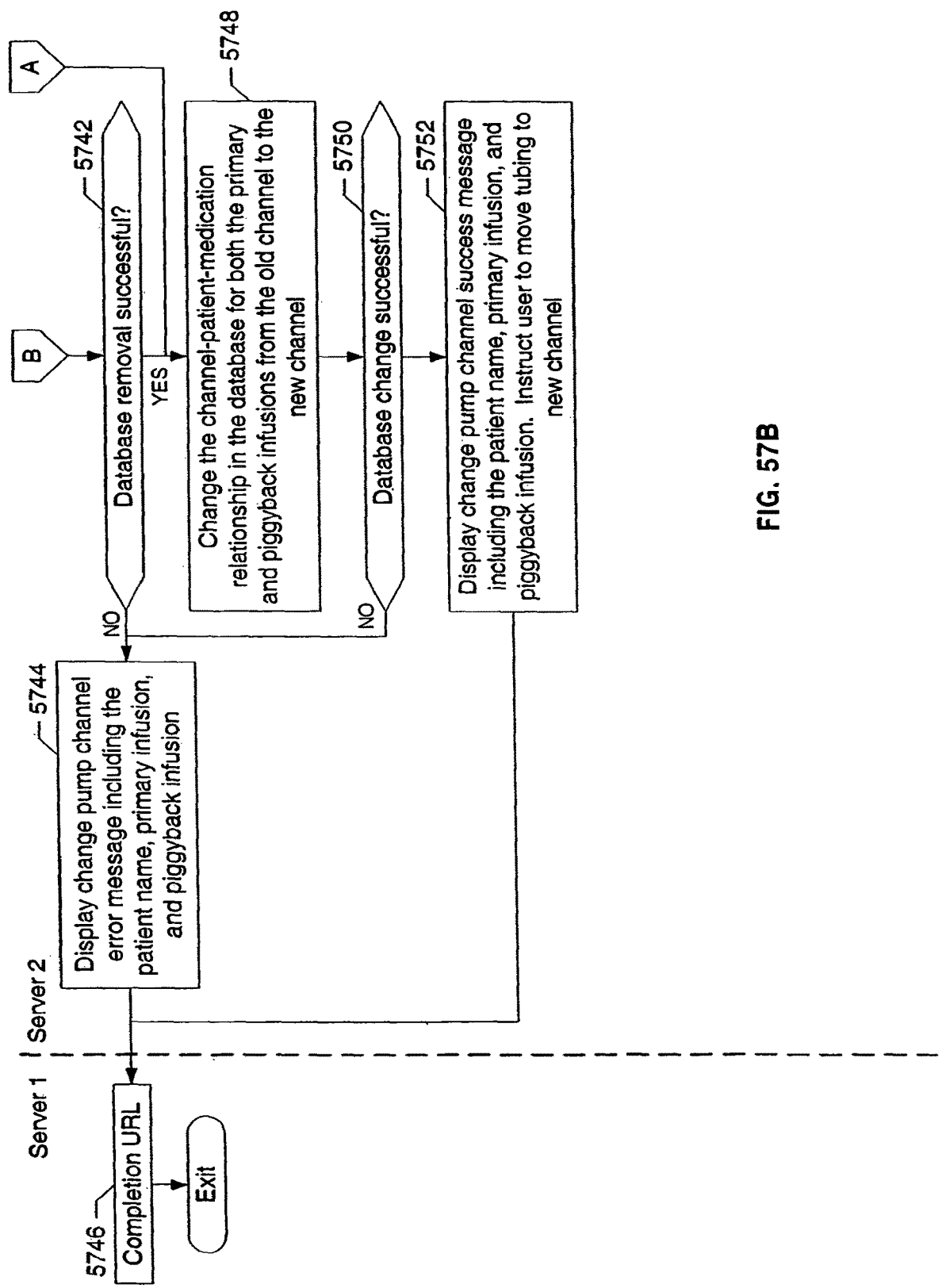

Subsequently, the second central server 108a determines if there are more items (e.g., medications) to administer for this patient 112 at block 5534. For example, the infusion order selected in block 5506 may require a primary infusion and a piggyback infusion. If there are more items (e.g., medications) to administer for this patient 112, the second central server 108a causes the digital assistant 118 to display the screen prompting the user to scan a machine-readable identifier associated with the medication 124 to be administered at block 5514. An example of a digital assistant display 118a prompting the user to scan a machine-readable identifier associated with the medication 124 is illustrated in FIG. 34. If there are no more items (e.g., medications) to administer for this patient 112, the second central server 108a causes the digital assistant 118 to display a screen showing the administration results at block 5536. An example of a digital assistant display 118a showing the administration results is illustrated in FIG. 57.

The administration results are also passed to the first central server 109. For example, the administration results may be passed to the first central server 109 as form variables (as if submitted from a web page). The first central server 109 then checks all of the administration results for any failures at block 5538. If there are no failures, the first central server 109 commits all of the new channel-patient-medication relationships to the first central server 109 database at block 5540. The first central server 109 then returns control to the second central server 108a by navigating to a predefined URL associated with the second central server 108a at block 5542. If there are one or more failures, the first central server 109 discards channel-patient-medication relationships associated with the failures and commits channel-patient-medication relationships associated with the successes to the first central server 109 database at block 5544. The failures may be associated with the second central server 108a and/or the first central server 109. Accordingly, the first central server 109 preferably communicates failures associated with the first central server 109 (e.g., an integrity failure) back to the second central server 108a when the first central server 109 returns control to the second central server 108a by navigating to a predefined URL associated with the second central server 108a at block 5546.

Returning to block 5530, if an automatic prescription comparison is selected, the second central server 108a transmits a "prescription comparison" XML document to the first central server 109 at block 5531. The "prescription comparison" XML document includes the patient identifier (e.g., wristband ID), the medication identifier (e.g., bag ID), a completion URL, and a cancellation URL. The completion URL is a network address used if a prescription match is found. The cancellation URL is a network address used if a prescription match is not found.

Once the first central server 109 receives the "prescription comparison" XML document, the first central server 109 determines if the "prescription comparison" XML document is valid at block 5548. For example, the first central server 109 may check if any data normally expected in a "prescription comparison" XML document is missing from the received "prescription comparison" XML document. If the first central server 109 determines that the "prescription comparison" XML document is not valid, the first central server 109 causes the digital assistant 118 to display an error message indicating to the user that the "prescription comparison" action could not be executed at block 5550. This display may include a reason such as which data was missing from the "prescription comparison" XML document. After the user presses an "OK" button to acknowledge the error message, the first central server 109 returns a cancellation code to the second central server 108*a* via the cancellation URL at block 5552.

If the first central server 109 determines that the "prescription comparison" XML document is valid, the first central server 109 initiates a channel scanning process 5554.

Generally, the channel scanning process 5554 prompts the user to scan a machine-readable identifier associated with the "new" pump channel (e.g., pump channel 103*a*) and determines if the scanned channel is available (e.g., not assigned to any patient 112; assigned to the current patient 112, but not in use; assigned to another patient 112 and overwritten; etc.). If the scanned channel is not available, the "administer infusion" action is cancelled. In such an event, the first central server 109 returns a cancel code to the second central server 108*a* via the cancellation URL. If the scanned channel is available, a new channel-patient-medication relationship is created. The channel scanning process 5554 is described in more detail below with reference to FIG. 56.

If the channel scanning process 5554 determines that the scanned channel is valid and available, the first central server 109 causes the digital assistant 118 to display a screen prompting the user to program the pump channel at block 5556. Preferably, the digital assistant display includes a "Compare" button and a "Cancel" button. If the user presses the "Cancel" button, the first central server 109 discards the new channel-patient-medication relationship at block 5558 and returns the cancellation code to the second central server 108*a* via the cancellation URL at block 5552. If the user presses the "Compare" button, the first central server 109 determines if communication with the pump channel is operating properly at block 5560. For example, the first central server 109 may determine that communication with the pump channel is not operating properly if status information has not been received from the channel within a predefined time period.

If communication with the pump channel is not operating properly, the first central server 109 causes the digital assistant 118 to display a screen indicating that a prescription comparison cannot be performed due to a loss of communication with the pump channel at block 5562. Again, the digital assistant display 118*a* preferably includes a "Compare" button and a "Cancel" button. If the user presses the "Cancel" button, the first central server 109 discards the new channel-patient-medication relationship at block 5558 and returns the cancellation code to the second central server 108*a* via the cancellation URL at block 5552. If the user presses the "Compare" button, the first central server 109 rechecks if communication with the pump channel is operating properly at block 5560.

If communication with the pump channel is operating properly, the first central server 109 determines if any data associated with this channel is missing at block 5564. For example, the first central server 109 may determine that data associated with this channel is missing if status information received from the channel is missing an expected sequence number. If channel data is missing, the first central server 109 causes the digital assistant 118 to display a screen indicating that a prescription comparison cannot be performed due to missing channel data at block 5564. Again, the digital assistant display 118*a* preferably includes a "Compare" button and a "Cancel" button. If the user presses the "Cancel" button, the first central server 109 discards the new channel-patient-medication relationship at block 5558 and returns the cancellation code to the second central server 108*a* via the cancellation URL at block 5552. If the user presses the "Compare" button, the first central server 109 rechecks if communication with the pump channel is operating properly at block 5560.

If no channel data is missing, the first central server 109 determines if the channel is already running at block 5568. For example, the first central server 109 may determine if the pump channel is running by reading status information received from the channel. If the channel is already running, the first central server 109 causes the digital assistant 118 to display a screen indicating that a prescription comparison cannot be performed because the channel is already running at block 5570. An example of a digital assistant display 118*a* indicating that a prescription comparison cannot be performed is illustrated in FIG. 42. The digital assistant display 118*a* may also indicate that the user should press a certain key on the pump 120 (e.g., start). Again, the digital assistant display 118*a* preferably includes a "Compare" button and a "Cancel" button. If the user presses the "Cancel" button, the first central server 109 discards the new channel-patient-medication relationship at block 5558 and returns the cancellation code to the second central server 108*a* via the cancellation URL at block 5552. If the user presses the "Compare" button, the first central server 109 rechecks if communication with the pump channel is operating properly at block 5572.

If communication with the pump channel is not operating properly, the first central server 109 causes the digital assistant 118 to display a screen indicating that a prescription comparison cannot be performed due to a loss of communication with the pump channel at block 5574. Again, the digital assistant display 118*a* preferably includes a "Compare" button and a "Cancel" button. If the user presses the "Cancel" button, the first central server 109 discards the new channel-patient-medication relationship at block 5558 and returns the cancellation code to the second central server 108*a* via the cancellation URL at block 5552. If the user presses the "Compare" button, the first central server 109 rechecks if communication with the pump channel is operating properly at block 5574. If communication with the pump channel is operating properly, the first central server 109 performs the requested prescription comparison at block 5576.

Returning to block 5568, if the channel is not running, the first central server 109 determines if the pump channel is setup to send rate information at block 5578. If the pump channel is not setup to send rate information, the first central server 109 causes the digital assistant 118 to display a screen indicating that a prescription comparison cannot be performed because the channel is not sending rate information at block 5580. An example of a digital assistant display 118*a* indicating that a prescription comparison cannot be performed is illustrated in FIG. 41. The digital assistant display 118*a* may also indicate that the user should press a certain key on the pump 120 (e.g., rate). Again, the digital assistant display 118a preferably includes a "Compare" button and a "Cancel" button. If the user presses the "Cancel" button, the first central server 109 discards the new channel-patient-medication relationship at block 5558 and returns the cancellation code to the second central server 108a via the cancellation URL at block 5552. If the user presses the "Compare" button, the first central server 109 rechecks if communication with the pump channel is operating properly at block 5572. If the pump channel is setup to send rate information, the first central server 109 performs the requested prescription comparison at block 5576.

As part of the prescription comparison, the first central server 109 uses the channel identifier obtained by the channel scanning process 5554 and the patient identifier transmitted by the second central server 108a to look up a medication identifier in the database (or two medication identifiers if a primary medication 124 and a piggyback medication 124 are both associated with this channel). The medication identifier(s) from the database are then compared to the scanned (or manually entered) medication identifier at block 5582. If one of the medication identifier(s) from the database does not match the scanned (or manually entered) medication identifier, the first central server 109 causes the digital assistant 118 to display an invalid medication notification at block 5584. For example, the digital assistant 118 may display a message that the scanned medication 124 is not associated with the scanned channel and indicate the actual medication 124 assigned to the scanned channel (both primary and piggyback if applicable). Again, the digital assistant display 118a preferably includes a "Compare" button and a "Cancel" button. If the user presses the "Cancel" button, the first central server 109 discards the new channel-patient-medication relationship at block 5558 and returns the cancellation code to the second central server 108a via the cancellation URL at block 5552. If the user presses the "Compare" button, the first central server 109 rechecks if communication with the pump channel is operating properly at block 5572.

As an additional part of the prescription comparison, the first central server 109 uses the channel identifier obtained by the channel scanning process 5554 and the patient identifier transmitted by the second central server 108a to look up a medication rate in the database. The medication rate from the database is then compared to the actual rate received from the pump channel at block 5585. If medication rate from the database does not match the actual rate received from the pump channel, the first central server 109 causes the digital assistant 118 to display a rate mismatch notification at block 5586. An example of a digital assistant display 118a with a mismatch notification is illustrated in FIG. 40. For example, the digital assistant 118 may display a message that the rate of the channel should be adjusted and indicate the correct value. Again, the digital assistant display 118a preferably includes a "Compare" button and a "Cancel" button. If the user presses the "Cancel" button, the first central server 109 discards the new channel-patient-medication relationship at block 5558 and returns the cancellation code to the second central server 108a via the cancellation URL at block 5552. If the user presses the "Compare" button, the first central server 109 rechecks if communication with the pump channel is operating properly at block 5572.

In addition, the digital assistant display 118a may include an "Accept Mismatch" button. If the user presses the "Accept Mismatch" button, the first central server 109 returns a mismatch code and the mismatching rates to the second central server 108a via the completion URL at block 5588. If medication rate from the database does match the actual rate received from the pump channel at block 5585, the first central server 109 causes the digital assistant 118 to display a match notification at block 5590. An example of a digital assistant display 118a with a match notification is illustrated in FIG. 39. Once the user accepts the match notification message, the first central server 109 returns a match code and the matching rate to the second central server 108a via the completion URL at block 5588.

Channel Scanning Process (for Administer Infusion Process)

Figure 55B:
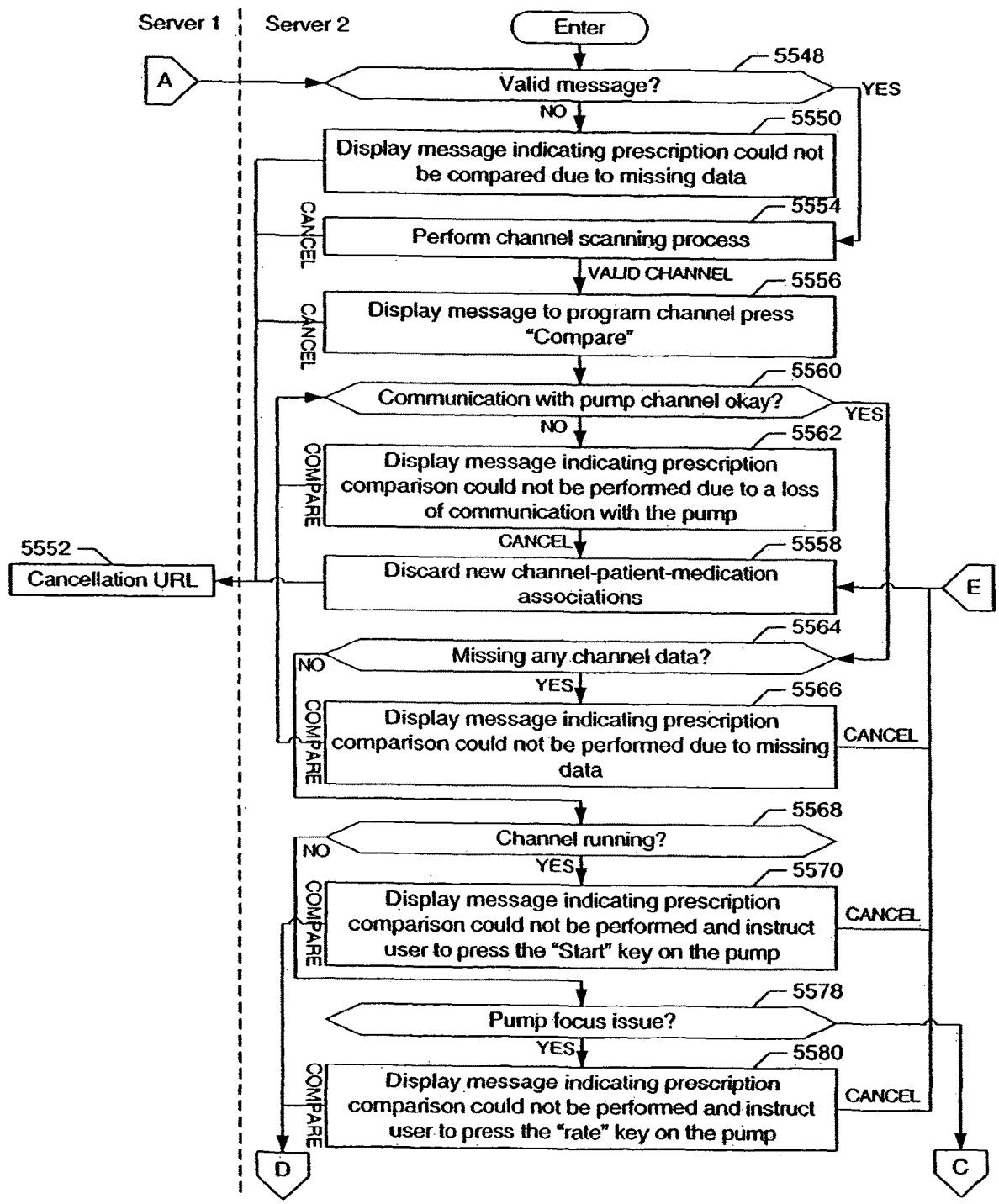
Figure 55C:
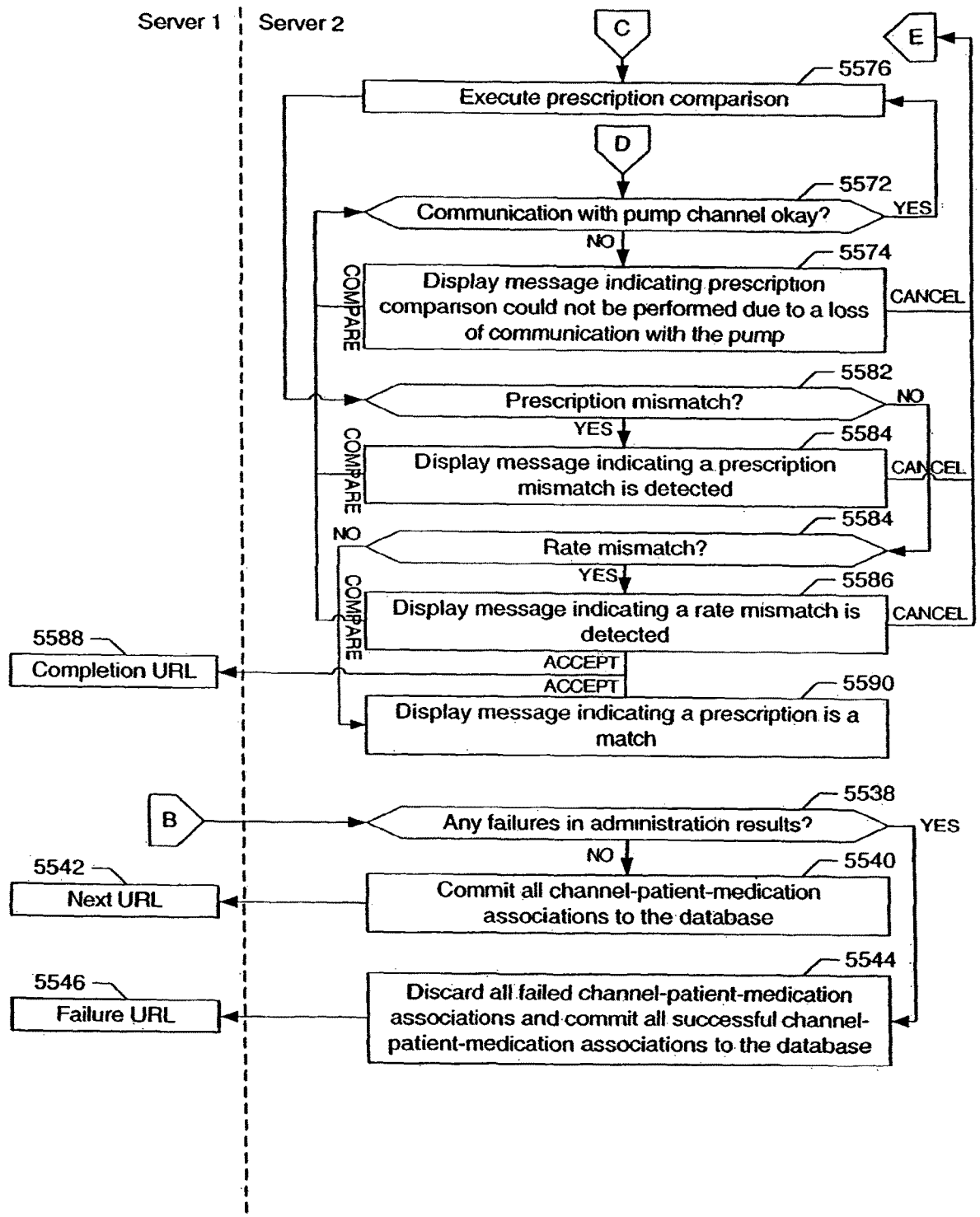
Figure 56:
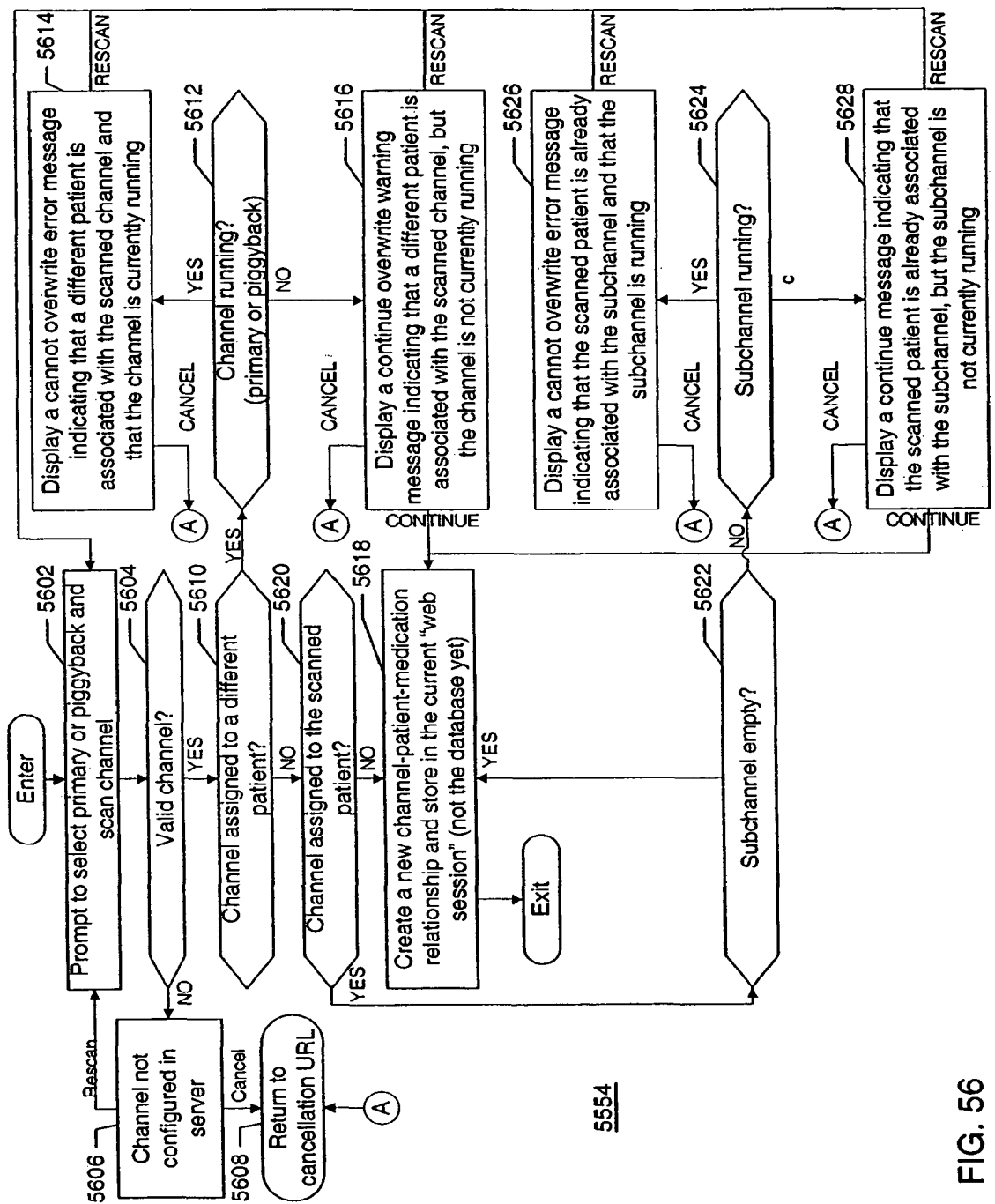
FIG. 56 is a flowchart of an example channel scanning process.

FIG. 56 illustrates an example of the channel scanning process 5554 used above with reference to FIG. 55. Generally, the channel scanning process 5554 prompts the user to scan a machine-readable identifier associated with a pump channel and determines if the scanned channel is available (e.g., assigned to the current patient 112, but not in use). If the scanned channel is not available, the "administer infusion" action is cancelled. In such an event, the first central server 109 returns a cancel code to the second central server 108a via the cancellation URL. If the scanned channel is available, a new channel-patient-medication relationship is created.

More specifically, the example channel scanning process 5554 begins when the first central server 109 causes the digital assistant 118 to display a screen prompting the user to select a sub-channel (e.g., primary or piggyback) and scan a machine-readable identifier associated with the channel at block 5602. An example of a digital assistant display 118a prompting the user to scan a machine-readable identifier associated with the channel is illustrated in FIG. 38. For example, the user may use the scanner of the digital assistant 118 to scan a barcode label associated with the channel. Alternatively, the user may manually enter the channel identifier into the digital assistant 118. In addition, the user may choose to skip the scanning process which causes a return to the second central server 108a via the completion URL or he may choose to cancel the scan which causes a return to the second central server 108a via the cancellation URL.

The channel identifier is then sent to the first central server 109 for verification at block 5604. The first central server 109 then attempts to lookup the channel identifier in the database. If the channel identifier does not exist as a valid channel identifier in the database (e.g., not properly formatted, not configured in the first central server 109, etc.), the first central server 109 causes the digital assistant 118 to display an invalid channel notification at block 5606. For example, the digital assistant 118 may display a message that the channel is not configured in the first central server 109 and include buttons allowing the user to rescan the channel identifier or cancel out of the operation. If the user chooses to cancel the operation, the first central server 109 preferably sends a cancel code to the second central server 108a via the cancellation URL at block 5608.

Once a valid channel identifier is obtained, the first central server 109 uses the channel identifier to look up a patient identifier in the database. The first central server 109 then compares the patient identifier from the database to the scanned (or manually entered) patient identifier at block 5610. If a valid patient identifier is present in the database, but the two patient identifiers do not match (i.e., the channel is assigned to a different patient 112), the first central server 109 checks the database to see if the channel is running (in either primary and/or piggyback mode) at block 5612.

If the channel is running, the first central server 109 causes the digital assistant 118 to display a "cannot overwrite" error message indicating that a different patient 112 is associated with the scanned channel and that the channel is currently running at block 5614. The error message may also include data indicative of the patient 112 that is associated with the scanned channel (e.g., patient's name), the primary medication 124, and/or the piggyback medication 124. Preferably, the user is given the option to cancel or rescan. If the user chooses to cancel the operation, the first central server 109 sends a cancel code to the second central server 108*a* via the cancellation URL at block 5608. If the user chooses to rescan, the first central server 109 causes the digital assistant 118 to display the screen prompting the user to select a sub-channel (e.g., primary or piggyback) and scan a machine-readable identifier associated with the channel at block 5602.

If the channel is not running, the first central server 109 causes the digital assistant 118 to display a "continue overwrite" warning message indicating that a different patient 112 is associated with the scanned channel, but the channel is not currently running at block 5616.

Preferably, the warning message indicates that continuing will overwrite existing data (e.g., remove the association with the other patient 112). The warning message may also include data indicative of the patient 112 that is associated with the scanned channel (e.g., patient's name), the primary medication 124, and/or the piggyback medication 124. Preferably, the user is given the option to cancel, rescan, or continue. If the user chooses to cancel the operation, the first central server 109 sends a cancel code to the second central server 108*a* via the cancellation URL at block 5608. If the user chooses to rescan, the first central server 109 causes the digital assistant 118 to display the screen prompting the user to select a sub-channel (e.g., primary or piggyback) and scan a machine-readable identifier associated with the channel at block 5602.

An example of a digital assistant display 118*a* prompting the user to scan a machine-readable identifier associated with the channel is illustrated in FIG. 38. If the user chooses to continue, the first central server 109 creates a new channel-patient-medication relationship and stores the new channel-patient-medication relationship in the current "web session" at block 5618. If this new channel-patient-medication relationship is ultimately kept, the first central server 109 commits the new channel-patient-medication relationship to the first central server 109 database block 5540 of FIG. 55 as described in detail above.

If a valid patient identifier is present in the database, and the two patient identifiers do match (i.e., the channel is assigned to this patient 112) at block 5620, the first central server 109 checks the database to see if the sub-channel is empty at block 5622. In other words, the first central server 109 checks that there is no primary infusion associated with this channel if the primary sub-channel was selected in block 5602 and checks that there is no piggyback infusion associated with this channel if the piggyback sub-channel was selected in block 5602. If the sub-channel is empty, the first central server 109 creates a new channel-patient-medication relationship and stores the new channel-patient-medication relationship in the current "web session" at block 5618. If the sub-channel is not empty, the first central server 109 checks the database to see if the sub-channel is running (in either primary and/or piggyback mode) at block 5624.

If the sub-channel is running, the first central server 109 causes the digital assistant 118 to display a "cannot overwrite" error message indicating that this patient 112 is already associated with the scanned channel and that the selected sub-channel is currently running at block 5626. The error message may also include data indicative of the patient 112 (e.g., patient's name), the primary medication 124, and/or the piggyback medication 124. Preferably, the user is given the option to cancel or rescan. If the user chooses to cancel the operation, the first central server 109 sends a cancel code to the second central server 108*a* via the cancellation URL at block 5608. If the user chooses to rescan, the first central server 109 causes the digital assistant 118 to display the screen prompting the user to select a sub-channel (e.g., primary or piggyback) and scan a machine-readable identifier associated with the channel at block 5602.

If the sub-channel is not running, the first central server 109 causes the digital assistant 118 to display a "continue" message indicating that this patient 112 is associated with the scanned channel, but the selected sub-channel is not currently running at block 5628. The message may also include data indicative of the patient 112 (e.g., patient's name), the primary medication 124, and/or the piggyback medication 124. Preferably, the user is given the option to cancel, rescan, or continue. If the user chooses to cancel the operation, the first central server 109 sends a cancel code to the second central server 108*a* via the cancellation URL at block 5608. If the user chooses to rescan, the first central server 109 causes the digital assistant 118 to display the screen prompting the user to select a sub-channel (e.g., primary or piggyback) and scan a machine-readable identifier associated with the channel at block 5602. If the user chooses to continue, the first central server 109 creates a new channel-patient-medication relationship and stores the new channel-patient-medication relationship in the current "web session" at block 5618. When the user presses continue again, the first central server 109 returns control to the current action (e.g., administer infusion).

Change Pump Channel Process

FIG. 57 A illustrates an example of a change pump channel process 5700. The change pump channel process 5700 may be used (e.g., by a nurse) to change an infusion from one pump channel to another pump channel without losing the channel-patient-medication relationship in the database. In general, the change pump channel process 5700 receives inputs from an electronic device, such as a digital assistant 118, which includes information indicating a change pump channel process is to be performed, information identifying which patient 112 is to be affected (e.g., patient ID), and information identifying which medication 124 for that patient 112 is to be affected (e.g., Rx ID). The process 5700 then sends this information to the first central server 109, which confirms that channel identification information matches the change pump channel order information.

More specifically, the example change pump channel process 5700 begins when the second central server 108*a* causes the digital assistant 118 to display a list of patients for selection at block 5702. An example of a digital assistant display showing a list of patients is illustrated in FIG. 24. The list of patients is preferably limited to patients associated with the user (e.g., a clinician 116) who is logged into that digital assistant 118 at the time. Once the user selects a patient 112, information identifying the selection and/or the patient 112 is transmitted from the digital assistant 118 back to the second central server 108*a*.

Communication between the digital assistant 118 and the second central server 108*a* may be via any suitable communication channel such as the wireless/wired network 102 described above.

The second central server 108*a* then causes the digital assistant 118 to display a list of actions at block 5704. An example of a digital assistant display showing a list of actions is illustrated in FIG. 25. The list of actions is preferably limited to actions associated with the selected patient 112. For example, a "change pump channel" action would only be available if an infusion associated with this patient 112 was currently listed in the second central server 108a database.

When the user selects the "change pump channel" action from the list of actions, information identifying the action selected is sent to the second central server 108a. In response, the second central server 108a causes the digital assistant 118 to display a screen prompting the user to scan a machine-readable identifier associated with the medication 124 to be affected by this "change pump channel" action at block 5706. An example of a digital assistant display prompting the user to scan a machine-readable identifier associated with the medication 124 is illustrated in FIG. 34. The user may use the scanner of the digital assistant 118 to scan the medication label 124a on a bag of medication 124 (e.g., a barcode on an infusion bag). Alternatively, the user may manually enter the medication identifier into the digital assistant 118.

The medication identifier is then sent to the second central server 108a for verification at block 5708. The second central server 108a attempts to lookup the medication identifier in the database. If the medication identifier (e.g., bag ID) does not exist as a valid medication identifier in the database, the second central server 108a causes the digital assistant 118 to display an invalid item notification at block 5710. Once the user acknowledges the invalid item notification (or the notification times out), the digital assistant 118 re-displays the screen prompting the user to scan a machine-readable identifier associated with the medication 124 to be affected by this "change pump channel" action at block 5706.

If the medication identifier (e.g., bag ID) does exist as a valid medication identifier in the database at block 5708, the second central server 108a transmits a "change pump channel" XML document to the first central server 109. The "change pump channel" XML document includes the patient identifier (e.g., selected from list in block 5702, the medication identifier (e.g., bag ID), a completion URL, and a cancellation URL. The completion URL is a network address used if the "change pump channel" action is attempted. The cancellation URL is a network address used if the "change pump channel" action fails.

Once the first central server 109 receives the "change pump channel" XML document, the first central server 109 determines if the "change pump channel" XML document is valid at block 5724. For example, the first central server 109 may check if any data normally expected in a "change pump channel" XML document is missing from the received "change pump channel" XML document. If the first central server 109 determines that the "change pump channel" XML document is not valid, the first central server 109 causes the digital assistant 118 to display an error message indicating to the user that the "change pump channel" action could not be executed at block 5726. This display may include a reason such as which data was missing from the "change pump channel" XML document. After the user presses an "OK" button to acknowledge the error message, the first central server 109 returns a failure code to the second central server 108a via the cancellation URL at block 5728.

If the first central server 109 determines that the "change pump channel" XML document is valid, the first central server 109 initiates a channel scanning process 5730. This channel scanning process 5730 is associated with the "old" channel (i.e., the user is attempting to move from and "old" channel to a "new" channel). Generally, the channel scanning process 5730 prompts the user to scan a machine-readable identifier associated with the "old" pump channel and determines if the scanned channel is associated with the patient identifier and the medication identifier (as described in more detail below with reference to FIG. 58. If the scanned channel is not associated with the patient identifier and the medication identifier, the "change pump channel" action is cancelled. In such an event, the first central server 109 returns a cancel code to the second central server 108a via the cancellation URL at block 5728.

If the scanned channel is associated with the patient identifier and the medication identifier (i.e., the old channel is valid), the first central server 109 causes the digital assistant 118 to display a message indicating the patient 112, the old channel of the primary infusion, and the old channel of the piggyback infusion at block 5732. Preferably, the digital assistant 118 also displays a message indicating that both infusions (primary and piggyback) are moved by this operation, along with a "Continue" button and a "Cancel" button. If the user presses the "Cancel" button, the first central server 109 returns a cancel code to the second central server 108a via the cancellation URL at block 5728.

If the user presses the "Continue" button, the first central server 109 initiates another channel scanning process 5734. This channel scanning process 5734 is associated with the "new" channel (i.e., the user is attempting to move from an "old" channel to a "new" channel).

Generally, the channel scanning process 5734 prompts the user to scan a machine-readable identifier associated with the "new" pump channel and determines if the scanned channel is available (e.g., not assigned to any patient 112; assigned to the current patient 112, but not in use; assigned to another patient 112 and overwritten; etc.). If the scanned channel is not available, the "change pump channel" action is cancelled. In such an event, the first central server 109 returns a cancel code to the second central server 108a via the cancellation URL at block 5728. The channel scanning process 5734 is described in more detail below with reference to FIG. 59.

If the scanned channel is associated with the patient identifier and the medication identifier (i.e., the new channel is valid), the first central server 109 determines if any other infusions are currently associated with the new channel at block 5736. If another infusion is already associated with the new channel, the first central server 109 causes the digital assistant 118 to display a message indicating that another infusion is currently associated with the new channel and a message asking the user if he/she would like to overwrite the current infusion at block 5738. Preferably, this message includes a "Yes" button, a "No" button, and a "Cancel" button. If the user presses the "Cancel" button, the first central server 109 returns a cancel code to the second central server 108a via the cancellation URL at block 5728. If the user presses the "No" button, the first central server 109 initiates another channel scanning process 5834.

If the user presses the "No" button, the first central server 109 attempts to remove the channel-patient-medication relationship in the database for the new channel at block 5740. If the attempt to remove the channel-patient-medication relationship in the database for the new channel is unsuccessful at block 5742, the first central server 109 causes the digital assistant 118 to display a "change pump channel" error message including the patient identifier, the medication identifier associated with the primary infusion that was not moved (if applicable), and the medication identifier associated with the piggyback infusion that was not moved (if applicable) at block 5744. Once the user acknowledges the "change pump channel" error message by pressing an "OK" button, the first central server 109 returns a failure code to the second central server 108*a* via the completion URL at block 5746.

If another infusion is not already associated with the new channel at block 5736, or the attempt to remove the channel-patient-medication relationship in the database for the new channel is successful at block 5742, the first central server 109 attempts to change the channel-patient-medication relationship in the database for both the primary and piggyback infusions from the old channel to the new channel at block 5748. If the attempt to move the channel-patient-medication relationship in the database from the old channel to the new channel is not successful at block 5750, the first central server 109 causes the digital assistant 118 to display the "change pump channel" error message.

If the attempt to move the channel-patient-medication relationship in the database from the old channel to the new channel is successful at block 5750, the first central server 109 causes the digital assistant 118 to display a "change pump channel" success message including the patient identifier, the medication identifier associated with the primary infusion that was moved (if applicable), and the medication identifier associated with the piggyback infusion that was moved (if applicable) at block 5752. Preferably, the display also includes a message to the user to move the tubing to the new channel. Once the user acknowledges the "change pump channel" success message by pressing an "OK" button, the first central server 109 returns a success code to the second central server 108*a* via the completion URL at block 5746.

Channel Scanning Process

Figure 58:
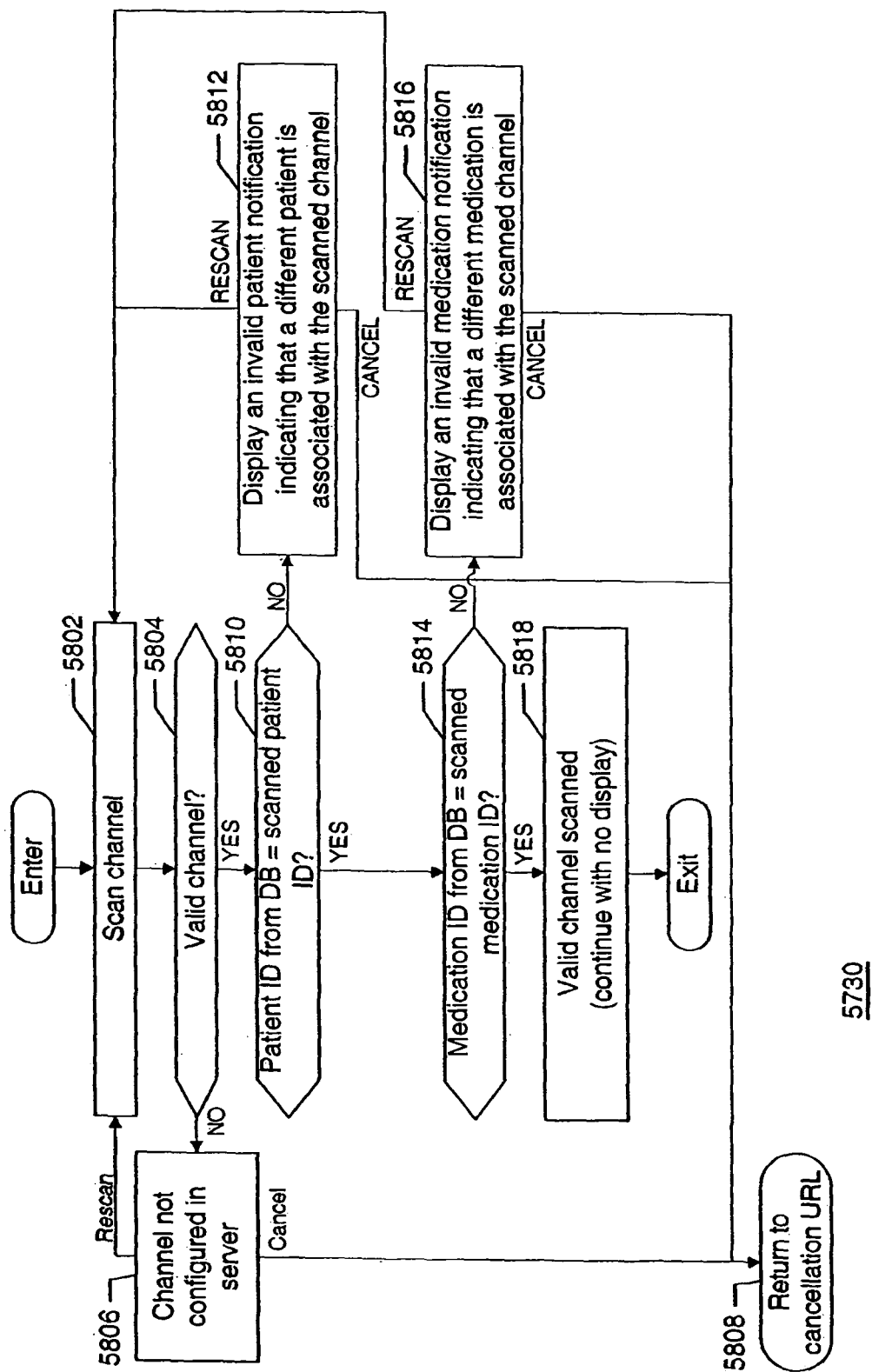
FIG. 58 is a flowchart of another example channel scanning process.

FIG. 58 illustrates an example of the channel scanning process 5730 used above with reference to FIG. 57. Generally, the channel scanning process 5730 prompts the user to scan a machine-readable identifier associated with a pump channel and determines if the scanned channel is associated with the previously scanned patient identifier and medication identifier. If the scanned channel is not associated with the patient identifier and the medication identifier, the current action (e.g., stop, discontinue, resume, channel change, remove pump, etc.) is cancelled.

More specifically, the example channel scanning process 5730 begins when the first central server 109 causes the digital assistant 118 to display a screen prompting the user to scan a machine-readable identifier associated with the channel at block 5802. An example of a digital assistant display 118*a* prompting the user to scan a machine-readable identifier associated with the channel is illustrated in FIG. 38. For example, the user may use the scanner of the digital assistant 118 to scan a barcode label associated with the channel.

Alternatively, the user may manually enter the channel identifier into the digital assistant 118. The channel identifier is then sent to the first central server 109 for verification at block 5804. The first central server 109 then attempts to look up the channel identifier in the database. If the channel identifier does not exist as a valid channel identifier in the database (e.g., not properly formatted, not configured in the first central server 109, etc.), the first central server 109 causes the digital assistant 118 to display an invalid channel notification at block 5806. For example, the digital assistant 118 may display a message that the channel is not configured in the first central server 109 and include buttons allowing the user to rescan the channel identifier or cancel out of the operation. If the user chooses to cancel the operation, the first central server 109 preferably sends a cancel code to the second central server 108*a* via the cancellation URL at block 5808.

Once a valid channel identifier is obtained, the first central server 109 uses the channel identifier to look up a patient identifier in the database. The patient identifier from the database is then compared to the scanned (or manually entered) patient identifier at block 5810. If the two patient identifiers do not match, the first central server 109 causes the digital assistant 118 to display an invalid patient notification at block 5812. For example, the digital assistant 118 may display a message that the scanned patient 112 is not associated with the scanned channel and indicate the actual patient 112 assigned to the scanned channel. Again, the PDA display may include buttons allowing the user to rescan the channel identifier or cancel out of the operation. If the user chooses to cancel the operation, the first central server 109 preferably sends a cancel code to the second central server 108*a* via the cancellation URL at block 5808.

Once a valid channel-patient relationship is established, the first central server 109 uses the channel identifier and the patient identifier to look up a medication identifier in the database (or two medication identifiers if a primary medication 124 and a piggyback medication 124 are both associated with this channel). The medication identifier(s) from the database are then compared to the scanned (or manually entered) medication identifier at block 5814. If one of the medication identifier(s) from the database does not match the scanned (or manually entered) medication identifier, the first central server 109 causes the digital assistant 118 to display an invalid medication notification at block 5816. For example, the digital assistant 118 may display a message that the scanned medication 124 is not associated with the scanned channel and indicate the actual medication 124 assigned to the scanned channel (both primary and piggyback if applicable). Again, the PDA display may include buttons allowing the user to rescan the channel identifier or cancel out of the operation. If the user chooses to cancel the operation, the first central server 109 preferably sends a cancel code to the second central server 108*a* via the cancellation URL at block 5808.

If a valid channel-patient-medication relationship is established, the first central server 109 indicates a valid channel scan occurred and returns control to the current action (e.g., administer, stop, discontinue, resume, channel change, remove pump, etc.) without issuing additional displays to the digital assistant 118 at block 5818.

Channel Scanning Process (New Channel)

Figure 59:
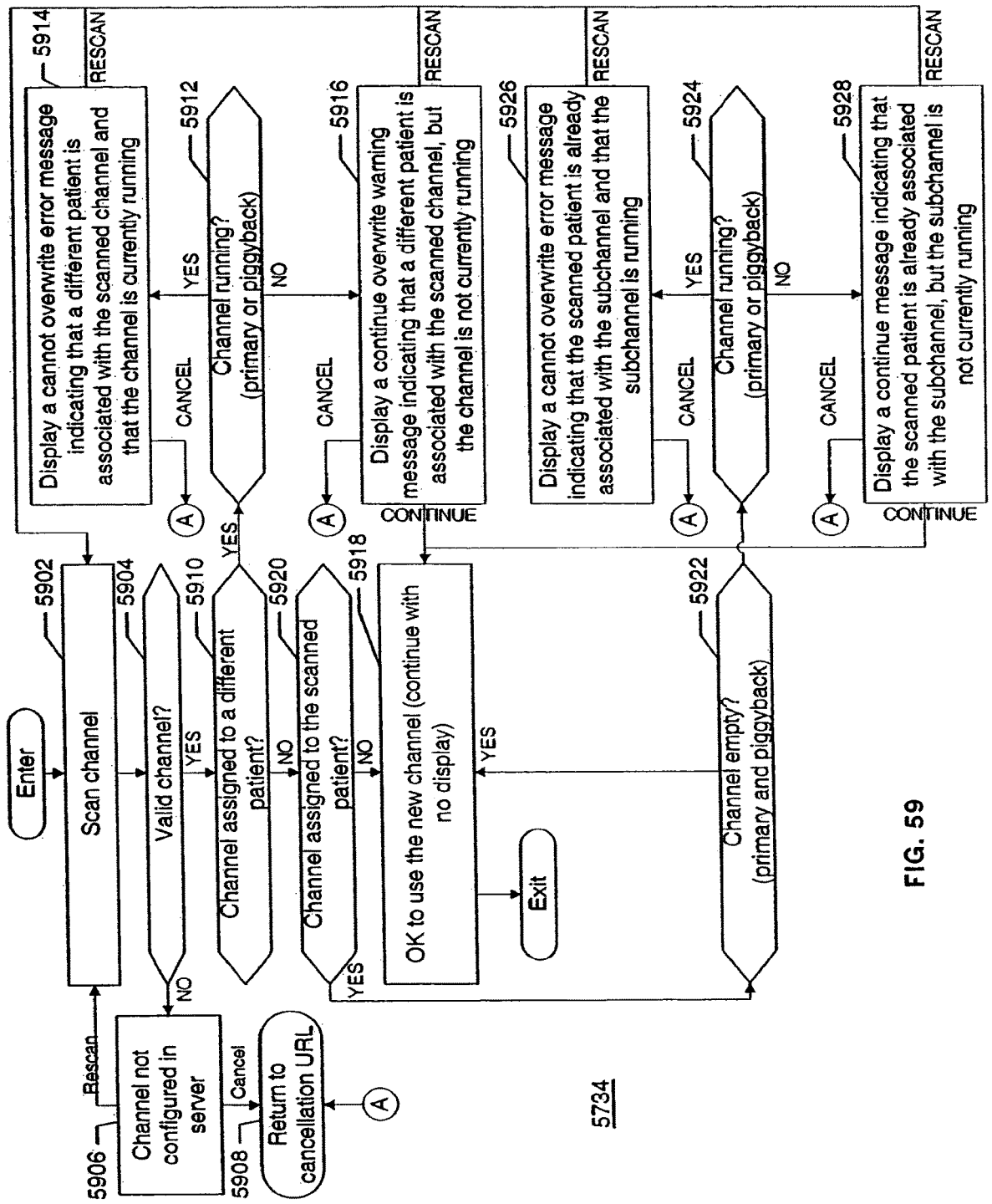
FIG. 59 is a flowchart of yet another example channel scanning process.

FIG. 59 illustrates an example of the channel scanning process 5734 used above with reference to FIG. 57. Generally, the channel scanning process 5734 prompts the user to scan a machine-readable identifier associated with a pump channel and determines if the scanned channel is available (e.g., assigned to the current patient 112, but not in use). If the scanned channel is not available, the current action (e.g., channel change) is cancelled.

More specifically, the example channel scanning process 5734 begins when the first central server 109 causes the digital assistant 118 to display a screen prompting the user to scan a machine-readable identifier associated with the channel at block 5902. An example of a digital assistant display 118*a* prompting the user to scan a machine-readable identifier associated with the channel is illustrated in FIG. 38. For example, the user may use the scanner of the digital assistant 118 to scan a barcode label associated with the channel.

Alternatively, the user may manually enter the channel identifier into the digital assistant 118. The channel identifier is then sent to the first central server 109 for verification at block 5904. The first central server 109 then attempts to lookup the channel identifier in the database.

If the channel identifier does not exist as a valid channel identifier in the database (e.g., not properly formatted, not configured in the first central server 109, etc.), the first central server 109 causes the digital assistant 118 to display an invalid channel notification at block 5906. For example, the digital assistant 118 may display a message that the channel is not configured in the first central server 109 and include buttons allowing the user to rescan the channel identifier or cancel out of the operation. If the user chooses to cancel the operation, the first central server 109 preferably sends a cancel code to the second central server 108*a* via the cancellation URL at block 5908.

Once a valid channel identifier is obtained, the first central server 109 uses the channel identifier to look up a patient identifier in the database. The first central server 109 then compares the patient identifier from the database to the scanned (or manually entered) patient identifier at block 5910. If a valid patient identifier is present in the database, but the two patient identifiers do not match (i.e., the channel is assigned to a different patient 112), the first central server 109 checks the database to see if the channel is running (in either primary and/or piggyback mode) at block 5912.

If the channel is running, the first central server 109 causes the digital assistant 118 to display a "cannot overwrite" error message indicating that a different patient 112 is associated with the scanned channel and that the channel is currently running at block 5914. The error message may also include data indicative of the patient 112 that is associated with the scanned channel (e.g., patient's name), the primary medication 124, and/or the piggyback medication 124. Preferably, the user is given the option to cancel or rescan. If the user chooses to cancel the operation, the first central server 109 sends a cancel code to the second central server 108*a* via the cancellation URL at block 5908. If the user chooses to rescan, the first central server 109 causes the digital assistant 118 to display the screen prompting the user to scan a machine-readable identifier associated with the channel at block 5902.

If the channel is not running, the first central server 109 causes the digital assistant 118 to display a "continue overwrite" warning message indicating that a different patient 112 is associated with the scanned channel, but the channel is not currently running at block 5916.

Preferably, the warning message indicates that continuing will overwrite existing data (e.g., remove the association with the other patient 112). The warning message may also include data indicative of the patient 112 that is associated with the scanned channel (e.g., patient's name), the primary medication 124, and/or the piggyback medication 124. Preferably, the user is given the option to cancel, rescan, or continue. If the user chooses to cancel the operation, the first central server 109 sends a cancel code to the second central server 108*a* via the cancellation URL at block 5908. If the user chooses to rescan, the first central server 109 causes the digital assistant 118 to display the screen prompting the user to scan a machine-readable identifier associated with the channel at block 5902. If the user chooses to continue, the first central server 109 causes the digital assistant 118 to display a message indicating that it is okay to use the selected channel at block 5918. When the user presses "continue" the first central server 109 returns control to the current action (e.g., administer, channel change, etc.) without issuing additional displays to the digital assistant 118.

If a valid patient identifier is present in the database, and the two patient identifiers do match (i.e., the channel is assigned to this patient 112) at block 5920, the first central server 109 checks the database to see if the channel is empty (e.g., no primary or piggyback infusion associated with this channel) at block 5922. If the channel is empty, the first central server 109 causes the digital assistant 118 to display the message indicating that it is okay to use the selected channel at block 5918. If the channel is not empty, the first central server 109 checks the database to see if the channel is running (in either primary and/or piggyback mode) at block 5924.

If the channel is running, the first central server 109 causes the digital assistant 118 to display a "cannot overwrite" error message indicating that this patient 112 is already associated with the scanned channel and that the channel is currently running at block 5926. The error message may also include data indicative of the patient 112 (e.g., patient's name), the primary medication 124, and/or the piggyback medication 124. Preferably, the user is given the option to cancel or rescan. If the user chooses to cancel the operation, the first central server 109 sends a cancel code to the second central server 108*a* via the cancellation URL at block 5908.

If the user chooses to rescan, the first central server 109 causes the digital assistant 118 to display the screen prompting the user to scan a machine-readable identifier associated with the channel at block 5902.

If the channel is not running, the first central server 109 causes the digital assistant 118 to display a "continue" message indicating that this patient 112 is associated with the scanned channel, but the channel is not currently running at block 5928. The message may also include data indicative of the patient 112 (e.g., patient's name), the primary medication 124, and/or the piggyback medication 124. Preferably, the user is given the option to cancel, rescan, or continue. If the user chooses to cancel the operation, the first central server 109 sends a cancel code to the second central server 108*a* via the cancellation URL at block 5908. If the user chooses to rescan, the first central server 109 causes the digital assistant 118 to display the screen prompting the user to scan a machine-readable identifier associated with the channel at block 5902. If the user chooses to continue, the first central server 109 causes the digital assistant 118 to display a message indicating that it is okay to use the selected channel at block 5918. When the user presses continue again, the first central server 109 returns control to the current action (e.g., channel change) without issuing additional displays to the digital assistant 118.

Stop/Discontinue Infusion Process

Figure 60:
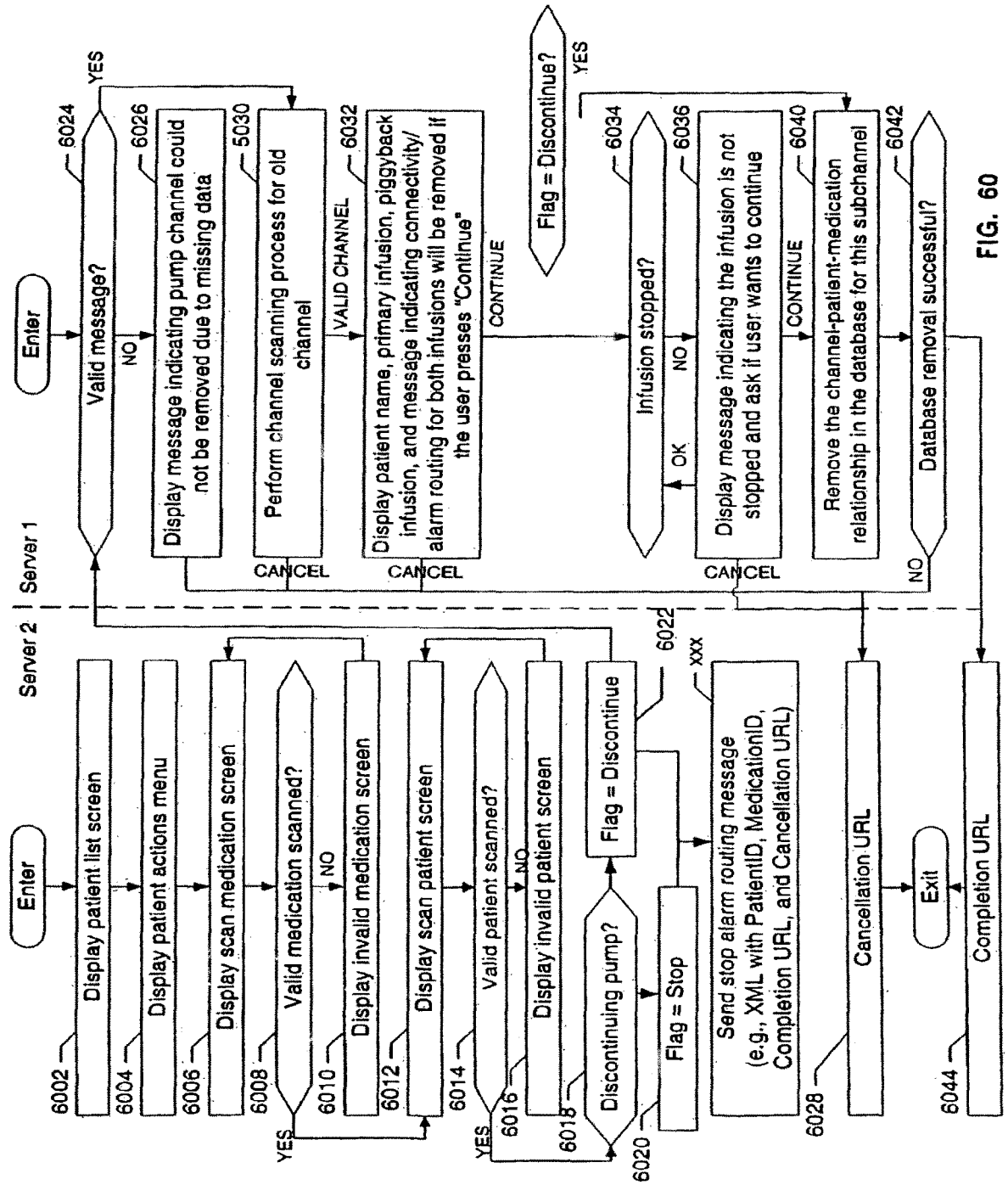
FIG. 60 is a flowchart of an example stop/discontinue infusion process.

FIG. 60 illustrates an example of a stop/discontinue infusion process 6000. The stop/discontinue infusion process 6000 may be used to temporarily stop (i.e., pause) an infusion process or completely discontinue (i.e., end) an infusion process. In general, the stop/discontinue infusion process 6000 receives inputs from an electronic device, such as a digital assistant 118, which includes information regarding whether a stop or a discontinue is to be performed, information identifying which patient 112 is to be affected (e.g., patient ID), and information identifying which medication 124 for that patient 112 is to be stopped or discontinued (e.g., Rx ID). The process 6000 then sends this information to the first central server 109, which confirms that channel identification information matches the stop/ discontinue order information and confirms that the correct infusion is stopped or discontinued.

More specifically, the example stop/discontinue infusion process 6000 begins when the second central server 108*a* causes the digital assistant 118 to display a list of patients at block 6002. An example of a digital assistant display 118*a* showing a list of patients is illustrated in FIG. 24. The list of patients is preferably limited to patients associated with the user (e.g., a clinician 116) who is logged into that digital assistant 118 at the time. Once the user selects a patient 112, information identifying the selection and/or the patient 112 is transmitted from the digital assistant 118 back to the second central server 108*a*. Communication between the digital assistant 118 and the second central server 108*a* may be via any suitable communication channel such as the wireless/wired network 102 described above. The second central server 108*a* then causes the digital assistant 118 to display a list of actions at block 6004. An example of a digital assistant display 118*a* showing a list of actions is illustrated in FIG. 25. The list of actions is preferably limited to actions associated with the selected patient 112. For example, a "stop infusion" action and a "discontinue infusion" action would only be available if an infusion associated with this patient 112 was currently in a running state.

When the user selects the "stop infusion" action or the "discontinue infusion" action from the list of actions, information identifying the action selected is sent to the second central server 108*a*. In response, the second central server 108*a* causes the digital assistant 118 to display a screen listing all running infusions for that patient 112 and prompting the user to scan a machine-readable identifier associated with the medication 124 to be stopped or discontinued at block 6006. An example of a digital assistant display 118*a* prompting the user to scan a machine-readable identifier associated with the medication 124 is illustrated in FIG. 34.

The user may use the scanner of the digital assistant 118 to scan the medication label 124*a* on a bag of medication 124 (e.g., a barcode on an infusion bag). Alternatively, the user may manually enter the medication identifier into the digital assistant 118.

The medication identifier is then sent to the second central server 108*a* for verification at block 6008. The second central server 108*a* attempts to lookup the medication identifier in the database. If the medication identifier (e.g., bag ID) does not exist as a valid medication identifier in the database, the second central server 108*a* causes the digital assistant 118 to display an invalid item notification at block 6010. Once the user acknowledges the invalid item notification (or the notification times out), the digital assistant 118 re-displays the screen prompting the user to scan a machine-readable identifier associated with the medication 124 to be stopped or discontinued at block 6006.

If the medication identifier (e.g., bag ID) does exist as a valid medication identifier in the database at block 6008, the second central server 108*a* causes the digital assistant 118 to display a screen prompting the user to scan a machine-readable identifier associated with the patient 112 at block 6012. An example of a digital assistant display 118*a* prompting the user to scan a machine-readable identifier associated with the patient 112 is illustrated in FIG. 36.

The user may use the scanner of the digital assistant 118 to scan a barcode label on a patient wristband 112*a*. Alternatively, the user may manually enter the patient identifier into the digital assistant 118. The patient identifier is then sent to the second central server 108*a* for verification at block 6014. The second central server 108*a* then attempts to lookup the patient identifier in the database. If the patient identifier (e.g., wristband ID) does not exist as a valid patient identifier in the database, the second central server 108*a* causes the digital assistant 118 to display an invalid patient notification at block 6016. Once the user acknowledges the invalid patient notification (or the notification times out), the digital assistant 118 re-displays the screen prompting the user to scan a machine-readable identifier associated with the patient 112 at block 6012.

If the patient identifier (e.g., wristband ID) does exist as a valid patient identifier in the database at block 6014, the second central server 108*a* may also prompt the user for a code indicative of the reason for the "stop infusion" action or the "discontinue infusion" action. If this reason code is not supplied, the system preferably displays a message to the user that a reason code must be supplied. In addition, the second central server 108*a* may timestamp the order and/or prompt the user for a time when the action is to occur. Still further, the second central server 108*a* preferably checks the status of the infusion order to determine if the infusion order is active or discontinued.

If the infusion order is active, the second central server 108*a* determines if the user is attempting to issue a "stop infusion" action or a "discontinue infusion" action based on the user selection from block 6004 at block 6018. If the user is attempting to issue a "stop infusion" action, the second central server 108*a* sets a "DCFlag" in a "stop infusion" XML document to "FALSE" at block 6020. If the user is attempting to issue a "discontinue infusion" action, the second central server 108*a* sets the "DCFlag" in the "stop infusion" XML document to "TRUE" at block 6022. Of course, any well-known method of indicating the state of a variable may be used.

The "stop infusion" XML document, including the patient identifier (e.g., wristband ID), the medication identifier (e.g., bag ID), a completion URL, a cancellation URL, and the DCFlag (indicating stop vs. discontinue) are then transmitted to the first central server 109.

The completion URL is a network address used if the infusion is successfully stopped or discontinued. The cancellation URL is a network address used if the "stop infusion" action or the "discontinue infusion" action fails or is cancelled.

Once the first central server 109 receives the "stop infusion" XML document, the first central server 109 determines if the "stop infusion" XML document is valid at block 6024. For example, the first central server 109 may check if any data normally expected in a "stop infusion" XML document is missing from the received "stop infusion" XML document. If the first central server 109 determines that the "stop infusion" XML document is not valid, the first central server 109 causes the digital assistant 118 to display an error message indicating to the user that the "stop infusion" action or the "discontinue infusion" action could not be executed at block 6026. This display may include a reason such as which data was missing from the "stop infusion" XML document. After the user presses an "OK" button to acknowledge the error message, the first central server 109 returns a failure code to the second central server 108*a* via the cancellation URL at block 6028.

If the first central server 109 determines that the "stop infusion" XML document is valid, the first central server 109 initiates a channel scanning process 5730. Generally, the channel scanning process 5730 prompts the user to scan a machine-readable identifier associated with the pump channel currently running the infusion to be stopped or discontinued and determines if the scanned channel is associated with the patient identifier and the medication identifier (as described in detail above with reference to FIG. 58. If the scanned channel is not associated with the patient identifier and the medication identifier, the "stop infusion" action or the "discontinue infusion" action is cancelled. In such an event, the first central server 109 returns a cancel code to the second central server 108*a* via the cancellation URL at block 6028.

If the scanned channel is associated with the patient identifier and the medication identifier (i.e., the channel is valid), the first central server 109 causes the digital assistant 118 to display a message indicating the patient 112 and infusion to be stopped including the details of the medication 124 to be stopped and the channel the medication 124 is on at block 6032.

Preferably, the PDA display also includes a "Continue" button and a "Cancel" button. In this manner, the user may manually stop the indicated infusion and then press the "Continue" button to inform the first central server 109 to check if the correct infusion was actually stopped or discontinued. Alternatively, the user may press the "Cancel" button, at which point the first central server 109 returns a cancel code to the second central server 108*a* via the cancellation URL at block 6028.

If the user presses the "Continue" button, the first central server 109 determines if the infusion was stopped by reading status information sent to the first central server 109 by the pump 120 at block 6034. If the pump 120 is unable to communicate with the first central server 109, the first central server 109 generates a loss of communication event for that channel. If communication with a channel is lost, the status of the infusion on that channel cannot be changed to "stopped" or "discontinued" until communication with that channel is restored. If communication is working properly, but the infusion was not stopped, the first central server 109 causes the digital assistant 118 to display a warning message indicating that the infusion was not stopped and indicating the patient 112 and infusion to be stopped at block 6036.

Preferably, the display also includes an "OK" button and a "Cancel" button. If the user presses the "OK" button, the first central server 109 checks again to see if the correct infusion was actually stopped or discontinued at block 6034. If the user presses the "Cancel" button, the first central server 109 returns a cancel code to the second central server 108*a* via the cancellation URL at block 6028.

If the infusion is stopped at block 6034, the first central server 109 checks if this is a "stop infusion" action or a "discontinue infusion" action. For example, the first central server 109 may check the state of a flag such as the DCFlag set by block 6020 or block 6022. If this is a "stop infusion" action (i.e., pause infusion), the first central server 109 returns a success code and DCFlag=FALSE to the second central server 108*a* via the completion URL at block 6044.

If instead this is a "discontinue infusion" action (i.e., end infusion), the first central server 109 preferably attempts to remove the database association between the patient identifier, the medication identifier, and the channel identifier for either the primary infusion or the piggyback infusion, but preferably not both at block 6040. If the user wants to stop or discontinue both a primary infusion and a piggyback infusion running on a channel, the user may execute the "stop infusion" action or the "discontinue infusion" action twice, once for each infusion. If the first central server 109 is not successful in removing the database association at block 6042, the first central server 109 returns a failure code to the second central server 108*a* via the cancellation URL at block 6028. If the first central server 109 is successful in removing the database association at block 6042, the first central server 109 returns a success code and DCFlag=TRUE to the second central server 108*a* via the completion URL at block 6044.

The first central server 109 removes the association between the patient identifier, the medication identifier, and the channel identifier for the selected infusion only if a "discontinue infusion" action is successful. Otherwise, the association is maintained. For example, if a "stop infusion" action is successful or a "discontinue infusion" action fails, the association between the patient identifier, the medication identifier, and the channel identifier is maintained. Similarly, the second central server 108*a* only updates the status of the infusion to "stopped" or "discontinued" upon receiving a success code from the first central server 109.

Any other result (e.g., cancel code or failure code) causes the second central server 108*a* to keep the infusion in its previous state. Preferably, at any point in the process 6000 the user has the option to cancel out of the process 6000. The Stop/Discontinue process may be utilized to document that the infusion was restarted for purposes of the MAR.

Resume Infusion Process

Figure 61:
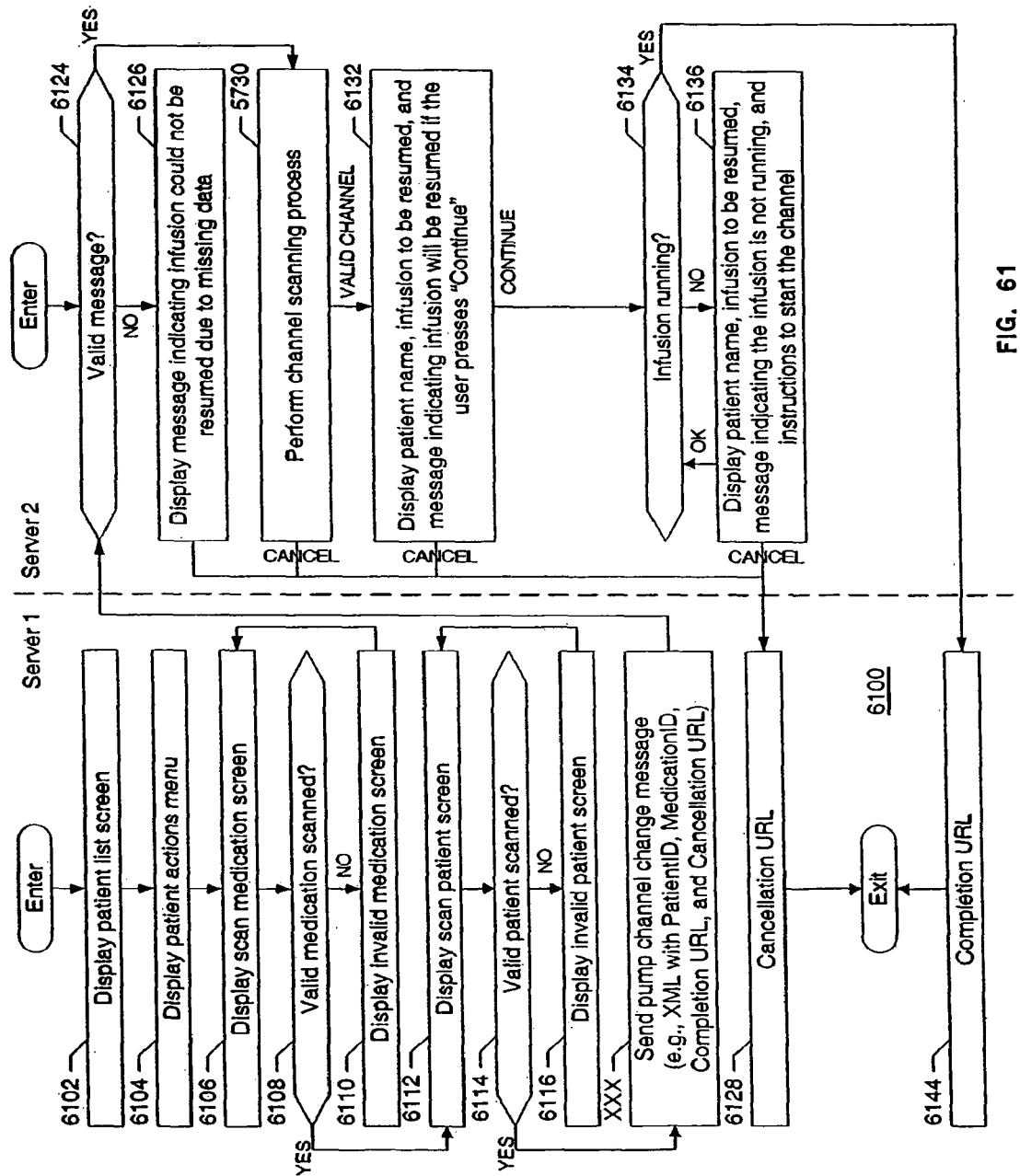
FIG. 61 is a flowchart of an example resume infusion process.

FIG. 61 illustrates an example of a resume infusion process 6100. The resume infusion process 6100 may be used to restart a stopped (i.e., paused) infusion process. However, the resume infusion process 6100 may not be used to restart a discontinued (i.e., ended) infusion process. In general, the resume infusion process 6100 receives inputs from an electronic device, such as a digital assistant 118, which includes information indicating a resume process is to be performed, information identifying which patient 112 is to be affected (e.g., patient ID), and information identifying which medication 124 for that patient 112 is to be resumed (e.g., Rx ID). The process 6100 then sends this information to the first central server 109, which confirms that channel identification information matches the resume order information and confirms that the correct infusion is resumed.

More specifically, the example resume infusion process 6100 begins when the second central server 108*a* causes the digital assistant 118 to display a list of patients at block 6102. An example of a digital assistant display 118*a* showing a list of patients is illustrated in FIG. 24. The list of patients is preferably limited to patients associated with the user (e.g., a clinician 116) who is logged into that digital assistant 118 at the time. Once the user selects a patient 112, information identifying the selection and/or the patient 112 is transmitted from the digital assistant 118 back to the second central server 108*a*. Communication between the digital assistant 118 and the second central server 108*a* may be via any suitable communication channel such as the wireless/wired network 102 described above. The second central server 108*a* then causes the digital assistant 118 to display a list of actions at block 6104. An example of a digital assistant display 118*a* showing a list of actions is illustrated in FIG. 25. The list of actions is preferably limited to actions associated with the selected patient 112. For example, a "resume infusion" action would only be available if an infusion associated with this patient 112 was currently in a stopped state.

When the user selects the "resume infusion" action from the list of actions, information identifying the action selected is sent to the second central server 108*a*. In response, the second central server 108*a* causes the digital assistant 118 to display a screen prompting the user to scan a machine-readable identifier associated with the medication 124 to be resumed at block 6106. An example of a digital assistant display 118*a* prompting the user to scan a machine-readable identifier associated with the medication 124 is illustrated in FIG. 34. The user may use the scanner of the digital assistant 118 to scan the medication label 124a on a bag of medication 124 (e.g., a barcode on an infusion bag). Alternatively, the user may manually enter the medication identifier into the digital assistant 118.

The medication identifier is then sent to the second central server 108a for verification at block 6108. The second central server 108a attempts to lookup the medication identifier in the database. If the medication identifier (e.g., bag ID) does not exist as a valid medication identifier in the database, the second central server 108a causes the digital assistant 118 to display an invalid item notification at block 6110. Once the user acknowledges the invalid item notification (or the notification times out), the digital assistant 118 re-displays the screen prompting the user to scan a machine-readable identifier associated with the medication 124 to be resumed at block 6106. If the user scans a machine-readable identifier associated with a medication 124 to be resumed, but the medication 124 has been discontinued, the second central server 108a preferably causes the digital assistant 118 to display a message to the user indicating that the medication 124 cannot be resumed due to its discontinued state.

If the medication identifier (e.g., bag ID) does exist as a valid medication identifier in the database at block 6108, and has not been discontinued, the second central server 108a causes the digital assistant 118 to display a screen prompting the user to scan a machine-readable identifier associated with the patient 112 at block 6112. An example of a digital assistant display 118a prompting the user to scan a machine-readable identifier associated with the patient 112 is illustrated in FIG. 36. The user may use the scanner of the digital assistant 118 to scan a barcode label on a patient wristband 112a. Alternatively, the user may manually enter the patient identifier into the digital assistant 118. The patient identifier is then sent to the second central server 108a for verification at block 6114. The second central server 108a then attempts to lookup the patient identifier in the database. If the patient identifier (e.g., wristband ID) does not exist as a valid patient identifier in the database, the second central server 108a causes the digital assistant 118 to display an invalid patient notification at block 6116. Once the user acknowledges the invalid patient notification (or the notification times out), the digital assistant 118 re-displays the screen prompting the user to scan a machine readable identifier associated with the patient 112 at block 6112.

If the patient identifier (e.g., wristband ID) does exist as a valid patient identifier in the database at block 6114, the second central server 108a may also prompt the user for a code indicative of the reason for the "resume infusion" action. If this reason code is not supplied, the system preferably displays a message to the user that a reason code must be supplied. In addition, the second central server 108a may timestamp the order and/or prompt the user for a time when the action is to occur. Still further, the second central server 108 a preferably checks the status of the infusion order to determine if the infusion order is active or discontinued.

If the infusion order is active, the second central server 108a transmits a "resume infusion" XML document to the first central server 109. The "resume infusion" XML document includes the patient identifier (e.g., wristband ID), the medication identifier (e.g., bag ID), a completion URL, and a cancellation URL. The completion URL is a network address used if the infusion is successfully resumed. The cancellation URL is a network address used if the "resume infusion" action fails or is cancelled.

Once the first central server 109 receives the "resume infusion" XML document, the first central server 109 determines if the "resume infusion" XML document is valid at block 6124. For example, the first central server 109 may check if any data normally expected in a "resume infusion" XML document is missing from the received "resume infusion" XML document. If the first central server 109 determines that the "resume infusion" XML document is not valid, the first central server 109 causes the digital assistant 118 to display an error message indicating to the user that the "resume infusion" action could not be executed at block 6126. This display may include a reason such as which data was missing from the "resume infusion" XML document. After the user presses an "OK" button to acknowledge the error message, the first central server 109 returns a failure code to the second central server 108a via the cancellation URL at block 6128.

If the first central server 109 determines that the "resume infusion" XML document is valid, the first central server 109 initiates the channel scanning process 5730. Generally, the channel scanning process 5730 prompts the user to scan a machine-readable identifier associated with the pump channel currently associated with the infusion to be resumed and determines if the scanned channel is associated with the patient identifier and the medication identifier (as described in detail above with reference to FIG. 58). If the scanned channel is not associated with the patient identifier and the medication identifier, the "resume infusion" action is cancelled. In such an event, the first central server 109 returns a cancel code to the second central server 108a via the cancellation URL at block 6128.

If the scanned channel is associated with the patient identifier and the medication identifier (i.e., the channel is valid), the first central server 109 causes the digital assistant 118 to display a message indicating the patient 112 and infusion to be resumed at block 6132. Preferably, the PDA display also includes a "Continue" button and a "Cancel" button. In this manner, the user may manually resume the indicated infusion and then press the "Continue" button to inform the first central server 109 to check if the correct infusion was actually resumed. Alternatively, the user may press the "Cancel" button, at which point the first central server 109 returns a cancel code to the second central server 108a via the cancellation URL at block 6128.

If the user presses the "Continue" button, the first central server 109 determines if the infusion was resumed by reading status information sent to the first central server 109 by the pump 120 at block 6134. If the pump 120 is unable to communicate with the first central server 109, the first central server 109 generates a loss of communication event for that channel. If communication with a channel is lost, the status of the infusion on that channel cannot be changed to "resumed" until communication with that channel is restored. If communication is working properly, but the infusion was not resumed, the first central server 109 causes the digital assistant 118 to display a warning message indicating that the infusion was not resumed and indicating the patient 112 and infusion to be resumed at block 6136. Preferably, the display also includes an "OK" button and a "Cancel" button. If the user presses the "OK" button, the first central server 109 checks again to see if the correct infusion was actually resumed at block 6134. If the user presses the "Cancel" button, the first central server 109 returns a cancel code to the second central server 108a via the cancellation URL at block 6128.

If the infusion is resumed at block 6134, the first central server 109 returns a success code to the second central server

108a via the completion URL at block 6144. The first central server 109 maintains the association between the patient identifier, the medication identifier, and the channel identifier for the selected infusion. The second central server 108a only updates the status of the infusion to "running" upon receiving a success code from the first central server 109. Any other result (e.g., cancel code or failure code) causes the second central server 108a to keep the infusion in its previous state. Preferably, if the user wants to resume both a primary infusion and a piggyback infusion running on a channel, the user may execute the "resume infusion" action twice, once for each infusion. The Resume process may be utilized to document that the infusion was restarted for purposes of the MAR.

Remove Pump Process

Figure 62:
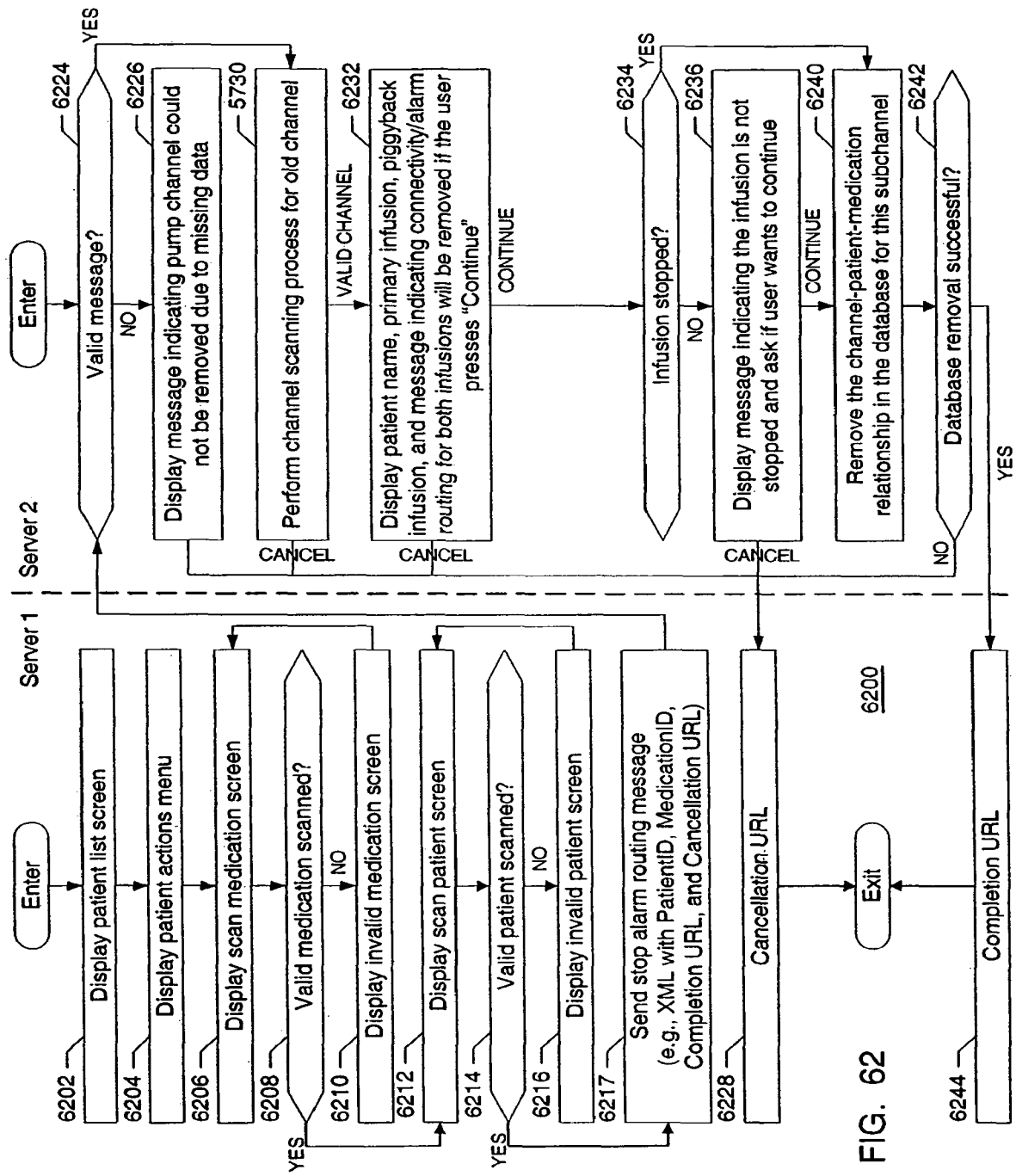
FIG. 62 is a flowchart of an example remove pump process.

FIG. 62 illustrates an example of a remove pump process 6200. The remove pump process 6200 may be used to terminate a channel-patient-medication relationship in the first central server 109 database independent of a discontinue infusion order existing in the pharmacy database and without going through the stop/discontinue infusion process 6000 describe above. In general, the remove pump process 6200 receives inputs from an electronic device, such as a digital assistant 118, which includes information indicating a remove pump process is to be performed, information identifying which patient 112 is to be affected (e.g., patient ID), and information identifying which medication 124 for that patient 112 is to be affected (e.g., Rx ID). The process 6200 then sends this information to the first central server 109, which confirms that channel identification information matches the remove pump order information and confirms that the correct pump 120 is removed.

More specifically, the example remove pump process 6200 begins when the second central server 108a causes the digital assistant 118 to display a list of patients for selection at block 6202. An example of a digital assistant display 118a showing a list of patients is illustrated in FIG. 24. The list of patients is preferably limited to patients associated with the user (e.g., a clinician 116) who is logged into that digital assistant 118 at the time. Once the user selects a patient 112, information identifying the selection and/or the patient 112 is transmitted from the digital assistant 118 back to the second central server 108a.

Communication between the digital assistant 118 and the second central server 108a may be via any suitable communication channel such as the wireless/wired network 102 described above.

The second central server 108a then causes the digital assistant 118 to display a list of actions at block 6204. An example of a digital assistant display 118a showing a list of actions is illustrated in FIG. 25. The list of actions is preferably limited to actions associated with the selected patient 112. For example, a "remove pump" action would only be available if an infusion associated with this patient 112 was currently listed in the first central server 109 database.

When the user selects the "remove pump" action from the list of actions, information identifying the action selected is sent to the second central server 108a. In response, the second central server 108a causes the digital assistant 118 to display a screen prompting the user to scan a machine-readable identifier associated with the medication 124 to be affected by this "remove pump" action at block 6206. An example of a digital assistant display 118a prompting the user to scan a machine-readable identifier associated with the medication 124 is illustrated in FIG. 34. The user may use the scanner of the digital assistant 118 to scan the medication label 124a on a bag of medication 124 (e.g., a barcode on an infusion bag). Alternatively, the user may manually enter the medication identifier into the digital assistant 118.

The medication identifier is then sent to the second central server 108a for verification at block 6208. The second central server 108a (or the digital assistant 118) checks if a properly formatted medication identifier was received. Preferably, the second central server 108a does not need to check if the medication identifier matches a current infusion in the second central server 108a database, because the purpose of the "remove pump" action is to remove associations from the first central server 109 database that have no corresponding infusions in the second central server 108a database.

If the medication identifier (e.g., bag ID) is not properly formatted, the second central server 108a causes the digital assistant 118 to display an invalid item notification at block 6210.

Once the user acknowledges the invalid item notification (or the notification times out), the digital assistant 118 re-displays the screen prompting the user to scan a machine-readable identifier associated with the medication 124 to be resumed at block 6206. If the medication identifier (e.g., bag ID) is properly formatted at block 6208, the second central server 108a causes the digital assistant 118 to display a screen prompting the user to scan a machine-readable identifier associated with the patient 112 at block 6212. An example of a digital assistant display 118a prompting the user to scan a machine-readable identifier associated with the patient 112 is illustrated in FIG. 36. The user may use the scanner of the digital assistant 118 to scan a barcode label on a patient wristband 112a.

Alternatively, the user may manually enter the patient identifier into the digital assistant 118. The patient identifier is then sent to the second central server 108a for verification at block 6214. The second central server 108a (or the digital assistant 118) then checks if a properly formatted patient identifier was received. Preferably, the second central server 108a does not need to check if the patient identifier matches a current infusion in the second central server 108a database, because the purpose of the "remove pump" action is to remove associations from the first central server 109 database that have no corresponding infusions in the second central server 108a database. However, the second central server 108a (or the digital assistant 118) may check if the patient identifier matches the patient 112 selected in block 6202.

If the patient identifier (e.g., wristband ID) is not properly formatted, or the patient identifier does not match the patient 112 selected in block 6202, the second central server 108a causes the digital assistant 118 to display an invalid patient notification at block 6216. Once the user acknowledges the invalid patient notification (or the notification times out), the digital assistant 118 re-displays the screen prompting the user to scan a machine-readable identifier associated with the patient 112 at block 6212.

If the patient identifier (e.g., wristband ID) is properly formatted and matches the patient 112 selected in block 6202 at block 6214, the second central server 108a transmits a "stop alarm routing" XML document to the first central server 109 at block 6217. The "stop alarm routing" XML document includes the patient identifier (e.g., wristband ID), the medication identifier (e.g., bag ID), a completion URL, and a cancellation URL. The completion URL is a network address used if the pump 120 is successfully removed. The cancellation URL is a network address used if the "remove pump" action fails or is cancelled.

Once the first central server 109 receives the "stop alarm routing" XML document, the first central server 109 determines if the "stop alarm routing" XML document is valid at block 6224. For example, the first central server 109 may check if any data normally expected in a "stop alarm routing" XML document is missing from the received "stop alarm routing" XML document. If the first central server 109 determines that the "stop alarm routing" XML document is not valid, the first central server 109 causes the digital assistant 118 to display an error message indicating to the user that the "stop alarm routing" action could not be executed at block 6226. This display may include a reason such as which data was missing from the "stop alarm routing" XML document. After the user presses an "OK" button to acknowledge the error message, the first central server 109 returns a failure code to the second central server 108*a* via the cancellation URL at block 6228.

If the first central server 109 determines that the "stop alarm routing" XML document is valid, the first central server 109 initiates the channel scanning process 5730. Generally, the channel scanning process 5730 prompts the user to scan a machine-readable identifier associated with the pump channel currently associated with the pump 120 to be removed and determines if the scanned channel is associated with the patient identifier and the medication identifier (as described in detail above with reference to FIG. 58. If the scanned channel is not associated with the patient identifier and the medication identifier, the "remove pump" action is cancelled. In such an event, the first central server 109 returns a cancel code to the second central server 108*a* via the cancellation URL at block 6228. If the scanned channel is associated with the patient identifier and the medication identifier (i.e., the channel is valid), the first central server 109 causes the digital assistant 118 to display a message indicating the patient 112 and infusion associated with this action at block 6232. Preferably, the PDA display also includes a "Continue" button and a "Cancel" button. In this manner, the user may manually stop the indicated infusion and then press the "Continue" button to inform the first central server 109 to check if the correct infusion was actually stopped. Alternatively, the user may press the "Cancel" button, at which point the first central server 109 returns a cancel code to the second central server 108*a* via the cancellation URL at block 6228.

If the user presses the "Continue" button, the first central server 109 determines if the infusion was stopped by reading status information sent to the first central server 109 by the pump 120 at block 6234. If the infusion was not stopped, the first central server 109 causes the digital assistant 118 to display a warning message indicating that the infusion was not stopped at block 6236. Preferably, the display also includes an "Continue" button and a "Cancel" button. If the user presses the "Cancel" button, the first central server 109 returns a cancel code to the second central server 108*a* via the cancellation URL at block 6228.

If the user presses the "Continue" button, the first central server 109 attempts to remove the database association between the patient identifier, the medication identifier, and the channel identifier for either the primary infusion or the piggyback infusion, but preferably not both at block 6240. If the user wants to stop alarm routing associated with both a primary infusion and a piggyback infusion running on a channel, the user may execute the "remove pump" action twice, once for each infusion. If the first central server 109 is not successful in removing the database association at block 6242, the first central server 109 returns a failure code to the second central server 108*a* via the cancellation URL at block 6228. If the first central server 109 is successful in removing the database association at block 6242, the first central server 109 returns a success code to the second central server 108*a* via the completion URL at block 6244.

The first central server 109 removes the association between the patient identifier, the medication identifier, and the channel identifier for the selected infusion—only if a "remove pump" action is successful. Otherwise, the association is maintained. The second central server 108*a* need not update the status of the "removed" infusion upon receiving a success code from the first central server 109.

Secure Communication Process

As described above, the system may include a plurality of digital assistants 118 and a plurality of medical devices (e.g., infusion pumps 120) communicating over a wired or wireless network. Because some of the data being transmitted is confidential medical data, the data is preferably encrypted and only communicated in the clear to authorized users and devices. In order to setup a new digital assistant 118 or medical device 120, a commissioning phase of the authentication process may be performed. Each time a commissioned device is powered up, an authentication process is preferably performed in order to verify communication is occurring with an authorized device and/or user. Once a device and/or user is authenticated, secure one way and/or two-way communication may occur in order to pass parameters, instructions, data, alarms, status information, and any other type of information between digital assistants, medical devices, and/or servers.

Figure 63:
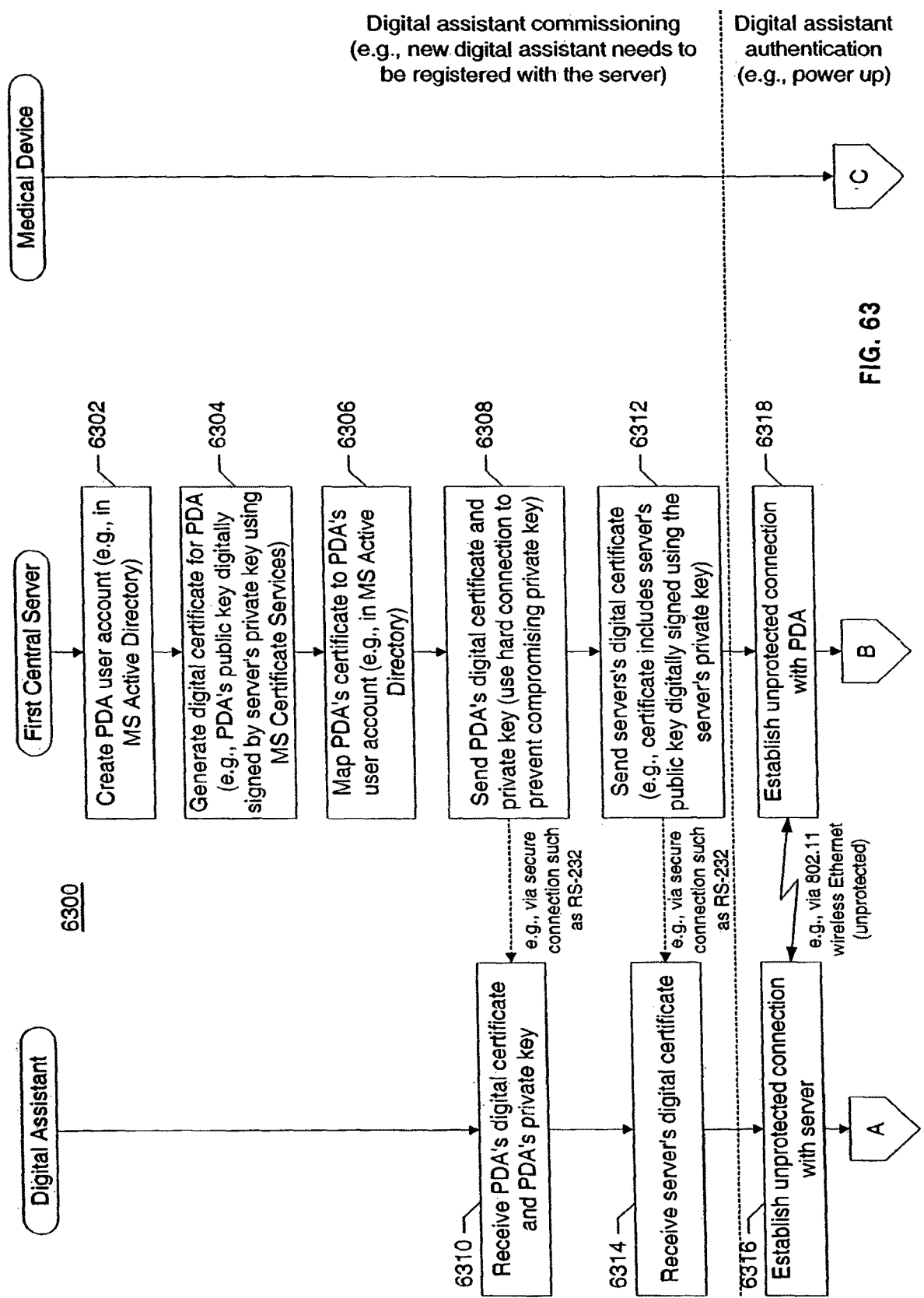
FIG. 63-FIG. 69 is a flowchart of an example authentication process.

Referring to FIG. 63, a digital assistant commissioning phase (i.e., server registration phase) of a secure communication process 6300 begins at block 6302 when the first central server 109 creates a digital assistant user account. For example, the digital assistant user account may be established using Microsoft Active Directory in a well-known manner. The first central server 109 then generates a digital certificate for the digital assistant 118 at block 6304. The digital certificate may be generated in any manner. For example, the digital certificate may be generated at the first central server 109 using Microsoft Digital Certificate Services in a well-known manner. The digital certificate preferably includes the digital assistant's public key digitally signed using the first central server's private key. In other words, the first central server 109 is acting as the certification authority (CA) for the digital assistant's digital certificate. Once the digital certificate is generated, the first central server 109 maps the digital certificate to the user account at block 6306.

The digital assistant's digital certificate and the digital assistant's private key are then sent by the first central server 109 at block 6308 to the digital assistant 118 at block 6310.

Preferably, the digital assistant's digital certificate and the digital assistant's private key are sent to the digital assistant 118 via a secure connection. For example, an RS-232 cable that is not connected to any other devices may be used. In addition, the first central server's digital certificate is sent by the first central server 109 at block 6312 to the digital assistant 118 at block 6314. Again, the first central server's digital certificate is preferably sent to the digital assistant 118 via a secure connection such as an RS-232 cable that is not connected to any other devices. At this point, the digital assistant 118 is commissioned (i.e., registered with the server).

Of course, any method of communicating with the digital assistant 118 may be used. In one example, the digital assistant's private key may be stored in a memory associated with the digital assistant 118 (e.g., an EPROM) at the time the digital assistant 118 is manufactured. In addition, each digital assistant 118 may have the same private key, with different identification codes used to distinguish one digital assistant 118 from another.

Each time a commissioned digital assistant 118 is turned on, the digital assistant 118 and the first central server 109 must perform an authentication process in order to move from an unsecured wireless connection to a secured wireless connection. In the example illustrated, the digital assistant 118 establishes an unsecured 802.11 (wireless Ethernet) connection with the first central server 109 at block 6316 and block 6318. Of course, any type of connection may be used, such as a wired connection or a connection using another protocol.

Figure 64:
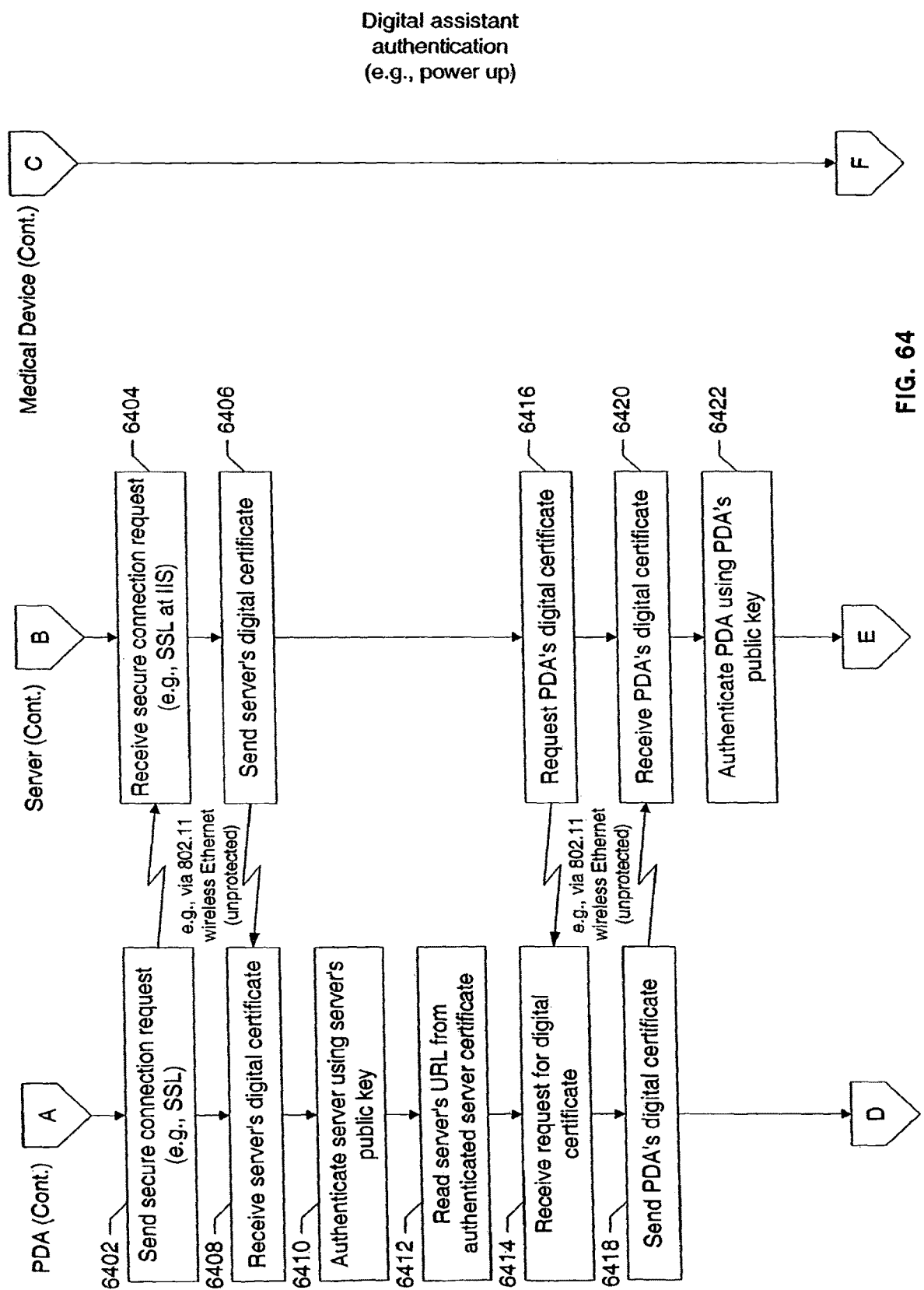

Turning to FIG. 64, at block 6402 the digital assistant 118 sends a request to the first central server 109 to establish a secure connection. The first central server 109 receives the digital assistant's request to establish a secure connection at block 6404. The first central server 109 responds to the request to establish a secure connection at block 6406 by sending a copy of the first central server's digital certificate to the digital assistant 118 over the unsecured connection. The digital assistant 118 receives the first central server's digital certificate at block 6408.

The digital assistant 118 uses the first central server's digital certificate to authenticate the first central server 109 at block 6410. In addition, at block 6412 the digital assistant 118 uses the first central server's digital certificate to retrieve an embedded uniform resource locator (URL) associated with the first central server 109. The digital assistant 118 can now request data and services from the retrieved URL knowing it is talking to the real first central server 109.

Next, at block 6414 the first central server 109 sends a request to the digital assistant 118 to establish the other half of the secure connection. The digital assistant 118 receives the first central server's request at block 6416. The digital assistant 118 responds to the request to establish a secure connection at block 6418 by sending a copy of the digital assistant's digital certificate to the first central server 109. The first central server 109 receives the digital assistant's digital certificate at block 6420.

Figure 65:
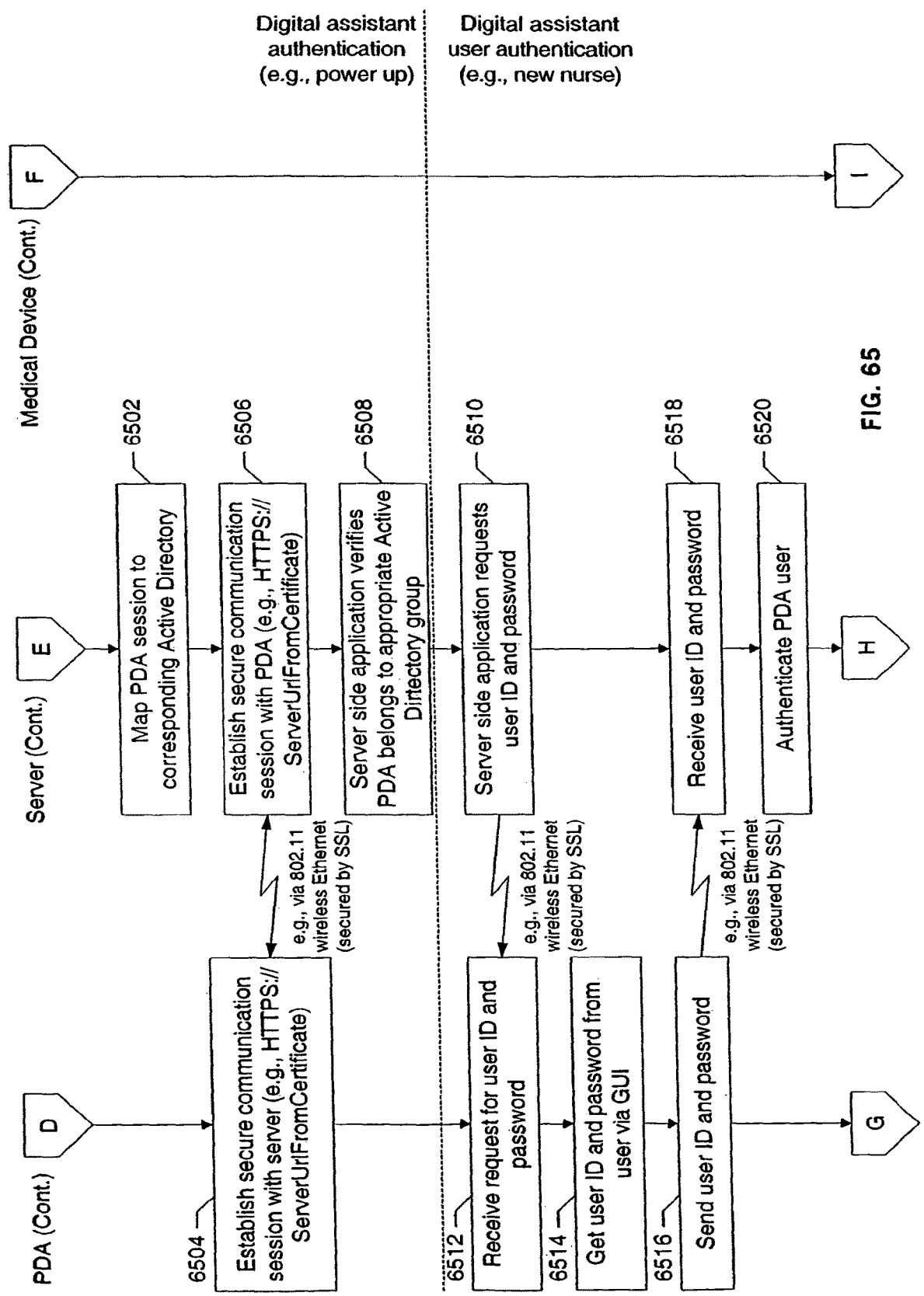

The first central server 109 uses the digital assistant's digital certificate to authenticate the digital assistant 118 at block 6422. The first central server 109 can now communicate with the digital assistant 118 knowing it is talking to a commissioned digital assistant 118. In addition, turning to FIG. 65, the first central server 109 establishes what files this digital assistant is authorized to access by mapping a session for the digital assistant user account to an active directory at block 6502.

Now that the digital assistant 118 is communicating with the first central server 109 over a secure connection, and the digital assistant 118 is cleared to access certain files on the first central server 109, at block 6504 the digital assistant 118 may establish a secure communication session with the first central server 109 by accessing the URL retrieved from the first central server's digital certificate. The first central server 109 also establishes the secure communication session at block 6506. In addition, an application on the first central server 109 verifies the digital assistant 118 belongs to the appropriate active directory at block 6508.

Although the digital assistant 118 may now be authenticated, the first central server 109 still does not know the identity of the user using the digital assistant 118. This is important because some users may have different access rights than other users, and certain alarms and other data are only sent to specific users. Accordingly, an application on the first central server 109 may request a user name and password from the user of the digital assistant 118 at block 6510. Once the digital assistant 118 receives the request for a user name and password at block 6512, the digital assistant 118 retrieves a user name and password from the user via a prompt on the digital assistant display 118a at block 6514. The user name and password are then sent by the digital assistant 118 at block 6516 and received by the first central server 109 at block 6518. The application on the first central server 109 may then authenticate the user at block 6520.

Once the user is authenticated on one server (e.g., the first central server 109), the authentication credentials may be used to automatically authenticate the digital assistant 118 on another server (e.g., second central server 108a). In one example, a user may only be authenticated if the user is authenticated on both the first central server 109 and the second central server 108a. Accordingly, the user name and password are preferably synchronized between the first central server 109 and the second central server 108a whenever a user name or password is created or modified.

After authenticating the user, the first central server 109 preferably returns a token that will be unique to the session between the user and the first central server 109. This session token is passed with each request (e.g., in an HTTP header or as a cookie) made to the first central server 109 as a means of authenticating the origin of the request and hence the destination of the response. Once this token is in place, the digital assistant 118 may roam from one wireless access point 114 to another seamlessly.

Figure 66:
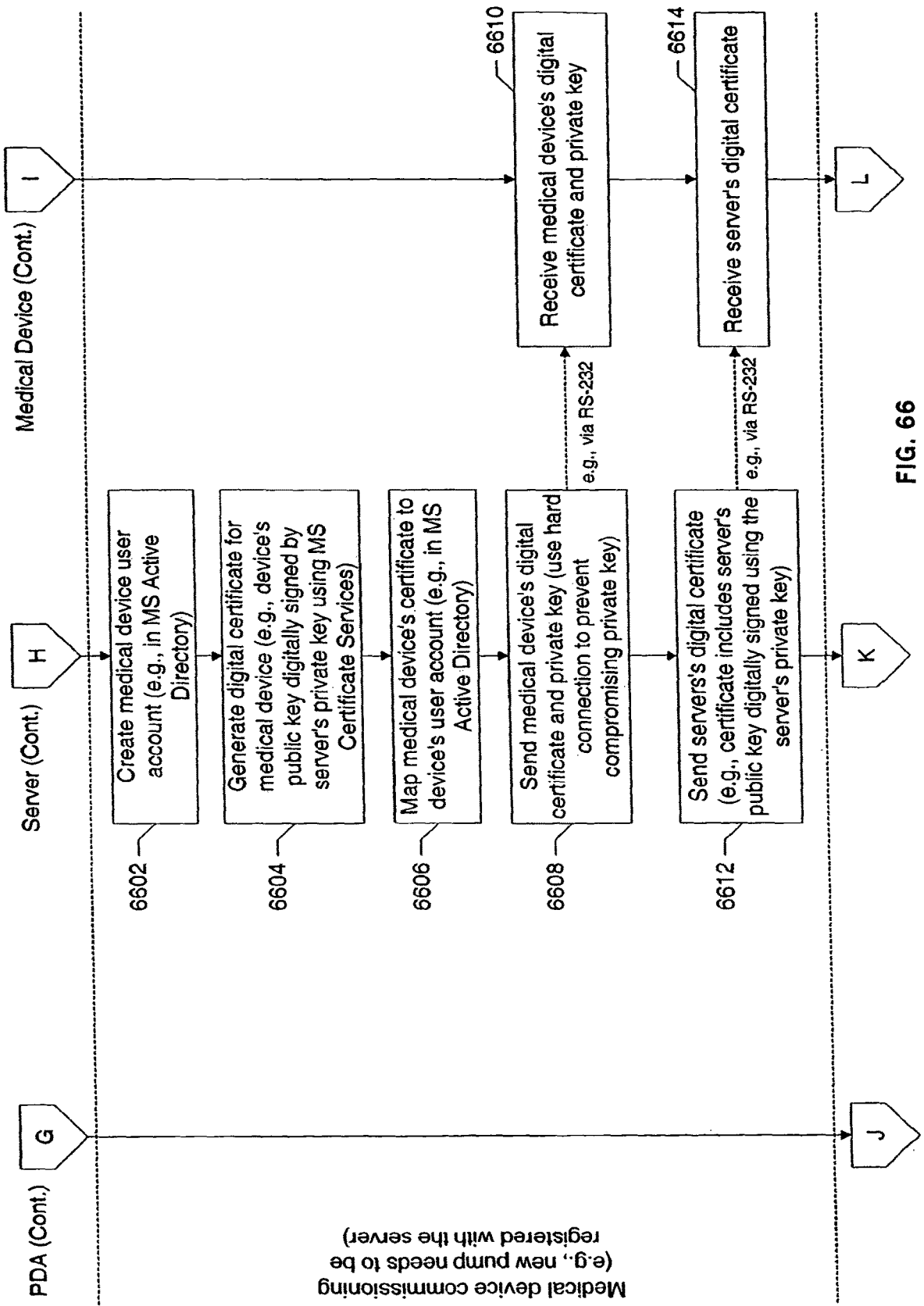

Turning to FIG. 66, the medical device commissioning phase (i.e., server registration phase) of the process 6300 begins at block 6602 when the first central server 109 creates a medical device user account. For example, the medical device user account may be established using Microsoft Active Directory in a well-known manner. The first central server 109 then generates a digital certificate for the medical device 120 at block 6604. The digital certificate may be generated in any manner. For example, the digital certificate may be generated at the first central server 109 using Microsoft Digital Certificate Services in a well known manner. The digital certificate preferably includes the medical device's public key digitally signed using the first central server's private key. In other words, the first central server 109 is acting as the certification authority (CA) for the medical device's digital certificate. Once the digital certificate is generated, the first central server 109 maps the digital certificate to the user account at block 6606.

The medical device's digital certificate and the medical device's private key are then sent by the first central server 109 at block 6608 to the medical device 120 at block 6610.

Preferably, the medical device's digital certificate and the medical device's private key are sent to the medical device 120 via a secure connection such as an RS-232 cable that is not connected to any other devices. In addition, the first central server's digital certificate is sent by the first central server 109 at block 6612 to the medical device 120 at block 6614. Again, the first central server's digital certificate is preferably sent to the medical device 120 via a secure connection such as an RS-232 cable that is not connected to any other devices. At this point, the medical device 120 is commissioned (i.e., registered with the server).

Of course, any method of communicating with the medical device 120 may be used. In one example, the medical device's private key may be stored in a memory associated with the medical device 120 (e.g., an EPROM) at the time the medical device 120 is manufactured. In addition, each medical device 120 may have the same private key, with different identification codes used to distinguish one medical device 120 from another.

Figure 67:
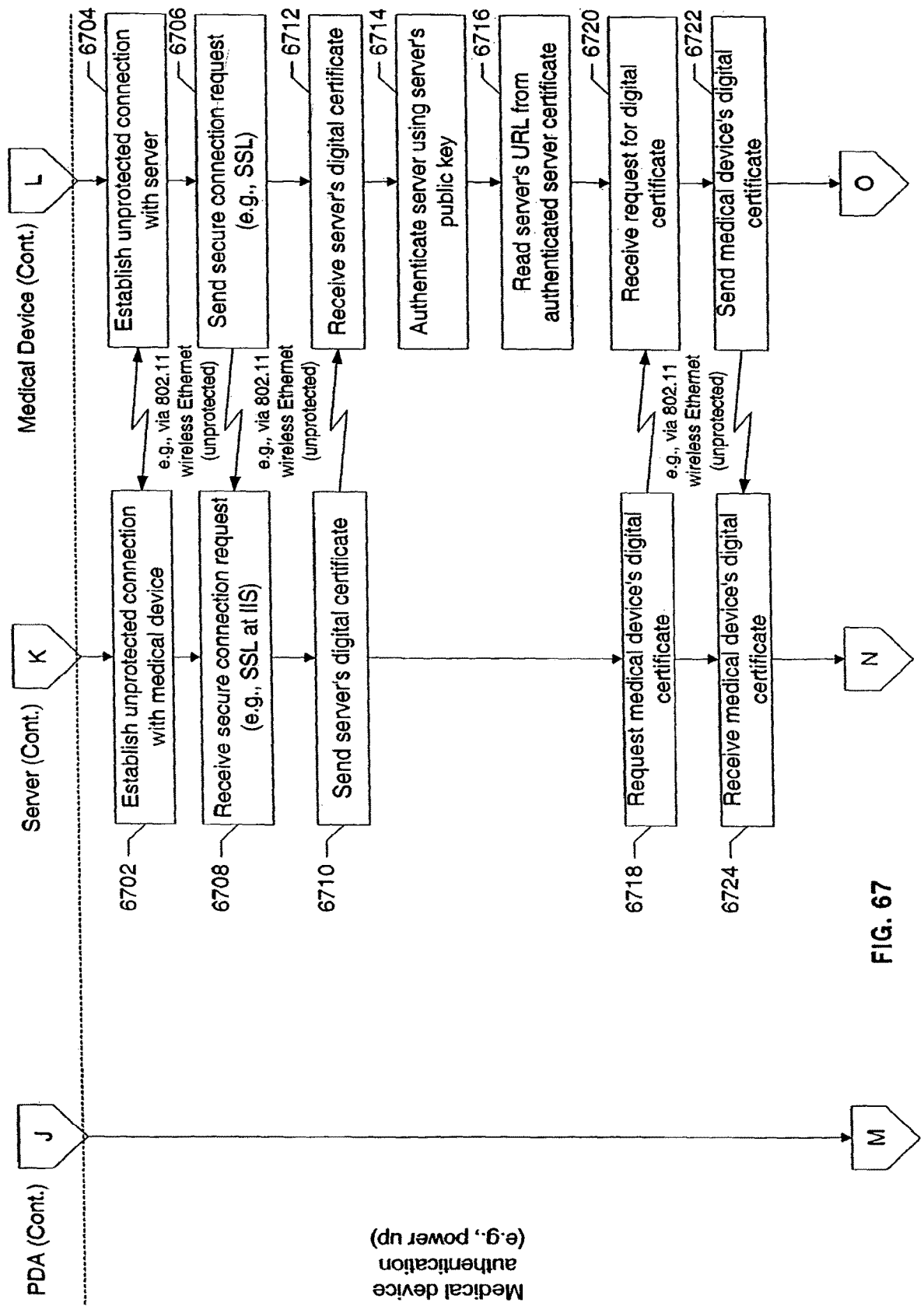

Each time a commissioned medical device 120 is turned on, the medical device 120 and the first central server 109 must perform an authentication process in order to move from an unsecured wireless connection to a secured wireless connection. In the example illustrated in FIG. 67, the medical device 120 establishes an unsecured 802.11 (wireless Ethernet) connection with the first central server 109 at block 6702 and block 6704. Of course, any type of connection may be used, such as a wired connection or a connection using another protocol.

Next, at block 6706 the medical device 120 sends a request to the first central server 109 to establish a secure connection. The first central server 109 receives the medical device's request to establish a secure connection at block 6708. The first central server 109 responds to the request to establish a secure connection at block 6710 by sending a copy of the first central server's digital certificate to the medical device 120 over the unsecured connection. The medical device 120 receives the first central server's digital certificate at block 6712.

The medical device 120 uses the first central server's digital certificate to authenticate the first central server 109 at block 6714. In addition, at block 6716 the medical device 120 uses the first central server's digital certificate to retrieve an embedded uniform resource locator (URL) associated with the first central server 109. The medical device 120 can now request data and services from the retrieved URL knowing it is talking to the real first central server 109.

Next, at block 6718 the first central server 109 sends a request to the medical device 120 to establish the other half of the secure connection. The medical device 120 receives the first central server's request at block 6720. The medical device 120 responds to the request to establish a secure connection at block 6722 by sending a copy of the medical device's digital certificate to the first central server 109. The first central server 109 receives the medical device's digital certificate at block 6724.

Figure 68:
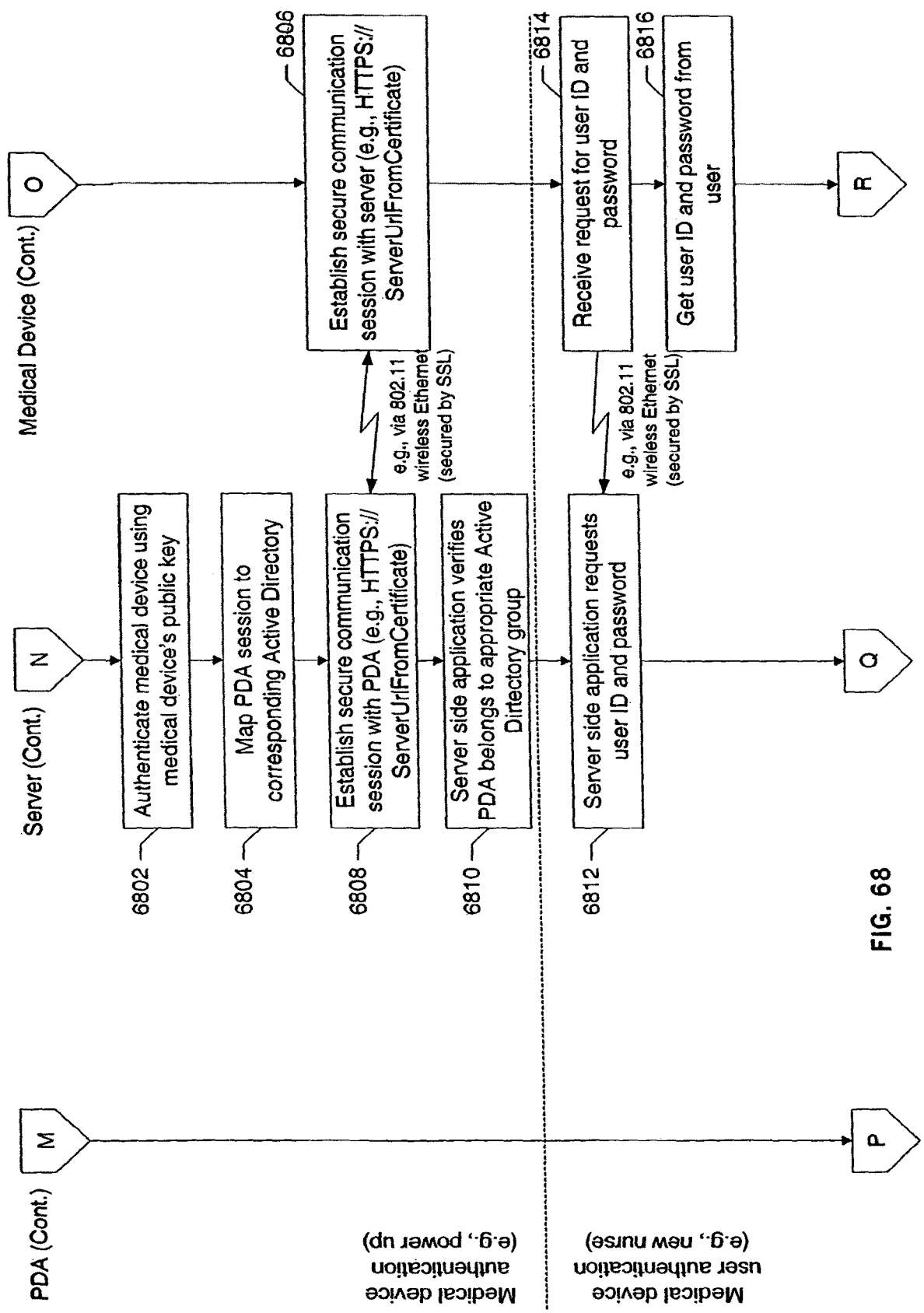

Turning to FIG. 68, the first central server 109 uses the medical device's digital certificate to authenticate the medical device 120 at block 6802. The first central server 109 can now communicate with the medical device 120 knowing it is talking to a commissioned medical device 120. In addition, the first central server 109 establishes what files this medical device 120 is authorized to access by mapping a session for the medical device user account to an active directory at block 6804.

Now that the medical device 120 is communicating with the first central server 109 over a secure connection, and the medical device 120 is cleared to access certain files on the first central server 109, at block 6806 the medical device 120 may establish a secure communication session with the first central server 109 by accessing the URL retrieved from the first central server's digital certificate. The first central server 109 also establishes the secure communication session at block 6808. In addition, an application on the first central server 109 verifies the medical device 120 belongs to the appropriate active directory at block 6810.

Although the medical device 120 may now be authenticated, the first central server 109 still does not know the identity of the user using the medical device 120. In many instances, no user will be associated with a medical device 120. In some applications, this may be important because some users may have different access rights than other users. In addition, a medical device may have different "roles." For example, a medical device may have a "one-way communication" role or a "two-way communication" role. In this manner, a medical device 120 capable of two-way communication may be placed in a system that expects only one-way communication devices. Similarly, a system that is capable of handling both one-way communication devices and two-way communication devices may need to be told the type of device that is connected.

Figure 69:
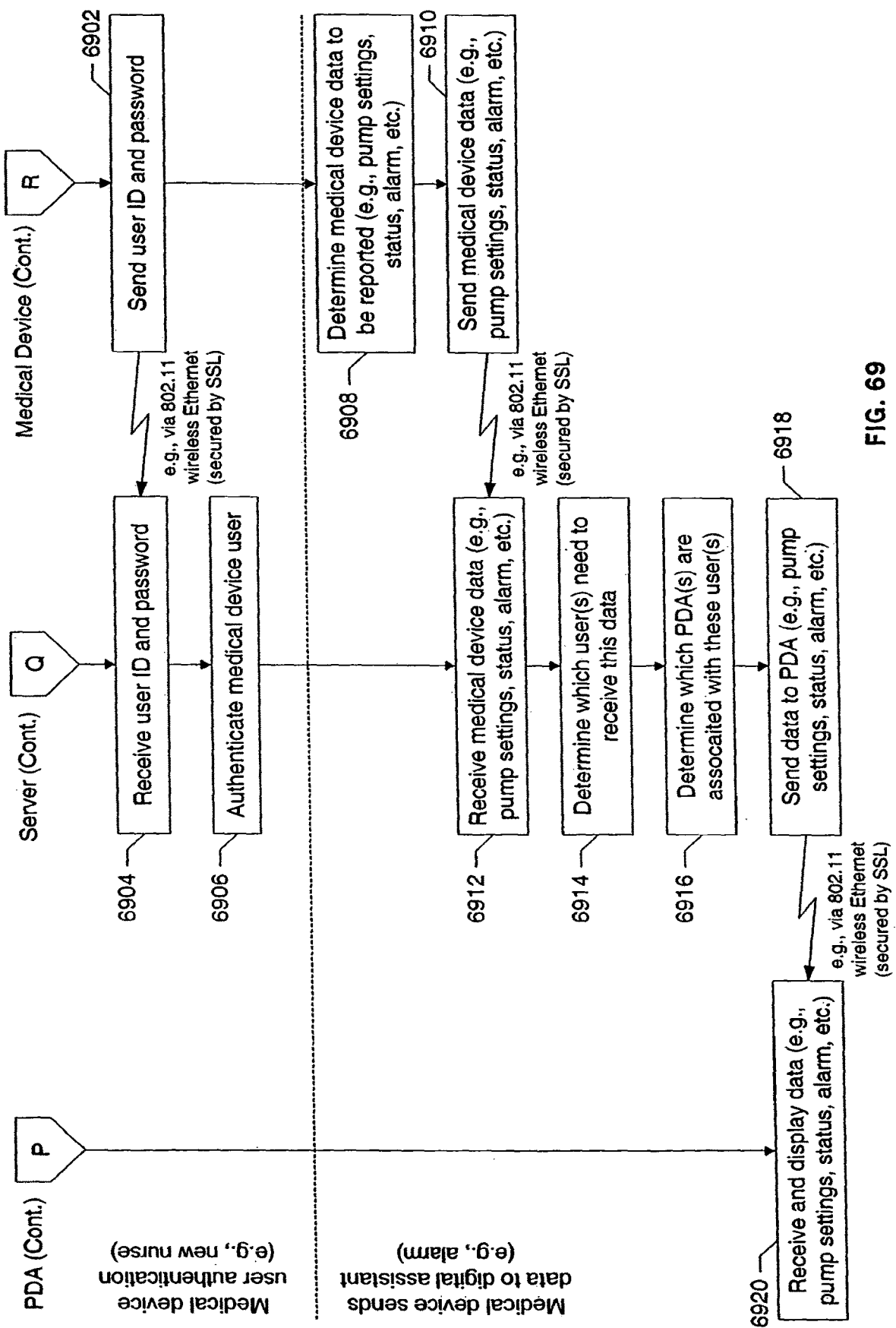

Accordingly, an application on the first central server 109 may request a user name and password from the user of the medical device 120 at block 6812. Once the medical device 120 receives the request for a user name and password at block 6814, the medical device 120 retrieves a user name and password from the user via a prompt on the medical device 120 or an associated digital assistant display 118*a* at block 6816. The user name and password are then sent by the medical device 120 (or other device) at block 6902 of FIG. 69 and received by the first central server 109 at block 6904. The application on the first central server 109 may then authenticate the user at block 6906.

Once the user is authenticated on one server (e.g., the first central server 109), the authentication credentials may be used to automatically authenticate the user on another server (e.g., second central server 108*a*). In one example, a user may only be authenticated if the user is authenticated on both the first central server 109 and the second central server 108*a*.

Accordingly, the user name and password are preferably synchronized between the first central server 109 and the second central server 108*a* whenever a user name or password is created or modified.

After authenticating the user, the first central server 109 preferably returns a token that will be unique to the session between the user and the first central server 109. This session token is passed with each request (e.g., in an HTTP header or as a cookie) made to the first central server 109 as a means of authenticating the origin of the request and hence the destination of the response.

Secure one-way communications may now be sent from the medical device 120 to the digital assistant 118. For example, the medical device 120 may report settings, generate alarms, etc. In the example illustrated, the medical device 120 determines data to be sent to the digital assistant 118 via the first central server 109 at block 6908. This data is then sent to the first central server 109 at block 6910 and received by the first central server 109 at block 6912. The first central server 109 may then determine which user(s) are authorized to receive this data at block 6914 and which digital assistant(s) 118 those users are currently associated with at block 6916. For example, a lookup table stored in the first central server 109 database may be used.

The first central server 109 then sends the data to the appropriate digital assistant(s) 118 at block 6918 and the digital assistant(s) 118 receive and display the data at block 6920. In addition, secure two-way communications may be accomplished. For example, a digital assistant 118 and/or the first central server 109 may send data, commands, setup information, or any other type of information to the medical device 120.

It should be emphasized that the above-described embodiments of the present invention, particularly, any "preferred" embodiments, are possible examples of implementations, merely set forth for a clear understanding of the principles of the invention. Many variations and modifications may be made to the above-described embodiment(s) of the invention without substantially departing from the spirit and principles of the invention. All such modifications are intended to be included herein within the scope of this disclosure and the present invention and protected by the following claims.

The invention is claimed as follows:

1. A pharmacy system for the automated transfer and processing of electronic medication order information to and from a computerized patient care system associated with a healthcare facility, the system comprising:
a pharmacy HL7 interface configured to
receive a first HL7 message including information relating to an electronic medication order for a medication that is to be prepared for intravenous administration to a patient, and
transmit a second HL7 message including information relating to preparation of the medication corresponding to the electronic medication order, the information from the second HL7 message being used to bill for the medication corresponding to the electronic medication order;
a pharmacy computer communicatively coupled to the pharmacy HL7 interface and configured to
process the electronic medication order, including accessing electronically at least one medication database or file using information included with the electronic medication order to identify one or more ingredients required to prepare the medication corresponding to the electronic medication order, and
transmit the information, the information including data indicative of the identified one or more ingredients relating to the preparation of the medication corresponding to the electronic medication order; and
a pharmacy workstation located at least in part within an environment suitable for preparing intravenously administered medications and communicatively coupled to the pharmacy computer, the pharmacy workstation configured to
provide instructions for preparing the medication corresponding to the electronic medication order, and
capture the information relating to preparation of the medication corresponding to the electronic medication order.

2. The system of claim 1, wherein the pharmacy computer is configured to
receive a message including information relating to an administration of the medication to the patient; and
responsive to receiving the message, transmit the information relating to the preparation of the medication corresponding to the electronic medication order.

3. The system of claim 1, wherein the pharmacy computer is communicatively coupled to an automatic filling and packaging system, the automatic filling and packaging system configured to automatically prepare the medication based on the electronic medication order and the one or more ingredients.

4. The system of claim 3, wherein the pharmacy computer includes a schedule generator configured to add the electronic medication order to a schedule specifying a predefined time period for preparing medications for patients.

5. The system of claim 4, wherein the automatic filling and packaging system uses the schedule to determine when to prepare the medication corresponding to the electronic medication order using the one or more ingredients.

6. The system of claim 3, wherein the pharmacy computer is configured to perform a calculation for a total parenteral nutrition medication order using at least one of patient height, patient weight, drug amount, diluent volume, concentration of ingredients, flow rate, and dependent quantities provided by the electronic medication order, and
wherein the automatic filling and packaging system is configured to prepare the medication based, in part, on the total parenteral nutrition medication order.

7. The system of claim 1, wherein the pharmacy workstation includes a display device configured to display the instructions including steps for a pharmacist to manually prepare the medication corresponding to the electronic medication order.

8. The system of claim 1, wherein the electronic medication order includes information for the preparation of at least one of a single dose infusion, an intermittent infusion, a continuous infusion, a sequence, a titration, a chemotherapy continuous infusion, a piggyback infusion, a large volume parenteral infusion, and a total parenteral nutritional admixture infusion.

9. The system of claim 1, wherein the pharmacy HL7 interface is configured to receive the electronic medication order from at least one of a clinician device, a computerized physician order-entry ("CPOE") system, and a pharmacy server.

10. The system of claim 1, wherein the pharmacy computer includes an algorithm for calculating a charge amount to be billed based on the information relating to the preparation of the medication corresponding to the electronic medication order.

11. The system of claim 1, wherein at least one of the pharmacy computer and the pharmacy workstation is communicatively coupled to a bar code scanner.

12. The system of claim 11, wherein at least one of the pharmacy computer and the pharmacy workstation is configured to use information from the bar code scanner to provide bar code verification of the one or more ingredients used to prepare the medication based on the electronic medication order.

13. The system of claim 1, wherein at least one of the pharmacy computer and the pharmacy workstation is configured to batch process the medication corresponding to the electronic medication order among other medications specified by respective electronic medication orders.

14. The system of claim 1, wherein at least one of the pharmacy computer and the pharmacy workstation is communicatively coupled to a memory that stores a plurality of instructions for preparing different medications, the at least one of the pharmacy computer and the pharmacy workstation being configured to select at least some of the instructions from the memory for the preparation of the medication corresponding to the electronic medication order.

15. The system of claim 1, wherein at least one of the pharmacy computer and the pharmacy workstation is communicatively coupled to a printer configured to print a bar code label for a medication container enclosing the medication corresponding to the electronic medication order.

16. The system of claim 1, wherein at least one of the pharmacy computer and the pharmacy workstation is configured to
manage an inventory of ingredients for preparing medications; and
update the inventory based on using the one or more ingredients for the preparation of the medication corresponding to the electronic medication order.

17. The system of claim 1, wherein the pharmacy HL7 interface is configured to determine a destination for the second HL7 message including at least one of a third-party financial system, an internal hospital information system, and an external hospital information system.

18. The system of claim 1, wherein the electronic medication order specifies at least one of (a) a dosage with a particular concentration of the medication, (b) a volume of the medication per unit of weight, (c) a dosage of the medication per a unit of body surface area, or (d) total dosage and duration.

19. The system of claim 18, wherein the medication order specifies the at least one of (a) to (d) over a time period.

20. The system of claim 18, wherein the pharmacy computer is configured to identify at least one of a concentration or a volume of at least one of the ingredients based on the medication order specifying the at least one of (a) to (d).

21. A pharmacy system for the automated transfer and processing of electronic medication order information to and from a computerized patient care system associated with a healthcare facility, the system comprising:

a pharmacy HL7 interface configured to
  receive a first HL7 message including information relating to an electronic medication order for a medication that is to be prepared for intravenous administration to a patient,
  receive information relating to preparation of the medication corresponding to the electronic medication order,
  generate a second HL7 message including the information relating to the preparation of the medication corresponding to the electronic medication order, and
  transmit the second HL7 message, the information from the second HL7 message being used to bill for the medication corresponding to the electronic medication order; and a pharmacy computer communicatively coupled to the pharmacy HL7 interface and configured to
  process electronically the electronic medication order, including accessing at least one medication database or file using information included with the electronic medication order to identify one or more ingredients required to prepare the medication corresponding to the electronic medication order,
  transmit the information, the information including data indicative of the identified one or more ingredients relating to the preparation of the medication corresponding to the electronic medication order to a pharmacy workstation for preparing the medication,
  receive a message including information relating to an administration of the medication to the patient, and
  responsive to receiving the message, transmitting to the pharmacy HL7 interface the information related to the preparation of the medication corresponding to the electronic medication order to generate the second HL7 message for billing for the medication.

22. The system of claim 21, wherein the pharmacy computer is configured to automatically trigger the transmission of the information related to the preparation of the medication to the pharmacy HL7 interface responsive to receiving the message.

23. The system of claim 21, wherein the pharmacy computer is configured to receive the message from at least one of an infusion pump that provided the intravenous administration to the patient, a medication administration server, or a pharmacy input device.

24. The system of claim 21, wherein the pharmacy computer includes an algorithm for calculating a charge amount to be billed based on the information relating to the preparation of the medication corresponding to the electronic medication order.

25. The system of claim 21, wherein the pharmacy HL7 interface is configured to determine a destination for the second HL7 message including at least one of a third-party financial system, an internal hospital information system, or an external hospital information system.

* * * * *